US012616746B2

(12) United States Patent
Ferguson et al.

(10) Patent No.: US 12,616,746 B2
(45) Date of Patent: May 5, 2026

(54) INFECTIOUS DISEASE ANTIGENS AND VACCINES

(71) Applicant: Gritstone bio, Inc., Emeryville, CA (US)

(72) Inventors: Andrew Ferguson, Hingham, MA (US); Raphael Rousseau, Los Altos, CA (US); Roman Yelensky, Newton, MA (US); James Xin Sun, Newton, MA (US); Matthew Joseph Davis, Scituate, MA (US); Karin Jooss, San Diego, CA (US); Amy Rachel Rappaport, Daly City, CA (US); Ciaran Daniel Scallan, San Francisco, CA (US); Leonid Gitlin, Foster City, CA (US); Christine Denise Palmer, Cambridge, MA (US)

(73) Assignee: Seattle Project Corp., Dover, DE (US)

( * ) Notice: Subject to any disclaimer, the term of this patent is extended or adjusted under 35 U.S.C. 154(b) by 652 days.

(21) Appl. No.: 17/937,751

(22) Filed: Oct. 3, 2022

(65) Prior Publication Data

US 2024/0050550 A1 Feb. 15, 2024

Related U.S. Application Data

(63) Continuation of application No. PCT/US2021/025828, filed on Apr. 5, 2021.

(60) Provisional application No. 63/005,160, filed on Apr. 3, 2020.

(51) Int. Cl.
| | |
|---|---|
| *A61K 39/00* | (2006.01) |
| *A61K 35/761* | (2015.01) |
| *A61K 38/00* | (2006.01) |
| *A61K 39/145* | (2006.01) |
| *A61P 31/16* | (2006.01) |
| *C12N 15/86* | (2006.01) |
| *B82Y 5/00* | (2011.01) |

(52) U.S. Cl.
CPC ............ *A61K 39/145* (2013.01); *A61P 31/16* (2018.01); *C12N 15/86* (2013.01); *A61K 2039/5256* (2013.01); *A61K 2039/545* (2013.01); *A61K 2039/55555* (2013.01); *B82Y 5/00* (2013.01)

(58) Field of Classification Search
CPC .......... A61P 35/00; A61P 37/04; A61P 35/02; C07K 14/005; C07K 14/705
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,722,848 | A | 2/1988 | Paoletti et al. |
| 4,837,028 | A | 6/1989 | Allen |
| 5,019,369 | A | 5/1991 | Presant et al. |
| 5,204,253 | A | 4/1993 | Sanford et al. |
| 5,240,846 | A | 8/1993 | Collins et al. |
| 5,279,833 | A | 1/1994 | Rose |
| 5,580,859 | A | 12/1996 | Felgner et al. |
| 5,589,466 | A | 12/1996 | Felgner et al. |
| 5,849,589 | A | 12/1998 | Tedder et al. |
| 5,891,994 | A | 4/1999 | Goldstein |
| 5,972,596 | A | 10/1999 | Pavlakis et al. |
| 6,083,716 | A | 7/2000 | Wilson et al. |
| 6,193,981 | B1 | 2/2001 | Goldstein |
| 6,376,236 | B1 | 4/2002 | Dubensky, Jr. et al. |
| 6,770,283 | B1 | 8/2004 | Garoff et al. |
| 8,093,021 | B2 | 1/2012 | Hurtado et al. |
| 8,216,834 | B2 | 7/2012 | Colloca et al. |
| 9,340,830 | B2 | 5/2016 | Lipson et al. |
| 9,416,370 | B2 | 8/2016 | Smith et al. |
| 10,055,540 | B2 | 8/2018 | Yelensky et al. |
| 11,504,421 | B2 | 11/2022 | Blair et al. |
| 11,510,973 | B2 | 11/2022 | Blair et al. |
| 12,109,257 | B2 | 10/2024 | Blair et al. |
| 2003/0114369 | A1 | 6/2003 | Takiguchi et al. |
| 2005/0271676 | A1 | 12/2005 | Sette et al. |
| 2006/0093623 | A1 | 5/2006 | Andrieu et al. |
| 2011/0293637 | A1 | 12/2011 | Hacohen et al. |
| 2011/0300205 | A1 | 12/2011 | Geall et al. |
| 2017/0199961 | A1 | 7/2017 | Yelensky et al. |
| 2018/0008690 | A1 | 1/2018 | Ng et al. |
| 2020/0010849 | A1 | 1/2020 | Blair et al. |
| 2021/0113673 | A1 | 4/2021 | Boucher et al. |
| 2022/0226453 | A1 | 7/2022 | Blair et al. |
| 2024/0067985 | A1 | 2/2024 | Blair et al. |
| 2025/0249084 | A1 | 8/2025 | Blair et al. |
| 2025/0270589 | A1 | 8/2025 | Blair et al. |

FOREIGN PATENT DOCUMENTS

| | | | |
|---|---|---|---|
| EP | 1371730 | A2 | 12/2003 |
| JP | 2007-518414 | A | 7/2007 |
| JP | 2019-511255 | A | 4/2019 |
| WO | 1991/006309 | A1 | 5/1991 |
| WO | 1993/024640 | A2 | 12/1993 |
| WO | 1995/13392 | A1 | 5/1995 |
| WO | 1996/013597 | A2 | 5/1996 |
| WO | 1996/018372 | | 6/1996 |

(Continued)

OTHER PUBLICATIONS

Brito et al., "Chapter Seven—Self-amplifying mRNA vaccines", Advances in Genetics, 2015, 89, book pp. 179-233: pdf pp. 1-10.*

(Continued)

*Primary Examiner* — Barry A Chestnut
(74) *Attorney, Agent, or Firm* — Goodwin Procter LLP

(57) ABSTRACT

Disclosed herein are compositions that include antigen-encoding nucleic acid sequences and/or antigen peptides. Also disclosed are nucleotides, cells, and methods associated with the compositions including their use as vaccines, including vectors and methods for a heterologous prime/boost vaccination strategy.

18 Claims, 19 Drawing Sheets

Specification includes a Sequence Listing.

(56) References Cited

FOREIGN PATENT DOCUMENTS

| | | | |
|---|---|---|---|
| WO | 1999/016884 | A1 | 4/1999 |
| WO | 2000/018433 | A2 | 4/2000 |
| WO | 200127291 | A1 | 4/2001 |
| WO | 200147955 | A2 | 7/2001 |
| WO | 2001/054719 | A2 | 8/2001 |
| WO | 2001/055177 | A2 | 8/2001 |
| WO | 2005/071093 | A2 | 8/2005 |
| WO | 2010037402 | A1 | 4/2010 |
| WO | 2011005799 | A2 | 1/2011 |
| WO | 2016081859 | A2 | 5/2016 |
| WO | 2016/122414 | A1 | 8/2016 |
| WO | 2016/187508 | A3 | 1/2017 |
| WO | 2017070626 | A2 | 4/2017 |
| WO | 2017/106638 | A1 | 6/2017 |
| WO | 2017/123652 | A1 | 7/2017 |
| WO | 2018/195357 | A1 | 10/2018 |
| WO | 2018/208856 | A1 | 11/2018 |
| WO | 2018/232330 | A1 | 12/2018 |
| WO | 2020/035609 | A2 | 2/2020 |
| WO | 2020/181240 | A1 | 9/2020 |
| WO | 2021/003348 | A1 | 1/2021 |
| WO | 2021203104 | A1 | 10/2021 |
| WO | 2021236854 | A1 | 11/2021 |
| WO | 2022/118226 | A1 | 6/2022 |
| WO | 2024238412 | A1 | 11/2024 |
| WO | 2025121052 | A1 | 6/2025 |

OTHER PUBLICATIONS

Aarnoudse et al., "TCR reconstitution in Jurkat reporter cells facilitates the identification of novel tumor antigens by cDNA expression clonin," International Journal of Vancer, May 1, 2002;99(1):7-13.

Abelin et al., "Complementary IMAC enrichment methods for HLA-associated phosphopeptide identification by mass spectrometry," Nature Protocols 10(9) (2015): 1308-1318.

Alexander et al., "Development of High Potency Universal DR-Restricted Helper Epitopes by Modification of High Affinity DR-Blocking Peptides." Immunity vol. 1, Issue 9 (1994): 751-761.

Altschul et al., "Basic Local Alignment Search Tool." Journal of Molecular Biology vol. 215, Issue 3 (1990): 403-410.

Amara et al., "Control of a mucosal challenge and prevention of AIDS by a multiprotein DNA/MVA vaccine." Science. Apr. 6, 2001;292(5514):69-74. doi: 10.1126/science.1058915.

Anders et al., "HTSeq-a Python framework to work with high-throughput sequencing data." Bioinformatics vol. 31, No. 2 (Jan. 15, 2015): 166-169.

Andreatta et al., "Accurate pan-specific prediction of peptide-MHC class II binding affinity with improved binding core identification." Immunogenetics 67, No. 11-12 (Nov. 2015): 641-650.

Andreatta et al., "Gapped sequence alignment using artificial neural networks: application to the MHC class I system," Bioinformatics, Feb. 15, 2016;32(4):511-7.

Banu et al., "Building and Optimizing a Virus-specific T Cell Receptor Library for Targeted Immunotherapy in Viral Infections." Scientific Reports, Feb. 25, 2014;4:1-10.

Barnstable et al., "Production of Monoclonal Antibodies to Group A Erythrocytes, HLA and Other Human Cell Surface Antigens—New Tools for Genetic Analysis," Cell vol. 14, 9-20, 1978.

Barouch et al., "Elicitation of high-frequency cytotoxic T-lymphocyte responses against both dominant and subdominant simian-human immunodeficiency virus epitopes by DNA vaccination of rhesus monkeys." Journal of Virology. Mar. 2001;75(5):2462-7. doi: 10.1128/JVI.75.5.2462-2467.2001.

Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.

Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.

Boegel et al., "HLA typing from RNA-Seq sequence reads," Genome Medicine, Dec. 22, 2012;4(12):1-12.

Boisvert et al., "A Quantitative Spatial Proteomics Analysis of Proteome Turnover in Human Cells," Molecular & Cellular Proteomics, Mar. 2012; 11(3):1-15.

Boshart et al., "A Very Strong Enhancer is Located Upstream of an Immediate Early Gene of Human Cytomegalovirus," Cell vol. 41, No. 2, 521-530, 1985.

Brumme Z.L, et al. "HLA-associated immune escape pathways in HIV-1 subtype B Gag, Pol and Nef proteins," PLoS One. Aug. 19, 2009;4(8)1-12.

Brumme, Z.L. "Pol protein, partial [Human immunodeficiency virus 1]," Online, www.ncbi.nlm.nih.gov/accession, Jul. 24, 2016 (2 pages).

Brumme, Z.L., "HIV-1 isolate D3521TOB8U from USA pol protein (pol) gene, partial cds," Online, www.ncbi.nlm.nih.gov/nuccore, Jul. 24, 2016, (2 pages).

Calis et al., "Properties of MHC Class I Presented Peptides That enhance immunogenicity." PLoS Comput Biol. vol. 9, Issue 10 (Oct. 24, 2013): e1003266, 13 pages.

Callendret et al., "Heterologous viral RNA export elements improve expression of severe acute respiratory syndrome (SARS) coronavirus spike protein and protective efficacy of DNA vaccines against SARS." Virology. Jul. 5, 2007;363 (2):288-302. doi: 10.1016/j.virol.2007.01.012.

Cancer Genome Atlas Research Network, "Comprehensive molecular profiling of lung adenocarcinoma," Nature, vol. 511, pp. 543-550, 2014.

Carithers et al., "A Novel Approach to High-Quality Postmortem Tissue Procurement: The GTEx Project," Biopreservation and Biobanking, vol. 13, No. 5, 311-319, Oct. 1, 2015.

Carreno et al., "A dendritic cell vaccine increases the breadth and diversity of melanoma neoantigen-specific T cells." Science, May 15, 2015;348(6236):803-8.

Carter et al., "Absolute quantification of somatic DNA alterations in human cancer," Nature Biotechnology vol. 30, No. 5, 413-421, 2012.

Cibulskis et al., "Sensitive detection of somatic point mutations in impure and heterogeneous cancer samples," Nature Biotechnology vol. 31, No. 3, pp. 213-219, 2013.

Cieslik et al., "The use of exome capture RNA-seq for highly degraded RNA with application to clinical cancer sequencing," Genome Research vol. 25, No. 9, 1372-1381, Sep. 1, 2015.

Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.

Cornet et al., "Optimal organization of a polypeptide-based candidate cancer vaccine composed of cryptic tumor peptides with enhanced immunogenicity," Vaccine vol. 24, No. 12, pp. 2102-2109, 2006.

Davis et al., "Alphavirus replicon particles as candidate HIV vaccines," IUBMB Life. Apr.-May 2002;53(4-5):209-211.

Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.

Desrichard et al., "Cancer neoantigens and applications for immunotherapy," Clinical Cancer Research vol. 22, No. 4, pp. 807-812, Feb. 15, 2016.

Duan et al., "Genomic and bioinformatic profiling of mutational neoepitopes reveals new rules to predict anticancer immunogenicity," Journal of Experimental Medicine, Oct. 20, 2014;211(11):2231-48.

Fang et al., "Stable antibody expression at therapeutic levels using the 2A peptide." Nature biotechnology 23, No. 5 (2005): 584-590.

Felgner et al., "Lipofection: a highly efficient, lipid-mediated DNA-transfection procedure." Proceedings of the National Academy of Sciences 84, No. 21 (1987): 7413-7417.

(56) References Cited

OTHER PUBLICATIONS

Frampton et al., "Development and validation of a clinical cancer genomic profiling test based on massively parallel DNA sequencing," Nature Biotechnology Nov. 2013;31(11):1023-31.

Frolov et al., "Cis-acting RNA elements at the 5' end of Sindbis virus genome RNA regulate minus- and plus-strand RNA synthesis," RNA vol. 7, No. 11, pp. 1638-1651, 2001.

Furney et al., "SF3B1 Mutations Are Associated with Alternative Splicing in Uveal Melanoma," Cancer Discovery vol. 3, Issue 10, pp. 1122-1129, 2013.

Gen Bank: AF394196.1—Simian adenovirus 25, complete genome, 15 pages, 2001.

Goldman et al, "HLA-DA monoclonal antibodies inhibit the proliferation of normal and chronic granulocytic leukaemia myeloid progenitor cell," British Journal of Haematology 52, No. 3 (1982): 411-420.

Gros et al., "Prospective identification of neoantigen-specific lymphocytes in the peripheral blood of melanoma patients," Nature Medicine vol. 22, Issue 4, pp. 433-438, Feb. 22, 2016.

Gubin et al., "Tumor neoantigens: Building a framework for personalized cancer immunotherapy," The Journal of Clinical Investigation, vol. 125, No. 9, pp. 3413-3421, Sep. 2015.

Hu et al., "Immunization Delivered by Lentiviral Vectors for Cancer and Infectious Diseases," Immunological Reviews, vol. 239, Issue 1, pp. 45-61, 2011.

Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.

Hung CF, et al. (2007), "DNA vaccines encoding li-PADRE generates potent PADRE-specific CD4+ T-cell immune responses and enhances vaccine potency," Mol. Ther., 15(6):1211-9.

Hunt et al., "Characterization of Peptides Bound to the Class I MHC Molecule HLA-A2. 1 by Mass Spectrometry," Science vol. 255, pp. 1261-1263, 1992.

Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.

Janetzki et al., "Guidelines for the automated evaluation of Elispot assays," Nature Protocols vol. 10, No. 7, pp. 1098-1115, Jul. 2015.

Jensen et al., "Improved methods for predicting peptide binding affinity to MHC class II molecules," Immunology vol. 154, Issue 3, pp. 394-406, 2018.

Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.

Skelly et al., "A powerful and flexible statistical framework for testing hypotheses of allele-specific gene expression from RNA-seq data," Genome Research vol. 21, No. 10, pp. 1728-1737, 2011.

Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.

Snyder et al., "Genetic Basis for Clinical Response to CTLA-4 Blockade in Melanoma," New England Journal of Medicine, vol. 371, No. 23, pp. 2189-2199, 2014.

Song et al., "Class: constrained transcript assembly of RNA-seq reads," BMC Bioinformatics, BioMed Central, 2013;14 Suppl 5(Suppl 5):1-8.

Stover et al., "New use of BCG for recombinant vaccines," Nature vol. 351, No. 6326, pp. 456-460, 1991.

Strauss et al., "The Alphaviruses: Gene Expression, Replication, and Evolution," Microbiological Reviews, vol. 58, No. 3, pp. 491-562, 1994.

Szoka et al., "Comparative properties and methods of preparation of lipid vesicles (liposomes)." Annual review of biophysics and bioengineering 9, No. 1 (1980): 467-508.

Tatsis et al., "Adenoviruses as vaccine vectors," Molecular Therapy vol. 10, No. 4, pp. 616-629, 2004.

Tran et al., "Cancer Immunotherapy Based on Mutation-Specific CD4+ T Cells in a Patient with Epithelial Cancer," Science vol. 344, No. 6184, pp. 641-645, 2014.

Van Allen et al., "Genomic correlates of response to CTLA-4 blockade in metastatic melanoma," Science vol. 350, No. 6257, pp. 207-211, Nov. 11, 2015.

Van Loo et al., "Allele-specific copy number analysis of tumors," Proceedings of the National Academy of Sciences, vol. 107, No. 39, pp. 16910-16915, 2010.

Verhoef et al., "Des-enkephalin-gamma-endorphin (DE gamma E): biotransformation in rat, dog and human plasma." Eur J Drug Metab Pharmacokinet. Oct.-Dec. 1986;11(4):291-302. doi: 10.1007/BF03189114.

Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.

Vitting-Seerup et al., "spliceR: an R package for classification of alternative splicing and prediction of coding potential from RNA-seq data," BMC Bioinformatics, vol. 15, Issue 1, pp. 1-7, 2014.

Walter et al., "Clonal Architecture of Secondary Acute Myeloid Leukemia," New England Journal of Medicine, vol. 366, Issue 12, pp. 1090-1098, 2012.

Wilkerson et al., "Integrated RNA and DNA sequencing improves mutation detection in low purity tumors," Nucleic Acids Research, Jul. 2014;42(13):1-12.

Wolff et al., "Direct gene transfer into mouse muscle in vivo." Science 247, No. 4949 (1990): 1465-1468.

Wu et al., "Targeting genes: delivery and persistent expression of a foreign gene driven by mammalian regulatory elements in vivo." Journal of Biological Chemistry 264, No. 29 (1989): 16985-16987.

Xu et al., "RNA CoMPASS: A Dual Approach for Pathogen and Host Transcriptome Analysis of RNA-Seq Datasets," PloS One, vol. 9, Issue 2, p. e89445, 2014.

Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.

Yadav et al., "Predicting immunogenic tumour mutations by combining mass spectrometry and exome sequencing," Nature, vol. 515, No. 7528, pp. 572-576, 2014.

Ye et al., "Pindel: a pattern growth approach to detect break points of large deletions and medium sized insertions from paired-end short reads," Bioinformatics vol. 25, No. 21, pp. 2865-2871, 2009.

Yoshida et al., "Splicing factor mutations and cancer," Wiley Interdisciplinary Reviews: RNA 5, No. 4 (2014): 445-459.

Zarling et al., "Identification of class I MHC-associated phosphopeptides as targets for cancer immunotherapy," Proceedings of the National Academy of Sciences, vol. 103, No. 40, pp. 14889-14894, 2006.

Zhang et al., "Intra-tumor Heterogeneity in Localized Lung Adenocarcinomas Delineated by Multi-region Sequencing," Science vol. 346, No. 6206, pp. 256-259, 2014.

Zhang, et al., "Peaks DB: De Novo Sequencing Assisted Database Search for Sensitive and Accurate Peptide Identification," Molecular & Cellular Proteomics, Apr. 2012;11(4):1-8.

Zhou et al., "A Chemical Genetics Approach for the Functional Assessment of Novel Cancer Genes," Cancer Research vol. 75, No. 10, pp. 1949-1958, May 15, 2015.

Zufferey et al., "Self-Inactivating Lentivirus Vector for Safe and Efficient In Vivo Gene Delivery," Journal of Virology vol. 72, No. 12, pp. 9873-9880, 1998.

McKay, et al. "Self-amplifying RNA SARS-CoV-2 lipid nanoparticle vaccine candidate induces high neutralizing antibody titers in mice," Biorxiv, Apr. 25, 2020, pp. 1-14.

Grifoni, A., et al., "A Sequence Homology and Bioinformatic Approach Can Predict Candidate Targets for Immune Responses to SARS-CoV-2," Cell Host Microbe. Apr. 8, 2020;27(4):671-680.

E. Fast, et al., "Potential T-cell and B-cell epitopes of 2019-nCOV." BioRxiv, (2020): Feb. 2020, Abstract.

Agnihothram, S., et al. "Development of a Broadly Accessible Venezuelan Equine Encephalitis Virus Replicon Particle Vaccine Platform," J Virol. May 14, 2018;92(11):e00027-18.

(56) References Cited

OTHER PUBLICATIONS

Tarke, A., et al., Comprehensive analysis of T Â cell immunodominance and immunoprevalence of SARS-CoV-2 epitopes in COVID-19 cases. Cell Rep Med. Feb. 16, 2021;2(2):1-20.

Grifoni Alba et al: "Targets of T Cell Responses to SARS-CoV-2 Coronavirus in Humans with COVID-19 Disease and Unexposed Individuals", Cell, Elsevier, Amsterdam NL, vol. 181, No. 7, May 14, 2020, p. 1489.

Dupuis et al., "Dendritic cells internalize vaccine adjuvant after intramuscular injection." Cell Immunol. May 25, 1998;186(1):18-27. doi: 10.1006/cimm.1998.1283.

UniProtKB Accession FOSJ75 (FOSJ75_RUBBR) Rubinisphaera brasiliensis (strain ATCC 49424 / DSM 5305 / JCM 21570 / NBRC 103401 / IFAM 1448) (Planctomyces brasiliensis) Uncharacterized protein, Jun. 3, 2011 [online]. [Retrieved on Sep. 24, 2021]. Retrieved from the internet: <URL: ht1ps://www.uniprot.org/uniprot/FOSJ75> Entire document.

UniProtKB Accession A0A1V4QDP4 (A0A1V4QDP4_9BACT) candidate division WOR-3 bacterium 4484_100 Uncharacterized protein, Jun. 7, 2017 [online]. [Retrieved on Sep. 24, 2021]. Retrieved from the internet: <URL: https://www.uniprot.org/uniprot/A0A1V4QDP4> Entire document.

Fisher et al., "The transmembrane domain of diphtheria toxin improves molecular conjugate gene transfer." Biochemical Journal 321, No. 1 (1997): 49-58.

Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.

Jose et al., "A structural and functional perspective of alphavirus replication and assembly," Future Microbiology, vol. 4, No. 7, pp. 837-856, 2009.

Käll et al., "Assigning Significance to Peptides Identified by Tandem Mass Spectrometry Using Decoy Databases," Journal of Proteome Research vol. 7, No. 01, pp. 29-34, 2008.

Käll et al., "Non-parametric estimation of posterior error probabilities associated with peptides identified by tandem mass spectrometry," Bioinformatics vol. 24, No. 16, pp. i42-i48, 2008.

Käll et al., "Semi-supervised learning for peptide identification from shotgun proteomics datasets," Nature Methods vol. 4, No. 11, pp. 923-925, 2007.

Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.

Kost et al., "The nucleotide sequence of the chick cytoplasmic b-actin gene," Nucleic Acids Research vol. 11, No. 23, pp. 8287-8301, 1983.

Kreiter et al., "Mutant MHC class II epitopes drive therapeutic immune responses to cancer," Nature, vol. 520, No. 7549, pp. 692-696, Apr. 2015.

Lam et al., "Nucleotide-resolution analysis of structural variants using BreakSeq and a breakpoint library," Nature Biotechnology vol. 28, No. 1, pp. 47-55 2010.

Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.

Lazzaro et al., "CD8 T-cell priming upon mRNA vaccination is restricted to bone-marrow-derived antigen-presenting cells and may involve antigen transfer from myocytes," Immunology, Oct. 2015;146(2):312-26.

Li et al., "RSEM: accurate transcript quantification from RNA-Seq data with or without a reference genome." BMC bioinformatics 12, No. 1 (2011): 323, 16 pages.

Liepe et al., "A large fraction of HLA class I ligands are proteasome-generated spliced peptides," Science vol. 354, No. 6310, Oct. 21, 2016.

Liu et al., "ATHLATES: accurate typing of human leukocyte antigen through exome sequencing," Nucleic Acids Research Aug. 2013;41(14):1-8.

Lu et al., "Efficient identification of mutated cancer antigens recognized by T cells associated with durable tumor regressions," Clinical Cancer Research vol. 20, No. 13, pp. 3401-3410, 2014.

Lundegaard et al., "State of the art and challenges in sequence based T-cell epitope prediction," Immunome Research vol. 6, No. 2, pp. 1-14, 2010.

Lundstrom, "Self-Replicating RNA Viruses for RNA Therapeutics." Molecules. Dec. 13, 2018;23(12):3310. doi: 10.3390/molecules23123310.

Lyons et al., "Influence of Human CD8 on Antigen Recognition by T-Cell Receptor-Transduced Cells," Cancer Research vol. 66, No. 23, pp. 11455-11461, 2006.

Magini et al, "Self-Amplifying mRNA Vaccines Expressing Multiple Conserved Influenza Antigens Confer Protection against Homologous and Heterosubtypic Viral Challenge," PLoS One. Aug. 15, 2016;11(8)1-25.

Maguire et al., "SF3B1 mutations constitute a novel therapeutic target in breast cancer," The Journal of Pathology vol. 235, No. 4 pp. 571-580, Mar. 2015.

Mannino et al., "Liposome mediated gene transfer." Biotechniques 6, No. 7 (1988): 682-690.

Maretty et al. "Bayesian transcriptome assembly," Genome Biology, 2014;15(10):1-11.

Mayor et al., "HLA typing for the next generation," PLoS One, May 27, 2015;10(5):1-12.

Mcgranahan et al., "Allele-specific HLA loss and immune escape in lung cancer evolution," Cell vol. 171, No. 6, pp. 1259-1271, 2017.

Mohammed et al., "Phosphorylation-dependent interaction between antigenic peptides and MHC class I: a molecular basis for the presentation of transformed self." Nature immunology 9, No. 11 (2008): 1236-1243.

Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.

Mose et al., "ABRA: improved coding indel detection via assembly-based realignment," Bioinformatics, vol. 30, No. 19, pp. 2813-2815, 2014.

Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.

Nielsen et al., "NN-align. An artificial neural network-based alignment algorithm for MHC class II peptide binding prediction," BMC Bioinformatics, Sep. 18, 2009;10:1-10.

Nielsen et al., "Prediction of MHC class II binding affinity using SMM-align, a novel stabilization matrix alignment method," BMC Bioinformatics, Jul. 4, 2007;8:1-12.

Nielsen et al., "The role of the proteasome in generating cytotoxic T-cell epitopes: insights obtained from improved predictions of proteasomal cleavage," Immunogenetics vol. 57, No. 1-2, pp. 33-41, 2005.

Panina-Bordignon et al., "Universally immunogenic T cell epitopes: promiscuous binding to human MHC class II and promiscuous recognition by T cells," European Journal of Immunology 19, No. 12 (1989): 2237-2242.

PCT/US2020/040630—International Preliminary Report on Patentability, Jan. 13, 2022, 15 pages.

PCT/US2020/040630—International Searech Report and Wirtten Opinion, Nov. 20, 2020, 23 pages.

PCT/US2021/025828—International Prelimiary Report on Patentability, Oct. 13, 2022, 10 pages.

PCT/US2021/025828—International Search Report and Written Opinion, Jul. 28, 2021, 13 pages.

Pearson et al., "MHC class I-associated peptides derive from selective regions of the human genome," The Journal of Clinical Investigation, vol. 126, No. 12, pp. 4690-4701, Dec. 1, 2016.

Pertea et al., "StringTie enables improved reconstruction of a transcriptome from RNA-seq reads," Nature Biotechnology vol. 33, No. 3, pp. 290-295, Mar. 2015.

Pushko et al., "Replicon-Helper Systems from Attenuated Venezuelan Equine Encephalitis Virus: Expression of Heterologous Genes

(56) References Cited

OTHER PUBLICATIONS in Vitro and Immunization against Heterologous Pathogens in Vivo," Virology vol. 239, No. 2, pp. 389-401, 1997.

Rajasagi et al., "Systematic identification of personal tumor-specific neoantigens in chronic lymphocytic leukemia," Blood, vol. 124, No. 3, pp. 453-462, 2014.

Rhême et al., "Alphaviral cytotoxicity and its implication in vector development," Experimental Physiology vol. 90, No. 1, pp. 45-52, 2005.

Riley et al., "Recent advances in nanomaterials for gene delivery—a review," Nanomaterials, Apr. 28, 2017;7(5):1-19.

Rivas et al., "Effect of predicted protein-truncating genetic variants on the human transcriptome," Science vol. 348, No. 6235, pp. 666-669, May 8, 2015.

Rizvi et al., "Mutational landscape determines sensitivity to PD-1 blockade in non-small cell lung cancer," Science, Apr. 3, 2015;348(6230):1-12.

Roberts et al., "Identification of novel transcripts in annotated genomes using RNA-Seq," Bioinformatics vol. 27, No. 17, pp. 2325-2329, 2011.

Roy et al., "Assessing long-distance RNA sequence connectivity via RNA-templated DNA-DNA ligation," Elife. Apr. 13, 2015;4:1-21.

Sakuma et al., "Lentiviral vectors: basic to translational," Biochemical Journal 443, No. 3 (2012): 603-618.

Saunders et al., Strelka: accurate somatic small-variant calling from sequenced tumor-normal sample pairs, Bioinformatics vol. 28, No. 14, pp. 1811-1817, 2012.

Schumacher et al., "Neoantigens in cancer immunotherapy," Science vol. 348, Issue 6230, pp. 69-74, Apr. 3, 2015.

Shukla et al., "Comprehensive analysis of cancer-associated somatic mutations in class I HLA genes," Nature Biotechnology vol. 33, No. 11. pp. 1152-1158, Nov. 2015.

* cited by examiner

FIG 7

Naïve
Teff
Tem
Tcm

SEQUENCE LISTING

```
Sequence total quantity: 70
SEQ ID NO: 1          moltype = DNA   length = 36519
FEATURE               Location/Qualifiers
misc_feature          1..36519
                      note = Description of Artificial Sequence: Synthetic
                      polynucleotide
source                1..36519
                      mol_type = other DNA
                      organism = synthetic construct
SEQUENCE: 1
ccatcttcaa taatatacct caaacttttt gtgcgcgtta atatgcaaat gaggcgtttg   60
aatttgggga ggaagggcgg tgattggtcg agggatgagc gaccgttagg ggcgggggcga  120
gtgacgtttt gatgacgtgg ttgcgaggag gagccagttt gcaagttctc gtgggaaaag  180
tgacgtcaaa cgaggtgtgg tttgaacacg gaaatactca attttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgt cagggaggag tatttgccga  360
```

-continued

```
gggccgagta gactttgacc gattacgtgg gggtttcgat taccgtgttt ttcacctaaa   420
tttccgcgta cggtgtcaaa gtccggtgtt tttacgtagg tgtcagctga tcgccaggqt   480
atttaaacct gcgctctcca gtcaagaggc cactcttgag tgccagcgag aagagttttc   540
tcctccgcgc cgcgagtcag atctacactt tgaaagatga ggcacctgag agacctgccc   600
gatgagaaaa tcatcatcgc ttccgagaac gagattctgg aactggtggt aaatgccatg   660
atgggcgacg accctccgga gcccccacc ccatttgaga caccttcgct gcacgatttg   720
tatgatctgg aggtggatgt gcccgaggac gatcccaatg aggaggcggt aaatgatttt   780
tttagcgatg ccgcgctgct agctgccgag gaggcttcga gctctagctc agacagcgac   840
tcttcactgc ataccctag acccggcaga ggtgagaaaa agatccccga gcttaaaggg   900
gaagagatgg acttgcgctg ctatgaggaa tgcttgcccc cgagcgatga tgaggacgag   960
caggcgatcc agaacgcagc gagccaggga gtgcaagccg ccagcgagag ctttgcgctg  1020
gactgcccgc ctctgcccgg acacggctgt aagtcttgtg aatttcatcg catgaatact  1080
ggagataaag ctgtgttgtg tgcactttgc tatatgagag cttacaacca ttgtgtttac  1140
agtaagtgtg attaagttga actttagagg gaggcagaga gcagggtgac tgggcgatga  1200
ctggtttatt tatgtatata tgttctttat ataggtcccg tctctgacgc agatgatgag  1260
accccaacta caaagtccac ttcgtcaccc ccagaaattg gcacatctcc acctgagaat  1320
attgttagac cagttcctgt tagagccact gggaggagag cagctgtgga atgtttggat  1380
gacttgctac agggtggggt tgaacctttg gacttgtgta cccggaaacg ccccaggcac  1440
taagtgccac acatgtgtgt ttacttgagg tgatgtcagt atttataggg tgtggagtgc  1500
aataaaaaat gtgttgactt taagtgcgtg gtttatgact caggggtggg gactgtgagt  1560
atataagcag gtgcagacct gtgtggttag ctcagagcgg catggagatt tggacggtct  1620
tggaagactt tcacaagact agacagctgc tagagaacgg ctcgaacgga gtctcttacc  1680
tgtggagatt ctgcttcggt ggcgacctag ctaggctagt ctacagggcc aaacaggatt  1740
atagtgaaca atttgaggtt attttgagag agtgttctgg tcttttttgac gctcttaact  1800
tgggccatca gtctcacttt aaccagagga tttcgagagc ccttgatttt actactcctg  1860
gcagaaccac tgcagcagta gcctttttg cttttattct tgacaaatgg agtcaagaaa  1920
cccatttcag cagggattac cagctggatt tcttagcagt agctttgtgg agaacatgga  1980
agtgccagcg cctgaatgca atctccggct acttgccggt acagccgcta gacactctga  2040
ggatcctgaa tctccaggag agtcccaggg cacgccaacg tcgccagcag cagcagcagg  2100
aggaggatca agaagagaac ccgagagccg gcctgaccc tccggcggag gaggaggagt  2160
agctgacctg tttcctgaac tgcgccgggt gctgactagg tcttcgagtg gtcgggagag  2220
ggggattaag cgggagaggc atgatgagac taatcacaga actgaactga ctgtgggtct  2280
gatgagtcgc aagcgcccag aaacagtgtg gtggcatgag gtgcagtcga ctggcacaga  2340
tgaggtgtcg gtgatgcatg agaggttttc tctagaacaa gtcaagactt gttggttaga  2400
gcctgaggat gattgggagg tagccatcag gaattatgcc aagctggctc tgaggccaga  2460
caagaagtac aagattacta agctgataaa tatcagaaat gcctgctaca tctcagggaa  2520
tggggctgaa gtggagatct gtctccagga aagggtggct ttcagatgct gcatgatgaa  2580
tatgtacccg ggagtggtgg gcatggatgg ggttaccttt atgaacatga ggttcagggg  2640
agatgggtat aatggcacgg tctttatggc caataccaag ctgacagtcc atggctgctc  2700
cttcttgggg tttaataaca cctgcatcga ggcctggggt caggtcggtg tgaggggctg  2760
cagttttttca gccaactgga tggggtcgt gggcaggacc aagagtatgc tgtccgtgaa  2820
gaaatgcttg tttgagaggt gccacctggg ggtgatgagc gagggcgaag ccagaatccg  2880
ccactgcgcc tctaccgaga cgggctgctt tgtgctgtgc aagggcaatg ctaagatcaa  2940
gcataatatg atctgtggag cctcggacga gcgcggctac cagatgctga cctgcgccgg  3000
cgggaacagc catatgctgg ccaccgtaca tgtggcttcc catgctcgca agccctggcc  3060
cgagttcgag cacaatgtca tgaccaggtg caatatgcat ctgggtgtccc gccgaggcat  3120
gttcatgccc taccagtgca acctgaatta tgtgaaggtg gtgctggagc ccgatgccat  3180
gtccagagtg agcctgacgg gggtgtttga catgaatgtg gaggtgtgga agattctgag  3240
atatgatgaa tccaagacca ggtgccgagc ctgcgagtgc ggagggaagc atgccaggtt  3300
ccagcccgtg tgtgtggatg tgacggagga cctgcgaccc gatcatttgg tgttgccctg  3360
caccgggacg gagttcggtt ccagcgggga agaatctgac tagagtgagt agtgttctga  3420
ggcggggggag gacctgcatg agggccagaa taactgaaat ctgtgctttt ctgtgtgttg  3480
cagcagcatg agcggaagcg gctcctttga gggaggggta ttcagccctt atctgacggg  3540
gcgtctcccc tcctgggcgg gagtgcgtca gaatgtgatg ggatccacgg tggacggccg  3600
gcccgtgcag cccgcgaact cttcaaccct gacctatgca acctgagct cttcgtcgtt  3660
ggacgcagct gccgccgcag ctgctgcatc tgccgccagc gccgtgcgcg gaatggccat  3720
gggcgccggc tactacggca ctctggtggc caactcgagt tccaccaata atcccgccag  3780
cctgaacgag gagaagctgt tgctgctgat ggcccagctc gaggccttga cccagcgcct  3840
gggcgagctg acccagcagg tggctcagct gcaggacgac acgcgggccg cggttgccac  3900
ggtgaaatcc aaataaaaaa tgaatcaata aataaacgga gacggttgtt gatttttaaca  3960
cagagtctga atctttattt gattttttcgc gcgcggtagg ccctggacca ccggtctcga  4020
tcattgagca cccggtggat ctttttccagg acccggtaga ggtgggcttg gatgttgagg  4080
tacatggca tgagcccgtc ccgggggtgg aggtagctcc attgcagggc ctcgtgctcg  4140
ggggtgggtgt tgtaaatcac ccagtcatag caggggcgga ggcatggtg ttgcacaata  4200
tctttgagga ggagactgat ggccacgggc agccctttgg tgtaggtgtt tacaaatctg  4260
ttgagctggg agggatgcat gcgggggggag atgaggtgca tcttggcctg gatcttgaga  4320
ttggcgatgt taccgcccag atcccgcctg gggttcatgt tgtgcaggac caccagcacg  4380
gtgtatccgg tgcacttggg gaatttatca tgcaacttgg aaggggaggc gtgaaagaat  4440
ttggcgacgc ctttgtgccc gcccaggttt tccatgcact catccatgat gatggcgatg  4500
ggcccgtggg cggcggcctg ggcaaagacg tttcgggggg cggacacatc atagtcgtgg  4560
tcctgggtga ggtcatcata ggccatttta atgaatttgg ggcggaggt gccggactgg  4620
gggacaaagg taccctcgat cccgggggcg tagttcccct cacagatctg catctcccag  4680
gctttgagct cggaggggggg gatcatgtcc acctgcgggg cgataaagaa cacggttttcc  4740
gggcggggg agatgagctg ggccgaaagc aagttccgga gcagtggga cttgccgagg  4800
ccggtggggc cgtagatgac cccgatgacc ggctgcaggt ggtagttgag ggagagacag  4860
ctgccgtcct cccggaggag ggggggccacc tcgttcatca tctcgcgcac gtgcatgttc  4920
tcgcgcacca gttccgccag gaggcgctct cccccaggg ataggagctc ctggagcgag  4980
gcgaagtttt tcagcggctt gagtccgtcg gccatgggca ttttgggagag ggtttgttgc  5040
aagagttcca ggcggtccca gagctcggtg atgtgctcta cggcatctcg atccagcaga  5100
```

```
cctcctcgtt tcgcgggttg ggacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcgggggc gtaggcgtcc gcgccgcagt gggcgcagac ggtctcgcac tccacgagcc   5520
aggtgaggtc gggctggtcg gggtcaaaaa ccagtttccc gccgttcttt ttgatgcgtt   5580
tcttaccttt ggtctccatg agctcgtgtc cccgctgggt gacaaagagg ctgtccgtga   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtccccctc gtccacatcc aggaaggtga ttggcttgta agtgtaggcc acgtgaccgg   5880
gggtcccggc cgggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
gggctcatt agtccagcag aggcgtccgc ccttgccgca gcaaagaggg ggcaggggt   6420
ccagcatgac ctcgtcgggg gggtcggcat cgatggtgaa gatgccggac aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgcccccg cggatgctgg cgcgcacgta gtcatacagc tcgtgcgagg   6720
gggcgaggag cccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg gggcacctcg gcccggttgt   7380
tgatgacctg ggcggcgagc acgatctcgt cgaagccgtt gatgttgtgg cccacgatgt   7440
agagttccac gaatcgcgga cggccctcga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcggggagt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg cgtttgatgt   7920
gatgaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtgat catgctgacg agcccgcgcg   8160
ggaggcaggt ccagacctcg cgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtcccccg tttcttcttg ggcggctggg gcgacggggg cggtgcctct tccatggtta   8460
gaagcggcgg cgaggacgcg cgccgggcgg caggggcggc tcgggccccg gaggcagggg   8520
cggcaggggc acgtcggcgc cgcgcgcggg taggttctgg tactcgcgcc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttgagatgc ggcccatgag ctgcgagaag gcgttcatgc ccgcctcgtt   8880
ccagacgcgg ctgtagacca cgacgccctc gggatcgcgg gcgcgcatga ccacctgacg   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggaggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgcgcgca tctccaggtg gccgggggg tccccgttgg gcaggagag   9480
ggcgctgacg atgcatctta tcaattgccc cgtaggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcggcggat   9660
gctgctggta atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
```

-continued

```
ctcgcccgcg cggccgtgca tgcgcgtgag cccgaagccg cgctggggct ggacgagcgc  9900
caggtcggcg acgacgcgct cggcgaggat ggcttgctgg atctgggtga gggtggtctg  9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agccctctt   10800
ttgttttgtt tgtttttgcc agatgcatcc cgtactgcgg cagatgcgcc cccaccaccc  10860
tccaccgcaa caacagcccc ctccacagcc ggcgcttctg ccccgccccc agcagcaact  10920
tccagccacg accgccgcgg ccgccgtgag cggggctgga cagagttatg atcaccagct  10980
ggccttggaa gagggcgagg ggctggccgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcgcgg cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacg tgctgaggac  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gaggggggaga gctactttga  11880
catgggccgg gacctgcact ggcagcccag ccgccggccc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgcccagag cgaggtgtac cagtccgggc cggactactt cttccagacc  12600
agtcgcagga gcttgcagac cgtgaacctg agccaggctt tcaagaactt gcagggcctg  12660
tggggcgtgc aggcccggt cggggaccgc gcgacggtgt cgagcctgct gacgccgaac  12720
tcgcgcctgc tgctgctgct ggtggcccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgccgct tgggccagga cgacccgggc  12900
aacctggaag ccaccctgaa cttttttgctg accaaccggt cgcagaagat cccgcccag   12960
tacgcgctca gcaccgagga ggagcgcatc ctgcgttacg tgcagcagag cgtgggcctg  13020
ttcctgatgc aggaggggc caccccagc gccgcgctcg acatgaccgc gcgcaacatg  13080
gagccagca tgtacgccag caacccgccg ttcatcaata aactgatgga ctacttgcat  13140
cggggcggcc ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcgcgcg tgcccgaggc cgccagtcct ttcccgagct tgcccttctc gctgaacagt  13440
atccgcagca gcgagctggg caggatcacg cgccccgcct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc aggggcccac gaaccggggc agcgccgacc gtaaacgccg gtggcacgac  13680
aggcagcggg gacagatgtg ggacgatgag gactccgccg acgacagcgg cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccat  13920
cgtacgagag cgtgatgcag caggcgatgg cggcggcggc gatgcagccc ccgctggagg  13980
ctccttacgt gccccgcgcg tacctggcgc ctacggaggg cggaacagc attcgttact   14040
cggagctggc accccttgtac gataccaccc ggttgtacct ggtggacaac aagtcggcgg  14100
acatcgcctc gctgaactac cagaacgacc acagcaactt cctgaccacc gtggtgcaga  14160
acaatgactt caccccacg gaggccagca cccagaccat caactttgac gagcgctcgc  14220
ggtggggcg ccagctgaaa accatcatgc acaccaacat gcccaacgtg aacgagttca  14280
tgtacagcaa caagttcaag gcgcgggtga tggtctcccg caagaccccc aatgggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggacccccgt gaccgagctg gtcatgcccg  14580
```

-continued

```
gggtgtacac caacgaggct ttccatcccg atattgtctt gctgcccggc tgcggggtgg   14640
acttcaccga gagccgcctc agcaacctgc tgggcattcg caagaggcag cccttccagg   14700
aaggcttcca gatcatgtac gaggatctgg aggggggcaa catccccgcg ctcctggatg   14760
tcgacgccta tgagaaaagc aaggaggatg cagcagctga agcaactgca gccgtagcta   14820
ccgcctctac cgaggtcagg ggcgataatt ttgcaagcgc cgcagcagtg gcagcggccg   14880
aggcggctga aaccgaaagt aagatagtca ttcagccggt ggagaaggat agcaagaaca   14940
ggagctacaa cgtactaccg gacaagataa acaccgccta ccgcagctgg tacctagcct   15000
acaactatgg cgaccccgag aagggcgtgc gctcctggac gctgctcacc acctcggacg   15060
tcacctgcgg cgtggagcaa gtctactggt cgctgcccga catgatgcaa gacccggtca   15120
ccttccgctc cacgcgtcaa gttagcaact acccggtggt gggcgccgag ctcctgcccg   15180
tctactccaa gagcttcttc aacgagcagg ccgtctactc gcagcagctg cgcgccttca   15240
cctcgcttac gcacgtcttc aaccgcttcc ccgagaacca gatcctcgtc cgcccgcccg   15300
cgcccaccat taccaccgtc agtgaaaacg ttcctgctct cacagatcac gggaccctgc   15360
cgctgcgcag cagtatccgg ggagtccagc gcgtgaccgt tactgacgcc agacgccgca   15420
cctgcccta cgtctacaag gccctgggca tagtcgcgcc gcgcgtcctc tcgagccgca   15480
ccttctaaat gtccattctc atctcgccca gtaataacac cggttggggc ctgcgcgcgc   15540
ccagcaagat gtacggaggc gctcgccaac gctccacgca acaccccgtg cgcgtgcgcg   15600
ggcacttccg cgctccctgg ggcgccttca agggccggcgt gcggtcgcgc accaccgtcg   15660
acgacgtgat cgaccaggtg gtggccgacg cgcgcaacta cacccccgcc gccgcgcccg   15720
tctccaccgt ggacgccgtc atcgacagcg tggtggccga cgcgcgccgg tacgcccgcg   15780
ccaagagccg gcggcggcgc atcgcccggc ggcaccggag caccccgcc atgcgcgcgg   15840
cgcgagcctt gctgcgcagg gccaggcgca cgggacgcag ggccatgctc agggcggca   15900
gacgcgcggc ttcaggcgcc agcgccggca ggacccggag acgggcggca acggcggcgg   15960
cagcggccat cgccagcatg tcccgcccgc ggcgagggaa cgtgtactgg gtgcgcgacg   16020
ccgccaccgg tgtgcgcgtg cccgtgcgca cccgcccccc tcgcacttga agatgttcac   16080
ttcgcgatgt tgatgtgtcc cagcggcgag gaggatgtcc aagcgcaaat tcaaggaaga   16140
gatgctccag gtcatcgcgc ctgagatcta cggccctgcg gtggtgaagg aggaaagaaa   16200
gccccgcaaa atcaagcggg tcaaaaagga caaaaaggaa gaagaaagtg atgtggacgg   16260
attggtggag tttgtgcgcg agttcgcccc ccggcggcgc gtgcagtggc gcgggcggaa   16320
ggtgcaaccg gtgctgagac ccggccaccac cgtggtcttc acgcccggcg agcgctccgg   16380
caccgcttcc aagcgctcct acgacgaggt gtacgggggat gatgatattc tggagcaggc   16440
ggccgagcgc ctgggcgagt ttgcttacgg caagcgcagc cgttccgcac cgaaggaaga   16500
ggcggtgtcc atcccgctgg accacggcaa ccccacgccg agcctcaagc ccgtgacctt   16560
gcagcaggtg ctgccgaccg cggcgccgcg ccgggggttc aagcgcgagg cgcgaggatct   16620
gtaccccacc atgcagctga tggtgcccaa gcgccagaag ctggaagacg tgctggagac   16680
catgaaggtg gacccggacg tgcagcccga ggtcaaggtg cggcccatca agcaggtggc   16740
cccgggcctg ggcgtgcaga ccgtggacat caagattccc acggagccca tggaaacgca   16800
gaccgagccc atgatcaagc ccagcaccag caccatggag gtgcagacgg atccctggat   16860
gccatcggct cctagtcgaa gaccccggcg caagtacggc ccggccagcc tgctgatgcc   16920
caactacgcg ctgcatcctt ccatcatccc cacgccgggc taccgcggca cgcgcttcta   16980
ccgcggtcat accagcagcc gccgccgcaa gaccaccact cgccgccgcc gtcgccgcac   17040
cgccgctgca accacccctg ccgccctggt gcggagagtg taccgccgcg gccgcgcacc   17100
tctgaccctg ccgcgcgcgc gctaccaccc gagcatcgcc atttaaactt tcgcctgctt   17160
tgcagatcaa tggccctcac atgccgcctt cgcgttccca ttacgggcta ccgaggaaga   17220
aaaccgcgcc gtagaaggct ggcggggaac gggatgcgtc gccaccacca ccggcggcgg   17280
cgcgccatca gcaagcggtt ggggggaggc ttcctgcccg cgctgatccc catcatcgcc   17340
gcggcgatcg gggcgatccc cggcattgct tccgtgacgg tgcaggcctc tcagcgccac   17400
tgagacacac ttggaaacat cttgtaataa accaatggac tctgacgctc ctggtcctgt   17460
gatgtgtttt cgtagacaga tggaagacat caattttttcg tccctggctc cgcgacacgg   17520
cacgcggccg ttcatgggca cctggagcga catcggcacc agccaactga acggggggcgc   17580
cttcaattgg agcagtctct ggagcgggct taagaatttc gggtccacgc ttaaaaccta   17640
tggcagcaag gcgtggaaca gcaccacagg gcaggcgctg agggataagc tgaaagagca   17700
gaacttccag cagaaggtgg tcgatgggct cgcctcgggc atcaacgggg tggtggacct   17760
ggccaaccag gccgtgcagc ggcagatcaa cagccgcctg gacccggtgc cgcccgccgg   17820
ctccgtggag atgccgcagg tggaggagga gctgcctccc ctggacaagc ggggcgagaa   17880
gcgaccccgc cccgatgcgc aggagacgct gctgacgcac acggacgagc cgccccgta   17940
cgaggaggcg gtgaaactgg gtctgcccac cacgcggccc atcgcgcccc tggccaccgg   18000
ggtgctgaaa cccgaaaagc ccgcgaccct ggacttgcct cctccccagc cttcccgccc   18060
ctctacagtg gctaagcccc tgccgtccgg ggccgtggcc cgccgcgcac ccggggggcac   18120
cgcccgccct catgcgaact ggcagagcac tctgaacagc atcgtgggtc tgggagtgca   18180
gagtgtgaag cgccgccgct gctattaaac ctaccgtagc gcttaacttg cttgtctgtg   18240
tgtgtatgta ttatgtcgcc gccgccgctg tccaccagaa ggaggagtga agaggcgcgt   18300
cgccgagttg caagatggcc accccatcga tgctgcccca gtgggcgtac atgcacatcg   18360
ccggacagga cgcttcggag tacctgagtc cgggtctgtc cagtttgcc gcgccacag   18420
acacctactt cagtctgggg aacaagttta ggaaccccac ggtggcgccc acgcacgatg   18480
tgaccaccga ccgcagccag cggctgacgc tgcgcttcgt gcccgtggac cgcgaggaca   18540
acacctactc gtacaaagtg cgctacacgc tggccgtggg cgacaaccgc gtgctggaca   18600
tggccagcac ctactttgac atccgcggcg tgctggatcg gggccctagc ttcaaaccct   18660
actccggcac cgcctacaac agtctggccc ccaaggagac acccaacact tgtcagtgaa   18720
catataaagc cgatggtgaa actgccacag aaaaaaccta tacatatgga aatgcacccg   18780
tgcagggcat taacatcaca aaagatggta ttcaacttgg aactgacacc gatgatcagc   18840
caatctacgc agataaaacc tatcagcctg aacctcaagt gggtgatgct gaatggcatg   18900
acatcactgg tactgatgaa aagtatggag gcagagctct taagcctgat accaaaatga   18960
agccttgtta tggttctttt gccaagccta ctaataaaga aggaggtcag gcaaatgtga   19020
aaacaggaac aggcactact aaagaatatg acatagacat ggctttcttt gacaacagaa   19080
gtgcggctgc tgctggccta gctccagaaa ttgttttgta tactgaaaat gtggatttgg   19140
aaactccaga tacccatatt gtatacaaag caggcacaga tgacagcagc tcttctatta   19200
atttgggtca gcaagccatg cccaacgagac ctaactacat tggtttcaga gacaacttta   19260
tcgggctcat gtactacaac agcactggca atatggggggt gctggccggt caggcttctc   19320
```

```
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100
tctacgccac cttcttcccc atggcgcaca acacggcctc cacgctcgag gccatgctgc 20160
gcaacgacac caacgaccag tccttcaacg actacctctc ggcggccaac atgctctacc 20220
ccatcccggc caacgccacc aacgtgccca tctccatccc ctcgcgcaac tgggccgcct 20280
tccgcggctg gtccttcacg cgtctcaaga ccaaggagac gccctcgctg ggctccgggt 20340
tcgacccta cttcgtctac tcgggtccca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctaaca ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760
ccatgcgcca gggccagccc taccccgcca actaccccta cccgctcatc ggcaagagcg 20820
ccgtcaccag cgtcacccag aaaaagttcc tctgcgacag ggtcatgtgg cgcatcccct 20880
tctccagcaa cttcatgtcc atgggcgcgc tcaccgacct cggccagaac atgctctatg 20940
ccaactccgc ccacgcgcta gacatgaatt tcgaagtcga ccccatggat gagtccaccc 21000
ttctctatgt tgtcttcgaa gtcttcgacg tcgtccgagt gcaccagccc caccgcggcg 21060
tcatcgaggc cgtctacctg cgcacccct tctcggccgg taacgccacc acctaagctc 21120
ttgcttcttg caagccatgg ccgcgggctc cggcgagcag gagctcaggg ccatcatccc 21180
cgacctgggc tgcgggccct acttcctggg caccttcgat aagcgcttcc cgggattcat 21240
ggccccgcac aagctggcct gcgccatcgt caacacggcc ggccgcgaga ccgggggcga 21300
gcactggctg gccttcgcct ggaacccgcg ctcgaacacc tgctacctct tcgacccctt 21360
cgggttctcg gacgagcgcc tcaagcagat ctaccagttc gagtacgagg gcctgctgcg 21420
ccgcagcgcc ctggccaccg aggaccgctg cgtcaccctg gaaaagtcca cccagaccgt 21480
gcagggtccg cgctcggccg cctgcgggct cttctgctgc atgttcctgc acgccttcgt 21540
gcactggccc gaccgcccca tggacaagaa ccccaccatg aacttgctga cggggggtgcc 21600
caacggcatg ctccagtcgc cccaggtgga acccaccctg cgccgcaacc aggaggcgct 21660
ctaccgcttc ctcaactccc actccgccta cttttcgctcc caccgcgcgc gcatcgagaa 21720
ggccaccgcc ttcgaccgca tgaatcaaga catgtaaacc gtgtgtgtat gttaaatgtc 21780
tttaataaac agcactttca tgttacacat gcatctgaga tgatttattt agaaatcgaa 21840
agggttctgc cgggtctcgg catggcccgc gggcagggac acgttgcgga actggtactt 21900
ggccagccac ttgaactcgg ggatcagcag tttgggcagc ggggtgtcgg ggaaggagtc 21960
ggtccacagc ttccgcgtca gttgcagggc gcccagcagg tcgggcgcgg agatcttgaa 22020
atcgcagttg ggaccgcgt tctgcgcgcg ggagttgcgg tacacggggt tgcagcactg 22080
gaacaccatc aggggccgggt gcttcacgct cgccagcacc gtcgcgtcgg tgatgctctc 22140
cacgtcgagg tcctcggcgt tggccatccc gaagggggtc atcttgcagg tctgccttcc 22200
catggtgggc acgcacccgg gcttgtggtt gcaatcgcag tgcaggggga tcagcatcat 22260
ctgggcctgg tcggcgttca tccccgggta catggccttc atgaaagcct ccaattgcct 22320
gaacgcctgc tgggccttgg ctccctcggt gaagaagacc ccgcaggact tgctagagaa 22380
ctggttggtg gcgcacccgg cgtcgtgcac gcagcagcgc gcgtcgttgt tggccagctg 22440
caccacgctg cgccccagc ggttctgggt gatcttggcc cggtcggggt tctccttcag 22500
cgcgcgctgc ccgttctcgc tcgccacatc catctcgatc atgtgctcct tctggatcat 22560
ggtgtcccg tgcaggcacc gcagcttgcc ctcggcctcg gtgcaccgt gcagccacag 22620
cgcgcacccg gtgcactccc agttcttgtg ggcgatctgg gaatgcgcgt gcacgaagcc 22680
ctgcaggaag cggcccatca tggtggtcag ggtcttgttg ctagtgaagg tcagcggaat 22740
gccgcggtgc tcctcgttga tgtacaggtg gcagatgcgg cggtacacct cgccctgctc 22800
gggcatcagc tggaagttgg ctttcaggtc ggtctccacg cggtagcggt ccatcagcat 22860
agtcatgatt tccataccct tctcccaggc cgagacgatg ggcaggctca tagggttctt 22920
caccatcatc ttagcgctag cagccgcggc caggggtcg ctctcgtcca gggtctcaaa 22980
gctccgcttg ccgtccttct cggtgatccg caccggggg tagctgaagc ccacggccgc 23040
cagctcctcc tcggcctgtc tttcgtcctc gctgtcctgg ctgacgtcct gcaggaccac 23100
atgcttggtc ttgcggggtt tcttcttggg cggcagcggc ggcggagatg ttggagatgg 23160
cgaggggggag cgcgagttct cgctcaccac tactatctct tcctcttctt ggtccgaggc 23220
cacgcggcgg taggtatgtc tcttcggggg cagagccgga ggcgacgggc tctcgccgcc 23280
gcgacttggc ggatggctgg cagagccct tccgcgttcg ggggtgcgct cccggcggc 23340
ctctgactga cttcctccgc ggccggccat tgtgttctcc tagggaggaa caacaagcat 23400
ggagactcag ccatcgccaa cctcgccatc tgcccccacc gccgacgaga agcagcagca 23460
gcagaatgaa agcttaaccg ccccgccgcc cagccccgcc acctccgacg cggccgtccc 23520
agacatgcaa gagatggagg aatccatcga gattgacctg ggctatgtga cgcccgcgga 23580
gcacgaggag gagctggcag tgcgcttttc acaagaagag atacaccaag aacagccaga 23640
gcaggaagca gagaatgagc agagtcaggc tgggctcgag catgacggcg actacctcca 23700
cctgagcggg gggaggaacg cgctcatcaa gcatctgacg gcgcaggcca ccatcgtcaa 23760
ggatcgcgct ctcgaccgca ccgaggtgcc cctcagcgtg gaggagctca gccgcgccta 23820
cgagttgaac ctcttctcgc cgcgcgtgcc ccccaagcgc cagcccaatg gcacctgcga 23880
gcccaacccg cgcctcaact tctacccggt cttcgcggtg cccgaggccc tggccaccta 23940
ccacatcttt ttcaagaacc aaaagatccc cgtctcctgc cgcgccaacc gcacccgcgc 24000
cgacgccctt ttcaacctgg gtcccggcgc ccgcctacct gatatcgcct ccttggaaga 24060
```

-continued

```
ggttcccaag atcttcgagg gtctgggcag cgacgagact cgggccgcga acgctctgca 24120
aggagaagga ggagagcatg agcaccacag cgccctggtc gagttggaag gcgacaacgc 24180
gcggctggcg gtgctcaaac gcacggtcga gctgacccat ttcgcctacc cggctctgaa 24240
cctgcccccc aaagtcatga gcgcggtcat ggaccaggtg ctcatcaagc gcgcgtcgcc 24300
catctccgag gacgagggca tgcaagactc cgaggagggc aagcccgtgg tcagcgacga 24360
gcagctggcc cggtggctgg gtcctaatgc tagtccccag agtttggaag agcggcgcaa 24420
actcatgatg gccgtggtcc tggtgaccgt ggagctggag tgcctgcgcc gcttcttcgc 24480
cgacgcggaa accctgcgca aggtcgagga gaacctgcac tacctcttca ggcacgggtt 24540
cgtgcgccag gcctgcaaga tctccaacgt ggagctgacc aacctggtct cctacatggg 24600
catcttgcac gagaaccgcc tggggcagaa cgtgctgcac accacctgc gcggggaggg 24660
ccggcgcgac tacatccgcg actgcgtcta cctctacctc tgccacacct ggcagacggg 24720
catgggcgtg tggcagcagt gtctggagga gcagaacctg aaagagctct gcaagctcct 24780
gcagaagaac ctcaagggtc tgtggaccgg gttcgacgag cgcaccaccg cctcggacct 24840
ggccgacctc attttccccg agcgcctcag gctgacgctg gcaacggcc tgcccgactt 24900
tatgagccaa agcatgttgc aaaactttcg ctctttcatc ctcgaacgct cggaatcct 24960
gcccgccacc tgctccgcgc tgccctcgga cttcgtgccg ctgaccttcc gcgagtgccc 25020
cccgccgctg tggagccact gctacctgct gcgcctggcc aactacctgg cctaccactc 25080
ggacgtgatc gaggacgtca gcggcgaggg cctgtctcgag tgccactgcc gctgcaacct 25140
ctgcacgccg caccgctccc tggcctgcaa ccccagctg ctgagcgaga cccagatcat 25200
cggcaccttc gagttgcaag ggcccagcga aggcgagggt tcagccgcca agggggtct 25260
gaaactcacc ccgggctgt ggacctcggc ctacttgcgc aagttcgtgc ccgaggacta 25320
ccatccttc gagatcaggt tctacgagga ccaatcccat cgcccaagg ccgagctgtc 25380
ggcctgcgtc atcacccagg gggcgatcct ggcccaattg caagccatcc agaaatcccg 25440
ccaagaattc ttgctgaaaa agggccgcgg ggtctacctc gacccccaga ccggtgagga 25500
gctcaacccc ggcttccccc aggatgcccc gaggaaacaa gaagctgaaa gtggagctgc 25560
cgcccgtgga ggatttggag gaagactggg agaacacgag tcaggcagag gaggaggaca 25620
tggaggaaga ctgggacagc actcaggcag aggaggacag cctgcaagac agtctggagg 25680
aagacgagga ggaggcagag gaggaggtgg aagaagcagc cgccgccaga ccgtcgtcct 25740
cggcggggga gaaagcaagc agcacggata ccatctccgc tccgggtcgg ggtcccgctc 25800
gaccacacag tagatgggac gagaccggac gattcccgaa ccccaccacc cagaccggta 25860
agaaggagcg gcagggatac aagtcctggc gggggcacaa aaacgccatc gtctcctgct 25920
tgcaggcctg cgggggcaac atctccttca cccggcgcta cctgctcttc caccgcgggg 25980
tgaactttcc ccgcaacatc ttgcattact accgtcacct ccacagcccc tactacttcc 26040
aagaagaggc agcagcagca gaaaaagacc agcagaaaac cagcagctag aaaatcccaca 26100
gcggcggcag caggtggact gaggatcgcg gcgaacgagc cggcgcaaac ccgggagctg 26160
aggaaccgga tctttcccac cctctatgcc atcttccagc agagtcgggg gcaggagcag 26220
gaactgaaag tcaagaaccg ttctctgcgc tcgctcaccc gcagttgtct gtatcacaag 26280
agcgaagacc aacttcagcg cactctcgag gacgccgagg ctctcttcaa caagtactgc 26340
gcgctcactc ttaaagagta gcccgcgccc gcccagtcgc agaaaaaggc gggaattacg 26400
tcacctgtgc ccttcgccct agccgcctcc acccatcatc atgagcaaag agattcccac 26460
gccttacatg tggagctacc agcccagat gggcctggcc gccggtgccg cccaggacta 26520
ctccacccgc atgaattggc tcagcgccgg gcccgcgatg atctcacggg tgaatgacat 26580
ccgcgcccac cgaaaccaga tactcctaga acagtcagcg ctcaccgcca cgcccccgcaa 26640
tcacctcaat ccgcgtaatt ggcccgccgc cctggtgtac caggaaattc cccagcccac 26700
gaccgtacta cttccgcgag acgcccaggc cgaagtccag ctgactaact caggtgtcca 26760
gctggcgggc ggcgccaccc tgtgtcgtca ccgccccgct cagggtataa agcggctggt 26820
gatccggggc agaggcacac agctcaacga cgaggtggtg agtcttcgc tgggtctgcg 26880
acctgacgga gtcttccaac tcgccggatc ggggagatct tccttcacgc ctcgtcaggc 26940
cgtcctgact ttggagagtt cgtcctcgca gccccgctcg ggtggcatcg gcactctcca 27000
gttcgtggag gagttcactc cctcggtcta cttcaacccc ttctccggct cccccggcca 27060
ctacccggac gagttcatcc cgaacttcga cgccatcagc gagtcggtgg acggctacga 27120
ttgaatgtcc catggtggcg cagctgacct agctcggctt cgacacctgg accactgccg 27180
ccgcttccgc tgcttcgctc gggatctcgc cgagtttgcc tactttgagc tgcccgagga 27240
gcaccctcag ggcccggccc acggagtgcg gatcgtcgtc gaaggggggcc tcgactccca 27300
cctgcttcgg atcttcagcc agcgtccgat cctggtcgag cgcgagcaag gacagaccct 27360
tctgactctg tactgcatct gcaaccaccc cggcctgcat gaaagtcttt gttgtctgct 27420
gtgtactgag tataataaaa gctgagatca gcgactactc cggacttccg tgtgttcctg 27480
aatccatcaa ccagtctttg ttcttcaccg ggaacgagac cgagctccag ctccagtgta 27540
agcccacaa gaagtacctc acctggctgt tccagggctc ccgatcgcc gttgtcaacc 27600
actgcgacaa cgacggagtc ctgctgagcg gccctgccaa ccttacttt tccacccgca 27660
gaagcaagct ccagctcttc caaccttcc tccccgggac ctatcagtgc gtctcgggac 27720
cctgccatca caccttccac ctgatcccga ataccacagc gtcgctcccc gctactaaca 27780
accaaactaa cctccaccaa cgccaccgtc gcgacctttc tgaatctaat actaccaccc 27840
acaccggagg tgagctccga ggtcaaccaa cctctgggat ttactacggc ccctgggagg 27900
tggttgggtt aatagcgcta ggcctagttg cgggtgggct tttggttctc tgctacctat 27960
acctcccttg ctgttcgtac ttagtggtgc tgtgttgctg gtttaagaaa tggggaagat 28020
caccctagtg agctgcggtg cgctggtggc ggtgttgctt tcgattgtgg gactgggcgg 28080
tgcggctgta gtgaaggaga aggccgatcc ctgcttgcat ttcaatccca acaaatgcca 28140
gctgagtttt cagcccgatg gcaatcggtg cgcggtactg atcaagtgcg gatgggaatg 28200
cgagaacgtg agaatcgagt acaataacaa gactcggaac aatactctcg cgtccgtgtg 28260
gcagcccggg gaccccgagt ggtacaccgt ctctgtcccc ggtgctgacg gctccccgcg 28320
caccgtgaat aatactttca tttttgcgca catgtgcgac acggtcatgt ggatgagcaa 28380
gcagtacgat atgtggcccc ccacgaagga gaacatcgtg gtcttctcca tcgcttacag 28440
cctgtgcacg gcgctaatca ccgctatcgt gtgcctgagc attcacatgc tcatcgctat 28500
tcgcccccaga aataatgccg aaaaagaaaa acagccataa cgttttttt cacacctttt 28560
tcagaccatg gcctctgtta aattttttgct tttatttgcc agtctcattg ccgtcattca 28620
tggaatgagt aatgagaaaa ttactatttta cactggcact aatcacacat tgaaaggtcc 28680
agaaaaagc acagaagttt catggtattg ttattttaat gaatcagatg tatctactga 28740
actctgtgga aacaataaca aaaaaaatga gagcattact ctcatcaagt ttcaatgtgg 28800
```

-continued

```
atctgactta accctaatta acatcactag agactatgta ggtatgtatt atggaactac   28860
agcaggcatt tcggacatgg aattttatca agtttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agctggaaca   29160
cttactaagt gttgaatttt aattttttag aaccatgaag atcctaggcc ttttaatttt   29220
ttctatcatt acctctgctc tatgcaattc tgacaatgag gacgttactg tcgttgtcgg   29280
atcaaattat acactgaaag gtccagcgaa gggtatgctt tcgtggtatt gctattttgg   29340
atctgacact acagaaactg aattatgcaa tcttaagaat ggcaaaattc aaaattctaa   29400
aattaacaat tatatatgca atggtactga tctgatactc ctcaatatca cgaaatcata   29460
tgctggcagt tacacctgcc ctggagatga tgctgacagt atgatttttt acaaagtaac   29520
tgttgttgat cccactactc cacctccacc caccacaact actcacacca cacacacaga   29580
tcaaaccgca gcagaggagg cagcaaagtt agccttgcag gtccaagaca gttcatttgt   29640
tggcattacc cctacacctg atcagccggtg tccggggctg ctagtcagcg gcattgtcgg   29700
tgtgctttcg ggattagcag tcataatcat ctgcatgttc atttttgctt gctgctatag   29760
aaggcttttac cgacaaaaat cagacccact gctgaacctc tatgtttaat tttttccaga   29820
gtcatgaagg cagttagcgc tctagttttt tgttctttga ttggcattgt tttttgcaat   29880
cctattccta aagttagctt tattaaagat gtgaatgtta ctgaggggg caatgtgaca   29940
ctggtaggtg tagagggtgc tgaaaacacc acctggacaa aataccacct caatgggtgg   30000
aaagatattt gcaattggag tgtattagtt tatacatgtg agggagttaa tcttaccatt   30060
gtcaatgcca cctcagctca aaatggtaga attcaaggac aaagtgtcag tgtatctaat   30120
gggtatttta cccaacatac ttttatctat gacgttaaag tcataccact gcctacgcct   30180
agcccaccta gcactaccac acagacaacc cacactacac agacaaccac atacagtaca   30240
ttaaatcagc ctaccaccac tacagcagca gaggttgcca gctcgtctgg ggtccgagtg   30300
gcatttttga tgtgggcccc atctagcagt cccactgcta gtaccaatga gcagactact   30360
gaattttttgt ccactgtcga gagccacacc acagctacct ccagtgcctt ctctagcacc   30420
gccaatctct cctcgctttc ctctacacca atcagtcccg ctactactcc tagccccgct   30480
cctcttccca ctccctgaa gcaaacagac ggcggcatgc aatggcagat caccctgctc   30540
attgtgatcg ggttggtcat cctggccgtg ttgctctact acatctttctg ccgccgcatt   30600
cccaacgcgc accgcaagcc ggtctacaag cccatcattg tcgggcagcc ggagccgctt   30660
caggtggaag ggggtctaag gaatcttctc ttctctttta cagtatggtg attgaactat   30720
gattcctaga caattcttga tcactattct tatctgcctc ctccaagtct gtgccaccct   30780
cgctctggtg gccaacgcca gtccagactg tattgggccc ttcgcctcct acgtgctctt   30840
tgccttcacc acctgcatct gctgctgtag catagtctgc ctgcttatca ccttcttcca   30900
gttcattgac tggatctttg tgcgcatcgc ctacctgcgc caccacccc agtaccgcga   30960
ccagcgagtg gcgcggctgc tcaggctcct ctgataagca tgcgggctct gctacttctc   31020
gcgcttctgc tgttagtgct cccccgtccc gtcgacccc ggtcccccac ccagtccccc   31080
gaggaggtcc gcaaatgcaa attccaagaa ccctggaaat tcctcaaatg ctaccgccaa   31140
aaatcagaca tgcatcccag ctggatcatg atcattggga tcgtgaacat tctggcctgc   31200
accctcatct cctttgtgat ttaccccctgc tttgactttg gttggaactc gccagaggcg   31260
ctctatctcc cgcctgaacc tgacacacca ccacagcaac ctcaggcaca cgcactacca   31320
ccactacagc ctaggccaca atacatgccc atattagact atgaggccga gccacagcga   31380
cccatgctcc ccgctattag ttacttcaat ctaaccggcg gagatgactg acccactggc   31440
caacaacaac gtcaacgacc ttctcctgga catggacggc cgcgcctcgg agcagcgact   31500
cgcccaactt cgcattcgcc agcagcagga gagagccgtc aaggagctgc aggatgcggt   31560
ggccatccac cagtgcaaga gaggcatctt ctgcctggtg aaacaggcca agatctccta   31620
cgaggtcact ccaaacgacc atcgcctctc ctacgagctc ctgcagcagc gccagaagtt   31680
cacctgcctg gtcggagtca accccatcgt catcacccag cagtctggcg ataccaaggg   31740
gtgcatccac tgctcctgcg actccccga ctgcgtccac actctgatca agaccctctg   31800
cggcctacgc gacctcctcc ccatgaacta atcacccct tatccagtga aataaagatc   31860
atattgatga tgattttaca gaaataaaaa ataatcattt gatttgaaat aaagatacaa   31920
tcatattgat gatttgagtt taacaaaaa ataaagaatc acttacttga aatctgatac   31980
caggtctctg tccatgtttt ctgccaacac cacttcactc ccctcttccc agctctggta   32040
ctgcaggccc cggcgggctg caaacttcct ccacacgctg aaggggatgt caaattcctc   32100
ctgtccctca atcttcattt tatcttctat cagatgtcca aaaagcgcgt ccgggtggat   32160
gatgacttcg accccgtcta cccctacgat gcagacaacg caccgaccgt gcccttcatc   32220
aacccccct tcgtctcttc agatggattc caagagaagc ccctgggggt gttgtccctg   32280
cgactggcca accccgtcac caccaagaac ggggaaatca ccctcaagct gggagagggg   32340
gtggacctcg attcctcggg aaaactcatc tccaacacgg ccaccaaggc cgccgccct   32400
ctcagttttt ccaacaacac catttccctt aacatggatc accccttta cactaaagat   32460
ggaaaattat ccttacaagt ttctccacca ttaaatatac tgagaacaag cattctaaac   32520
acactagctt taggttttgg atcaggttta ggactccgtg gctctgcctt ggcagtacag   32580
ttagtctctc cacttacatt tgatactgat ggaaacataa agcttacctt agacagaggt   32640
ttgcatgtta caacaggaga tgcaattgaa agcaacataa gctgggctaa aggtttaaaa   32700
tttgaagatg gagccatagc aaccaacatt ggaaatgggt tagagtttgg aagcagtagt   32760
acagaaacag gtgttgatga tgcttaccca atccaagtta aacttggatc tggccttagc   32820
tttgacagta caggagccat aatggctggt aacaaagaag acgataaacc cactttgtgg   32880
acaacacctg atccatcacc aaactgtcaa atactcgcag aaaatgatgc aaaactaaca   32940
ctttgcttga ctaaatgtgg tagtcaaata ctggccactg tgtcagtctt agttgtagga   33000
agtgaaacc taaccccat tactggcacc gtaagcagtg ctcaggtgtt tctacgtttt   33060
gatgcaaacg gtgttctttt aacagaacat tctacactaa aaaaatactg ggggtatagg   33120
caggagata gcatagatgg cactccatat accaatgctg taggattcat gcccaattta   33180
aaagcttatc caaagtcaca taagttctact actaaaaata atatagtagg gcaagtatac   33240
atgaatggag atgtttcaaa acctatgctt ctcactataa ccctcaatgg tactgatgac   33300
agcaacagta catattcaat gtcatttctca tacacctgga ctaatggaag ctatgttgga   33360
gcaacatttg gggctaactc ttataccttc tcatacatcg cccaagaatg aacactgtat   33420
cccaccctgc atgccaaccc ttcccacccc actctgtgga acaaactctg aaacacaaaa   33480
taaaataaag ttcaagtgtt ttattgattc aacagttta caggattcga gcagttattt   33540
```

-continued

```
ttcctccacc ctcccaggac atggaataca ccaccctctc cccccgcaca gccttgaaca   33600
tctgaatgcc attggtgatg gacatgcttt tggtctccac gttccacaca gtttcagagc   33660
gagccagtct cgggtcggtc agggagatga aaccctccgg gcactccgc  atctgcacct   33720
cacagctcaa cagctgagga ttgtcctcgg tggtcgggat cacggttatc tggaagaagc   33780
agaagagcgg cggtgggaat catagtccgc gaacgggatc ggccggtggt gtcgcatcag   33840
gccccgcagc agtcgctgcc gccgccgctc cgtcaagctg ctgctcaggg ggtccgggtc   33900
cagggactcc ctcagcatga tgcccacggc cctcagcatc agtcgtctgg tgcggcgggc   33960
gcagcagcgc atgcggatct cgctcaggtc gctgcagtac gtgcaacaca gaaccaccag   34020
gttgttcaac agtccatagt tcaacacgct ccagccgaaa ctcatcgcgg gaaggatgct   34080
acccacgtgg ccgtcgtacc agatcctcag gtaaatcaag tggtgccccc tccagaacac   34140
gctgcccacg tacatgatct ccttgggcat gtggcggttc accacctccc ggtaccacat   34200
caccctctgg ttgaacatgc agcccggat  gatcctgcgg aaccacaggg ccagcaccgc   34260
cccgcccgcc atgcagcgaa gagaccccgg gtcccggcaa tggcaatgga ggaccaccg   34320
ctcgtacccg tggatcatct gggagctgaa caagtctatg ttggcacagc acaggcatat   34380
gctcatgcat ctcttcagca ctctcaactc ctcgggggtc aaaaccatat cccagggcac   34440
ggggaactct tgcaggacag cgaacccgc  agaacagggc aatcctcgca cagaacttac   34500
attgtgcatg gacagggtat cgcaatcagg cagcaccggg tgatcctcca ccagagaagc   34560
gcgggtctcg gtctcctcac agcgtggtaa gggggccggc cgatacgggt gatggcggga   34620
cgcggctgat cgtgttcgcg accgtgtcat gatgcagttg ctttcggaca ttttcgtact   34680
tgctgtagca gaacctggtc cgggcgctgc acaccgatcg ccggcggcgg tctcggcgct   34740
tggaacgctc ggtgttgaaa ttgtaaaaca gccactctct cagaccgtgc agcagatcta   34800
gggcctcagg agtgatgaag atcccatcat gcctgatggc tctgatcaca tcgaccaccg   34860
tggaatgggc cagacccagc cagatgatgc aattttgttg ggtttcggtg acggcggggg   34920
agggaagaac aggaagaacc atgattaact tttaatccaa acggtctcgg agtacttcaa   34980
aatgaagatc gcggagatgg cacctctcgc ccccgctgtg ttggtggaaa ataacagcca   35040
ggtcaaaggt gatacggttc tcgagatgtt ccacggtggc ttccagcaaa gcctccacgc   35100
gcacatccag aaacaagaca atagcgaaag cgggagggtt ctctaattcc tcaatcatca   35160
tgttacactc ctgcaccatc cccagataat tttcattttt ccagccttga atgattcgaa   35220
ctagttcctg aggtaaatcc aagccagcca tgataaagag ctcgcgcaga gcgccctcca   35280
ccggcattct taagcacacc ctcataattc caagatattc tgctcctggt tcacctgcag   35340
cagattgaca agcggaatat caaaatctct gccgcgatcc ctgagctcct ccctcagcaa   35400
taactgtaag tactctttca tatcctctcc gaaattttta gccataggac caccaggaat   35460
aagattaggg caagccacag tacagataaa ccgaagtcct ccccagtgag cattgccaaa   35520
tgcaagactg ctataagcat gctggctaga cccggtgata tcttccagat aactggacag   35580
aaaatcgccc aggcaatttt taagaaaatc aacaaaagaa aaatcctcca ggtggacgtt   35640
tagagcctcg ggaacaacga tgaagtaaat gcaagcggtg cgttccagca tggttagtta   35700
gctgatctgt agaaaaaaca aaaatgaaca ttaaaccatg ctagcctggc gaacaggtgg   35760
gtaaatcgtt ctctccagca ccaggcaggc cacggggtct ccggcgcgac cctcgtaaaa   35820
attgtcgcta tgattgaaaa ccatcacaga gagacgttcg cggtggccgg cgtgaatgat   35880
tcgacaagat gaatacaccc ccggaacatt ggcgtccgcg agtgaaaaaa agcgcccgag   35940
gaagcaataa ggcactacaa tgctcagtct caagtccagc aaagcgatgc catgcggatg   36000
aagcacaaaa ttctcaggtg cgtacaaaat gtaattactc ccctcctgca caggcagcaa   36060
agccccgat  ccctccaggt acacatacaa agcctcacgc ttcatagctt accgagcagc   36120
agcacacaac aggcgcaaga gtcagagaaa ggctgagctc taacctgtcc acccgctctc   36180
tgctcaatat atagcccaga tctacactga cgtaaaggcc aaagtctaaa aatacccgcc   36240
aaataatcac acacgcccag cacacgccca gaaaccggtg acacactcaa aaaaaatacg c   36300
gcacttcctc aaacgcccaa aactgccgtc atttccgggt tcccacgcta cgtcatcaaa   36360
acacgacttt caaattccgt cgaccgttaa aaacgtcacc cgccccgccc ctaacggtcg   36420
cccgtctctc agccaatcag cgccccgcat ccccaaattc aaacacctca tttgcatatt   36480
aacgcgcaca aaaagtttga ggtatattat tgatgatgg                         36519
```

SEQ ID NO: 2        moltype = DNA   length = 31588
FEATURE             Location/Qualifiers
misc_feature        1..31588
                    note = Description of Artificial Sequence: Synthetic
                    polynucleotide
source              1..31588
                    mol_type = other DNA
                    organism = synthetic construct
SEQUENCE: 2

```
ccatcttcaa taatatacct caaacttttt gtgcgcgtta atatgcaaat gaggcgtttg   60
aatttgggga ggaagggcgg tgattggtcg agggatgagc gaccgttagg ggcggggcga   120
gtgacgtttt gatgacgtgg ttgcgaggag gagccagttc gcaagttctc gtgggaaaag   180
tgacgtcaaa cgaggtgtgg tttgaacacg gaaatactca attttcccgc gctctctgaa   240
aggaaatgag gtgtttctgg gcggatgcaa gtgaaaacgg gccatttttcg cgcgaaaact   300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cggtgtcaaa gtccggtgtt tttacgtagg tgtcagctga tcgccagggt   480
atttaaacct gcgctctcca gtcaagaggc cactcttgag tgccagcgag aagagtttta   540
tcctccgcgc cgcgagtcag atctacactt tgaaagtagg gataacaggg taatgacatt   600
gattattgac tagttgttaa tagtaatcaa ttacgggggtc attagttcat agcccatata   660
tggagttccg cgttacataa cttacggtaa atggcccgcc tggctgaccg cccaacgacc   720
cccgcccatt gacgtcaata atgacgtatg ttcccatagt aacgccaata gggactttcc   780
attgacgtca atgggtggag tatttacggt aaactgccca cttggcagta catcaagtgt   840
atcatatgcc aagtccgccc cctattgacg tcaatgacgg taaatggccc gcctggcatt   900
atgcccagta catgacctta cgggactttc ctacttggca gtacatctac gtattagtca   960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataacccgc  ccgttgacg  caaatgggcg   1140
```

-continued

```
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
ccgggatgtt ccaggcactg tccgaaggct gcacaccta tgatattaac cagatgctga    1320
atgtcctggg agaccaccag gtctctggcc tggagcagct ggagagcatc atcaacttcg    1380
agaagctgac cgagtggaca agctccaatg tgatgcctat cctgtcccca ctgaccaagg    1440
gcatcctggg cttcgtgttt accctgacag tgccttctga gcggggcctg tcttgcatca    1500
gcgaggcaga cgcaaccaca ccagagtccg ccaatctggg cgaggagatc ctgtctcagc    1560
tgtacctgtg gcccgggtg acatatcact ccccttctta cgcctatcac cagttcgagc     1620
ggagagccaa gtacaagaga cacttcccag gctttggcca gtctctgctg ttcggctacc    1680
ccgtgtacgt gttcggcgat tgcgtgcagg gcgactggga tgccatccgg tttagatact    1740
gcgcaccacc tggatatgca ctgctgaggt gtaacgacac caattattcc gccctgctgg     1800
cagtgggcgc cctggaggc cctcgcaatc aggattggct gggcgtgcca aggcagctgg       1860
tgacacgcat gcaggccatc cagaacgcag gcctgtgcac cctggtggca atgctggagg     1920
agacaatctt ctggctgcag gcctttctga tggccctgac cgacagcggc cccaagacaa     1980
acatcatcgt ggattcccag tacgtgatgg gcatctccaa gccttcttc caggagtttg      2040
tggactggga gaacgtgagc ccagagctga attccaccga tcagccattc tggcaggcag     2100
gaatcctggc aaggaacctg gtgccatatg tggccacagt gcagggccag aatctgaagt     2160
accaggccaa gagcctggtc atcagcgcct ccatcatcgt gtttaacctg ctggagctgg     2220
agggcgacta tcgggacgat ggcaacgtgt gggtgcacac cccactgagc cccagaacac     2280
tgaacgcctg ggtgaaggcc gtggaggaga agaagggcat cccagtgcac ctggagctgg     2340
cctccatgac caatatggag ctgatgtcta gcatcgtgca ccagcaggtg aggacatacg     2400
gacccgtgtt catgtgcctg ggaggcctgc tgaccatggt gcaggagcc gtgtggctga      2460
cagtgcgggt gctggagctg ttcagagccg cccagctggc caacgatgtg gtgctgcaga     2520
tcatggagct gtgcggagca gccttctgcc aggtgtgcca caccacagtg ccatggccca     2580
atgcctcct gaccccaag tggaacaatg agacaacaca gcctcagatc gccaactgta      2640
gcgtgacga cttcttcgtg tggctgcact actatacgt gagggatacc ctgtgacccc       2700
gcgtgacata ccacatgaat aagtacgcct atcacatgct ggagaggcgc gccaagtata    2760
agagaggccc tggcccaggc gcaaagtttg tggcagcatg gaccctgaag gccgccgccg     2820
gccccggccc cggccagtat atcaaggcta acagtaagtt cattggaatc acagagctgg     2880
gacccggacc tggataatga gtttaaactc ccatttaaat gtgagggtta atgcttcgag     2940
cagacatgat aagatacatt gatgagtttg gacaaaccac aactagaatg cagtgaaaaa     3000
aatgctttat ttgtgaaatt tgtgatgcta ttgctttatt tgtaaccatt ataagctgca    3060
ataaacaagt taacaacaac aattgcattc attttatgtt tcaggttcag ggggagatgt    3120
gggaggtttt ttaaagcaag taaaacctct acaaatgtgg taaaataact ataacggtcc    3180
taaggtagcg agtgagtagt gttctggggc gggggaggac ctgcatgagg gccagaataa    3240
ctgaaatctg tgcttttctg tgtgttgcag cagcatgagc ggaagcggct cctttgaggg    3300
aggggtattc agcccttatc tgacgggggcg tctcccctcc tgggcgggag tgcgtcagaa   3360
tgtgatggga tccacggtgg acggccggcc cgtgcagccc gcgaactctt caaccctgac    3420
ctatcaacc ctgagctctt cgtcgttgga cgcagctgcc gccgcagctg ctgcatctgc     3480
cgccagcgcc gtgcgcggaa tggccatggg cgccggctac tacggcactc tggtggccaa    3540
ctcgagttcc accaataatc ccgccagcct gaacgaggag aagctgttgc tgctgatggc    3600
ccagctcgag gccttgaccc agcgcctggg cgagctgacc cagcaggtgg ctcagctgca    3660
ggagcagacg cgggccgcgg ttgccacggt gaaatccaaa taaaaaatga atcaataaat    3720
aaacggagac ggttgttgat tttaacacag agtctgaatc tttatttgat ttttcgcgcg    3780
cggtaggccc tggaccaccg gtctcgatca ttgagcaccc ggtggatctt tccaggacc      3840
cggtagaggt gggcttggat gttgaggtac atgggcatga gcccgtcccg ggggtggagg    3900
tagctccatt gcagggcctc gtgctcgggg gtggtgttgt aaatcaccca gtcatagcag    3960
gggcgcaggg catggtgttg cacaatatct ttgaggagga gactgatggc cacgggcagc     4020
cctttggtgt aggtgtttac aaatctgttg agctgggagg gatgcatgcg gggggagatg     4080
aggtgcatct tggcctggat cttgagattg gcgatgttac cgcccagatc ccgcctgggg    4140
ttcatgttgt gcaggaccac cagcacggtg tatccggtgc acttgggtga tttatcatgc     4200
aacttggaag ggaaggcgtg aaagaatttg gcgacgcctt gtgcccgcc caggttttcc      4260
atgcactcat ccatgatgat ggcgatgggc ccgtgggcgg cggcctgggc aaagacgttt     4320
cggggggtcgg acacatcata gttgtggtcc tgggtgaggt catcataggc cattttaatg    4380
aatttggggc ggaagggtgcc ggactgggg acaaaggtac cctcgatccc gggggcgtag    4440
ttcccctcac agatctgcat ctcccaggct ttgagctcgg aggggggggat catgtccacc    4500
tgcggggcga taagaacac ggtttccggg gcgggggaga tgagctgggc cgaaagcaag     4560
ttccggagca gctgggactt gccgcagccg gtggggccgt agatgacccc gatgaccggc    4620
tgcaggtggt agttgaggga gagacagctg ccgtcctccc ggaggagggg ggccacctcg    4680
ttcatcatct cgcgcacgtg catgttctcg cgcaccagt ccgccaggag gcgctctccc      4740
cccaggata ggagctcctg gagcgaggcg aagttttca gcggcttgag tccgtcggcc       4800
atgggcattt tggagagggt ttgttgcaag agttccaggc ggtcccagag ctcggtgatg    4860
tgctctacgg catctcgatc cagcagacct cctcgtttcg cgggttggga cggctgcggg    4920
agtagggcac cagacgatgg gcgtccacgc agccaggg ccggtccttc cagggtcgca      4980
gcgtccgcgt cagggtggtc tccgtcacgg tgaaggggt cgcgccgggc tgggcgcttg     5040
cgaggtgcg cttcaggctc atccggctgg tcgaaaacg ctcccgatcg gcgccctgcg      5100
cgtcggccag gtagcaattg accatgagtt cgtagttgag cgcctcggcc gcgtggcctt     5160
tggcgcggag cttacctttg gaagtctgcc cgcaggcggg acagaggagg gacttgaggg     5220
cgtagagctt gggggcgagg aagacggact cggggccggg gctgtccgcg ggcagtggg       5280
cgcagacggt ctcgcactcc acgagccagg tgaggtcggg ctggtcgggg tcaaaaacca    5340
gtttcccgcc gttcttttg atgcgtttct tacctttggt ctccatgagc tcgtgtcccc     5400
gctgggtgac aaagaggctg tccgtgtccc cgtagaccga ctttatgggc cggtcctcga    5460
gcggtgtgcc gcggtcctcc tcgtagagga accccgccca ctccgagacg aaagcccggg    5520
tccaggccac cacgaaggag gccacgtggg acgggtgtcc accagcgggt                5580
ccaccttttc cagggtatgc aaacacatgt ccccctcgtc cacatccagg aaggtgattg    5640
gcttgtaagt gtaggccacg tgaccggggg tcccggccgg gggggtataa aagggtgcgg    5700
gtccctgctc gtcctcactg tcttccggat cgctgtccag gagcgccagc tgttgggta      5760
ggtattccct ctcgaaggcg ggcatgacct cggcactcag gttgtcagtt tctagaaacg    5820
aggaggattt gatattgacg gtgccggcgg agatgccttc caagagcccc tcgtccatct    5880
```

-continued

```
ggtcagaaaa gacgatcttt ttgttgtcga gcttggtggc gaaggagccg tagagggcgt    5940
tggagaggag cttggcgatg gagcgcatgg tctggttttt ttccttgtcg gcgcgctcct    6000
tggcggcgat gttgagctgc acgtactcgc gcgccacgca cttccattcg gggaagacgg    6060
tggtcagctc gtcgggcacg attctgacct gccagccccg attatgcagg gtgatgaggt    6120
ccacactggt ggccacctcg ccgcgcaggg gctcattagt ccagcagagg cgtccgccct    6180
tgcgcgagca gaagggggc aggggtcca gcatgacctc gtcggggggg tcggcatcga    6240
tggtgaagat gccgggcagg aggtcggggt caaagtagct gatggaagtg gccagatcgt    6300
ccagggcagc ttgccattcg cgcacggcca gcgcgcgctc gtagggactg aggggcgtgc    6360
cccagggcat gggatgggta agcgcggagg cgtacatgcc gcagatgtcg tagacgtaga    6420
ggggctcctc gaggatgccg atgtaggtgg ggtagcgacg cccccgcag atgctggcgc    6480
gcacgtagtc atacagctcg tgcgaggggg cgaggagccc cgggcccagg ttggtgcgac    6540
tgggctttc ggcgcggtag acgatctggc ggaaaatggc atgcgagttg gaggagatgg    6600
tgggcctttg gaagatgttg aagtgggcgt ggggcagtcc gaccgagtcg cggatgaagt    6660
gggcgtagga gtcttgcagc ttggcgacga gctcggcggt gactaggacg tccagagcgc    6720
agtagtcgag ggtctcctgg atgatgtcat acttgagctg tcccttttgt ttccacagct    6780
cgcggttgag aaggaactct tcgcggtcct tccagtactc ttcgagggggg aacccgtcct    6840
gatctgcacg gtaagagcct agcatgtaga actggttgac ggccttgtag gcgcagcagc    6900
ccttctccac ggggagggcg taggcctggg cggccttgcg cagggaggtg tgcgtgaggg    6960
cgaaagtgtc cctgaccatg accttgagga actggtgctt gaagtcgata tcgtcgcagc    7020
cccctgctc ccagagctgg aagtccgtgc gcttcttgta ggcggggttg ggcaaagcga    7080
aagtaacatc gttgaagagg atcttgcccg cgcgggggcat aaagttgcga gtgatgcgga    7140
aaggttgggg cacctcggcc cggttgttga tgacctgggg gcgggagcacg atctcgtcga    7200
agccgttgat gttgtggccc acgatgtaga gttccacgaa tcgcggacgg cccttgacgt    7260
ggggcagttt cttgagctcc tcgtaggtga gctcgtcggg gtcgctgagc ccgtgctgct    7320
cgagcgccca gtcggcgaga tggggggttgg cgcggaggaa ggaagtccag agatccacgg    7380
ccagggcggt ttgcagacgg tcccggtact gacggaactg ctgcccgacg gccatttttt    7440
cggggggtgac gcagtagaag gtgcggggggt ccccgtgcca gcgatcccat ttgagctgga    7500
gggcgagatc gagggcgagc tcgacgagcc ggtcgtcccc ggagagtttc atgaccagca    7560
tgaaggggac gagctgcttg ccgaaggacc ccatccaggt gtaggtttcc acatcgtagg    7620
tgaggaagag cctttcggtg cgaggatgcg agccgatggg gaagaactgg atctcctgcc    7680
accaattgga ggaatggctg ttgatgtgat ggaagtagaa atgccgacgg cgcgccgaac    7740
actcgtgctt gtgtttatac aagcggccac agtgctcgca acgctgcacg ggatgcacgt    7800
gctgcacgag ctgtacctga gttcctttga cgaggaattt cagtgggaag tggagtcgtg    7860
gcgcctgcat ctcgtgctgt actacgtcgt ggtggtcggc ctggccctct tctgcctcga    7920
tggtggtcat gctgacgagc ccgcgcggga ggcaggtcca gacctcggcg cgagcgggtc    7980
ggagagcgag gacgagggcg cgcaggccgg agctgtccag ggtcctgaga cgctgcggag    8040
tcaggtcagt gggcagcggc ggcgcgcggt tgacttgcag gagttttttcc agggcgcgcg    8100
ggaggtccag atggtacttg atctccaccg cgccattggt ggcgacgtcg atggcttgca    8160
gggtcccgtg ccccctgggt gtgaccaccg tcccccgttt cttcttgggc ggctgggggcg    8220
acggggggcgg tgcctcttcc atggttagaa gcggcggcga ggacgcgcgc gcgggcggcag    8280
gggcggctcg gggcccggag gcaggggcgg caggggcacg tcggcgccgc gcgcgggtag    8340
gttctggtac tgcgcccgga gaagactggc gtgagcgacg acgcgacggt tgacgtcctg    8400
gatctgacgc ctctgggtga aggccacggg acccgtgagt ttgaacctga aagagagttc    8460
gacagaatca atctcggtat cgttgacggc ggcctgccgc aggatctctt gcacgtcgcc    8520
cgagttgtcc tggtaggcga tctcggtcat gaactgctcg atctcctcct cttgaaggtc    8580
tccgcggccg gcgcgctcca cggtggccgc gaggtcgttg gagatgcggc ccatgagctg    8640
cgagaaggcg ttcatgcccg cctcgttcca gacgcgggctg tagaccacga cgcccctcggg    8700
atcgcgggcg cgcatgacca cctgggcgag gttgagctcc acgtggcgcg tgaagaccgc    8760
gtagttgcag aggcgctggt agaggtagtt gagcgtggtg gcgatgtgct cggtgacgaa    8820
gaaatacatg atccagcggc ggagcggcat ctcgctgacg tcgcccagcg cctccaaacg    8880
ttccatggcc tcgtaaaagt ccacggcgga gttgaaaaac tgggagttgc gcgccgagac    8940
ggtcaactcc tcctccagaa gacggatgag ctcggcgatg gtggcgcgca cctcgcgctc    9000
gaaggcccccc gggagttcct ccacttcctc ttcttcctcc tccactaaca tctcttctac    9060
ttcctcctca ggcggcagtg gtggcggggg aggggggcctg cgtcgccggc ggcgcacggg    9120
cagacggtcg atgaagcgct cgatggtctc gccgcgccgg cgtcgcatgg tctcggtgac    9180
ggcgcgcccg tcctcgcggg gccgcagcgt gaagacgccg ccgcgcatct ccaggtggcc    9240
ggggggggtcc ccgttgggca gggagagggc gctgacgatg catcttatca attgccccgt    9300
agggactccg cgcaaggacc tgagcgtctc gagatccacg ggatctgaaa accgctgaac    9360
gaaggcttcg agccagtcgc agtcgcaagg taggctgagc acggtttctt ctggcggggtc    9420
atgttggttg ggagcgggggc gggcgatgct gctggtgatg aagttgaaat aggcggttct    9480
gagacgcgcg atggtggcga ggagcaccag gtctttgggc ccggcttgct ggatgcgcag    9540
acggtcggcc atgccccagg cgtggtcctg acacctggcc aggtccttgt agtagtcctg    9600
catgagccgc tccacgggca cctcctcctc gcccgcgcgg ccgtgcatgc gcgtgagccc    9660
gaagccgcgc tggggctgga cgagcgccag gtcggccacg acgcgctcgg cgaggatggc    9720
ttgctggatc tgggtgaggg tggtctggaa gtcatcaaag tcgacgaagc ggtggtaggc    9780
tccggtgttg atggtgtagg agcagttggc catgacggac cagttgacgg tctggtggcc    9840
cggacgcacg agctcgtggt acttgaggcg cgagtaggcg cgcgtgtcga agatgtagtc    9900
gttgcaggtg cgcaccaggt actggtagcc gatgaggaag tgcggcggcg gctggcggta    9960
gagcggccat cgctcggtgg cgggggggcgc gggcgcgagg tcctcgagca tggtgcgggg    10020
gtagccgtag atgtacctgg acatccaggt gatgccgacg gcggtggtgg aggcgcgcgg    10080
gaactcgcgg acgcggttcc agatgttgcg cagcggcagg aagtagttca tggtgggcac    10140
ggtctggccc gtgaggcgcg cgcagtcgtg gatgctctat acgggcaaaa acgaaagcgg    10200
tcagcggctc gactccgtgg cctggaggct aagcgaacgg gttgggctgc gcgtgtaccc    10260
cggttcgaat ctcgaatcag gctggagccg cagctaacgt ggtattggca ctcccgtctc    10320
gacccaagcc tgcaccaacc ctccaggata cggaggcggg tcgtttttgca acttttttttt    10380
ggaggccgga tgagactagt aagcgcggaa agcggccgac cgcgatggct cgctgccgta    10440
gtctggagaa gaatcgccag ggttgcgttg cggtgtgccc cggttcgagg ccggccggat    10500
tccgcggcta acgagggcgt ggctgccccg tcgtttccaa gaccccatag ccagccgact    10560
tctccagtta cggagcgagc ccctcttttg ttttgtttgt ttttgccaga tgcatcccgt    10620
```

```
actgcggcag atgcgccccc accaccctcc accgcaacaa cagccccctc cacagccggc   10680
gcttctgccc ccgcccagc agcaacttcc agccacgacc gccgcggccg ccgtgagcgg    10740
ggctggacag agttatgatc accagctggc cttggaagag ggcgagggc tggcgcgcct     10800
gggggcgtcg tcgccggagc ggcacccgcg cgtgcagatg aaaagggacg ctcgcgaggc   10860
ctacgtgccc aagcagaacc tgttcagaga caggagcggc gaggagcccg aggagatgcg    10920
cgcggcccgg ttccacgcgg ggcgggagct gcggcgcggc ctggaccgaa agagggtgct    10980
gagggacgag gatttcgagg cggacgagct gacggggatc agccccgcgc gcgcgcacgt    11040
ggccgcggcc aacctggtca cggcgtacga gcagaccgtg aaggaggaga gcaacttcca    11100
aaaatccttc aacaaccacg tgcgcaatcct gatcgcgcgc gaggaggtga ccctgggcct    11160
gatgcacctg tgggacctgc tggaggccat cgtgcagaac cccaccagca agccgctgac    11220
ggcgcagctg ttcctggtgg tgcagcatag tcgggacaac gaagcgttca gggaggcgct    11280
gctgaatatc accgagcccg agggccgctg gctcctggac ctggtgaaca ttctgcagag    11340
catcgtggtg caggagcgcg ggctgccgct gtccgagaag ctggcggcca tcaacttctc    11400
ggtgctgagt ttgggcaagt actacgctag gaagatctac aagaccccgt acgtgcccat    11460
agacaaggag gtgaagatcg acgggtttta catgcgcatg accctgaaag tgctgaccct    11520
gagcgacgat ctggggggtgt accgcaacga caggatgcac cgtgcggtga gcgccagcag    11580
gcggcgcgag ctgagcgacc aggagctgat gcatagtctg cagcggggccc tgaccggggc     11640
cgggaccgag ggggagagct acttttgacat gggcgcggac ctgcactggc agccagccg     11700
ccgggccttg gaggcggcgg caggaccecta cgtagaagag gtggacgatg aggtggacga    11760
ggagggcgag tacctggaag actgatggcc cgaccgtatt tttgctagat gcaacaacaa     11820
cagccaccte ctgatcccgc gatgcgggcg gcgctgcaga gccagccgtc cggcattaac    11880
tcctcggacg attggaccca ggccatgcaa cgcatcatgg cgctgacgac ccgcaacccc    11940
gaagcctttta gacagcagcc ccaggccaac cggctctcgg ccatcctgga ggccgtggtg    12000
ccctcgcgct ccaaccccac gcacgagaag gtcctggcca tcgtgaacgc gctggtggag    12060
aacaaggcca tccgcggcga cgaggccggc ctggtgtaca acgcgctgct ggagcgcgtg    12120
gcccgctaca acagcaccaa cgtgcagacc aacctggacc gcatggtgac cgacgtgcgc    12180
gaggccgtgg cccagcgcga gcggttccac cgcgagtcca acctgggatc catggtggc     12240
ctgaacgcct tcctcagcac ccagcccgcc aacgtgcccc ggggccagga ggactacacc    12300
aacttcatca gcgccctgcg cctgatggtg accgaggtgc cccagagcga ggtgtaccag    12360
tccggccgg actacttctt ccagaccagt cgccagggct tgcagaccgt gaacctgagc    12420
caggcttttca agaacttgca gggcctgtgg ggcgtgcagg ccccggtcgg ggaccgcgcg    12480
acggtgtcga gcctgctgac gccgaactcg cgcctgctgc tgctgctggt ggccccccttc    12540
acggacagcg gcagcatcaa ccgcaactcg tacctgggct acctgattaa cctgtaccgc    12600
gaggccatcg gccaggcgca cgtggacgag cagacctacc aggagatcac ccacgtgagc    12660
cgcgccctgg gccaggacga cccgggcaac ctggaagcca ccctgaactt tttgctgacc    12720
aaccggtcgc agaagatccc gccccagtac gcgctcagca ccgaggagga gcgcatcctg    12780
cgttacgtgc agcagagcgt gggcctgttc ctgatgcagg aggggccac ccccagcgcc     12840
gcgctcgaca tgaccgcgcg caacatggag cccagcatgt acgccagcaa ccgcccgttc    12900
atcaataaac tgatggacta cttgcatcgg gcggccgcca tgaactctga ctatttcacc    12960
aacgccatcc tgaatcccca ctggctcccg ccgccggggt tctacacggg cgagtacgac    13020
atgcccgacc ccaatgacgg gttcctgtgg gacgatgtgg acagcagcgt gttctccccc     13080
cgaccggggtg ctaacgagcg cccccttgtgg aagaaggaag gcagcgaccg acgcccgtcc    13140
tcggcgctgt ccggccgcga gggtgctgcc gcggcgggtac ccgaggccgc cagtccttc     13200
ccgagcttgc ccttctcgct gaacagtatc cgcagcagcg agctgggcag gatcacgcgc    13260
ccgcgcttgc tgggcgaaga ggagtacttg aatgactcgc tgttgagacc cgagcgggag    13320
aagaacttcc ccaataacgg gatagaaagc ctggtggaca agatgagccg ctggaagacg    13380
tatgcgcagg agcacaggga cgatccccgg gcgtcgcagg gcggggcagc     13440
gccgccgta aacgccggtg gcacgacagg cagcggggac agatgtggga cgatgaggac    13500
tccgccgacg acagcagcgt gttggacttg ggtgggagtg gtaacccgtt cgctcacctg    13560
cgcccccgta tcgggcgcat gatgtaagag aaaccgaaaa taaatgatac tcaccaaggc    13620
catggcgacg agcgtgcgtt cgtttcttct ctgttgttgt tgtatctagt atgatgaggc    13680
gtgcgtaccc ggagggtcct cctccctcgt acgagagcgt gatgcagcag gcgatggcgg    13740
cggcggcgat gcagcccccg ctggaggctc cttacgtgcc cccgcggtac ctggcgccta    13800
cggaggggcg gaacagcatt cgttactcgg agctggcacc cttgtacgat accaccggt     13860
tgtacctggt ggacaacaag tcggcggaca tcgcctcgct gaactaccag aacgaccaca    13920
gcaacttcct gaccaccgtg gtgcagaaca atgacttcac ccccacggag gccagccacc    13980
agaccatcaa cttttgacgag cgctcgcggt ggggcggcca gctgaaaacc atcatgcaca    14040
ccaacatgcc caacgtgaac gagttcatgt acagcaacaa gttcaaggcg cgggtgatgg    14100
tctcccgcaa gacccccaat ggggtgacag tgacagagga ttatgatgt agtcaggatg     14160
agctgaagta tgaatgggtg gaatttgagc tgcccgaagg caacttctcg gtgaccatga    14220
ccatcgacct gatgaacaac gccatcatcg acaattactt ggcggtgggg cggcagaacg    14280
gggtgctgga gagcgacatc ggcgtgaagt tcgacactag gaacttcagg ctgggctggg    14340
accccgtgac cgagctggtc atgcccgggg tgtacaccaa cgaggctttc catcccgata    14400
ttgtcttgct gcccggctgc ggggtgactt tcaccgagga ccgcctcagc aacctgctgg    14460
gcattcgcaa gaggcagccc ttccaggaag gcttccagat catgtacgag gatctcggag     14520
ggggcaacat ccccgcgctc ctggatgtcg acgcctatga gaaaagcaag gaggatgcag    14580
cagctgaagc aactgcagcc gtagctaccg cctctaccga ggtcagggc gataattttg     14640
caagcgccgc agcagtggca gcggccgagg cggctacaac gt actaccgac aagataaaca    14700
agccggtgga gaaggatagc aagaacagga gctacaacgt actaccggac aagataaaca    14760
ccgcctaccg cagctggtac ctagcctaca actatggcga ccccgagaag ggcgtgcgct    14820
cctgacgct gctcaccacc tcggacgtca cctgcggcgt ggagcaagtc tactggtcgc    14880
tgcccgacat gatgcaagac ccggtcacct tccgctccac gcgtcaagtt agcaactacc    14940
cggtggtggg cgccgagctc ctgccccgtct actccaagag cttcttcaac gagcaggccg    15000
tctactcgca gcagctgcgc gccttcacct cgcttacgca cgtcttcaac cgcttccccg    15060
agaaccagat cctccgtccgc ccgcccgcgc ccaccattac caccgtcagt gaaaacgttc    15120
ctgctctcac agatcacggg accctgccgc tgcgcagcag tatccgggga gtccagcgcg    15180
tgaccgttac tgacgccaga cgccgcacct gcccctacgt ctacaaggcc ctgggcatag    15240
tcgcgccgcg cgtcctctcg agccgcacct tctaaatgtc cattctcatc tcgcccagta    15300
ataacaccgg ttggggcctg cgcgcgccca gcaagatgta cggaggcgct cgccaacgct    15360
```

```
ccacgcaaca ccccgtgcgc gtgcgcgggc acttccgcgc tccctggggc gccctcaagg   15420
gccgcgtgcg gtcgcgcacc accgtcgacg acgtgatcga ccaggtggtg gccgacgcgc   15480
gcaactacac ccccgccgcc gcgcccgtct ccaccgtgga cgccgtcatc gacagcgtgg   15540
tggccgacgc gcgccggtac gcccgcgcca agagccggcg gcggcgcatc gcccggcggc   15600
accggagcac ccccgccatg cgcgcgggcg gagccttgct gcgcagggcc aggcgcacgg   15660
gacgcagggc catgctcagg gcggccagac gcgcgggcttc aggcgccagc gccggcagga   15720
cccggagacg cgcggccacg gcggcggcag cggccatcgc cagcatgtcc cgcccgcggc   15780
gagggaacgt gtactgggtg cgcgacgccg ccaccggtgt gcgcgtgccc gtgcgcaccc   15840
gccccctcg cacttgaaga tgttcacttc gcgatgttga tgtgtcccag cggcgaggag   15900
gatgtccaag cgcaaattca aggaagagat gctccaggtc atcgcgcctg agatctacgg   15960
ccctgcggtg gtgaaggagg aaagaaagcc ccgcaaaatc aagcgggtca aaaaggacaa   16020
aaaggaagaa gaaagtgatg tggacggatt ggtggagttt gtgcgcgagt tcgcccccg   16080
gcggcgcgtg cagtggcgcg ggcggaaggt gcaaccggtg ctgagacccg gcaccaccgt   16140
ggtcttcacg cccggcgagc gctccggcac cgcttccaag cgctcctacg acgaggtgta   16200
cggggatgat gatattctgg agcaggcggc cgagcgcctg ggcgagtttg cttacggcaa   16260
gcgcagccgt tccgcaccga aggaagaggc ggtgtccatc ccgctggacc acggcaaccc   16320
cacgccgagc ctcaagcccg tgaccttgca gcaggtgctg ccgaccgcgg cgccgcgccg   16380
ggggttcaag cgcgaggggcg aggatctgta ccccaccatg cagctgatgg tgcccaagcg   16440
ccagaagctg gaagacgtgc tggagaccat gaaggtggac ccggacgtgc agcccgaggt   16500
caaggtgcgg cccatcaagc aggtggcccc gggcctgggc gtgcagaccg tggacatcaa   16560
gattcccacg gagcccatgg aaacgcagac cgagcccatg atcaagccca gcaccagcac   16620
catggaggtg cagacggatc cctggatgcc atcggctcct agtcgaagac ccggcgcaa   16680
gtacggcgcg gccagcctgc tgatgcccaa ctacgcgctg catccttcca tcatccccac   16740
gccgggctac cgcggcacgc gcttctaccg cggtcatacc agcagccgcc gccgcaagac   16800
caccactcgc cgccgccgtc gccgcaccgc cgctgcaacc accctgccg cctggtgcg   16860
gagagtgtac cgccgcgggcc gcgcacctct gaccctgccg gccgcgcgct accaccgcag   16920
catcgccatt taaactttcg cctgctttgc agatcaatgg ccctcacatg ccgccttcgc   16980
gttcccatta cgggctaccg aggaagaaaa ccgcgccgta gaaggctggc ggggaacggg   17040
atgcgtcgcc accaccaccg gcggcggcgc gccatcagca agcggttggg gggaggcttc   17100
ctgcccgcgc tgatccccat catcgcccgcg gcgatcgggg cgatccccgg cattgcttcc   17160
gtggcggtgc aggcctctca gcgccactga gacacacttg gaaacatctt gtaataaacc   17220
aatggactct gacgctcctg gtcctgtgat gtgttttcgt agacagatgg aagacatcaa   17280
ttttccgtcc ctggctccgc gacacggcac gcggccgttc atgggcacct ggagcgacat   17340
cggcaccagc caactgaacg ggggcgcctt caattggagc agtctctgga gcgggcttaa   17400
gaatttcggg tccacgctta aaacctatgg cagcaaggcg tggaacagca ccacagggca   17460
ggcgctgagg gataagctga aagagcagaa cttccagcag aaggtggtcg atgggctcgc   17520
ctcgggcatc aacgggggtgg tggacctggc caaccaggcc gtgcagcggc agatcaacag   17580
ccgcctggac ccggtgccgc ccgccggctc cgtggagatg ccgcaggtgg aggaggagct   17640
gcctcccctg gacaagcggg gcgagaagcg accccgcccg gatgcggagg agacgctgct   17700
gacgcacacg gacgagccgc ccccgtacga ggaggcggtg aaaactgggtc tgcccaccac   17760
gcggcccatc gcgcccctgg ccaccggggt gctgaaaccc gaaaagcccg cgaccctgga   17820
cttgcctcct ccccagcctt cccgcccctc tacagtggct aagcccctgc cgccggtggc   17880
cgtggccgcc gcgcgacccg ggggcaccgc ccgccctcat gcgaactggc agagcactct   17940
gaacagcatc gtgggtctgg gagtgcgagag tgtgaagcgc cgccgctgct attaaaccta   18000
ccgtagcgct taacttgctt gtctgtgtgt gtatgtatta tgtcgccgcc gccgctgtcc   18060
accagaagga ggagtgaaga ggcgcgtcgc cgagttgcaa gatggccacc ccatcgatgc   18120
tgccccagtg ggcgtacatg cacatcgccg gacaggacgc ttcggagtac ctgagtccgg   18180
gtctggtgca gtttgcccgc gccacagaca cctacttcag tctgtgggaac aagttttagga   18240
accccacggt ggcgcccacg cacgatgtga ccaccgaccg cagccagcgg ctgacgctgc   18300
gcttcgtgcc cgtggaccgc gaggacaaca cctactcgta caaagtgcgc tacacgctgg   18360
ccgtggacga caaccgcgtg ctggacatgg ccagcacca ctttgacatc cgcggcgtgg   18420
tggatcgggg ccctagcttc aaaccctact ccggcaccgc ctacaacagt ctggccccca   18480
agggagcacc caacacttgt cagtggacat ataaagccga tggtgaaact gccacagaaa   18540
aaacctatac atatgaaat gcaccgtgc agggcattaa catcacaaaa gatggtattc   18600
aacttggaac tgacaccgat gatcagccaa tctacgcaga taaaacctat cagcctgaac   18660
ctcaagtggg tgatgctgaa tggcatgaca tcactggtac tgatgaaaag tatggaggca   18720
gagctcttaa gcctgatacc aaaatgaagc cttgttatgg ttcttttgcc aagcctacta   18780
ataaagaagg aggtcaggca aatgtgaaaa caggaacagg cactactaaa gaatatgaca   18840
tagacatggc tttctttgac aacagaagtg cggctgctgc tggcctagct ccagaaattg   18900
ttttgtatac tgaaaatgtg gatttggaaa ctccagatac ccatattgta tacaaagcag   18960
gcacagatga cagcagctct tctattaatt tgggtcagca agccatgccc aacagaccta   19020
actacattgg tttcagagac aactttatcg ggctcatgta ctacaacagc actggcaata   19080
tggggggtgct ggcggtcag gcttctcagc tgaatgctgt ggttgacttg caagacagaa   19140
acaccgagct gtcctaccag ctcttgcttg actctctgga tgcagaacc cggtatttca   19200
gtatgtggaa tcaggcggtg gacagctatg atcctgatgt gcgcattatt gaaaatcatg   19260
gtgtggagga tgaacttccc aactattgtt tccctctgga tgctgttggc agaacagata   19320
cttatcaggg aattaaggct aatggaactg atcaaaccac atggaccaaa gatgacagtg   19380
tcaatgatgc taatgagata ggcaagggta atccattcgc catggaaatc aacatccaag   19440
ccaacctgtg gaggaacttc ctctacgcca acgtggccct gtacctgccc gactcttaca   19500
agtacacgcc ggccaatgtt accctgccca ccaacaccaa cacctacgat tacatgaacg   19560
gccgggtggt ggcgccctcg ctggtggact cctacatcaa catcggggcg cgctggtcgc   19620
tggatcccat ggacaacgtg aaccccttca accaccaccg caatgcgggg ctgcgctacc   19680
gctccatgct cctgggcaac gggcgctacg tgcccttcca catccaggtg ccccagaaat   19740
ttttcgccat caagaaccct ctgctcctgc cgcggtccta cacctccgag tggaacttcc   19800
gcaaggacgt caacatgatc ctgcagagct ccctcggcaa cgacctgcgc acggacgggg   19860
cctccatctc cttcaccagc atcaacctct acgccacctt cttccccatg gcgcacaaca   19920
cggcctccac gctcgaggcc atgctgcgca acgacaccaa cgaccagtcc ttcaacgact   19980
acctctcggg ggcaacatg ctctacccca tcccggccaa cgccaccaac gtgcccatct   20040
ccatcccctc gcgcaactgg gccgccttcc gcggctggtc cttcacgcgt ctcaagacca   20100
```

-continued

```
aggagacgcc ctcgctgggc tccgggttcg acccctactt cgtctactcg ggctccatcc   20160
cctacctcga cggcaccttc tacctcaacc acaccttcaa gaaggtctcc atcaccttcg   20220
actcctccgt cagctggccc ggcaacgacc ggctcctgac gcccaacgag ttcgaaatca   20280
agcgcaccgt cgacggcgag ggctacaacg tggcccagtg caacatgacc aaggactggt   20340
tcctggtcca gatgctggcc cactacaaca tcggctacca gtgcttctac gtgcccgagg   20400
gctacaagga ccgcatgtac tccttcttcc gcaacttcca gcccatgagc cgccaggtgg   20460
tggacgaggt caactacaag gactaccagg ccgtcaccct ggcctaccag cacaacaact   20520
cgggcttcgt cggctacctc gcgcccacca tgcgccaggg ccagccctac cccgccaact   20580
accctaccc gctcatcggc aagagcgccg tcaccagcgt cacccagaaa aagttcctct   20640
gcgacagggt catgtggcgc atcccettct ccagcaactt catgtccatg ggcgcgctca   20700
ccgacctcgg ccagaacatg ctctatgcca actccgccca cgcgctagac atgaatttcg   20760
aagtcgaccc catggatgag tccacccttc tctatgttgt cttcgaagtc ttcgacgtcg   20820
tccgagtgca ccagccccac cgcggcgtca tcgaggccgt ctacctgcgc accccttct   20880
cggccggtaa cgccaccacc taagctcttg cttcttgcaa gccatggccg cgggctccgg   20940
cgagcaggag ctcagggcca tcatccgcga cctgggctgc gggccctact tcctgggcac   21000
cttcgataag cgcttcccgg gattcatggc cccgcacaag ctggcctgcg ccatcgtcaa   21060
cacggccggc cgcgagaccg ggggcgagca ctggctggcc ttcgcctgga acccgcgctc   21120
gaacacctgc tacctcttcg accccttcgg gttctcggac gggccctca agcagatcta   21180
ccagttcgag tacgagggcc tgctgcgccg cagcgccctg gccaccgagg accgctgcgt   21240
caccctggaa aagtccaccc agaccgtgca gggtccgcgc tcggccgcct gcgggctctt   21300
ctgctgcatg ttcctgcacg ccttcgtgca ctggcccgac cgcccatgg acaagaaccc   21360
caccatgaac ttgctgacgg gggtgcccaa cggcatgctc cagtcgcccc aggtggaacc   21420
caccctgcgc cgcaaccagg aggcgctcta ccgcttcctc aactcccact ccgcctactt   21480
tcgctcccac cgcgcgcgca tcgagaaggc caccgcctt c gaccgcatga atcaagacat   21540
gtaaaccgtg tgtgtatgtt aaatgtcttt aataaacagc actttcatgt tacacatgca   21600
tctgagatga tttatttaga aatcgaaagg gttctgccgg gtctcggcat ggcccgcggg   21660
cagggacacg ttgcggaact ggtacttggc cagccacttg aactcgggga tcagcagttt   21720
gggcagcggg gtgtcgggga aggagtcggt ccacagcttc cgcgtcagtt gcagggcgcc   21780
cagcaggtcg ggcgcggaga tcttgaaatc gcagttggga cccgcgttct gcgcgcggga   21840
gttgcggtac acggggttgc agcactggaa caccatcagg gccgggtgct tcacgctcgc   21900
cagcaccgtc gcgtcggtga tgctctccac gtcgaggtcc tcggcgttgg ccatcccgaa   21960
gggggtcatc ttgcaggtct gccttccat ggtgggcacg cacccggggct tgtggttgca   22020
atcgcagtgc aggggggatca gcatcatctg ggcctggtcg gcgttcatcc ccgggtacat   22080
ggccttcatg aaagcctcca attgcctgaa cgcctgctgg gcctggctc cctcggtgaa   22140
gaagaccccg caggacttgc tagagaactg gttggtggcg caccggcgt cgtgcacgca   22200
gcagcgcgcg tcgttgttgg ccagctcac cacgctgcgc ccccagcggt tctgggtgat   22260
cttggcccgg tcggggttct ccttcagcgc gcgctgcccg ttctcgctcg ccacatccat   22320
ctcgatcatg tgctccttct ggatcatggt ggtcccgtgc aggcaccgca gcttgccctc   22380
ggcctcggtg caccggtgca gccacagcgc gcacccggtg cactcccagt tcttgtgggc   22440
gatctgggaa tgcgcgtgca cgaagccctg caggaagcgg cccatcatgg tggtcagggt   22500
cttgttgcta gtgaaggtca gcggaatgcc gcggtgctcc tcgttgatgt acaggtggca   22560
gatgcggcgg tacacctcgc cctgctcggg catcagctgg aagttggctt tcaggtcggt   22620
ctccacgcag tagcggtcca tcagcatagt catgatttcc ataccccttct cccaggccga   22680
gacgatgggc aggctcatag ggttcttcac catcatctta gcgctagcag ccgcggccag   22740
ggggtcgctc tcgtccaggg tctcaaagct ccgcttgccg tccttctcgg tgatccgcac   22800
cggggggtag ctgaagccca cggccgccag ctcctcctcg gcctgtcttt cgtcctcgct   22860
gtcctggctg acgtcctgca ggaccacatg cttggtcttg cggggtttct tcttgggcgg   22920
cagcggcggc ggagatgttg gagatggcga gggggagcgc gagttctcgc tcaccactac   22980
tatctcttcc tcttcttggt ccgaggccac gcggcggtag gtatgtctct tcggggggcag   23040
aggcggaggc gacgggctct cgccgccgcg acttggcgga tggctggcag agcccttcc   23100
gcgttcgggg gtgcgctccc ggcggcgctc tgactgactt cctccgcggc cggccattgt   23160
gttctcctag ggaggaacaa caagcatgga gactcagcca tcgccaacct cgccatctgc   23220
ccccaccgcc gacgagaagc agcagcagca gaatgaaagc ttaaccgccc cgccgccag   23280
ccccgccacc tccgacgcgg ccgtcccaga catgcaagag atggaggaat ccatcgagat   23340
tgacctgggc tatgtgacgc cgcggaacca cgaggaggag ctggcagtgc gctttttcaca   23400
agaaagagata caccaagaac agccagagca ggaagcagag aatgagcaga gtcaggctgg   23460
gctcgagcat gacggcgact acctccacct gagcgggggg gaggacgcgc tcatcaagca   23520
tctggcccgg caggccacca tcgtcaagga tgcgctgctc gaccgcaccg aggtgcccct   23580
cagcgtggag gagctcagcc gcgcctacga gttgaacctc ttctcgccgc gcgtgcccc   23640
caagcgccag cccaatggca cctgcgagcc caaccgcgc ctcaacttct acccggtctt   23700
cgcggtgccc gaggccctgg ccacctacca catctttttc aagaaccaaa agatccccgt   23760
ctcctgccgc gccaaccgca cccgcgccga cgcccttttc aacctgggtc ccggcgcccg   23820
cctacctgat atcgcctcct tggaagaggt tcccaagatc ttcgagggtc tgggcagcga   23880
cgagactcgg gccgcgaacg ctctgcaagg agaaggagga gagcatggac accacagcgc   23940
cctggtcgag ttggaaggcg acaacgcgcg gctggcggtg ctcaaacgca cggtcgagct   24000
gacccattc gcctacccgg ctctgaacct gccccccaaa gtcatgagcg cggtcatgga   24060
ccaggtgctc atcaagcgcg cgtcgcccat ctccgaggac gagggcatgc aagactccga   24120
ggagggcaag cccgtggtca gcgacgagca gctggcccgg tggctgggtc ctaatgctag   24180
tccccagagt ttggaagagc ggcgcaaact catgatggcc ggtggtcctg tgaccgtgga   24240
gctggagtgc ctgcgccgct tcttcgccga cgcggagacc ctgcgcaagg tcgaggagaa   24300
cctgcactac ctcttcaggc acgggttcgt cgcgccaggcc tgcaagatct ccaacgtgga   24360
gctgaccaac ctggtctcct acatgggcat cttgcacgag aaccgcctgg ggcagaacgt   24420
gctgcacacc accctgcgcg gggaggcccg cgcgcgactac atccgcgact cgtctacct   24480
ctacctctgc cacacctggc agacgggcat gggcgtgtgg cagcagtgtc tggaggaaca   24540
gaacctgaaa gagctctgca agctcctgca gaagaacctc aagggtctgt ggaccggggt   24600
cgacgagcgc accaccgcct cggacctggc cgacctcatt ttccccgagc gcctcaggct   24660
gacgctcgcg aacggcctgc ccgactttat gagccaaagc atgttgcaaa actttcgctc   24720
tttcatcctc gaacgctccg gaatcctgcc cgccacctgc tccgcgctgc cctcggactt   24780
cgtgccgctg accttccgcg agtgcccccc gccgctgtgg agccactgct acctgctgcg   24840
```

-continued

```
cctggccaac tacctggcct accactcgga cgtgatcgag gacgtcagcg gcgagggcct   24900
gctcgagtgc cactgccgct gcaacctctg cacgccgcac cgctccctgg cctgcaaccc   24960
ccagctgctg agcgagaccc agatcatcgg caccttcgag ttgcaagggc ccagcgaagg   25020
cgagggttca gccgccaagg ggggtctgaa actcaccccg gggctgtgga cctcggccta   25080
cttgcgcaag ttcgtgcccg aggactacca tcccttcgag atcaggttct acgaggacca   25140
atcccatccg cccaaggccg agctgtcggc ctgcgtcatc acccaggggg cgatcctggc   25200
ccaattgcaa gccatccaga aatcccgcca agaattcttg ctgaaaaagg gccgcggggt   25260
ctacctcgac ccccagaccg gtgaggagct caaccccggc ttcccccagg atgccccgag   25320
gaaacaagaa gctgaaagtg gagctgccgc ccgtggagga tttggaggaa gactgggaga   25380
acagcagtca ggcagaggag gaggagatgg aggaagactg ggacagcact caggcagagg   25440
aggacagcct gcaagacagt ctggaggaag acgaggagga ggcagaggag gaggtggaag   25500
aagcagccgc cgccagaccg tcgtcctcgg cgggggagaa agcaagcagc acggatacca   25560
tctccgctcc gggtcggggt cccgctcgac cacacagtag atgggacgag accggacgat   25620
tcccgaaccc caccacccag accggtaaga aggagcggca aggatacaag tcctggcgga   25680
ggcacaaaaa cgccatcgtc tcctgcttgc aggcctgcgg gggcaacatc tccttcaccc   25740
ggcgctacct gctcttccac cgcggggtga actttccccg caacatcttg cattactacc   25800
gtcacctcca cagcccctac tacttccaag aagaggcagc agcagcagaa aaagaccagc   25860
agaaaaccag cagctagaaa atcccacagcg gcggcagcag gtggactgag gatcgcggcg   25920
aacgagccgg cgcaaacccg ggagctgagg aaccggatct ttcccaccct ctatgccatc   25980
ttccagcaga gtcggggcga ggagcaggaa ctgaaagtca agaaccgttc tctgcgctcg   26040
ctcacccgca gttgtctgta tcacaagagc gaagaccaac ttcagcgcac tctcgaggac   26100
gccgagcgtc tcttcaacaa gtactgcgcg ctcactctta aagagtagcc cgcgcccgcc   26160
cagtcgcaga aaaaggcggg aattacgtca cctgtgccct tcgccctagc cgcctccacc   26220
catcatcatg agcaaagaga ttcccacgcc ttacatgtgg agctaccagc cccagatgggg   26280
cctgccgcgc ggtgccgccc aggactactc caccccgcatg aattggctca gcgccggggc   26340
cgcgatgatc tcacgggtga atgacatccg cgcccaccga aaccagatac tcctagaaca   26400
gtcagcgctc accgccacgc cccgcaatca cctcaatccg cgtaattggc ccgccgccct   26460
ggtgtaccag gaaattcccc agcccacgac cgtactactt ccgcgagacg cccaggccga   26520
agtccagctg actaactcag gtgtccagct ggcgggcggc gccaccctgt gtcgtcaccg   26580
ccccgctcag ggtataaagc ggctggtgat ccggggcaga ggcacacagc tcaacgacga   26640
ggtggtgagc tcttcgctgg gtctgcgacc tgacggagtc ttccaactcg ccggatcggg   26700
gagatcttcc ttcacgcctc gtcaggccgt cctgactttg gagagttcgt cctcgcagcc   26760
ccgctcgggt ggcatcggca ctctccagtt cgtggaggag ttcactccct cggtctactt   26820
caaccccttc tccggctccc ccggccacta cccggacgag ttcatcccga acttcgacgc   26880
catcagcgag tcggtggacg gctacgattg aaactaatca cccccttatc cagtgaaata   26940
aagatcatat tgatgatgat tttacagaaa taaaaaataa tcatttgatt tgaaataaag   27000
atacaatcat attgatgatt tgagtttaac aaaaaaataa agaatcactt acttgaaatc   27060
tgataccagg tctctgtcca tgttttctgc caacaccact tcactccct cttcccagct   27120
ctggtactgc aggccccggc gggctgcaaa cttcctccac acgctgaagg ggatgtcaaa   27180
ttcctcctgt ccctcaatct tcattttatc ttctatcaga tgtccaaaaa gcgcgtccgg   27240
gtggatgatg acttcgaccc cgtctacccc tacgatgcag acaacgcacc gaccgtgccc   27300
ttcatcaacc ccccttcgt ctcttcagat ggattccaag agaagcccct ggggggtgttg   27360
tccctgcgac tggccgaccc cgtcaccacc aagaacgggg aaatcaccct caagctggga   27420
gagggggtgg acctcgattc ctcgggaaaa ctcatctcca cacggccac caaggccgcc   27480
gcccctctca gttttccaa caacaccatt tcccttaaca tggatcaccc cttttacact   27540
aaagatggaa aattatcctt acaagtttct ccaccattaa atatactgag aacaagcatt   27600
ctaaacacac tagctttagg ttttggatca ggtttaggac tccgtggctc tgccttggca   27660
gtacagttag tctctccact tacatttgat actgatggaa acataaagct taccttagac   27720
agaggtttgc atgttacaac aggagatgca attgaaagca acataagctg ggctaaaggt   27780
ttaaaatttg aagatggagc catagcaacc aacattggaa atgggttaga gtttggaagc   27840
agtagtacag aaacaggtgt tgatgatgct tacccaatcc aagttaaact tggatctgac   27900
cttagctttg acagtacagg agccataatg gctggtaaca agaagacga taaactcact   27960
ttgtggacaa cacctgatcc atcaccaaac tgtcaaatac tcgcagaaaa tgatgcaaaa   28020
ctaacacttt gcttgactaa atgtggtagt caaatactgg ccactgtgtc agtcttagtt   28080
gtaggaagtg gaaacctaaa ccccattact ggcaccgtaa gcagtgctca ggtgtttcta   28140
cgttttgatg caaacggtgt tctttttaaca gaacattcta cactaaaaaa atactggggg   28200
tataggcagg gagatagcat agatggcact ccatatacca atgctgtagg attcatgccc   28260
aatttaaaag cttatccaaa gtcacaaagt tctactacta aaaataatat agtagggcaa   28320
gtatacatga atggagatgt ttcaaaacct atgcttctca ctataacct caatggtact   28380
gatgacagca acagtacata ttcaatgtca ttttcataca cctggactaa tggaagctat   28440
gttggagcaa catttgggc taactcttat accttctcat acatcgccca agaatgaaca   28500
ctgtatccca ccctgcatgc caaccccttcc caccccactc tgtggaacaa actctgaaac   28560
acaaataaa ataaagttca agtgttttat tgattcaaca gtttacagg attcgagcag   28620
ttattttcc tccaccctcc caggacatgg aatacaccac cctctccccc cgcacagctt   28680
tgaacatctg aatgccattg gtgatggaca tgcttttggt ctccacgttc cacacagttt   28740
cagagcgagc cagtctcggg tcggtcaggg agatgaaacc ctccgggcac tcccgcatct   28800
gcacctcaca gctcaacagc tgaggattgt cctcggtggt cgggatcacg gttatctgga   28860
agaagcagaa gagcggcggt gggaatcata gtccgcgaac gggatcggcc ggtggtgtcg   28920
catcaggccc cgcagcagtc gctgccgccg ccgctccgtc aagctgctgc tcaggggggtc   28980
cgggtccagg gactccctca gcatgatgcc cacggccctc agcatcagtc gtctggtgcg   29040
gcgggcgcag cagcccatgc ggatctcgct caggtcgctg cagtacgtgc aacacagaac   29100
caccaggttg ttcaacagtc catagttcaa cacgctccag ccgaaactca tcgcgggaag   29160
gatgctaccc acgtggccgt cgtaccagat cctcaggtaa atcaagtggt gcccctcca   29220
gaacacgtcg cccacgtaca tgatctcctt gggcatgtgg cggttcacca cctcccggta   29280
ccacatcacc ctctggttga acatgcagcc ccggatgatc ctgcggaacc acagggccag   29340
caccgcccccg cccgccatgc agcgaagaga ccccgggtcc cggcaatggc aatgaggac   29400
ccaccgctcg tacccgtgga tcatctggga gctgaacaag tctatgttgg cacagcacag   29460
gcatatgctc atgcatctct tcagcactct caactcctcg ggggtcaaaa ccatatccca   29520
gggcacgggg aactcttgca ggacagcgaa ccccgcagaa cagggcaatc ctcgcacaga   29580
```

-continued

```
acttacattg tgcatggaca gggtatcgca atcaggcagc accgggtgat cctccaccag  29640
agaagcgcgg gtctcggtct cctcacagcg tggtaagggg gccggccgat acgggtgatg  29700
gcgggacgcg gctgatcgtg ttcgcgaccg tgtcatgatg cagttgcttt cggacatttt  29760
cgtacttgct gtagcagaac ctggtccggg cgctgcacac cgatcgccgg cggcggtctc  29820
ggcgcttgga acgctcggtg ttgaaattgt aaaacagcca ctctctcaga ccgtgcagca  29880
gatctagggc ctcaggagtg atgaagatcc catccatgcct gatggctctg atcacatcga  29940
ccaccgtgga atgggccaga cccagccaga tgatgcaatt ttgttgggtt tcggtgacgg  30000
cgggggaggg aagaacagga agaaccatga ttaactttta atccaaacgg tctcggagta  30060
cttcaaaatg aagatcgcgg agatggcacc tctcgccccc gctgtgttgg tggaaaataa  30120
cagccaggtc aaaggtgata cggttctcga gatgttccac ggtggcttcc agcaaagcct  30180
ccacgcgcac atccagaaac aagacaatag cgaaagcggg agggttctct aattcctcaa  30240
tcatcatgtt acactcctgc accatcccca gataattttc attttccag ccttgaatga  30300
ttcgaactag ttcctgaggt aaatccaagc cagccatgat aaagagctcg cgcagagcgc  30360
cctccaccgg cattcttaag cacaccctca taattccaag atattctgct cctggttcac  30420
ctgcagcaga ttgacaagcg gaatatcaaa atctctgccg cgatccctga gctcctccct  30480
cagcaataac tgtaagtact ctttcatatc ctctccgaaa tttttagcca taggaccacc  30540
aggaataaga ttagggcaag ccacagtaca gataaaccga agtcctcccc agtgagcatt  30600
gccaaatgca agactgctat aagcatgctg gctagacccg gtgatatctt ccagataact  30660
ggacagaaaa tcgcccaggc aatttttaag aaaatcaaca aaagaaaaat cctccaggtg  30720
gacgtttaga gcctcgggaa caacgatgaa gtaaatgcaa gcggtgcgtt ccagcatggt  30780
tagttagctg atctgtagaa aaaacaaaaa tgaacattaa accatgctag cctggcgaac  30840
aggtgggtaa atcgttctct ccagcaccag gcaggccagg gggtctccgg cgcgaccctc  30900
gtaaaaattg tcgctatgat tgaaaaccat cacagagaga cgttcccggt ggccggcgtg  30960
aatgattcga caagatgaat acaccccggg aacattggcg tccgcgagtg aaaaaaagcg  31020
cccgaggaag caataaggca ctacaatgct cagtctcaag tccagcaaag cgatgccatg  31080
cggatgaagc acaaaattct caggtgcgta caaaatgtaa ttactcccct cctgcacagg  31140
cagcaaagcc cccgatccct ccaggtacac atacaaagcc tcagcgtcca tagcttaccg  31200
agcagcagca cacaacaggc gcaagagtca gagaaaggct gagctctaac ctgtccaccc  31260
gctctctgct caatatatag cccagatcta cactgacgta aaggccaaag tctaaaaata  31320
cccgccaaat aatcacacac gcccagcaca cgcccagaaa ccggtgacac actcaaaaaa  31380
atacgcgcac ttcctcaaac gcccaaaact gccgtcattt ccgggttccc acgctacgtc  31440
atcaaaacac gactttcaaa ttccgtcgac cgttaaaaac gtcacccgcc ccgcccctaa  31500
cggtcgcccg tctctcagcc aatcagcgcc ccgcatcccc aaattcaaac acctcatttg  31560
catattaacg cgcacaaaaa gtttgagg                                     31588
```

```
SEQ ID NO: 3          moltype = DNA  length = 11447
FEATURE               Location/Qualifiers
source                1..11447
                      mol_type = other DNA
                      organism = Venezuelan equine encephalitis virus
SEQUENCE: 3
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacgggcc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatgggggt ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctcct tccatgaatt cgcctacgag agtctgagaa  2160
cacgaccagc cgctccttac caagtaccaa ccatagggg gtatgcgtg ccaggatcag  2220
gcaagtctgg catcattaaa agcgcagtca ccaaaaaaga tctagtggtg agcgccaaga  2280
```

```
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataaagac   2460
ctaaaaaggc agtgctctgc ggggatccca aacagtgcgg ttttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaaagctcact   3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgcctatagcg cggcagttca agtttttcccg ggtatgcaaa ccgaaatcct   3900
cacttgaaga gacggaagtt ctgtttgtat tcattgggta cgatcgcaag gcccgtacgc    3960
acaatcctta caagctttca tcaaccttga ccaacatttta tacaggttcc agactccacg    4020
aagccggatg tgcaccctca tatcatgtgg tgcgaggggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttccat     4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggaggct agcgtgacca   5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc     5520
caggcgtgaa tagggtgatc actagagagg agctcgaggc gcttaccccg tcacgcactc    5580
ctagcaggtc ggtctcgaga accagcctgg tctccaaccc gccaggcgta aataggtga     5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgc     5820
tcgaccaaga aaaagaagaa ttactacgca agaaattaca gttaaatccc acacctgtca    5880
acagaagcag ataccagtcc aggaaggtgg agaacatgaa agccataaca gctagacgta    5940
ttctgcaagg cctagggcat tatttgaagg cagaagaaa agtggagtgc taccgaaccc      6000
tgcatcctgt tcctttgtat tcatctagtg tgaaccgtgc cttttcaagc cccaaggtcg    6060
cagtggaagc ctgtaacgcc atgttgaaag agaactttcc gactgtgcct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatcgg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaaacta   6960
aatttaaatt cggagccatg atgaaatctg gaatgttcct cacactgttt gtgaacacag    7020
```

```
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgttcccg ttccagccaa tgtatccgat gcagccaatg ccctatcgca acccgttcgc    7620
ggccccgcgc aggccctggt tccccagaac cgaccctttt ctggcgatgc aggtgcagga    7680
attaacccgc tcgatggcta acctgacgtt caagcaacgc cgggacgcgc cacctgaggg    7740
gccatccgct aagaaaccga agaaggaggc ctcgcaaaaa cagaaagggg gaggccaagg    7800
gaagaagaag aagaaccaag ggaagaagaa ggctaagaca gggccgccta atccgaaggc    7860
acagaatgga aacaagaaga agaccaacaa gaaaccaggc aagagacagc gcatggtcat    7920
gaaattggaa tctgacaaga cgttcccaat catgttggaa gggaagataa acggctacgc    7980
ttgtgtggtc ggagggaagt tatttcaggcc gatgcatgtg gaaggcaaga tcgacaacga    8040
cgttctggcc gcgcttaaga cgaagaaagc atccaaatac gatcttgagt atgcagatgt    8100
gccacagaac atgcgggccg atacattcaa atacacccat gagaaacccc aaggctatta    8160
cagctggcat catggagcag tccaatatga aaatgggcgt ttcacggtgc cgaaaggagt    8220
tggggccaag ggagacagcg gacgaccat tctggataac cagggacggg tggtcgctat     8280
tgtgctggga ggtgtgaatg aaggatctag gacagcccct tcagtcgtca tgtggaacga    8340
gaagggagtt accgtgaagt atactccgga gaactgcgag caatggtcac tagtgaccac    8400
catgtgtctg ctcgccaatg tgacgttccc atgtgctcaa ccaccaattt gctacgacag    8460
aaaaccagca gagactttgg ccatgctcag cgttaacgtt gacaacccgg gctacgatga    8520
gctgctggaa gcagctgtta agtgccccgg aaggaaaagg agatccaccg aggagctgtt    8580
taaggagtat aagctaacgc gcccttacat ggccagatgc atcagatgtg cagttgggag    8640
ctgccatagt ccaatagcaa tcgaggcagt aaagagcgac gggcacgacg gttatgttag    8700
acttcagact tcctcgcagt atggcctgga ttcctccggc aacttaaagg gcaggaccat    8760
gcggtatgac atgcacggga ccattaaaga gataccacta catcaagtgt cactccatac    8820
atctcgcccg tgtcacattg tggatgggca cggttatttc ctgcttgcca ggtgcccggc    8880
aggggactcc atcaccatgg aatttaagaa agattccgtc acacactcct gctcggtgcc    8940
gtatgaagtg aaatttaatc ctgtaggcag agaactctat actcatcccc cagaacacgg    9000
agtagagcaa gcgtgccaag tctacgcaca tgatgcacag aacagaggag cttatgtcga    9060
gatgcacctc ccggggctcag aagtggacag cagtttggtt tccttgagcg gcagttcagt    9120
caccgtgaca cctcctgttg ggactagcgc cctggtggaa tgcgagtgtg gcggcacaaa    9180
gatctccgag accatcaaca agacaaaaca gttcagccag tgcacaaaga aggagcagta    9240
cagagcatat cggctgcaga acgataagtg ggtgtataat tctgacaaac tgcccaaagc    9300
agcgggagcc accttaaaag gaaaactgca tgtcccattc ttgctggcag acggcaaatg    9360
caccgtgcct ctagcaccag aacctatgat aaccttyggt ttcagatcag tgtcactgaa    9420
actgcaccct aagaatccca catatctaac cacccgccaa cttgctgatg agcctcacta    9480
cacgcacgag ctcatatctg aaccagctgt taggaatttt accgtcaccg aaaaagggtg    9540
ggagtttgta tggggaaacc acccgccgaa aaggttttgg gcacaggaaa cagcacccgg    9600
aaatccacat gggctaccgc acgaggtgat aactcattat taccacagat accctatgtc    9660
caccatcctg ggtttgtcaa tttgtgccgc cattgcaacc gtttccgttg cagcgtctac    9720
ctggctgttt tgcagatcta gagttgcgtg cctaactcct taccggctaa cacctaacgc    9780
taggatacca tttttgtctgg ctgtgctttg ctgcgccggc actgcccggg ccgagaccac    9840
ctgggagtcc ttggatcacc tatggaacaa taaccaacag atgttctgga ttcaattgct    9900
gatccctctg gccgccttga tcgtagtgac tcgcctgctc aggtgcgtgt gctgtgtcgt    9960
gccttttttta gtcatggccg gcgccgcagg cgccggcgcc tacgagcacg cgaccacgat    10020
gccgagccaa gcgggaatct cgtataacac tatagtcaac agagcaggct acgcaccact    10080
ccctatcagc ataacaccaa caaagatcaa gctgatacct acagtgaact ggagtacgt    10140
cacctgccac tacaaaacag gaatggattc accagccatc aaatgctgcg gatctcagga    10200
atgcactcca acttacaggc ctgatgaaca gtgcaaagtc ttcacaggggg tttacccgtt    10260
catgtggggt ggtgcatatt gcttttgcga cactgagaac acccaagtca gcaaggccta    10320
cgtaatgaaa tctgacgact gccttgcgga tcatgctgaa gcatataaag cgcacacagc    10380
ctcagtgcag gcgttcctca acatcacagt gggagaacac tctattgtga ctaccgtgta    10440
tgtgaatgga gaaactcctg tgaatttcaa tgggggtcaaa ttaactgcag gtccgctttc    10500
cacagcttgg acacccttttg atcgcaaaat cgtgcagtat gccggggaga tctataatta    10560
tgatttttcct gagtatgggg caggacaacc aggagcattt ggagatatac aatccagaac    10620
agtctcaagc tcagatctgt atgccaatac caacctagtg ctgcagagac ccaaagcagg    10680
agcgatccac gtgccataca ctcaggcacc ttcgggtttt gagcaatgga agaaaagataa    10740
agctccatca ttgaaattta ccgcccccttt cggatgcgaa atatatcaa accccattcg    10800
cgccgaaaac tgtgctgtag ggtcaattcc attagccttt gacattcccg acgccttgtt    10860
caccaggggtg tcagaaacac cgacacttttc agcggccgaa tgcactctta acgagtgcgt    10920
gtattcttcc gactttggtg ggatcgccac ggtcaagtac tcggccagca agtcaggcaa    10980
gtgcgcagtc catgtgccat cagggactgc taccctaaaa gaagcagcag tcgagctaac    11040
cgagcaaggc tcggcgacta tccatttctc gaccgcaaat atccacccgg agttcaggct    11100
ccaaatatgc acatcatatg ttacgtgcaa aggtgattgt caccccccga aagaccatat    11160
tgtgacacac cctcagtatc acgcccaaac atttacagcc gcggtgtcaa aaaccgcgtg    11220
gacgtggtta acatccctgc tgggaggatc agccgtaatt attataattg gcttggtgct    11280
ggctactatt gtggccatgt acgtgctgac caaccagaaa cataattgaa tacagcagca    11340
attggcaagc tgcttacata gaactcgcgg cgattggcat gccgccttaa aattttttatt    11400
ttattttttc ttttctttc cgaatcggat tttgttttta atatttc                   11447
```

```
SEQ ID NO: 4          moltype = DNA   length = 9577
FEATURE               Location/Qualifiers
misc_feature          1..9577
                      note = Description of Artificial Sequence: Synthetic
```

-continued

```
                        polynucleotide
source                  1..9577
                        mol_type = other DNA
                        organism = synthetic construct
SEQUENCE: 4
atgggcggcg catgagagaa gcccagacca attacctacc caaaatggag aaagttcacg   60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacgagcc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatgaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgaag 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgctggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacgggg 2040
aataccgtgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgccg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga ataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagg gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcaac aattgaagg 3540
gcagaactgt cctggtggtc ggggaaaagt tgtccgtccc aggcaaaatg ttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatgttta cgctgacagg gccagcgaaa 3840
gcatcattgg tgctatagcg cggcagttca gttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg aggtggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
```

-continued

```
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtcggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc   5520
caggcgtgaa tagggtgatc actagagagg agctcgaggc gcttaccccg tcacgcactc   5580
ctagcaggtc ggtctcgaga accagcctgg tctccaaccc gccaggcgta aataggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaagaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgcattatata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaaacta   6960
aatttaaatt cggagccatg atgaaatctg gaatgttcct cacactgttt gtgaaccaag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggccctat aactctctac ggctaacctg aatggactac gactctagaa tagtctttaa   7560
ttaagccacc atggcaggca tgtttcaggc gctgagcgaa ggctgcacccc gtatgatat   7620
taaccagatg ctgaacgtgc tgggcgatca tcaggtctca ggccttgagc agcttgagag   7680
tataatcaac tttgaaaaac tgactgaatg gaccagttct aatgttatgc ctatcctgtc   7740
tcctctgaca aagggcatcc tgggcttcgt gtttaccctg accgtgcctt ctgagagagg   7800
acttagctgc attagcgaag cggatgcgac caccccggaa agcgcgaacc tgggcgaaga   7860
aattctgagc cagctgtatc tttggccaag ggtgacctac cattccccta gttatgctta   7920
ccaccaattt gaaagacgag ccaaatataa aagacacttc cccggctttg gccagagcct   7980
gctgtttggc taccctgtgt acgtgttcgg cgattgcgtg cagggcgatt gggatgcgat   8040
tcgctttcgc tattgcgcgc cgccgggcta tgcgctgctg cgctgcaacg ataccaacta   8100
tagcgctctg ctggctgtgg gggccctaga aggacccagg aatcaggact ggcttggtgt   8160
cccaagacaa cttgtaactc ggatgcaggc tattcagaat gccggcctgt gtaccctggt   8220
ggccatgctg gaagagacaa tcttctggct gcaagcgttt ctgatggcgc tgaccgatag   8280
cggcccgaaa accaacatta ttgttggatag ccagtatgtg atgggcatta gcaaaccgag   8340
ctttcaggaa tttgtggatt gggaaaacgt gagcccggaa ctgaacagca ccgatcagcc   8400
gttttggcaa gccggaatcc tggccagaaa tctggtgcct atggtggcca cagtgcaggg   8460
ccagaacctg aagtaccagg tcagtcact agtcatctct gcttctatca ttgtcttcaa   8520
cctgctggaa ctggaaggtg attatcgaga tgatggcaac gtgtgggtgc ataccccgct   8580
gagcccgcgc accctgaacg cgtgggtgaa agcggtggaa gaaaaaaaag gtattccagt   8640
tcacctagag ctggccagta tgaccaacat ggagctcatg agcagtattg tgcatcagca   8700
ggtcagaaca tacggccccg tgttcatgtg tctcggcgga ctgcttacaa tggtggctgg   8760
tgctgtgtgt ctgacagtgc gagtgctcga gctgttccgg ccgcgcagc tggccaacga   8820
cgtggtcctc cagatcatga gctttgtgtgg tgcagcgttt cgcaggtgt gccataccac   8880
cgtgccgtgg ccgaacgcga gcctgacccc gaaatggaac aacgaaacca ccagccca   8940
gatcgccaac tgcagcgtgt atgacttttt tgtgtggctc cattattatt ctgttcgaga   9000
cacactttgg ccaggggtga cctaccatat gaacaaatat gcgtatcata tgctggaaag   9060
acgagccaaa tataaaagag gaccaggacc tggcgctaaa tttgtggccg cctgacact   9120
gaaagccgct gctggtcctg gacctggcca gtacatcaag gccaacagca gttcatcgg   9180
```

-continued

```
catcaccgaa ctcggacccg gaccaggctg atgattcgaa cggccgtatc acgcccaaac   9240
atttacagcc gcggtgtcaa aaaccgcgtg gacgtggtta acatccctgc tgggaggatc   9300
agccgtaatt attataattg gcttggtgct ggctactatt gtggccatgt acgtgctgac   9360
caaccagaaa cataattgaa tacagcagca attggcaagc tgcttacata gaactcgcgg   9420
cgattggcat gccgccttaa aattttttatt ttatttttttc ttttcttttc cgaatcggat   9480
tttgttttta atatttcaaa aaaaaaaaaa aaaaaaaaaa aaaaaaaaaa aaaaaaaaaa   9540
aaaaaaaaaa aaaaaaaaaa aaaaaaaaaa aaaaaaa                             9577

SEQ ID NO: 5            moltype = DNA   length = 11447
FEATURE                 Location/Qualifiers
source                  1..11447
                        mol_type = other DNA
                        organism = Venezuelan equine encephalitis virus
SEQUENCE: 5
atgggcggcg catgagagaa gcccagacca attacctacc caaaatggag aaagttcacg   60
ttgacatcga ggaagacagc ccattcctca gagctttgca gcggagcttc ccgcagtttg   120
aggtagaagc caagcaggtc actgataatg accatgctaa tgccagagcg tttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct cgccgccgtc atgagcgacc   420
ctgacctgga aactgagact atgtgcctcc acgacgacga gtcgtgtcgc tacgaaggge   480
aagtcgctgt ttaccaggat gtatacgcgg ttgacggacc gacaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactag agttagttgc gacgggtacg   900
tcgttaaaag aatagctatc agtccaggcc tgtatggcaa gccttcaggc tatgctgcta   960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac ctttttgcccg   1200
tagtggccca ggcatttgct aggtgggcaa aggaatataa ggaagatcaa gaagatgaaa   1260
ggccactagg actacgagat agacagttag tcatgggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctgggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtaa   1800
taacacactc tggccgaaaa gggcgttatg ccgtggaacc ataccatggt aaagtagtgg   1860
tgccagaggg acatgcaata cccgtccagg acttttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctcctt ccatgaattt cgcctacgag agtctgagaa   2160
cacgaccagc cgctccttac caagtaccaa ccataggggt gtatgggctg gccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc tttttgcttgt catgcaggta ctctcagagc gctcataagc attataagac   2460
ctaaaaaggc agtgctctgc ggggatcccca aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgtaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttttc tgcacccact gttccgttat ccattaggaa taatcactgg gataactcc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttttcttc attcgtcagc aaattgaagg   3540
gcagaactgt cctggtcgtc gggaaaaagt tgtccgtgca agcaaaatg gttgactggt   3600
tgtcagaccg gcctgaggct accttcagag ctcggctgga tttaggcatc ccaggtgatg   3660
tgcccaaata tgcataaata tttgttaatg tgaggacccc atataaatac catcactatc   3720
agcagtgtga agaccatgcc attaagctta gcatgttgac caagaaagct tgtctgcatc   3780
tgaatccccg cggaacctgt gtcagcatag gttatggtta cgctgacagg gccagcgaaa   3840
gcatcattgg tgctatagcg cggcagttca agtttttcccg ggtatgcaaa ccgaaatcct   3900
```

-continued

```
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct  agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctcgcga gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtaa aatcaaggta tgaaaccgta ggaacttcaa   7440
tcatagttat ggccatgact actctagcta gcagtgttaa atcattcagc tacctgagag   7500
gggccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgacccttt  ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga gaccaacaa  gaaaccaggc aagagacagc gcatggtcat   7920
gaaattggaa tctgacaaga cgttcccaat catgttggaa gggagaataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcggggccg atacattcaa atacacccat gagaaacccc aaggctatta   8160
cagctggcat catggagcag tccaatatga aaatgggcgt ttcacggtgc cgaaaggagt   8220
tgggggccaag ggagacagcg gacgaccat tctggataac cagggacggg tggtcgctat   8280
tgtgctggga ggtgtgaatg aaggatctga gacagcccct tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg ctacgatga    8520
gctgctggaa gcagctgtta agtgccccgg aaggaaaagg agatccaccg aggagctgtt   8580
taaggagtat aagctaacgc gccccttacat ggccagatgc atcagatgtg cagttgggag   8640
```

-continued

```
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
agggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggtttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttgatcacc tatggaacaa taaccaacag atgttctgga ttcaattgct   9900
gatccctctg gccgccttga tcgtagtgac tcgcctgctc aggtgcgtgt gctgtgtcgt   9960
gcctttttta gtcatggccg gcgccgcagg cgccggcgcc tacgagcacg cgaccacgat   10020
gccgagccaa gcgggaatct cgtataacac tatagtcaac agagcaggct acgcaccact   10080
ccctatcagc ataacaccaa caaagatcaa gctgatacct acagtgaact tggagtacgt   10140
cacctgccac tacaaaacag gaatggattc accagccatc aaatgctgcg gatctcagga   10200
atgcactcca acttacaggc ctgatgaaca gtgcaaagtc ttcacagggg tttacccgtt   10260
catgtggggt ggtgcatatt gcttttgcga cactgagaac acccaagtca gcaaggccta   10320
cgtaatgaaa tctgacgact gccttgcgga tcatgctgaa gcatataaag cgcacacagc   10380
ctcagtgcag gcgttcctca acatcacagt gggagaacac tctattgtga ctaccgtgta   10440
tgtgaatgga gaaactcctg tgaatttcaa tgggtcaaa ttaactgcag gtccgctttc   10500
cacagcttgg acacccttg atcgcaaaat cgtgcagtat gccggggaga tctataatta   10560
tgattttcct gagtatgggg caggacaacc aggagcattt ggagatatac aatccagaac   10620
agtctcaagc tcagatctgt atgccaatac caacctagtg ctgcagagac ccaaagcagg   10680
agcgatccac gtgccataca ctcaggcacc ttcgggtttt gagcaatgga agaaagataa   10740
agctccatca ttgaaattta ccgcccctt cggatgcgaa atatatacaa accccattcg   10800
cgccgaaaac tgtgctgtag ggtcaattcc attagccttt gacattcccg acgccttgtt   10860
caccaggggtg tcagaaacac cgacactttc agcggccgaa tgcactctta acgagtgcgt   10920
gtattcttcc gactttggtg ggatcgccac ggtcaagtac tcggccagca agtcaggcaa   10980
gtgcgcagtc catgtgccat cagggactgc taccctaaaa gaagcagcag tcgagctaac   11040
cgagcaaggg tcggcgacta tccatttctc gaccgcaaat atccacccgg agttcaggct   11100
ccaaatatgc acatcatatg ttacgtgcaa aggtgattgt caccccccga aagaccatat   11160
tgtgacacac cctcagtatc acgcccaaac atttacagcc gcggtgtcaa aaaccgcgtg   11220
gacgtggtta acatccctgc tgggaggatc agccgtaatt attataattg gcttggtgct   11280
ggctactatt gtggccatgt acgtgctgac caaccagaaa cataattgaa tacagcagca   11340
attggcaagc tgcttacata gaactcgcgg cgattggcat gccgccttaa aattttatt   11400
ttattttttc ttttctttc cgaatcggat tttgttttta atatttc              11447
```

```
SEQ ID NO: 6              moltype = DNA   length = 7894
FEATURE                   Location/Qualifiers
misc_feature             1..7894
                          note = Description of Artificial Sequence: Synthetic
                          polynucleotide
source                    1..7894
                          mol_type = other DNA
                          organism = synthetic construct
```

SEQUENCE: 6
```
atgggcggcg catgagagaa gcccagacca attacctacc caaaatggag aaagttcacg   60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct cgccgccgtc atgagcgacc   420
ctgacctgga aactgagact atgtgcctcc acgacgacga gtcgtgtcgc tacgaagggc   480
aagtcgctgt ttaccaggat gtatacgcgc ttgacggacc gacaagtctc tatcaccaag   540
ccaataaggg agttagagtc gcctactgga taggctttga caccaccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatgggggtg ttgttgggct tttagaaggc   1320
```

-continued

```
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctgggtccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtga   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtgatgcaaa ccgaaatcct   3900
cacttgaaga gacggaagtt ctgtttgtat tcattgggta cgatcgcaag gcccgtacgc   3960
acaatcctta caagctttca tcaaccttga ccaacatttta tacaggttcc agactccacg   4020
aagccggatg tgcaccctca tatcatgtgg tgcgagggga tattgccacg gccaccgaag   4080
gagtgattat aaatgctgct aacagcaaag dacaacctgg cggagggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggaa   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gacgatcatc atcgaagagg   5160
aagaagagga tagcataagt ttgctgtcag atggcccgac ccaccaggtg ctgcaagtca   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340
gcgggggcaac gtcagccgag actaactctt acttcgcaaa gagtatggag tttctggcgc   5400
gaccggtgcc tgcgcctcga acagtattca ggaaccctcc acatcccctc ccgccacaca   5460
gaacaccgtc acttgcaccc agcagggcct gctcgagaac cagcctagtt tccacccgc   5520
caggcgtgaa tagggtgatc actagagagg agctcgaggc gcttacccg tcacgcactc   5580
ctagcaggtc ggtctcgaga accagcctgg tctccaaccc gccaggcgta aataggtgta   5640
ttacaagaga ggagtttgag gcgttcgtag cacaacaaca atgacggttt gatgcggtg   5700
catacatctt ttcctccgac accggtcaag ggcatttaca acaaaaatca gtaaggcaaa   5760
cggtgctatc cgaagtggtg ttggagagga ccgaattcga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agcctaaca gctagacgta   5940
ttctgcaagg cctaggggcat tatttgaagg cagaaggaaa agtggagtgc taccgaaccc   6000
tgcatcctgt tcctttgtat tcatctagtg tgaaccgtgc cttttcaagc cccaaggtcg   6060
```

```
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgtagga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaaattaa 6480
aaggaccaaa agctgctgct cttttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gactatcacg cccaaacatt 7560
tacagccgcg gtgtcaaaaa ccgcgtggac gtggttaaca tccctgctgg aggatcagc 7620
cgtaattatt ataattggct tggtgctggc tactattgtg gccatgtacg tgctgaccaa 7680
ccagaaacat aattgaatac agcagcaatt ggcaagctgc ttacatagaa ctcgcggcga 7740
ttggcatgcc gccttaaaat ttttatttta ttttttcttt tcttttccga atcggatttt 7800
gttttaata tttcaaaaaa aaaaaaaaaa aaaaaaaaaa aaaaaaaaaa aaaaaaaaaa 7860
aaaaaaaaaa aaaaaaaaaa aaaaaaaaaa aaaa                               7894
```

```
SEQ ID NO: 7            moltype = DNA  length = 7893
FEATURE                 Location/Qualifiers
misc_feature           1..7893
                        note = Description of Artificial Sequence: Synthetic
                         polynucleotide
source                 1..7893
                        mol_type = other DNA
                        organism = synthetic construct
SEQUENCE: 7
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaca tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggcttta caccaccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactga gttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatgggggt ttgttgggct tttagaaggc 1320
acaagataac atctatttat aagcgcccgg ataeccaaac catcatcaaa gtgaacacgg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcataagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggaa 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctcct tccatgaatt cgcctacgag agtctgagaa 2160
cacgaccagc cgctccttac caagtaccaa ccatagggggt gtatgcgtg ccaggatcag 2220
gcaagtctgg catcattaaa agcgcagtca ccaaaaaaga tctagtggtg agcgccaaga 2280
```

-continued

```
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataaagac  2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaaagctcact  3180
cagcagagat agtattgaac caactatgcg tgaggttctt tggactcgat ctggactccg   3240
gtctatttttc tgcacccact gttccgttat ccattaggaa taatcactgg gataactccc  3300
cgtcgcctaa catgtacggg ctgaataaag aagtggtccg tcagctctct cgcaggtacc   3360
cacaactgcc tcgggcagtt gccactggaa gagtctatga catgaacact ggtacactgc  3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacatttta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacaa   5340
gcgggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaagaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac agagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaaacta   6960
aatttaaatt cggagccatg atgaaatctg gaatgttcct cacactgttt gtgaacacag   7020
```

-continued

```
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccctaaaa aggctgttta agcttggcaa acctctggca gcagacgatg  7320
aacatgatga tgacaggaga agggcattgc atgaagagtc aacacgctgg aaccgagtgg  7380
gtattcttc agagctgtgc aaggcagtag aatcaaggta tgaaaccgta ggaacttcca  7440
tcatagttat ggccatgact actctagcta gcagtgttaa atcattcagc tacctgagag  7500
gggccctat aactctctac ggctaacctg aatggactac gactatcacg cccaaacatt  7560
tacagccgcg gtgtcaaaaa ccgcgtggac gtggttaaca tccctgctgg gaggatcagc  7620
cgtaattatt ataattggct tggtgctggc tactattgtg gccatgtacg tgctgaccaa  7680
ccagaaacat aattgaatac agcagcaatt ggcaagctgc ttacatagaa ctcgcggcga  7740
ttggcatgcc gccttaaaat tttattta ttttctttt cttttccgaa tcggatttg  7800
ttttaatat ttcaaaaaaa aaaaaaaaaa aaaaaaaaaa aaaaaaaaaa aaaaaaaaaa  7860
aaaaaaaaaa aaaaaaaaaa aaa                                         7893
```

SEQ ID NO: 8                moltype = DNA  length = 7927
FEATURE                   Location/Qualifiers
misc_feature             1..7927
                          note = Description of Artificial Sequence: Synthetic
                          polynucleotide
source                    1..7927
                          mol_type = other DNA
                          organism = synthetic construct

SEQUENCE: 8

```
taatacgact cactatagga tgggcggcgc atgagagaag cccagaccaa ttacctaccc  60
aaaatggaga aagttcacgt tgacatcgag gaagacagcc cattcctcag agctttgcag  120
cggagcttcc cgcagtttga ggtagaagcc aagcaggtca ctgataatga ccatgctaat  180
gccagagcgt tttcgcatct ggcttcaaaa ctgatcgaaa cggaggtgga cccatccgac  240
acgatccttg acattggaag tgcgcccgcc cgcagaatgt attctaagca caagtatcat  300
tgtatctgtc cgatgagatg tgcggaagat ccggacagat tgtataagta tgcaactaag  360
ctgaagaaaa actgtaagga aataactgat aaggaattgg acaagaaaat gaaggagctc  420
gccgccgtca tgagcgaccc tgacctggaa actgagacta tgtgcctcca cgacgacgag  480
tcgtgtcgct acgaagggca agtcgctgtt taccaggatg tatacgcggt tgacggaccg  540
acaagtctct atcaccaagc caataaggga gttagagtcg cctactggat aggctttgac  600
accaccccct ttatgtttaa gaacttggct ggagcatatc catcatactc taccaactgg  660
gccgacgaaa ccgtgttaac ggctcgtaac ataggcctat gcagctctga cgttatggag  720
cggtcacgta gagggatgtc cattcttaga aagaagtatt tgaaaccatc caacaatgtt  780
ctattctctg ttggctcgac catctaccac gagaagaggg acttactgag gagctggcac  840
ctgccgtctg tatttcactt acgtggcaag caaaattaca catgtcggtg tgagactata  900
gttagttgcg acgggtacgt cgttaaaaga atagctatca gtccaggcct gtatgggaag  960
ccttcaggct atgctgctac gatgcaccgc gagggattcc tgtgctgcaa agtgacagac  1020
acattgaacg gggagagggt ctcttttccc gtgtgcacat atgtgccagc tacattgtgt  1080
gaccaaatga ctggcatact ggcaacagat gtcagtgcgg acgacgcgca aaaactgctg  1140
gttgggctca accagcgtat agtcgtcaac ggtcgcaccc agagaaacac caataccatg  1200
aaaaattacc ttttgcccgt agtggcccag gcatttgcta ggtgggcaaa ggaatataag  1260
gaagatcaag aagatgaaag gccactagga ctacgagata gacagttagt catggggtgt  1320
tgttgggctt ttagaaggca caagataaca tctatttata agcgcccgga tacccaaacc  1380
atcatcaaag tgaacagcga tttccactca ttcgtgctgc ccaggatagg cagtaacaca  1440
ttggagatcg ggctgagaac aagaatcagg aaaatgttag aggagcacaa ggagccgtca  1500
cctctcatta ccgccgagga cgtacaagaa gctaagtgcg cagccgatga ggctaaggag  1560
gtgcgtgaag ccgaggagtt gcgcgcagct ctaccacctt tggcagctga tgttgaggag  1620
cccactctgg aagccgatgt cgacttgatg ttacaagagg ctggggccgg ctcagtggag  1680
acacctcgtg gcttgataaa ggttaccagc tacgctggcg aggacaagat cggctcttac  1740
gctgtgcttt ctccgcaggc tgtactcaag agtgaaaaat tatcttgcat ccaccctctc  1800
gctgaacaag tcatagtgat aacacactct ggccgaaaag ggcgttatgc cgtggaacca  1860
taccatggta aagtagtggt gccagaggga catgcaatac ccgtccagga ctttcaagct  1920
ctgagtgaaa gtgccaccat tgtgtacaac gaacgtgagt cgtaaacag gtacctgcac  1980
catattgcca cacatggagg agcgctgaac actgatgaag aatattacaa aactgtcaag  2040
cccagcgagc acgacgggcga atacctgtac gacatcgaca ggaaacagtg cgtcaagaaa  2100
gaactagtca ctgggctagg gctcacaggc gagctggtgg atcctccctt ccatgaattc  2160
gcctacgaga gtctgagaac acgaccagcc gctccttacc aagtaccaac catagggtg  2220
tatggcgtgc caggatcagg caagtctggc atcattaaaa gcgcagtcac caaaaaagat  2280
ctagtggga gcgccaagaa agaaaactgt gcagaaatta taagggacgt caagaaaatg  2340
aaagggctgg acgtcaatgc cagaactgtg gactcagtgc tcttgaatgg atgcaaacac  2400
cccgtagaga ccctgtatat tgacgaagct ttttgcttgtc atgcaggtac tctcagagcg  2460
ctcatagcca ttataagacc taaaaaggca gtgctctgcg gggatcccaa acagtgcggt  2520
ttttaaca tgatgtgcct gaaagtgcat tttaaccacg agattgcac acaagtcttc  2580
cacaaaagca tctctcgccg ttgcactaaa tctgtgactt cggtcgtctc aaccttgttt  2640
tacgacaaaa aaatgagaac gacgaatccg aaagagacta agattgtgat tgacactacc  2700
ggcagtacca aacctaagca ggacgatctc attctcactt gtttcagagg gtgggtgaag  2760
cagttgcaaa tagattacaa aggcaacgaa ataatgacgg cagctgcctc tcaagggctg  2820
acccgtaaag gtgtgtatgc cgttcggtac aaggtgaatg aaaatcctct gtacgcaccc  2880
acctcagaac atgtgaacgt cctactgacc cgcacggaag acggcatcgt gtggaaaaca  2940
ctagccggcg acccatggat aaaaacactg actgccaagt accctgggaa tttcactgcc  3000
acgatagagg agtggcaagc agagcatgat gccatcatga ggcacatctt ggagagaccg  3060
gaccctaccg acgtcttcca gaataaggca aacgtgtgtt gggccaaggc tttagtgccg  3120
gtgctgaaga ccgctggcat agacatgacc actgaacaat ggaacactgt ggattatttt  3180
gaaacggaca aagctcactc agcagagata gtattgaacc aactatgcgt gaggttcttt  3240
```

```
ggactcgatc tggactccgg tctattttct gcacccactg ttccgttatc cattaggaat  3300
aatcactggg ataactcccc gtcgcctaac atgtacgggc tgaataaaga agtggtccgt  3360
cagctctctc gcaggtaccc acaactgcct cgggcagttg ccactggaag agtctatgac  3420
atgaacactg gtacactgcg caattatgat ccgcgcataa acctagtacc tgtaaacaga  3480
agactgcctc atgctttagt cctccaccat aatgaacacc cacagagtga cttttcttca  3540
ttcgtcagca aattgaaggg cagaactgtc ctggtggtcg gggaaaagtt gtccgtccca  3600
ggcaaaatgg ttgactggtt gtcagaccgg cctgaggcta ccttcagagc tcggctggat  3660
ttaggcatcc caggtgatgt gcccaaatat gacataaatat ttgttaatgt gaggaccoca  3720
tataaatacc atcactatca gcagtgtgaa gaccatgcca ttaagcttag catgttgacc  3780
aagaaagctt gtctgcatct gaatcccggc ggaacctgtg tcagcatagg ttatggttac  3840
gctgacaggg ccagcgaaag catcattggt gctatagcgc ggcagttcaa gttttcccgg  3900
gtatgcaaac cgaaatcctc acttgaagag acggaagttc tgtttgtatt cattgggtac  3960
gatcgcaagg cccgtacgca caatccttac aagctttcat caaccttgac caacatttat  4020
acaggttcca gactccacga agccggatgt gcaccctcat atcatgtggt gcgaggggat  4080
attgccacgg ccaccgaagg agtgattata aatgctgcta acagcaaagg acaacctggc  4140
ggaggggtgt gcggagcgct gtataagaaa ttcccggaaa gcttcgattt acagccgatc  4200
gaagtaggaa aagcgcgact ggtcaaaggt gcagctaaac atatcattca tgccgtagga  4260
ccaaacttca acaaagtttc ggaggttgaa ggtgacaaac agttggcaga ggcttatgag  4320
tccatcgcta agattgtcaa cgataacaat tacaagtcag tagcgattcc actgttgtcc  4380
accggcatct tttccgggaa caaagatcga ctaacccaat cattgaacca tttgctgaca  4440
gctttagaca ccactgatgc agatgtagcc atatactgca gggacaagaa atgggaaatg  4500
actctcaagg aagcagtggc taggagagaa gcagtggagg agatatgcat atccgacgac  4560
tcttcagtga cagaacctga tgcagagctg gtgagggtgc atccgaagag ttctttggct  4620
ggaaggaagg gctacagcac aagcgatggc aaaactttct catatttgga agggaccaag  4680
tttcaccagg cggccaagga tatagcagaa attaatgcca tgtggcccgt tgcaacggag  4740
gccaatgagc aggtatgcat gtatatcctc ggagaaagca tgagcagtat taggtcgaaa  4800
tgccccgtcg aagagtcgga agcctccaca ccacctagca cgctgccttg cttgtgcatc  4860
catgccatga ctccagaaag agtacagcgc ctaaaagcct cacgtccaga acaaattact  4920
gtgtgctcat cctttccatt gccgaagtat agaatcactg gtgtgcagaa gatccaatgc  4980
tcccagccta tattgttctc accgaaagtg cctgcgtata ttcatccaag gaagtatctc  5040
gtggaaacac caccggtaga cgagactccg gagccatcgg cagagaacca atccacagag  5100
gggacacctg aacaaccacc acttataacc gaggatgaga ccaggactag aacgcctgag  5160
ccgatcatca tcgaagagga agaagaggat agcataagtt tgctgtcaga tggcccgacc  5220
caccaggtgc tgcaagtcga ggcagacatt cacgggccgc cctctgtatc tagctcatcc  5280
tggtccattc ctcatgcatc cgactttgat gtggacagtt tatccatact tgacaccctg  5340
gagggagcta gcgtgaccag cggggcaacg tcagccgaga ctaactctta cttcgcaaag  5400
agtatggagt ttctggcgcg accggtgcct gcgcctcgaa cagtattcag gaaccctcca  5460
catcccgctc cgcgcacaag aacaccgtca cttgcaccca gcagggcctg ctcgagaacc  5520
agcctagttt ccacccgcc aggcgtgaat agggtgatca ctagagagga gctcgaggcg  5580
cttaccccgt cacgcactcc tagcaggtcg gtctcgagaa ccagcctggt ctccaacccg  5640
ccaggcgtaa atagggtgat tacaagagag gagtttgagg cgttcgtagc acaacaacaa  5700
tgacggtttg atgcgggtgc atacatcttt tcctccgaca ccggtcaagg gcatttacaa  5760
caaaaatcag taaggcaaac ggtgctatcc gaagtggtgt tggagaggac cgaattggag  5820
atttcgtatg ccccgcgcct cgaccaagaa aaagaagaat tactacgcaa gaaattacag  5880
ttaaatccca cacctgctaa cagaagcaga taccagtcca ggaaggtgga gaacatgaaa  5940
gccataacag ctagacgtat tctgcaaggc ctagggcatt atttgaaggc agaaggaaaa  6000
gtggagtgct accgaaccct gcatcctgtt cctttgtatt catctagtgt gaaccgtgcc  6060
ttttcaagcc ccaaggtcgc agtggaagcc tgtaacgcca tgttgaaaga gaactttccg  6120
actgtggctt cttactgtat tattccgag tacgatgcct atttggacat ggttgacgga  6180
gcttcatgct gcttagacac tgccagtttt tgccctgcaa agctgcgcag ctttccaaag  6240
aaacactcct atttggaacc cacaatacga tcggcagtgc cttcagcgat ccagaacacg  6300
ctccagaacg tcctggcagc tgccacaaaa agaaattgca atgtcacgca aatgagagaa  6360
ttgcccgtat tggattcggc ggcctttaat gtggaatgct tcaagaaata tgcgtgtaat  6420
aatgaatatt gggaaacgtt taaagaaaac cccatcaggc ttactgaaga aaacgtggta  6480
aattacatta ccaaattaaa aggaccaaaa gctgctgctc tttttgcgaa gacacataat  6540
ttgaatatgt tgcaggacat accaatggac aggtttgtaa tggacttaaa gagagacgtg  6600
aaagtgactc caggaacaaa acatactgaa gaacggccca aggtacaggt gatccaggct  6660
gccgatccgc tagcaacagc gtatctgtgc ggaatccacc gagagctggt taggagatta  6720
aatgcggtcc tgcttccgaa cattcataca ctgtttgata tgtcggctga agactttgac  6780
gctattatag ccgagcactt ccagcctggg gattgtgttc tggaaactga catcgcgtcg  6840
tttgataaaa gtgaggacga cgccatggct ctgaccgcgt taatgattct ggaagactta  6900
ggtgtggacg cagagctgtt gacgctgatt gaggcggctt cggcgaaat ttcatcaata  6960
catttgccca ctaaaactaa attttaaattc ggagccatga tgaaatctgg aatgttcctc  7020
acactgtttg tgaacacgat cattaacatt gtaatcgcaa gcagagtgat gagaaccgtg  7080
ctaaccggat caccatgtgc agcattcatt ggagatgaca atatcgtgaa aggagtcaaa  7140
tcggacaaat taatggcaga caggtgcgcc acctggttga atatggaagt caagattata  7200
gatgctgtgt tgggcgagaa agcgccttat ttctgtggag ggtttatttt gtgtgactcc  7260
gtgaccggca cagcgtgccg tgtggcagac cccctaaaaa ggctgtttaa gcttggcaaa  7320
cctctggcag cagacgatga acatgatgat gacaggagga ggcattgca tgaagagtca  7380
acacgctgga accgagtggg tattcttca gagctgtgca aggcagtaga atcaaggtat  7440
gaaaccgtag gaacttccat catagttatg gccatgacta ctctagctag cagtgttaaa  7500
tccattcagct acctgagagg ggcccctata actctacg gctaacctga atggactacg  7560
actatcacgc ccaaacattt acagccgcgg tgtcaaaaac cgcgtggacg tggttaacat  7620
cctggtgggg aggatcagcc gtaattatta taattggctt ggtgctggct actattgtgg  7680
ccatgtacgt gctgaccaac cagaaacata attgaataca gcagcaattg gcaagctgct  7740
tacatagaac tcgcggcgat tggcatgccg ccttaaaatt tttattttat tttttctttt  7800
cttttccgaa tcgatttttg ttttaatat ttcaaaaaa aaaaaaaaaa aaaaaaaaaa  7860
aaaaaaaaaa aaaaaaaaaa aaaaaaaaaa aaaaaaaaaa aaaaaaaaaa aaatacgtag  7920
tttaaac                                                            7927
```

-continued

```
SEQ ID NO: 9            moltype = DNA  length = 7926
FEATURE                 Location/Qualifiers
misc_feature            1..7926
                        note = Description of Artificial Sequence: Synthetic
                        polynucleotide
source                  1..7926
                        mol_type = other DNA
                        organism = synthetic construct
SEQUENCE: 9
taatacgact cactatagga taggcggcgc atgagagaag cccagaccaa ttacctaccc    60
aaaatggaga aagttcacgt tgacatcgag gaagacagcc cattcctcag agctttgcag   120
cggagcttcc cgcagtttga ggtagaagcc aagcaggtca ctgataatga ccatgctaat   180
gccagagcgt tttcgcatct ggcttcaaaa ctgatcgaaa cggaggtgga cccatccgac   240
acgatccttg acattggaag tgcgcccgcc cgcagaatgt attctaagca caagtatcat   300
tgtatctgtc cgatgagatg tgcggaagat ccggacagat tgtataagta tgcaactaag   360
ctgaagaaaa actgtaagga aataactgat aaggaattgg acaagaaaat gaaggagctc   420
gccgccgtca tgagcgaccc tgacctggaa actgagacta tgtgcctcca cgacgacgag   480
tcgtgtcgct acgaagggca agtcgctgtt taccaggatg tatacgcggt tgacggaccg   540
acaagtctct atcaccaagc caataaggga gttagagtcg cctactggat aggctttgac   600
accaccccct ttatgtttaa gaacttggct ggagcatatc catcatactc taccaactgg   660
gccgacgaaa ccgtgttaac ggctcgtaac ataggcctac gagctctga cgttatggag   720
cggtcacgta gagggatgtc cattcttaga aagaagtatt tgaaaccatc caacaatgtt   780
ctattctctg ttggctcgac catctaccac gagaagaggg acttactgag gagctggcac   840
ctgccgtctg tatttcactt acgtggcaag caaaattaca catgtcggtg tgagactata   900
gttagttgcg acgggtacgt cgttaaaaga atagctatca gtccaggcct gtatgggaag   960
ccttcaggct atgctgctac gatgcaccgc gagggattct tgtgctgcaa agtgacagac  1020
acattgaacg gggagagggt ctcttttccc gtgtgcacgt atgtgccagc tacattgtgt  1080
gaccaaatga ctggcatact ggcaacagat gtcagtgcgg acgacgcgca aaaactgctg  1140
gttgggctca accagcgtat agtcgtcaac ggtcgcaccc agagaaacac caataccatg  1200
aaaaattacc ttttgcccgt agtggcccag gcatttgcta ggtgggcaaa ggaatataag  1260
gaagatcaag aagatgaaag gccactagga ctacgagata gacagttagt catggggtgt  1320
tgtttgggctt ttagaaggca caagataaca tctatttata agcgcccgga tacccaaacc  1380
atcatcaaag tgaacagcga tttccactca ttcgtgctgc caggatagg cagtaacaca  1440
ttggagatcg ggctgagaac aagaatcagg aaaatgttag aggagcacaa ggagccgtca  1500
cctctcatta ccgccgagga cgtacaagaa gctaagtgcg cagccgatga ggctaaggag  1560
gtgcgtgaag ccgaggagtt gcgcgcagct ctaccacctt tggcagctga tgttgaggag  1620
cccactctgg aagccgatgt cgacttgatg ttacaagagg ctggggccgg ctcagtggag  1680
acacctcgtg gcttgataaa ggttaccagc tacgatggcg aggacaagat cggctcttac  1740
gctgtgcttt ctccgcaggc tgtactcaag agtgaaaat tatcttgcat ccaccctctc  1800
gctgaacaag tcatagtgat aacacactct ggccgaaaag ggcgttatgc cgtggaacca  1860
taccatggta aagtagtggt gccagaggga catgcaatac ccgtccagga ctttcaagct  1920
ctgagtgaaa gtgccaccat tgtgtacaac gaacgtgagt tcgtaaacag gtacctgcac  1980
catattgcca cacatggagg agcgctgaac actgatgaag aatattacaa aactgtcaag  2040
cccagcgagc acgacggcga atacctgtac gacatcgaca ggaaacagtg cgtcaagaaa  2100
gaactagtca ctgggctagg gctcacaggc gagctggtgg atcctccctt ccatgaattc  2160
gcctacgaga gtctgagaac acgaccagcc gctccttacc aagtaccaac cataggggtg  2220
tatgccgtgc caggatcagg caagtctggc atcattaaaa gcgcagtcac caaaaaagat  2280
ctagtggtga gcgccaagaa agaaaactgt gcagaaatta aagggacgt caagaaaatg  2340
aaagggctgg acgtcaatgc cagaactgtg gactcagtgc tcttgaatgg atgcaaacac  2400
ccggtagaga ccctgtatat tgacgaagct tttgcttgtc atgcaggtac tctcagacgc  2460
ctcatagcca ttataagacc taaaaaggca gtgctctgcg gggatcccaa acagtgcggt  2520
ttttttaaca tgatgtgcct gaaagtgcat tttaaccacg agatttgcac acaagtcttc  2580
cacaaaagca tctctcgccg ttgcactaaa tctgtgactt cggtcgtctc aaccttgttt  2640
tacgacaaaa aaatgagaac gacgaatccg aaagagacta agattgtgat tgacactacc  2700
ggcagtacca aacctaagca ggacgatctc attctcactt gtttcagagg gtgggtgaag  2760
cagttgcaaa tagattacaa aggcaacgaa ataatgacgg cagctgcctc tcaagggctg  2820
acccgtaaag gtgtgtatgc cgttcggtac aaggtgaatg aaaatcctct gtacgcaccc  2880
acctcagaac atgtgaacgt cctactgacc cgcacgcgag accgcatcgt gtggaaaaca  2940
ctagccggcg acccatggat aaaaacactg actgccaagt accctgggaa tttcactgac  3000
acgatagagg agtggcaagc agagcatgat gccatcatga ggcacatctt ggagagaccg  3060
gaccctaccg acgtcttcca gaataaggca aacgtgtgtt gggccaaggc tttagtgccg  3120
gtgctgaaga ccgctggcat agacatgacc actgaacaat ggaacactgt ggattatttt  3180
gaaacggaca aagctcactc agcagagata gtattgaaac aactatgtgg agggttctac  3240
ggactcgatc tggactccgg tctatttttct gcacccactg ttccgttatc cattaggaat  3300
aatcactggg ataactcccc gtcgcctaac atgtacgggc tgaataaaga agtggtccgt  3360
cagctctctc gcaggtaccc acaactgcct cgggcagttg ccactggaag agtctatgac  3420
atgaacactg gtacactgcg caattatgat ccgcgcataa acctagtacc tgtaaacaga  3480
agactgcctc atgctcttagt cctccaccat aatgaacacc cacagagtga ctttttcttca  3540
ttcgtcagca aattgaaggg cagaactgtc ctggtggtcg gggaaaagtt gtccgtccca  3600
ggcaaaatgg ttgactggtt gtcagaccgg cctgaggcta ccttcagagc tcggctggat  3660
ttaggcatcc caggtgatgt gcccaaatat gacataatat ttgttaatgt gaggacccca  3720
tataaatacc atcactatca gcagtgtgaa gaccatgcca ttaagcttag catgttgacc  3780
aagaaagctt gtctgcatct gaatcccggg ggaacctgtc tcagcatagg ttatggttac  3840
gctgacaggg ccagcgaaag catcattggt gctatagcgc ggcagttcaa gttttcccgg  3900
gtatgcaaac cgaaatcctc acttgaagag acggaagttc tgtttgtatt cattgggtac  3960
gatcgcaagg cccgtacgca caatccttac aagctttcat caaccttgac caacatttat  4020
acaggttcca gactccacga agccggatgt gcaccctcat atcatgtggt gcgaggggat  4080
attgccacgg ccaccgaagg agtgattata aatgctgcta cagcaaagg acaacctggc  4140
```

```
ggaggggtgt gcggagcgct gtataagaaa ttcccggaaa gcttcgattt acagccgatc   4200
gaagtaggaa aagcgcgact ggtcaaaggt gcagctaaac atatcattca tgccgtagga   4260
ccaaacttca acaaagtttc ggaggttgaa ggtgacaaac agttggcaga ggcttatgag   4320
tccatcgcta agattgtcaa cgataacaat tacaagtcag tagcgattcc actgttgtcc   4380
accggcatct tttccgggaa caaagatcga ctaacccaat cattgaacca tttgctgaca   4440
gctttagaca ccactgatgc agatgtagcc atatactgca gggacaagaa atgggaaatg   4500
actctcaagg aagcagtggc taggagagaa gcagtggagg agatatgcat atccgacgac   4560
tcttcagtga cagaacctga tgcagagctg gtgagggtgc atccgaagag ttctttggct   4620
ggaaggaagg gctacagcac aagcgatggc aaaactttct catatttgga agggaccaag   4680
tttcaccagg cggccaagga tatagcagaa attaatgcca tgtggcccgt tgcaacggag   4740
gccaatgagc aggtatgcat gtatatcctc ggagaaagca tgagcagtat taggtcgaaa   4800
tgccccgtcg aagagtcgga agcctccaca ccacctagca cgctgccttg cttgtgcatc   4860
catgccatga ctccagaaag agtacagcgc ctaaaagcct cacgtccaga acaaattact   4920
gtgtgctcat cctttccatt gccgaagtat agaatcactg gtgtgcagaa gatccaatgc   4980
tcccagccta tattgttctc accgaaagtg cctgcgtata ttcatccaag gaagtatctc   5040
gtggaaacac caccggtaga cgagactccg gagccatcgg cagagaacca atccacagag   5100
gggacacctg aacaaccacc acttataacc gaggatgaga ccaggactag aacgcctgag   5160
ccgatcatca tcgaagagga agaagaggat agcataagt tgctgtcaga tggcccgacc   5220
caccaggtgc tgcaagtcga ggcagacatt cacgggccgc cctctgtatc tagctcatcc   5280
tggtccattc ctcatgcatc cgactttgat gtggacagtt tatccatact tgacaccctg   5340
gagggagcta gcgtgaccag cggggcaacg tcagccgaga ctaactctta cttcgcaaag   5400
agtatggagt ttctggcgcg accggtgcct gcgcctcgaca cagtattcag gaaccctcca   5460
catcccgctc cgcgcacaag aacaccgtca cttgcaccca gcagggcctg ctcgagaacc   5520
agcctagttt ccaccccgcc aggcgtgaat agggtgatca ctagagagga gctcgaggcg   5580
cttacccgt cacgcactcc tagcaggtcg gtctcgagaa ccagcctggt ctccaacccg   5640
ccaggcgtaa ataggggtgat tacaagagag gagtttgagg cgttcgtagc acaacaacaa   5700
tgacggtttg atgcgggtgc atacatcttt tcctccgaca ccggtcaagg gcatttacaa   5760
caaaaatcag taaggcaaac ggtgctatcc gaagtggtgt tggagaggac cgaattggag   5820
atttcgtatg ccccgcgcct cgaccaagaa aaagaagaat tactacgcaa gaaattacag   5880
ttaaatccca cacctgctaa cagaagcaga taccagtcca ggaaggtgga gaacatgaaa   5940
gccataacag ctagacgtat tctgcaaggc ctagggcatt atttgaaggc agaaggaaaa   6000
gtggagtgct accgaaccct gcatcctgtt cctttgtatt catctagtgt gaaccgtgcc   6060
ttttcaagcc ccaaggtcgc agtggaagcc tgtaacgcca tgttgaaaga gaactttccg   6120
actgtggctt cttactgtat tattccagag tacgatgcct atttggacat ggttgacgga   6180
gcttcatgct gcttagacac tgccagtttt tgccctgcaa agctgcgcag ctttccaaag   6240
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
aaagtgactc caggaacaaa acatactgaa gaacggccca aggtacaggt gatccaggct   6660
gccgatccgc tagcaacagc gtatctgtgc ggaatccacc gagagctggt taggagatta   6720
aatgcggtcc tgcttccgaa cattcataca ctgtttgata tgtcggctga agactttgac   6780
gctattatag ccgagcactt ccagcctggg gattgtgttc tggaaactga catcgcgtcg   6840
tttgataaaa gtgaggacga cgccatggct ctgaccgcgt taatgattct ggaagactta   6900
ggtgtggacg cagagctgtt gacgctgatt gaggcggctt tcggcgaaat ttcatcaata   6960
catttgccca ctaaaactaa atttaaattc ggagccatga tgaaatctgg aatgttcctc   7020
acactgtttg tgaacacagt cattaacatt gtaatcgcaa gcagagtgtt gagagaacgg   7080
ctaaccggat caccatgtgc agcattcatt ggagatgaca atatcgtgaa aggagtcaaa   7140
tcggacaaat taatggcaga caggtgcgcc acctggttga atatggaagt caagattata   7200
gatgctgtgg tgggcgagaa agcgccttat ttctgtggag ggtttatttt gtgtgactcc   7260
gtgaccggca cagcgtgccg tgtggcagac cccctaaaaa ggctgtttaa gcttggcaaa   7320
cctctggcag cagacgatga acatgatgat gacaggagaga gggcattgca tgaagagtca   7380
acacgctgga accgagtggg tattctttca gagctgtgca aggcagtaga atcaaggtat   7440
gaaaccgtag gaacttccat catagttatg gccatgacta ctctagctag cagtgttaaa   7500
tcattcagct acctgagagg ggcccctata actctacg gctaacctga atggactacg   7560
actatcacgc ccaaacattt acagccgcgg tgtcaaaaac cgcgtggacg tggttaacat   7620
ccctgctggg aggatcagcc gtaattatta taattggctt ggtgctggct actattgtgg   7680
ccatgtacgt gctgaccaac cagaaacata attgaataca gcacaattg gcaagctgct   7740
tacatagaac tcgcggcgat tggcatgccg ccttaaaatt tttattttat ttttctttc   7800
ttttccgaat cggattttgt ttttaatatt tcaaaaaaaa aaaaaaaaaa aaaaaaaaaa   7860
aaaaaaaaaa aaaaaaaaaa aaaaaaaaaa aaaaaaaaaa aaaaaaaaaa aatacgtagt   7920
ttaaac                                                              7926
```

```
SEQ ID NO: 10           moltype = DNA  length = 36519
FEATURE                 Location/Qualifiers
misc_feature            1..36519
                        note = Description of Artificial Sequence: Synthetic
                        polynucleotide
source                  1..36519
                        mol_type = other DNA
                        organism = synthetic construct
SEQUENCE: 10
ccatcttcaa taatatacct caaactttt gtgcgcgtta atatgcaaat gaggcgtttg   60
aatttgggga ggaagggcgg tgattggtcg agggatgagc gaccgttagg ggcggggcga   120
gtgacgtttt tgatgacgtgg ttgcgaggag gagccagttt gcaagttctc gtgggaaaag   180
tgacgtcaaa cgaggtgtgg tttgaacacg gaaatactca attttcccgc gctctctgac   240
aggaaatgag gtgtttctgg gcggatgcaa gtgaaaacgg gccattttcg cgcgaaaact   300
```

-continued

```
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gccccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc atacccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
accccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tcttttttgac gctcttaact   1800
tgggccatca gtctcacttt aaccagagga tttcgagagc ccttgatttt actactcctg   1860
gcagaaccac tgcagcagta gccttttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctgaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctgggt caggtcggtg tgaggggctg   2760
cagtttttca gccaactgga tggggtcgt gggcaggacc aagagtatgc tgtccgtgaa   2820
gaaatgcttg tttgagaggt gccacctggg ggtgatgagc gagggcgaag ccagaatccg   2880
ccactcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca gccctggcc   3060
cgagttcgag cacaatgtca tgaccaggtg caatatgcat ctgggggtcc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggaggaagc atgccaggtt   3300
ccagcccgtg tgtgtggatg tgacggagga cctgcgacc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggagggta ttcagcctt atctgacggg   3540
gcgtctcccc tcctgggcgg gagtgcgtca gaatgtgatg ggatccacgg tggacggccg   3600
gcccgtgcag cccgcgaact cttcaacct gacctatgca accctgagct cttcgtcgtt   3660
ggacgcagct gccgccgcag ctgctgcatc tgccgccagc gccgtgcgcg gaatggccat   3720
gggcgccggc tactacggca ctctggtggc caactcgagt tccaccaata tcccgccag   3780
cctgaacgag gagaagctgt tgctgctgat ggcccagctc gaggccttga cccagccgct   3840
gggcgagctc acccagcagt tggctcagct gcaggagcag acgcgggccg cggttgccac   3900
ggtgaaatcc aaataaaaaa tgaatcaata aataaacgga gacggttgtt gattttaaca   3960
cagagtctga atctttattt gattttttcgc gcgcggtagg ccctggacca ccggtctcga   4020
tcattggagca cccggtggat ctttttccagg acccggtaga ggtgggcttg gatgttgagg   4080
tacatgggca tgagcccgtc ccgggggtgg aggtagctcc attgcaggcc ctcgtgctcg   4140
ggggtggtgt tgtaaatcac ccagtcatag caggggcgca gggcatggtg ttgcacaata   4200
tctttggagga ggagactgat ggccacgggc agccctttgg tgtaggtgtt tacaaatctg   4260
ttgagctggg agggatgcat gcgggggggag atgaggtgca tcttgcctg gatcttgaga   4320
ttggcgatgt taccgcccag atcccgcctg gggttcatgt tgtgcaggac caccagcacg   4380
gtgtatccgg tgcacttggg gaatttatca tgcaacttgg aagggaaggc gtgaaagaat   4440
ttggcgacgc ctttgtgccc gcccaggttt ccatgcact catccatgat gatggcgatg   4500
ggcccgtggg cggcggcctg ggcaaagacg tttcggggggt cggacacatc atagttgtgg   4560
tcctgggtga ggtcatcata ggccatttta atgaatttgg ggcggagggt gccggactgg   4620
gggacaaagg tacctcgat cccggggggcg tagttccct cacagatctg catctcccag   4680
gctttgagct cggaggggggg gatcatgtcc acctgcgggt cgataaagaa cacggttttcc   4740
ggggcggggg agatgagctg ggccgaaagc aagttccgga gcagctggga cttgccgcag   4800
ccggtgggc cgtagatgac cccgatgacc ggctgcaggt ggtagttgag ggagagacag   4860
ctgccgtcct cccggaggag gggggccacc tcgttcatca tctcgcgcac gtgcatgttc   4920
tcgcgcacca gttccgccag gaggcgctct cccccaggg ataggagctc ctggagcgag   4980
gcgaagtttt tcagcggctt gagtccgtcg gccatgggca tttttggagag ggtttgttgc   5040
```

-continued

```
aagagttcca ggcggtccca gagctcggtg atgtgctcta cggcatctcg atccagcaga  5100
cctcctcgtt tcgcgggttg ggacggctgc gggagtaggg caccagacga tgggcgtcca  5160
gcgcagccag ggtccggtcc ttccagggtc gcagcgtccg cgtcagggtg gtctccgtca  5220
cggtgaaggg gtgcgcgccg ggctgggcgc ttgcgagggt gcgcttcagg ctcatccggc  5280
tggtcgaaaa ccgctcccga tcggcgccct gcgcgtcggc caggtagcaa ttgaccatga  5340
gttcgtagtt gagcgcctcg gccgcgtggc ctttggcgcg gagcttacct ttggaagtct  5400
gcccgcaggc gggacagagg agggacttga gggcgtagag cttgggggcg aggaagacgg  5460
actcgggggc gtaggcgtcc gcgccgcagt gggcgcagac ggtctcgcac tccacgagcc  5520
aggtgaggtc gggctggtcg gggtcaaaaa ccagtttccc gccgttcttt ttgatgcgtgt  5580
tcttaccttt ggtctccatg agctcgtgtc cccgctgggt gacaaagagg ctgtccgtgt  5640
ccccgtagac cgactttatg ggccggtcct cgagcggtgt gccgcggtcc tcctcgtaga  5700
ggaaccccgc ccactccgag acgaaagccc gggtccaggc cagcacgaag gaggccacgt  5760
gggacgggta gcggtcgttg tccaccagcg ggtccacctt ttccagggta tgcaaacaca  5820
tgtccccctc gtccacatcc aggaaggtga ttggcttgta agtgtaggcc acgtgaccgg  5880
gggtcccggc cgggggggta taaaagggtg cgggtccctg ctcgtcctca ctgtcttccg  5940
gatcgctgtc caggagcgcc agctgttggg gtaggtattc cctctcgaag gcgggcatga  6000
cctcggcact caggttgtca gtttctagaa acgaggagga tttgatattg acggtgccgg  6060
cggagatgcc tttcaagagc ccctcgtcca tctggtcaga aaagacgatc tttttgttgt  6120
cgagcttggt ggcgaaggag ccgtagaggg cgttggagag gagcttggcg atggagcgca  6180
tggtctggtt ttttttccttg tcggcgcgct ccttggcggc gatgttgagc tgcacgtact  6240
cgcgcgccac gcacttccat tcggggaaga cggtggtcag ctcgtcgggc acgattctga  6300
cctgccagcc ccgattatgc agggtgatga ggtccacact ggtggccacc tcgccgcgca  6360
ggggctcatt agtccagcag aggcgtccgc ccttgcgcga gcagaagggg ggcaggggt  6420
ccagcatgac ctcgtcgggg gggtcggcat cgatggtgaa gatgccgggc aggaggtcgg  6480
ggtcaaagta gctgatggaa gtggccagat cgtccagggc agcttgccat tcgcgcacg  6540
ccagcgcgcg ctcgtaggga ctgaggggcg tgccccaggc catgggatgg gtaagcgagg  6600
aggcgtacat gccgcagatg tcgtagacgt agaggggctc ctcgaggatg ccgatgtagg  6660
tggggtagca gcgcccccg cggatgctgg cgcgcacgta gtcatacagc tcgtgcgagg  6720
gggcgaggag ccccgggccc aggttggtgc gactgggctt ttcggcgcgg tagacgatct  6780
ggcggaaaat ggcatgcgag ttggaggaga tggtgggcct ttggaagatg ttgaagtgga  6840
cgtggggcag tccgaccgag tcgcggatga agtgggcgta ggagtcttgc agcttggcga  6900
cgagctcggc ggtgactagg acgtccagag cgcagtagtc gagggtctcc tggatgatgt  6960
catacttgag ctgtcccttt tgtttccaca gctcgcggtt gagaaggaac tcttcgcggt  7020
ccttccagta ctcttcgagg gggaacccgt cctgatctgc acggtaagag cctagcatgt  7080
agaactggtt gacggccttg taggcgcagc agccctctc cacgggaggg gcgtaggcct  7140
gggcggcctt gcgcagggag gtgtgcgtga gggcgaaagt gtccctgacc atgaccttga  7200
ggaactggtg cttgaagtcg atatcgtcgc agcccccctg ctcccagagc tggaagtccg  7260
tgcgcttctt gtaggcgggg ttgggcaaag cgaaagtaac atcgttgaag aggatcttgc  7320
ccgcgcgggg cataaagttg cgagtgatgc ggaaaggttg gggcacctcg gcccggttgt  7380
tgatgacctg ggcggcgagc acgatctcgt cgaagccgtt gatgttgtgg cccacgatgt  7440
agagttccac gaatcgcgga cggccccttga cgtggggcag tttcttgagc tcctcgtagg  7500
tgagctcgtc gggggtcgctg agcccgtgct gctcgagcgc ccagtcggcg agatgggggt  7560
tggcgcggag gaaggaagtc cagagatcca cggccaggcc ggtttgcaga cggtcccggt  7620
actgacggaa ctgctgcccg acggccattt tttcggggggt gacgcagtag aaggtgcggg  7680
ggtccccgtg ccagcgatcc catttgagct ggagggcgag atcgagggcg agctcgacga  7740
gccggtcgtc cccggagagt ttcatgacca gcatgaaggg gacgagctgc ttgccgaagg  7800
accccatcca ggtgtaggtt tccacatcgt aggtgaggaa gagcctttcg gtgcgaggat  7860
gcgagccgat ggggaagaac tggatctcct gccaccaatt ggaggaatgg ctgttgatgt  7920
gatggaagta gaaatgccga cggcgcgccg aacactcgtg cttgtgttta tacaagcggc  7980
cacagtgctc gcaacgctgc acgggatgca cgtgctgcac gagctgtacc tgagttcctt  8040
tgacgaggaa tttcagtggg aagtggagtc gtggcgccg catctcgtgc tgtactacgt  8100
cgtggtggtc ggcctggccc tcttctgcct cgatggtggt catgctgacg agcccgcgcg  8160
ggaggcaggt ccagacctcg gcgcgagcgg gtcggagagc gaggacgagg gcgcgcaggc  8220
cggagctgtc cagggtcctg agacgctgcg gagtcaggtc agtgggcagc ggcggcgcgc  8280
ggttgacttg caggagtttt tccagggcgc gcgggaggtc cagatggtac ttgatctcca  8340
ccgcgccatt ggtggcgacg tcgatggctt gcagggtccc gtgccctgg ggtgtgacca  8400
ccgtcccccg tttcttcttg ggcggtctgg gcgacggggg cggtgcctct tccatggtta  8460
gaagcggcg cgaggacgcg cgccgggcgg caggggcggc tcggggcccg gaggcagggg  8520
cggcaggggc acgtcggcgc cgcgcgcggg taggttctgg tactgcgcccc ggagaagact  8580
ggcgtgagcg acgacgcgac ggttgacgtc ctggatctga cgcctctggg tgaaggccac  8640
gggacccgtg agtttgaacc tgaaagagag ttcgacagaa tcaatctcgg tatcgttgac  8700
ggcggcctgc cgcaggatct cttgcacgtc gcccgagttg tcctggtagg cgatctcggt  8760
catgaactgc tcgatctcct cctcttgaag gtctccgcgg ccggcgcgct ccacggtggc  8820
cgcgaggtcg ttggagatgc ggcccatgag ctgcgagaag gcgttcatgc cgcctcgtt  8880
ccagacgcgg ctgtagacca cgacgccctc gggatcgcgg gcgcgcatga ccacctgggc  8940
gaggttgagc tccacgtggc gcgtgaagac cgcgtagttg cagaggcgct ggtagaggta  9000
gttgagcgtg gtggcgatgt gctcggtgac gaagaaatac atgatccagc ggcggagcgg  9060
catctcgctg acgtcgccca gcgcctccaa acgttccatg gcctcgtaaa agtccacggc  9120
gaagttgaaa aactgggagt tgcgcgccga gacggtcaac tcctcctcca gaagacggat  9180
gagctcggcg atggtggcgc gcacctcgcg ctcgaaggcc cccgggagtt cctccacttc  9240
ctcttcttcc tcctccacta acatctcttc tacttcctcc tcaggcggca gtggtggcgg  9300
gggaggggggc ctgcgtcgcc ggcggcgcac gggcagacgg tcgatgaagc gctcgatggt  9360
ctcgccgcgc cggcgtcgca tggtctcggt gacgcgcgc ccgtcctcgc ggggccgcag  9420
cgtgaagacg ccgccgcgca tctccaggtg gccgggggtg gcaggggagg ggcgctgacg  9480
ggcgctgacg atgcatctta tcaattgccc cgtagggact ccgcgcaagg acctgagcgt  9540
ctcgagatcc acgggatctg aaaaccgctg aacgaaggct tcgagccagt cgcagtcgca  9600
aggtaggctg agcacggttt cttctggcgg gtcatgttgg ttgggagcgg ggcggcgat  9660
gctgctggtg atgaagttga aataggcggt tctgagacgg cggatggtgg cgaggagcac  9720
caggtctttg ggcccggctt gctggatgcg cagacggtcg gccatgcccc aggcgtggtc  9780
```

```
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgt   10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagaccccca tagccagccg acttctccag ttacggagcg agccctctt   10800
ttgtttttgtt tgttttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcaa  11340
cctgatcgcg cgcgaggagg tgaccctggg cctgatgcac ctgtgggacc tgctgaggc   11400
catcgtgcag aaccccacca gcaagccgct gacggcgcag ctgttcctgg tggtgcagca  11460
tagtcgggac aacgaagcgt tcaggaggc gctgctgaat atcaccgagc ccgagggccg   11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagcgagcg accaggagct   11820
gatgcatagt ctgcagcggg ccctgaccgg ggccggacc gaggggaga gctactttga   11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccgggggcca ggaggactac accaacttca tcagcgccct gcgcctgatg  12540
gtgaccgagg tgcccagag cgaggtgtac cagtccgggc gactacttt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gacgtgcag   12840
gagcagacct accaggagat cacccacgtg agccgcgcc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggaggggc cacccccagc gccgcgctcg acatgacccg gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggtctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggccg tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact ccccaataa cgggatagaa  13560
agcctggtgg acaagatgag ccgctggaag acgtatgcgc aggagcacag cgacgatccc  13620
cgggcgtcgc aggggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggaggct cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcg ccagctgaaa accatcatgc acaccaacat gcccaacgtg aacgagttca  14280
tgtacagcaa caagttcaag gcgcgggtga tggtctcccg caagacccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
```

-continued

```
agttcgacac taggaacttc aggctgggct gggaccccgt gaccgagctg gtcatgcccg   14580
gggtgtacac caacgaggct ttccatcccg atattgtctt gctgcccggc tgcggggtgg   14640
acttcaccga gagccgcctc agcaacctgc tgggcattcg caagaggcag cccttccagg   14700
aaggcttcca gatcatgtac gaggatctgg aggggggcaa catccccgcg ctcctggatg   14760
tcgacgccta tgagaaaagc aaggaggatg cagcagctga agcaactgca gccgtagcta   14820
ccgcctctac cgaggtcagg ggcgataatt ttgcaagcgc cgcagcagtg gcagcggccg   14880
aggcggctga aaccgaaagt aagatagtca ttcagccggt ggagaaggat agcaagaaca   14940
ggagctacaa cgtactaccg gacaagataa acaccgccta ccgcagctgg tacctagcct   15000
acaactatgg cgaccccgag aagggcgtgc gctcctggac gctgctcacc acctcggacg   15060
tcacctgcgg cgtggagcaa gtctactggt cgctgcccga catgatgcaa gacccggtca   15120
ccttccgctc cacgcgtcaa gttagcaact acccggtggt gggcgccgag ctcctgcccg   15180
tctactccaa gagcttcttc aacgagcagg ccgtctactc gcagcagctg cgcgccttca   15240
cctcgcttac gcacgtcttc aaccgcttcc ccgagaacca gatcctcgtc cgcccgcccg   15300
cgcccaccat taccaccgtc agtgaaaacg ttcctgctct cacagatcac gggaccctgc   15360
cgctgcgcag cagtatccgg ggagtccagc gcgtgaccgt tactgacgcc agacgccgca   15420
cctgccccta cgtctacaag gccctgggca tagtcgcgcc gcgcgtcctc tcgagccgca   15480
ccttctaaat gtccattctc atctcgccca gtaataacac cggttggggc ctgcgcgcgc   15540
ccagcaagat gtacggaggc gctcgccaac gctccacgca acaccccgtg cgcgtgcccg   15600
ggcacttccg cgctccctgg ggcgccctca agggccgcgt gcggtcgcgc accaccgtcg   15660
acgacgtgat cgaccaggtg gtggccgacg cgcgcaacta cacccccgcc gccgcgcccg   15720
tctccaccgt ggacgccgtc atcgacagcg tggtggccga cgcgcgccgg tacgcccgcg   15780
ccaagagccg gcggcggcgc atcgcccggc ggcaccggag caccccgcc atgcgcgcg    15840
cgcgagcctt gctgcgcagg gccaggcgca cgggacgcag ggccatgctc agggcggcca   15900
gacgcgcggc ttcaggcgcc agcgccggca ggacccggag acgcgcggcc acggcggcgg   15960
cagcggccat cgccagcatg tcccgcccgc ggcgagggaa cgtgtactgg gtgcgcgacg   16020
ccgccaccgg tgtgccgctg cccgtgcgca cccgcccccc tcgcacttga agatgttcac   16080
ttcgcgatgt tgatgtgtcc cagcggcgag gaggatgtcc aagcgcaaat tcaaggaaga   16140
gatgctccag gtcatcgcgc ctgagatcta cggccctgcg gtggtgaagg aggaaagaaa   16200
gccccgcaaa atcaagcggg tcaaaaagga caaaaaggaa gaagaaagtg atgtggacgg   16260
attggtggag tttgtgcgcg agttcgcccc ccggcggcgc gtgcagtggc gcgggcggaa   16320
ggtgcaaccg gtgctgagac ccggcaccac cgtggtcttc acgcccggcg agcgctccgg   16380
caccgcttcc aagcgctcct acgacgaggt gtacggggat gatgatattc tggagcaggc   16440
ggccgagcgc ctgggcgagt ttgcttacgg caagcgcagc cgttccgcac cgaaggaaga   16500
ggcggtgtcc atcccgctgg accacggcaa ccccacgccg agcctcaagc ccgtgacctt   16560
gcagcaggtg ctgccgaccg cggcgccgcg ccgggggttc aagcgcgagg gcgaggatct   16620
gtacccacc atgcagctga tggtgcccaa gcgccagaag ctggaagacg tgctggagac    16680
catgaaggtg gacccggacg tgcagcccga ggtcaaggtg cggcccatca agcaggtggc   16740
cccgggcctg ggcgtgcaga ccgtggacat caagattccc acggagccca tggaaacgca   16800
gaccgagccc atgatcaagc ccagcaccag caccatggag gtgcagacgg atccctggat   16860
gccatcggct cctagtcgaa gaccccggcg caagtacggc gcggccagcc tgctgatgcc   16920
caactacgcg ctgcatcctt ccatcatccc cacgccgggc taccgcggca cgcgcttcta   16980
ccgcggtcat accagcagcc gccgccgcaa gaccaccact cgccgccgcc gtcgccgcac   17040
cgccgctgca accacccctg ccgccctggt gcggagagtg taccgccgcg gccgcgcac    17100
tctgaccctg ccgcgcgcgc gctaccaccc gagcatcgcc atttaaactt tcgcctgctt   17160
tgcagatcaa tggccctcac atgccgcctt cgcgttccca ttacgggcta ccgaggaaga   17220
aaaccgcgcc gtagaaggct ggcggggaac gggatgcgtc gccaccacca ccggcggcgg   17280
cgcgccatca gcaagcggtt ggggggaggc ttcctgcccg cgctgatccc catcatcgcc   17340
gcggcgatcg gggcgatccc cggcattgct tccgtggcgg tgcaggcctc tcagcgccac   17400
tgagacacac ttggaaacat cttgtaataa accaatggac tctgacgctc ctggtcctgt   17460
gatgtgtttt cgtagacaga tggaagacat caattttcg tccctggctc cgcgacacgg   17520
cacgcggccg ttcatgggca cctggagcga catcggcacc agcaactga acggggggcg   17580
cttcaattgg agcagtctct ggagcgggct taagaatttc gggtccacgc ttaaaaccta   17640
tggcagcaag gcgtggaaca gcaccacagg gcaggcgctg agggataagc tgaaagagca   17700
gaacttccag cagaaggtgg tcgatgggct cgcctcgggc atcaacgggg tggtggacct   17760
ggccaaccag gccgtgcagc ggcagatcaa cagccgcctg gacccggtgc cgcccgccgg   17820
ctccgtggag atgccgcagg tggaggagga gctgcctccc ctggacaagc ggggcgagaa   17880
gcgaccccgc cccgatgcgg aggagacgct gctgacgcac acggacgagc cgcccccgta   17940
cgaggaggcg gtgaaactgg gtctgcccac cacgcggccc atcgcgcccc tggccaccgg   18000
ggtgctgaaa cccgaaaagc ccgcgaccct ggacttgcct cctccccagc cttcccgccc   18060
ctctacagtg gctaagcccc tgccgccggt ggccgtgacg cgcgccgcgac ccgggggcac  18120
cgccgcgcct catgcgaact ggcagagcac tctgaacagc atcgtgggtc tgggagtgca   18180
gagtgtgaag cgccgcgct gctattaaac ctaccgtagc gcttaacttg cttgtctgtg   18240
tgtgtatgta ttatgtcgcc gccgccgctg tccaccagaa ggaggagtga agaggcgcgt   18300
cgccgagttg caagatgccc accccatcga tgctgcccca tgtgggcgtac atgcacatcg   18360
ccggacagga cgcttcggag tacctgagtc cgggtctggt gcagtttgcc cgcgccacag   18420
acacctactt cagtctgggg aacaagttta ggaaccccac ggtggcgccc acgcacgatg   18480
tgaccaccga ccgcagccag cggctgacgc tgcgcttcgt gcccgtggac cgcgaggaca   18540
acacctactc gtacaaagtg cgctacacgc tggccgtggg cgacaaccagc gtgctggaca   18600
tggccagcac ctactttgac atccgcgcg tgctggatcg gggccctagc ttcaaaccct   18660
actccggcac cgcctacaac agtctggccc ccaaggagc acccaacact tgtcagtgga   18720
catataaagc cgatggtgaa actgccacag aaaaaaccta tacatatgga aatgcacccg   18780
tgcagggcat taacatcaca aaagatggta ttcaacttgg aactgacacc gatgatcagc   18840
caatctacgc agataaaacc tatcagcctg aacctcaagt gggtgatgct gaatggcatg   18900
acatcactgg tactgatgag aagtatggag gcagagctct taagcctgat accaaaatga   18960
agcccttgtta tggttctttt gccaagccta ctaataaaga aggaggtcag gcaaatgtga   19020
aaacaggaac aggcactact aaagaatatg acatagacat ggctttctt gacaacagaa    19080
gtgcggctgc tgctggccta gctccagaaa ttgtttgta tactgaaaat gtggatttgg    19140
aaactccaga tacccatatt gtatacaaag caggcacaga tgacagcagc tcttctatta   19200
atttgggtca gcaagccatg cccaacagac ctaactacat tggtttcaga gacaactta    19260
```

-continued

```
tcgggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga acccggtatt tcagtatgtg gaatcaggcg gtggacagct  19440
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctacg  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat gctcctgggc aacgggcgct  19920
acgtgccctt ccacatccag gtgccccaga aatttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcgcgctg gtccttcacg cgtctcaaga ccaaggagac gccctcgctg ggctccgggt  20340
tcgacccccta cttcgtctac tcgggctcca tccccctacct cgacggcacc ttctacctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtgcaacatg accaaggact ggttcctggt ccagatgctg gcccactaca  20580
acatcggcta ccaggcttc tacgtgcccg agggctacaa ggaccgcatg tactccttct  20640
tccgcaactt ccagcccatg agccgccagg tggtggacga ggtcaactac aaggactacc  20700
aggccgtcac cctggcctac cagcacaaca actcgggctt cgtcggctac ctcgcgccca  20760
ccatgcgcca gggccagccc tacccgccca actacccca cccgctcatc ggcaagagcg  20820
ccgtcaccag cgtcacccag aaaaagttcc tctgcgacag ggtcatgtgg cgcatccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggtcg gccttcgcct ggaaccggcg ctcgaacacc tgctacctct tcgaccccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccg gccttcgcct ggaaccggcg ctcgaacacc tgctacctct tcgaccccctt  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggaccgacgt tctgcgcgcg ggagttgcag tacacggggt tgcagcactg  22080
gaacaccatc agggccgggt gcttcacgct cgccagcacc gtcgcgtcgg tgatgctctc  22140
cacgtcgagg tcctcggccgt tggccatccc gaaggggggtc atcttgcagg tctgccttcc  22200
catggtgggc acgcacccgg gcttgtggtt gcaatcgcag tgcagggggga tcagcatcat  22260
ctggcctggg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcaccgcg gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacaccct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctcg ctgacgtcct gcaggaccac  23100
atgcttggtc ttgcggggtt tcttcttggg cggcagcggc ggcggagatg ttggagatgc  23160
cgaggggggag cgcgagttct cgctcaccac tactatctct tcctcttctt ggtccgaggc  23220
cacgcggcgg taggtatgtc tcttcggggg cagaggcgga ggcgacgggc tctcgcccgc  23280
gcgacttggc ggatggctgg cagagccccct tccgcgttcg ggggtgcgct ccgcgcggcg  23340
ctctgactga cttcctccgc ggccggccat tgtgttcctc tagggaggaa caacaagcat  23400
ggagactcag ccatcgccaa cctcgccatc tgccccccacc gccgacgaga agcagcagca  23460
gcagaatgaa agcttaaccg ccccgccgcc cagcccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tgggctcgga catgacgggc actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg caccctgcga  23880
gcccaacccg cgcctcaact tctacccggt cttcgccggtg cccgaggccc tggccaccta  23940
ccacatcttt ttcaagaacc aaaagatccc cgtctcctgc cgcgccaacc gcaccccgcgc  24000
```

```
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgcgg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca aggggggtct  25260
gaaactcacc ccggggctgt ggacctcggc ctacttgcgg aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttcccc aggatgcccc gaggaaacaa gagctgaaa gtggagccgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cggggggcaac atctccttca cccggcgcta cctgctcttc caccgcgggg  25980
tgaactttcc ccgcaacatc ttgcattact accgtcacct ccacagcccc tactacttcg  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agcccagat gggcctggcc gccggtgccg cccaggacta  26520
ctccaccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccg cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct ccccgggtca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgaggcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccggac ctatcagtgc gtctcgggac  27720
cctgccatca caccttccac ctgatcccga ataccacagc gtcgctcccc gctactaaca  27780
accaaactaa cctccaccaa cgccaccgtc gcgaccttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgctgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatacttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgcatcgt gtgcctgagc attcacatgc tcatcgctat  28500
tcgccccaga aataatgccg aaaaagaaa acagccataa cgttttttt cacacctttt  28560
tcagaccatg gcctctgtta aattttgct tttatttgcc agtctcattg ccgtcattca  28620
tggaatgagt aatgagaaaa ttactatta cactggcact aatcacacat tgaaaggtcc  28680
agaaaaagcc acagaagttt catggtattg ttattttaat gaatcagatg tatctactga  28740
```

-continued

```
actctgtgga aacaataaca aaaaaaatga gagcattact ctcatcaagt ttcaatgtgg   28800
atctgactta accctaatta acatcactag agactatgta ggtatgtatt atggaactac   28860
agcaggcatt tcggacatgg aattttatca agtttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agctggaaca   29160
cttactaagt gttgaatttt aattttttag aaccatgaag atcctaggcc ttttaatttt   29220
ttctatcatt acctctgctc tatgcaattc tgacaatgag gacgttactg tcgttgtcgg   29280
atcaaattat acactgaaag gtccagcgaa gggtatgctt tcgtggtatt gctattttgg   29340
atctgacact acagaaactg aattatgcaa tcttaagaat ggcaaaattc aaaattctaa   29400
aattaacaat tatatatgca atggtactga tctgatactc ctcaatatca cgaaatcata   29460
tgctggcagt tacacctgcc ctggagatga tgctgacagt atgatttttt acaaagtaac   29520
tgttgttgat cccactactc cacctccacc caccacaact actcacacca cacacacaga   29580
tcaaaccgca gcagaggagg cagcaaagtt agccttgcag gtccaagaca gttcatttgt   29640
tggcattacc cctacacctg atcagcggtg tccggggctg ctagtcagcg gcattgtcgg   29700
tgtgctttcg ggattagcag tcataatcat ctgcatgttc attttttgctt gctgctatag   29760
aaggctttac cgacaaaaat cagacccact gctgaacctc tatgtttaat tttttccaga   29820
gtcatgaagg cagttagcgc tctagttttt tgttctttga ttggcattgt tttttgcaat   29880
cctattccta aagttagctt tattaaagat gtgaatgtta ctgagggggg caatgtgaca   29940
ctggtaggtg tagagggtgc tgaaaacacc acctggacaa aataccacct caatgggtgg   30000
aaagatattt gcaattggag tgtattagtt tatacatgtg agggagttaa tcttaccatt   30060
gtcaatgcca cctcagctca aaatggtaga attcaaggac aaagtgtcag tgtatctaat   30120
gggtatttta cccaacatac ttttatctat gacgttaaag tcataccact gcctacgcct   30180
agcccaccta gcactaccac acagacaacc cacactacac agacaaccac atacagtaca   30240
ttaaatcagc ctaccaccac tacagcagca gaggttgcca gctcgtctgg ggtccgagtg   30300
gcatttttga tgttggcccc atctagcagt cccactgcta gtaccaatga gcagactact   30360
gaatttttgt ccactgtcga gagccacacc acagctacct ccagtgcctt ctctagcacc   30420
gccaatctct cctcgctttc ctctacacca atcagtcccg ctactactcc tagccccgct   30480
cctcttccca ctcccctgaa gcaaacagac ggcggcatgc aatggcagat caccctgctc   30540
attgtgatcg ggttggtcat cctggccgtg ttgctctact acatcttctg ccgccgcatt   30600
cccaacgcgc accgcaagcc ggtctacaag cccatcattg tcgggcagcc ggagccgctt   30660
caggtggaag ggggtctaag gaatcttctc ttctcttta cagtatggtg attgaactat   30720
gattcctaga caattcttga tcactattct tatctgcctc ctccaagtct gtgccaccct   30780
cgctctggtg gccaacgcca gtccagactg tattgggccc ttcgctcct acgtgctctt   30840
tgccttcacc acctgcatct gctgctgtag catagtctgc ctgcttatca ccttcttcca   30900
gttcattgac tggatctttg tgcgcatcgc ctacctgcgc caccacccc agtaccgcga   30960
ccagcgagtg gcgcggctgc tcaggctcct ctgataagca tgcgggctct gctacttctc   31020
gcgcttctgc tgttagtgct cccccgtccc gtcgaccccc ggtcccccac ccagtcccca   31080
gaggaggtcc gcaaatgcaa attccaagaa ccctggaaat tcctcaaatg ctaccgccaa   31140
aaatcagaca tgcatcccag ctggatcatg atcattggga tcgtgaacat tctggcctgc   31200
accctcatct cctttgtgat ttaccccctgc tttgactttg gttggaactc gccagaggcg   31260
ctctatctcc cgcctgaacc tgacacacca ccacagcaac ctcaggcaca cgcactacca   31320
ccactacagc ctaggccaca atacatgccc atattagact atgaggccga gccacagcga   31380
cccatgctcc ccgctattag ttacttcaat ctaaccggcg gagatgactg acccactggc   31440
caacaacaac gtcaacgacc ttctcctgga catggacggc cgcgcctcgg agcagcgact   31500
cgcccaactt cgcattcgcc agcagcagga gagagccgtc aaggagctgc aggatgcggt   31560
ggccatccac cagtgcaaga gaggcatctt ctgcctggtg aaacaggcca agatctccta   31620
cgaggtcact ccaaacgacc atcgcctctc ctacgagctc ctgcagcagc gccagaagtt   31680
cacctgcctg gtcggagtca accccatcgt catcacccag cagtctggcg ataccaaggg   31740
gtgcatccac tgctcctgcg actcccccga ctgcgtccac actctgatca agacccctgtc   31800
cggcctccgc gacctcctcc ccatgaacta atcacccct tatccagtga aataaagatc   31860
atattgatga tgattttaca gaaataaaaa ataatcattt gatttgaaat aaagatacaa   31920
tcatattgat gatttgagtt aacaaaaaa ataaagaatc acttacttga aatctgatac   31980
caggtctctg tccatgtttt ctgccaacac cacttcactc ccctcttccc agctctggta   32040
ctgcaggccc cggcgggctg caaacttcct ccacacgctg aaggggatgt caaattcctc   32100
ctgtccctca atcttcattt tatcttctat cagatgtcca aaaagcgcgt ccgggtggat   32160
gatgacttcg accccgtcta cccctacgat gcagacaacg caccgaccgt gcccttcatc   32220
aaccccccct tcgtctcttc agatggattc caagagaagc ccctgggggt gttgtccctg   32280
cgactggccg accccgtcac caccaagaac ggggaaatca ccctcaagct gggagaggggg   32340
gtggacctcg attcctcggg aaaactcatc tccaacacgg ccaccaaggc cgcgcccct   32400
ctcagtttt ccaacaacac catttcctt aacatggatc accctttta cactaaagat   32460
ggaaaattat ccttacaagt ttctccacca ttaaatatac tgagaacaag cattctaaac   32520
acactagctt taggttttgg atcaggttta ggactccgtg gctctgcctt ggcagtacag   32580
ttagtctctc cacttacatt tgatactgat ggaaacataa agcttacctt agacagaggt   32640
ttgcatgtta caacaggaga tgcaattgaa agcaacataa gctgggctaa aggtttaaaa   32700
tttgaagatg gagccatagc aaccaacatt ggaaatgggt tagagtttgg aagcagtagt   32760
acagaaacag gtgttgatga tgcttaccca atccaagtta aacttggatc tggccttagc   32820
tttgacagta caggagccat aatggctggt aacaaagaag acgataaact cactttgtgg   32880
acaacacctg atccatcacc aaactgtcaa atactcgcag aaaatgatgc aaaactaaca   32940
ctttgcttga ctaaatgtgg tagtcaaata ctggccactg tgtcagtctt agttgtagga   33000
agtggaaacc taaaccccat tactggcacc gtaagcagtc tcaggtgtt tctacgtttt   33060
gatgcaaacg tgtgttcttt aacagaacat tctcactaa aaaaatactg ggggtatagg   33120
cagggaacag gcatagatgg cactccatat accagttcat ggattcat gcccaattta   33180
aaagcttatc caaagtcaca aagttctact actaaaaata atatagtagg gcaagtatac   33240
atgaatggag atgtttcaaa acctatgctt ctcactataa ccctcaatgg tactgatgac   33300
agcaacagta catattcaat gtcatttcca tacacctgga ctaatggaag ctatgttgga   33360
gcaacatttg gggctaactc ttataccttc tcatacatcg cccaagaatg aacactgtat   33420
cccacccgc atgccaaccc ttcccacccc actctgtgga acaaactctg aaacacaaa   33480
```

```
taaaataaag ttcaagtgtt ttattgattc aacagtttta caggattcga gcagttattt  33540
ttcctccacc ctcccaggac atggaataca ccaccctctc ccccgcaca gccttgaaca   33600
tctgaatgcc attggtgatg gacatgcttt tggtctccac gttccacaca gtttcagagc   33660
gagccagtct cgggtcggtc agggagatga aaccctccgg gcactccgc atctgcacct    33720
cacagctcaa cagctgagga ttgtcctcgg tggtcgggat cacggttatc tggaagaagc   33780
agaagagcgg cggtgggaat catagtccgc gaacgggatc ggccggtggt gtcgcatcag   33840
gccccgcagc agtcgctgcc gccgccgctc cgtcaagctg ctgctcaggg ggtccgggtc   33900
cagggactcc ctcagcatga tgcccacggc cctcagcatc agtcgtctgg tgcggcgggc   33960
gcagcagcgc atgcggatct cgctcaggtc gctgcagtac gtgcaacaca gaaccaccag   34020
gttgttcaac agtccatagt tcaacacgct ccagccgaaa ctcatcgcgg gaaggatgct   34080
acccacgtgg ccgtcgtacc agatcctcag gtaaatcaag tggtgccccc tccagaacac   34140
gctgcccacg tacatgatct ccttgggcat gtggcggttc accacctccc ggtaccacat   34200
caccctctgg ttgaacatgc agccccggat gatcctgcgg aaccacaggg ccagcaccgc   34260
cccgcccgcc atgcagcgaa gagacccgg gtcccggcaa tggcaatgga ggacccaccg    34320
ctcgtacccg tggatcatct gggagctgaa caagtctatg ttggcacagc acaggcatat   34380
gctcatgcat ctcttcagca ctctcaactc ctcgggggtc aaaaccatat cccagggcac   34440
ggggaactct tgcaggacag cgaaccccgc agaacagggc aatcctcgca cagaacttac   34500
attgtgcatg gacagggtat cgcaatcagg cagcaccggg tgatcctcca ccagagaagc   34560
gcgggtctcg gtctcctcac agcgtggtaa gggggccggc cgatacgggt gatggcggga   34620
cgcggctgat cgtgttcgcg accgtgtcat gatgcagttg ctttcggaca ttttcgtact   34680
tgctgtagca gaacctggtc cgggcgctgc acaccgatcg ccggcggcgg tctcggcgct   34740
tggaacgctc ggtgttgaaa ttgtaaaaca gccactctct cagaccgtgc agcagatcta   34800
gggcctcagg agtgatgaag atcccatcat gcctgatggc tctgatcaca tcgaccaccg   34860
tggaatgggc cagacccagc cagatgatgc aattttgttg ggtttcggtg acggcggggg   34920
agggaagaac aggaagaacc atgattaact tttaatccaa acggtctcgg agtacttcaa   34980
aatgaagatc gcggagatgg cacctctcgc ccccgctgtg ttggtggaaa ataacagca    35040
ggtcaaaggt gatacggttc tcgagatgtt ccacggtggc ttccagcaaa gcctccacgc   35100
gcacatccag aaacaagaca atagcgaaag cgggagggtt ctctaattcc tcaatcatca   35160
tgttacactc ctgcaccatc cccagataat tttcattttt ccagccttga atgattcgaa   35220
ctagttcctg aggtaaatcc aagccagcca tgataaagag ctcgcgcaga gcgccctcca   35280
ccggcattct taagcacacc ctcataattc caagatattc tgctcctggt tcacctgcag   35340
cagattgaca agcggaatat caaaatctct gccgcgatcc ctgagctcct ccctcagcaa   35400
taactgtaag tactctttca tatcctctcc gaaattttta gccataggac caccaggaat   35460
aagattaggg caagccacag tacagataaa ccgaagtcct ccccagtgag cattgccaaa   35520
tgcaagactg ctataagcat gctggctaga cccggtgata tcttccagat aactggacag   35580
aaaatcgccc aggcaatttt taagaaaatc aacaaaagaa aaatcctcca ggtggacgtt   35640
tagagcctcg ggaacaacga tgaagtaaat gcaagcggtg cgttccagca tggttagtta   35700
gctgatctgt agaaaaaaca aaaatgaaca ttaaaccatg ctagcctggc gaacaggtgg   35760
gtaaatcgtt ctctccagca ccaggcaggc cacggggtct ccggcgcgac cctcgtaaaa   35820
attgtcgcta tgattgaaaa ccatcacaga gagacgttcc cggtggcggg cgtgaatgat   35880
tcgacaagat gaatacaccc ccggaacatt ggcgtccgcg agtgaaaaaa agcgcccgag   35940
gaagcaataa ggcactacaa tgctcagtct caagtccagc aaagcgatgc catgcggatg   36000
aagcacaaaa ttctcaggtg cgtacaaaat gtaattactc ccctcctgca caggcagcaa   36060
agcccccgat ccctccaggt acacatacaa agcctcagcg tccatagctt accgagcagc   36120
agcacacaac aggcgcaaga gtcagagaaa ggctgagctc taacctgtcc acccgctctc   36180
tgctcaatat atagcccaga tctacactga cgtaaaggcc aaagtctaaa aatacccgcc   36240
aaataatcac acacgcccag cacacgccca gaaaccgggtg acacactcaa aaaaatacgc   36300
gcacttcctc aaacgcccaa aactgccgtc atttccgggt tcccacgcta cgtcatcaaa   36360
acacgacttt caaattccgt cgaccgttaa aaacgtcacc cgccccgccc ctaacggtcg   36420
cccgtctctc agccaatcag cgccccgcat ccccaaattc aaacacctca tttgcatatt   36480
aacgcgcaca aaaagtttga ggtatattat tgatgatgg                          36519
```

SEQ ID NO: 11          moltype = DNA   length = 31867
FEATURE                Location/Qualifiers
misc_feature           1..31867
                       note = Description of Artificial Sequence: Synthetic
                       polynucleotide
source                 1..31867
                       mol_type = other DNA
                       organism = synthetic construct
SEQUENCE: 11

```
ccatcttcaa taatatacct caaacttttt gtgcgcgtta atatgcaaat gaggcgtttg   60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag   180
tgacgtcaaa cgaggtgtgg tttgaacacg gaaatactca attttcccgc gctctctgac   240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cgtgtcaaa gtccggtgtt tttacgtagg tgtcagctga tcgccagggt    480
atttaaacct gcgctctcca gtcaagaggc cactcttgag tgccagcgag aagagttttc   540
tcctccgcgc cgcgagtcag atctacactt tgaaagtagg gataacaggg taatgacatt   600
gattattgac tagttgttaa tagtaatcaa ttacggggtc attagttcat agcccatata   660
tggagttccg cgttacataa cttacggtaa atggcccgc tggctgaccg cccaacgacc    720
cccgcccatt gacgtcaata atgacgtatg ttcccatagt aacgccaata gggactttcc   780
attgacgtca atgggtggag tatttacggt aaactgccca cttggcagta catcaagtgt   840
atcatatgcc aagtccgccc cctattgacg tcaatgacgg taaatggccc gcctggcatt   900
atgcccagta catgacctta cgggactttc ctacttggca gtacatctac gtattagtca   960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
```

-continued

```
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
tgagcaaggc cgaggagctg ttcaccgggg tggtgcccat cctggtcgag ctggacggcg   1320
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgaggggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg ggggaggacc tgcatgaggg ccagaataac tgaaatctgt gcttttctgt   2340
gtgttgcagc agcatgagcg gaagcggctc ctttgagggg gggattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
tctcgatcat tgagcacccg gtggatcttt tccaggaccc ggtagaggtg ggcttggatg   2940
ttgaggtaca tgggcatgag cccgtcccgg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acggcgaggc ctttggtgta ggtgtttaca   3120
aatctgttga gctgggaggg atgcatgcgg ggggagatga ggtgcatctt ggcctggatc   3180
ttgagattgg cgatgttacc gcccagatcc cgcctgggt tcatgttgtg caggaccacc   3240
agcacggtgt atccggtgca cttggggaat ttatcatgca acttggaagg gaaggcgtga   3300
aagaatttgg cgacgccttt gtgcccgccc aggttttcca tgcactcatc catgatgatg   3360
gcgatggggc cgtgggcggc ggcctggca aagacgtttc ggggtcgga cacatcatag   3420
ttgtggtcct gggtgaggtc atcataggcc attttaatga atttggggcg gagggtgccg   3480
gactggggga caaaggtacc ctcgatcccg ggggcgtagt tccctcaca gatctgcatc   3540
tcccaggctt tgagctcgga ggggggatc atgtccacct gcggggcgat aaagaacacg   3600
gtttccgggg cggggagat gagctggcc gaaagcaagt tccggagcag ctgggacttg   3660
ccgcagccgg tggggccgta gatgacccg atgaccggct gcaggtggta gttgaggag   3720
agacagctgc cgtcctcccg gaggaggggg gccacctcgt tcatcatctc gcgcacgtgc   3780
atgttctcgc gcaccagttc cgccaggagg cgctctcccc ccaggatag gagctcctgg   3840
agcgaggcga agttttttcag cggcttgagt ccgtcgggca tgggcatttt ggagaggggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagcgc agccagggtc cggtccttcc agggtcgcag cgtccgcgtc agggtggtct   4080
ccgtcacggt gaaggggtgc gcgccgggtc gggcgcttgc gagggtgcgc ttcaggctcg   4140
tccggctggt cgaaaaccgc tcccgatcgg cgcctgcgc gtcggccagg tagcaattga   4200
ccatgagttc gtagttgagc gcctcggccg cgtggccttt ggcgcggagc ttaccttgg   4260
aagtctgccc gcaggcggga cagaggaggg acttgagggc gtagagcttg ggggcgagga   4320
agacggactc ggggcgtag gcgtccgcgc cgcagtgggc gcagacggtc tcgcactcca   4380
cgagccaggt gaggtcgggc tggtcggggt caaaaaccag tttcccgccg ttctttttga   4440
tgcgtttctt accttttggtc tccatgagct cgtgtccccg ctgggtgaca aagaggctgt   4500
ccgtgtcccc gtagaccgac tttatgggcc ggtcctcgag cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc caccttttcc agggtatgca   4680
aacacatgtc cccctcgtcc acatccagga aggtgattgg cttgtaagtg taggccacgt   4740
gaccgggggt cccggccggg ggggtataaa agggtgcggg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattcacgg   4920
tgccggcgga gatgcctttc aagagcccct cgtccatctg gtcagaaaag acgatctttt   4980
tgttgtcgag cttggtggcg aaggagccgg agagggcgtt ggagaggagc ttggcgatgg   5040
agcgcatggt ctgttttttt tccttgtcgg cgcgctcctt ggcggcgatg ttgagctgca   5100
cgtactcgcg cgccacgcac ttccattcgg ggaagacggt ggtcagctcg tcgggcacga   5160
ttctgacctg ccagcccga ttatgcaggg tgatgaggtc cacactggtg gccacctcgc   5220
cgcgcagggg ctcattagtc cagcagaggc gtccgccctt gcgcgagcag aaggggggca   5280
gggggtccag catgacctcg tcgggggggt cggcatcgat ggtgaagatg ccgggcagga   5340
ggtcggggtc aaagtagctg atggaagtgg ccagatcgtc cagggcagct tgccattcgc   5400
gcacggccag cgcgctctcg tagggactga ggggcgtgcc ccaggcatg ggatgggtaa   5460
gcgcggaggc gtacatgccg cagatgtcgt agacgtagag ggtcctcg aggatgccga   5520
tgtaggtggg gtagcagcgc cccccgcgga tgctggcgcg cacgtagtca tacagctcgt   5580
gcgaggggc gaggagcccc gggcccaggt tggtgcgact gggctttccg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
```

```
tgatgtcata cttgagctgt cccttttgtt tccacagctc gcggttgaga aggaactctt   5880
cgcggtcctt ccagtactct tcgaggggga acccgtcctg atctgcacgg taagagccta   5940
gcatgtagaa ctggttgacg gccttgtagg cgcagcagcc cttctccacg gggagggcgt   6000
aggcctgggc ggccttgcgc agggaggtgt gcgtgagggc gaaagtgtcc ctgaccatga   6060
ccttgaggaa ctggtgcttg aagtcgatat cgtcgcagcc cccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg gggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccattttttc gggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg gggcggctgg ggcccggagg   7380
caggggcggc aggggcacgt cggcgccgcg cgcgggtagg ttctggtact gcgcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgaag ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcgggggga gggggcctgc gtcgccggcg gcgcacgggc agacggtcga tgaagcgctc   8220
gatggtctcg ccgcgccggc gtcgcatggt ctcggtgacg gcgcgccgt cctcgcgggg   8280
ccgcagcgtg aagacgccgc cgcgcatctc caggtggccg ggggggtccc cgttgggcag   8340
ggagagggcg ctgacgatga atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggca ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagcca atgaggaagt gcggcggcgg ctggcggtag agcggccatc gctcggtggc   9060
ggggcgcgcg ggcgcgaggt cctcgagcat ggtgcggtag tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cgggcaaaaa cgaaagcggt cagcggctcg actccgtggc   9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa ctttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggacgccgat   9660
cctcttttgt tttgtttgtt tttgccagat gcatcccgta ctgcggcaga tgcgcccca   9720
ccaccctcca ccgcaacaac agcccctcc acagccggcg cttctgcccc cgccccagca   9780
gcaacttcca gccacgaccg ccgcggccgc cgtgagcggg gctggacaga gttatgatca   9840
ccagctggcc ttggaagagg gcgaggggct ggcgcgcctg ggggcgtcgt cgcgggagcg   9900
gcacccgccc gtgcagatga aaagggacgc tcgcgagcgc tacgtgccca agcagaacct   9960
gttcagagac aggagcggcg aggagcccga ggagatgcgc gcggcccggt tccacgcggg   10020
gcgggagctg cggcgcggcc tggaccgaaa gagggtgctg agggacgagg atttcgaggc   10080
ggacgagctg acggggatca gccccgcgcg cgcgcacgtg gccgcggcca acctggtcac   10140
ggcgtacgag cagaccgtga aggaggagag caacttccaa aaatccttca acaaccacgt   10200
gcgcacccctg atcgcgcgcg atgaggtgac cctgggcgcg atgcacctgt gggacctgct   10260
ggaggccatc gtgcagaacc ccaccagcaa gccgctgacg gcgcagctgt cctggtggt   10320
gcagcatagt cgggacaacg aagcgttcag ggaggcgctg ctgaatatca ccgagcccga   10380
gggccgctgg ctcctggacc tggtgaacat tctgcagagc atcgtggtgc aggagcgcgg   10440
gctgccgctg tccgagaagc tggcggccat caacttctcg gtgctgagtt tgggcaagta   10500
ctacgctagg aagatctaca agaccccgta cgtgcccata gacaaggagg tgaagatcga   10560
```

-continued

```
cgggttttac atgcgcatga ccctgaaagt gctgaccctg agcgacgatc tgggggtgta    10620
ccgcaacgac aggatgcacc gtgcggtgag cgccagcagg cggcgcgagc tgagcgacca    10680
ggagctgatg catagtctgc agcgggccct gaccgggggcc gggaccgagg gggagagcta    10740
ctttgacatg ggcgcggacc tgcactggca gcccagccgc cgggccttgg aggcggcggc    10800
aggaccctac gtagaagagg tggacgatga ggtggacgag gagggcgagt acctggaaga    10860
ctgatggcgc gaccgtattt ttgctagatg caacaacaac agccacctcc tgatcccgcg    10920
atgcgggcgg cgctgcagag ccagccgtcc ggcattaact cctcggacga ttggacccag    10980
gccatgcaac gcatcatggc gctgacgacc cgcaaccccg aagcctttag acagcagccc    11040
caggccaacc ggctctcggc catcctggag gccgtggtgc cctcgcgctc caacccccag    11100
cacgagaagg tcctggccat cgtgaacgcg ctggtggaga acaaggccat ccgcggcgac    11160
gaggccggcc tggtgtacaa cgcgctgctg gagcgcgtgg cccgctacaa cagcaccaac    11220
gtgcagacca acctggaccg catggtgacc gacgtgcgcg aggccgtggc ccagcgcgag    11280
cggttccacc gcgagtccaa cctgggatcc atggtggcgc tgaacgcctt cctcagcacc    11340
cagcccgcca acgtgccccg gggccaggag gactacacca acttcatcag cgccctgccgc    11400
ctgatggtga ccgaggtgcc ccagagcgag gtgtaccagt ccgggccgga ctacttcttc    11460
cagaccagtc gccagggctt gcagaccgtg aacctgagcc aggctttcaa gaacttgcag    11520
ggcctgtggg gcgtgcaggc cccggtcggg gaccgcgcga cggtgtcgag cctgctgacg    11580
ccgaactcgc gcctgctgct gctgctggtg gcccccttca cggacagcgg cagcatcaac    11640
cgcaactcgt acctgggcta cctgattaac ctgtaccgcg aggccatcgg ccaggcgcac    11700
gtggacgagc agacctacca ggagatcacc cacgtgagcc gcgccctggg ccaggacgac    11760
ccgggcaacc tggaagccac cctgaacttt ttgctgacca accggtcgca gaagatcccg    11820
ccccagtacg cgctcagcac cgaggaggag cgcatcctgc gttacgtgca gcagagcgtg    11880
ggcctgttcc tgatgcagga ggggggccacc cccagcgccg cgctcgacat gaccgcgcgc    11940
aacatggagc ccagcatgta cgccagcaac cgcccgttca tcaataaaact gatggactac    12000
ttgcatcggg cggccgccat gaactctgac tatttcacca acgccatcct gaatcccac     12060
tggctcccgc cgccggggtt ctacacgggc gagtacgaca tgcccgaccc caatgacggg    12120
ttcctgtggg acgatgtgga cagcagcgtg ttctccccccc gaccgggtgc taacgagcgc    12180
cccttgtgga agaaggaagg cagcgaccga cgccgtcct cggcgctgtc cggccgcgag     12240
ggtgctgccg cggcggtgcc cgaggccgcc agtcctttcc cgagcttgcc cttctcgctg    12300
aacagtatcc gcagcagcga gctgggacag atcacgcgcc gcgcttgct gggcgaagag     12360
gagtacttga atgactcgct gttgagaccc gagcgggaga agaacttccc caataacggg    12420
atagaaagcc tggtggacaa gatgagccgc tggaagacgt atgcgcagga gcacagggac    12480
gatccccggg cgtcgcaggg ggccacgagc cggggcagcg ccgcccgtaa acgccggtgg    12540
cacgacaggc agcgggggaca gatgtgggac gatgaggact ccgccgacga cagcagcgtg    12600
ttggacttgg gtgggagtgg taacccgttc gctcacctgc gccccgtat cgggcgcatg     12660
atgtaagaga aaccgaaaat aaatgatact caccaaggcc atggcgacca gcgtgcgttc    12720
gtttcttctc tgttgttgtt gtatctagta tgatgaggcg tgcgtacccg gagggtcctc    12780
ctccctcgta cgagagcgtg atgcagcagg cgatggcggc ggcggcgatg cagccccgc     12840
tggaggctcc ttacgtgccc ccgcggtacc tggcgcctac ggagggggcg aacagcattc    12900
gttactcgga gctggcaccc ttgtacgata ccacccggtt gtacctggtg gacaacaagt    12960
cggcggacat cgcctcgctg aactaccaga acgaccacag caacttcctg accaccgtgg    13020
tgcagaacaa tgacttcacc cccacggagg ccagcacccca gaccatcaac tttgacgagc    13080
gctcgccggtg gggcggccag ctgaaaacca tcatgcacc caacatgccc aacgtgaacg    13140
agttcatgta cagcaacaag ttcaaggcgc gggtgatggt ctcccgcaag accccccaatg    13200
gggtgacagt gacagaggat tatgatggta gtcaggatga gctgaagtat gaatgggtgg    13260
aatttgagct gcccgaaggc aacttctcgg tgaccatgac catcgacctg atgaacaacg    13320
ccatcatcga caattacttg gcggtggggc ggcagaacgg ggtgctggag agcgacatcg    13380
gcgtgaagtt cgacactagg aacttcaggc tgggctggga ccccgtgacc gagctggtca    13440
tgcccggggt gtacaccaac gaggctttcc atcccgatat tgtcttgctg cccggctgcg    13500
gggtggactt caccgagagc cgcctcagca acctgctggg cattcgcaag aggcagccct    13560
tccaggaagg cttccagatc atgtacgagg atctggaagg gggcaacatc cccgcgctcc     13620
tggatgtcga cgcctatgag aaaagcaagg aggatgcagc agctgaagca actgcagccg    13680
tagctaccgc ctctaccgag gtcaggggcg ataattttgc aagcgccgca gcagtggcag    13740
cggccgaggc ggctgaaacc gaaagtaaga tagtcattca gccggtggag aaggatagca    13800
agaacaggag ctacaacgta ctaccggaca agataaacac cgcctaccgc agctggtacc    13860
tagcctacaa ctatggcgac cccgagaagg gcgtgcgctc ctggacgctg ctcaccacct    13920
cggacgtcac ctgcggcgtg gagcaagtct actggtcgct gcccgacatg atgcaagacc    13980
cggtcacctt ccgctccacg cgtcaagtta gcaactaccc ggtggtgggc gccgagctcc    14040
tgcccgtcta ctccaagagc ttcttcaacg agcaggccgt ctactcgcag cagtcgacgg    14100
ccttcacctc gcttacgcac gtcttcaacc gcttccccga gaaccagatc ctcgtccgcc    14160
cgcccgcgcc caccattacc accgtcagtg aaaacgttcc tgctctcaca gatcacggga    14220
ccctgccgct gcgcagcagt atccggggag tccagcgcgt gaccgttact gacgccagac    14280
gccgcacctg ccccctacgtc tacaaggccc tgggcatagt cgcgccgcgc gtcctctcga    14340
gccgcacctt ctaaatgtcc attctcatct cgcccagtaa taacaccggt tggggcctgc    14400
gcgcgcccag caagatgtac ggaggcgctc gccaacgctc cacgcaacac cccgtcgcgcg    14460
tgcgcgggca cttccgcgct ccctgggggcg ccctcaaggg ccgcgtgcgg tcgcgcacca    14520
ccgtcgacga cgtgatcgac caggtggtgg ccgacgcgcg caactacacc cccgccgccg    14580
cgcccgtctc caccgtggac gccgtcatcg acagcgtggt ggcgacgcg cgccggtacg     14640
cccgcgccaa gagccggcgg cggcatcg cccggcgca ggagcaatcc cccgccatgc    14700
gcgcggcgcg agccttgctg cgcagggcca ggcgcacggg acgcagggcc atgctcaggg    14760
cggccagacg cgcggcttca ggcgccagcg ccggcaggac ccggagacgc gcggccacgg    14820
cggcggcagc ggccatcgcc agcatgtccc gcccgcggcg agggaacgtg tactgggtgc    14880
gcgacgcgc caccggtgtg cgcgtgcccg tgcgcacccg cccccctcgc acttgaagat    14940
gttcacttcg cgatgttgat gtgtcccagc ggcgaggagg atgtccaagc gcaaattcaa    15000
ggaagagatg ctccaggtca tcgcgcctga gatctacgac cctgcggtgg tgaaggagga    15060
aagaaagccc cgcaaaatca agcgggtcaa aaaggacaaa aaggaagaag aaagtgatgt    15120
ggacggattg gtggagtttg tgcgcgagtt cgccccccgg cggcgcgtgc agtggcgcgg    15180
gcggaaggtg caaccggtgc tgagacccgg caccaccgtg gtcttcacgc ccggcgagcg    15240
ctccggcacc gcttccaagc gctcctacga cgaggtgtac ggggatgatg atattctgga    15300
```

-continued

```
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc ggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat ttttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc acggggtggt  16620
ggacctggcc aaccaggccg tgcagccggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccaccg  17340
acgatgtgac caccgaccgc agccagcggc tgacgctgcg cttcgtgccc gtggaccgga  17400
aggacaacac ctactcgtac aaaagtgcgct cacacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct ttctttgaca  17940
acagaagtgc ggctgctgct ggcctagctc cagaaattgt tttgtatact gaaaatgtgg  18000
atttggaaac tccagatacc catattgtat acaaagcagg cacagatgac agcagctctt  18060
ctattaattt gggtcagcaa gccatgccca acagacctaa ctacattggt ttcagagaca  18120
actttatcgg gctcatgtac tacaacagca ctggcaatat gggggtgctg gccggtcagg  18180
cttctcagct gaatgctgtg gttgacttgc aagacagaaa caccgagctg tcctaccagc  18240
tcttgcttga ctctctgggt gacagaaccc ggtatttcag tatgtggaat caggcggtgg  18300
acagctatga tcctgatgtg cgcattattg aaaatgcagt tgtggaggat gaacttccca  18360
actattgttt ccctctggat gctgttggca gaacagatac ttatcaggga attaaggcta  18420
atggaactga tcaaaccaca tggaccaaag atgcagtgt caatgatgct aatgagatag  18480
gcaagggtaa tccattcgcc atggaaatca acatccaagc caacctgtgg aggaacttcc  18540
tctacgacaa cgtggccctg tacctgcccg actcttacaa gtacacgcg gccaatgtta  18600
ccctgcccac caacaccaac acctacgatt acatgaacgg ccgggtggtg gcgccctcgc  18660
tggtggactc ctacatcaac atcggggcgc gctggtcgct ggatcccatg gacaacgtga  18720
acccttcaa ccaccaccgc aatgcggggc tgcgctaccg ctccatgctc ctgggcaacg  18780
ggcgctacgt gcccttccac atccaggtgc cccagaaatt tttcgccatc aagagagctcc  18840
tgctcctgcc cgggtcctac acctacgagt ggaacttccg caaggacgtc aacatgatcc  18900
tgcagagctc cctcggcaac gacctgcgca cggacgggc ctccatctcc ttcaccagca  18960
tcaacctcta cgccaccttc ttccccatgg cgcacaacac ggcctccacg ctcgaggcca  19020
tgctgcgcaa cgacaccaac gaccagtcct tcaacgacta cctctcggcg gccaacatgc  19080
tctaccccat cccggccaac gccaccaacg tgcccatctc catcccctcg cgcaactgga  19140
ccgccttccg cggctggtcc ttcacgcgtc tcaagaccaa gggagacgcc tcgctgggct  19200
ccgggttcga ccctacttc gtctactcgg gctccatccc ctacctcgac ggcaccttct  19260
acctcaacca caccttcaag aaggtctcca tcaccttcga ctcctccgtc agctggcccg  19320
gcaacgaccg gctcctgacg cccaacgagt tcgaaatcaa gcgcaccgtc gacggcgagg  19380
gctacaacgt ggcccagtgc aacatgacca aggactggtt cctggtccag atgctggcc  19440
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcacccctg cctaccagc acaacaactc gggcttcgtc ggctacctcg  19620
cgcccaccat gcgccagggc cagccctacc ccgccaacta cccctacccg ctcatcggca  19680
agagcgccat caccagcgtc acccagaaaa agttcctctg cgacaggggtc atgtggcgca  19740
tcccccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccaccccttct ctatgttgtc ttcgaagtct tcgacgtcgt ccgagtgcac cagcccacc  19920
gcggcgtcat cgaggccgtc tacctgcgca ccccccttctc ggccggtaac gccaccacct  19980
aagctcttgc ttcttgcaag ccatggccgc gggctccggc gagcaggagc tcagggccat  20040
```

-continued

```
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
cccccttcggg ttctcggacg agcgcctcaa gcagatctac cagttcgagt acgagggcct  20280
gctgcgccgc agcgccctgg ccaccgagga ccgctgcgtc accctggaaa agtccaccca  20340
gaccgtgcag ggtccgcgct cggccgcctg cgggctcttc tgctgcatgt tcctgcacgc  20400
cttcgtgcac tggcccgacc gccccatgga caagaacccc accatgaact tgctgacggg  20460
ggtgcccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg caggggcgcc agcaggtgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag ggggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
ttgcctgaac gcctgctggg ccttggctcc ctcggtgaag aagaccccgc aggacttgct  21240
agagaactgg ttggtggcgc acccggcgtc gtgcacgcag cagcgcgcgt cgttgttggc  21300
cagctgcacc acgctgcgcc cccagcgctt ctgggtgatc ttggccccgg tcggggttctc  21360
cttcagcgcg cgctgccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca taccctctc ccaggccgag acgatgggca ggctcatagg  21780
gttcttcacc atcatcttag cgctagcagc cgcggccagg gggtcgctct cgtccagggt  21840
ctcaaagctc cgcttgccgt ccttctcggg gatccgcacc gggggggtagc tgaagcccac  21900
ggccgccagc tcctcctcgg cctgtcttc gtcctcgctg tcctggctga cgtcctgcag  21960
gaccacatgc ttggtcttgc ggggtttctt cttgggcggc agcggcggcg gagatgttgg  22020
agatggcgag ggggagcgcg agttctcgct caccactact atctcttcct cttcttggtc  22080
cgaggccacg cggcggtagg tatgtctctt cggggggcaga ggcggaggcg acgggctctc  22140
gccgccgcga cttggcggat ggctggcaga gccccttccg cgttcggggg tgcgctcccg  22200
gcggcgctct gactgacttc ctccgcgcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
cgtcccagac atgcaagaga tggaggaatc catcgagatt gacctgggct atgtgacgcc  22440
cgcggagcac gaggaggagc tggcagtgcg ctttttcacaa gaagagatac accaagaaca  22500
gccagagcag gaagcagaga atgagcagag tcaggctggg ctcgagcatg acggcgacta  22560
cctccacctg agcggggggg aggacgcgct catcaagcat catcaagcgc aggccaccat  22620
cgtcaaggat gcgctgctcg accgcaccga ggtgcccctc agcgtggagg agctcagccg  22680
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
cacctaccac atcttttca agaaccaaaa gatccccgtc tcctgccgcg caacccgcac  22860
ccgcgccgac gcccttttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgggg ctggcggtgc tcaaacgcac ggtcgagctg acccatttcg cctacccggc  23100
tctgaacctg cccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggccggt ggctgggtcc taatgctagt ccccagagtt tggaagagcg  23280
gcgcaaactc atgatggccg tggtcctggt gaccgtggac ctggagtgcc tgcgccgctt  23340
cttcgccgac gcggagaccc tgcgcaaggt cgaggagaac ctgcactacc tcttcaggca  23400
cggggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggccccg cgcgactaca tccgcgactg cgtctacctc tacctctgcc acacctggca  23580
gacgggcatg ggcgtgtggc agcagtgtct ggaggagcag aacctgaaag agctctgcaa  23640
gctcctgcag aagaacctca aggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc cgccacctgct ccgcgctgcc ctcggacttc gtgcgctgca cttcccggca  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caaccttctc acgccgcacc gctccctggc ctgcaacccc cagctgctga gcgagaccca  24060
gatcatcggc accttcgagt tgcaagggcc cagcgaaggc gagggtttca ccgccaaggg  24120
gggtctgaaa ctcacccgg gcgtgtggac ctcggcctac ttggcgcaagt tcgtgcccga  24180
ggactaccat ccccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aacccggct tccccaggga tgccccgagg aaacaagaag ctgaaagtgg  24420
agctgccgcc cgtggaggat ttggaggaag actgggaaac cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc ggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
```

```
cctgcttgca ggcctgcggg ggcaacatct ccttcacccg gcgctacctg ctcttccacc   24840
gcggggtgaa ctttccccgc aacatcttgc attactaccg tcacctccac agccccctact  24900
acttccaaga agaggcagca gcagcagaaa aagaccagca gaaaaccagc agctagaaaa   24960
tccacagcgg cggcagcagg tggactgagg atcgcggcga acgagccggc gcaaacccgg   25020
gagctgagga accggatctt tcccaccctc tatgccatct tccagcagag tcggggggcag 25080
gagcaggaac tgaaagtcaa gaaccgttct ctgcgctcgc tcacccgcag ttgtctgtat   25140
cacaagagcg aagaccaact tcagcgcact ctcgaggacg ccgaggctct cttcaacaag   25200
tactgcgcgc tcactcttaa agagtagccc gcgcccgccc agtcgcagaa aaaggcggga   25260
attacgtcac ctgtgccctt cgccctagcc gcctccaccc atcatcatga gcaaagagat   25320
tcccacgcct tacatgtgga gctaccagcc ccagatgggc ctggccgccg gtgccgccca   25380
ggactactcc acccgcatga attggctcag cgccgggccc gcgatgatct cacgggtgaa   25440
tgacatccgc gcccaccgaa accagatact cctagaacag tcagcgctca ccgccacgcc   25500
ccgcaatcac ctcaatccgc gtaattggcc cgccgccctg gtgtaccagg aaattcccca   25560
gcccacgacc gtactacttc cgcgagacgc ccaggccgaa gtccagctga ctaactcagg   25620
tgtccagctg gcgggcggcg ccaccctgtg tcgtcaccgc cccgctcagg gtataaagcg   25680
gctggtgatc cggggcagag gcacacagct caacgacgag gtggtgagct cttcgctggg   25740
tctgcgacct gacggagtct tccaactcgc cggatcgggg agatcttcct tcacgcctcg   25800
tcaggccgtc ctgactttgg agagttcgtc ctcgcagccc cgctcgggtg gcatcggcac   25860
tctccagttc gtgggaggagt tcactccctc ggtctacttc aacccctttct ccggctcccc   25920
cggccactac ccggacgagt tcatcccgaa cttcgacgcc atcagcgagt cggtggacgg   25980
ctacgattga atgtcccatg gtggcgcagc tgacctagct cggcttcgac acctggacca   26040
ctgccgcacg ttccgctgct tcgctcggga tctcgccgag tttgcctact ttgagctgac   26100
cgaggagcac cctcagggcc cggcccacgg agtgcggatc gtcgtcgaag ggggcctcga   26160
ctcccaccctg cttcggatct tcagccagcg tccgatcctg gtcgagcgcg agcaaggaca   26220
gacccttctg actctgtact gcatctgcaa ccaccccggc ctgcatgaaa gtctttgttg   26280
tctgctgtgt actgagtata ataaaaagctg agatcagcga ctactccgga cttccgtgtg   26340
ttcctgaatc catcaaccag tctttgttct tcaccgggaa cgagaccgag ctccagctcc   26400
agtgtaagcc ccacaagaag tacctcacct ggctgttcca gggctccccg atcgccgttg   26460
tcaaccactg cgacaacgac ggagtcctgc tgagcggccc tgccaacctt actttttcca   26520
cccgcagaag caagctccag ctcttccaac ccttcctccc cggacctat cagtgcgtct   26580
cgggaccctg ccatcacacc ttccacctga tcccgaatac cacagcgtcg ctccccgcta   26640
ctaacaacca aactaacctc caccaacgcc accgtcgcga cggccacaat acatgcccat   26700
attagactat gaggccgagc cacagcgacc catgctcccc gctattagtt acttcaatct   26760
aaccggcgga gatgactgac ccactggcca acaacaacgt caacgacctt ctcctggaca   26820
tggacggccg cgcctcggag cagcgactcg cccaacttcg cattcgccag cagcaggaga   26880
gagccgtcaa ggagctgcag gatgcggtgg ccatccacca gtgcaagaga ggcatcttct   26940
gcctggtgaa acaggccaag atctcctacg aggtcactcc aaacgaccat cgcctctcct   27000
acgagctcct gcagcagcgc cagaagttca cctgcctggt cggagtcaac cccatcgtca   27060
tcacccagca gtctggcgat accaaggggt gcatccactg ctcctgcgac tcccccgact   27120
gcgtccacac tctgatcaag accctctgcg gcctccgcga cctcctcccc atgaactaat   27180
cacccccctta tccagtgaaa taaagatcat attgatgatg atttacaga aataaaaaat    27240
aatcatttga tttgaaataa agatacaatc atattgatga tttgagttta acaaaaaaat   27300
aaagaatcac ttacttgaaa tctgatacca ggtctctgtc catgtttct gccaacacca    27360
cttcactccc ctcttccag ctctggtact gcaggcccccg gcgggctgca aacttcctcc   27420
acacgctgaa ggggatgtca aattcctcct gtccctcaat cttcatttta tcttctatca   27480
gatgtccaaa aagcgcgtcc gggtggatga tgacttcgac cccgtctacc cctacgatgc   27540
agacaacgca ccgaccgtgc ccttcatcaa cccccccttc gtctcttcag atggattcca   27600
agagaagccc ctgggggtgt tgtccctgcg actggccgac cccgtcacca ccaagaacgg   27660
ggaaatcacc ctcaagctgg gagaggggt ggacctcgat tcctcgggaa aactcatctc   27720
caacacggcc accaaggccg ccgcccctct cagttttttcc aacaacacca tttcccttaa   27780
catggatcac ccctttttaca ctaaagatgg aaaattatcc ttacaagttt ctccaccatt   27840
aaatatactg agaacaagca ttctaaacac actagcttta ggttttggat caggtttagg   27900
actccgtggc tctgccttgg cagtacagtt agtctctcca cttacatttg atactgatgg   27960
aaaacataaag cttaccttag acagaggttt gcatgttaca acaggagatg caattgaaag   28020
caacataagc tgggctaaag gtttaaaatt tgaagatgga gccatagcaa ccaacattgg   28080
aaatgggtta gagtttggaa gcagtagtac agaaacaggt gttgatgatg cttacccaat   28140
ccaagttaaa cttggatctg gccttagctt tgacagtaca ggagccataa tggctggtaa   28200
caaagaagac gataaactca ctttgtggac aacacctgat ccatcaccaa actgtcaaat   28260
actcgcagaa aatgatgcaa aactaacact ttgcttgact aaatgtggta gtcaaatact   28320
ggccactgtg tcagtcttag ttgtaggaag tggaaaccta aaccccatta ctggcaccgt   28380
aagcagtgct caggtgtttc tacgtttttga tgcaaacggt gttctttttaa cagaacattc   28440
tacactaaaa aaatactggg ggtataggca gggagatagc atagatggca ctccatatac   28500
caatgctgta ggattcatgc ccaatttaaa agcttatcca aagtcacaaa gttctactac   28560
taaaaataat atagtagggc aagtatacat gaatggaaac tatgttcaaaac ctatgcttct  28620
cactataacc ctcaatggta ctgatgacaa caacagtaca tattcaatgt catttttcata  28680
cacctggact aatggaaagct atgttggagc aacatttggg gctaactctt ataccttctc   28740
atacatcgcc caagaatgaa cactgtatcc caccctgcat gccaaccctt cccaccccac    28800
tctgtggaac aaactctgaa acacaaaata aaataaagtt caagtgtttt attgattcaa   28860
cagtttttaca ggattcgagc agttattttt cctccaccct cccaggacat ggaatacacc    28920
accctctccc cccgcacagc cttgaacatc tgaatgccat tggtgatgga catgctttttg   28980
gtctccacgt tccacacagt ttcagagcga gccagtctcg ggtcggtcag gggagatgaaa   29040
ccctccgggc actcccgcat ctgcacctca cagctcaaca gctgaggatt gtcctcggtg    29100
gtcgggatca cggttatctg gaagaagcag aagagcggcg gtgggaatca tagtccgcga   29160
acgggatcgg ccggtggtgt cgcatcaggc ccgcagcaag tcgctgccgc cgccgctccg   29220
tcaagctgct gctcaggggg tccgggtcca gggactccct cagcatgatg cccacgacgcc  29280
tcagcatcag tcgtctggtg cggcgggcgc agcagcgcat gcggatccg ctcaggtcgc     29340
tgcagtacgt gcaacacaga accaccaggt tgttcaacag tccatagttc aacacgctcc   29400
agccgaaact catcgcggga aggatgctac ccacgtggcc gtcgtaccag atcctcaggt   29460
aaatcaagtg gtgcccctc cagaacacgc tgcccacgta catgatctcc ttgggcatgt     29520
```

-continued

```
ggcggttcac cacctcccgg taccacatca ccctctggtt gaacatgcag ccccggatga   29580
tcctgcggaa ccacagggcc agcaccgccc cgcccgccat gcagcgaaga gaccccgggt   29640
cccggcaatg gcaatggagg acccaccgct cgtaccgtg gatcatctgg gagctgaaca   29700
agtctatgtt ggcacagcac aggcatatgc tcatgcatct cttcagcact ctcaactcct   29760
cggggtcaa aaccatatcc cagggcacgg ggaactcttg caggacagcg aaccccgcag   29820
aacagggcaa tcctcgcaca gaacttacat tgtgcatgga cagggtatcg caatcaggca   29880
gcaccgggtg atcctccacc agagaagcgc gggtctcggt ctcctcacag cgtggtaagg   29940
gggccggccg atacgggtga tggcgggacg cggctgatcg tgttcgcgac cgtgtcatga   30000
tgcagttgct ttcggacatt ttcgtacttg ctgtagcaga acctggtccg ggcgctgcac   30060
accgatcgcc ggcggcggtc tcggcgcttg gaacgctcgg tgttgaaatt gtaaaacagc   30120
cactctctca gaccgtgcag cagatctagg gcctcaggag tgatgaagat cccatcatgc   30180
ctgatggctc tgatcacatc gaccaccgtg gaatgggcca gacccagcca gatgatgcaa   30240
ttttgttggg tttcggtgac ggcgggggag ggaagaacag gaagaaccat gattaacttt   30300
taatccaaac ggtctcggag tacttcaaaa tgaagatcgc gggagatggca cctctcgccc   30360
ccgctgtgtt ggtggaaaat aacagccagg tcaaaggtga tacggttctc gagatgttcc   30420
acggtggctt ccagcaaagc ctccacgcgc acatccagaa acaagacaat agcgaaagcg   30480
ggaggggttct ctaattcctc aatcatcatg ttacactcct gcaccatccc cagataattt   30540
tcatttttcc agccttgaat gattcgaact agttcgtgag gtaaatccaa gccagccatg   30600
ataaagagct cgcgcagagc gccctccacc ggcattctta agcacaccct cataattcca   30660
agatattctg ctcctggttc acctgcagca gattgacaag cggaatatca aaatctctgc   30720
cgcgatccct gagctcctcc ctcagcaata actgtaagta ctctttcata tcctctccga   30780
aatttttagc cataggacca ccaggaataa gattaggcga agcacagta cagatcaaacc  30840
gaagtcctcc ccagtgagca ttgccaaatg caagactgct ataagcatgc tggctagacc   30900
cggtgatatc ttccagataa ctggacagaa aatcgcccag gcaattttta agaaaatcaa   30960
caaaagaaaa atcctccagg tggacgttta gagcctcggg aacaacgatg aagtaaatgc   31020
aagcggtgcg ttccagcatg gttagttagc tgatctgtag aaaaaacaaa aatgaacatt   31080
aaaccatgct agcctggcga acaggtgggg aaatcgttct ctccagcacc aggcaggcca   31140
cggggtctcc ggcgcgaccc tcgtaaaaat tgtcgctatg attgaaaacc atcacagaga   31200
gacgttcccg gtgcggcg tgaatgattc gacaagatga atacaccccc ggaacattgg   31260
cgtccgcgag tgaaaaaaag cgcccgagga agcaataagg cactacaatg ctcagtctca   31320
agtccagcaa agcgatgcca tgcggatgaa gcacaaaatt ctcaggtgcg tacaaaatgt   31380
aattactccc ctcctgcaca ggcagcaaag ccccgatcc ctccaggtac acatacaaag   31440
cctcagcgtc catagcttac cgagcagcag cacacaacag gcgcaagagt cagagaaagg   31500
ctgagctcta acctgtccac ccgctctctg ctcaatatat agcccagatc tacactgacg   31560
taaaggccaa agtctaaaaa tacccgccaa ataatcacac acgcccagca cacgcccaga   31620
aaccggtgac acactcaaaa aaatacgcgc acttcctcaa acgcccaaaa ctgccgtcat   31680
ttccggggttc ccacgctacg tcatcaaaac acgactttca aattccgtcg accgttaaaa   31740
acgtcaccccg ccccgcccct aacggtcgcc cgtctctcag ccaatcagcg ccccgcatcc   31800
ccaaattcaa acacctcatt tgcatattaa cgcgcacaaa aagtttgagg tatattattg   31860
atgatgg                                                             31867
```

```
SEQ ID NO: 12          moltype = DNA  length = 32788
FEATURE                Location/Qualifiers
misc_feature           1..32788
                       note = Description of Artificial Sequence: Synthetic
                        polynucleotide
source                 1..32788
                       mol_type = other DNA
                       organism = synthetic construct
SEQUENCE: 12
ccatcttcaa taatatacct caaactttt gtgcgcgtta atatgcaaat gaggcgtttg   60
aatttgggga ggaagggcgg tgattggtcg agggatgagc gaccgttagg ggcgggcga   120
gtgacgtttt gatgacgtgg ttgcgaggag gagccagttt gcaagttctc gtgggaaaag   180
tgacgtcaaa cgaggtgtgg tttgaacacg gaaatactca attttcccgc gctctctgac   240
aggaaatgag gtgtttctgg gcggatgcaa gtgaaaacgg gccatttttcg cgcgaaaact   300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cggtgtcaaa gtccggtgtt tttacgtagg tgtcagctga tcgccagggt   480
atttaaacct gcgctctcca gtcaagaggc cactcttgag tgccagcgag aagagtttc   540
tcctccgcgc cgcgagtcag atctcacctt tgaaagtagg gataacaggg taatgacatt   600
gattattgac tagttgttaa tagtaatcaa ttacggggtc attagttcat agcccatata   660
tggagttccg cgttacataa cttacggtaa atggcccgcc tggctgaccg cccaacgacc   720
cccgcccatt gacgtcaata atgacgtatg ttcccatagt aacgccaata gggactttcc   780
attgacgtca atgggtggag tatttacggt aaactgccca cttggcagta catcaagtgt   840
atcatatgcc aagtccgccc cctattgacg tcaatgacgg taaatggccc gcctggcatt   900
atgcccagta catgacctta cgggactttc ctacttggca gtacatctac gtattagtca   960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgt tgacg caaatgggcg   1140
gtaggcgtgt acggtgggag gtctatataa gcagagctcg tttagtgaac cgtcagatcg   1200
cctgaacgc catccacgct gttttgacct ccatagaaga cagcgatcgc gccaccatgg   1260
ccgggatgtt ccaggcactg tccgaaggct gcacccta tgatattaac cagatgctga   1320
atgtcctggg agacaccag gtctctggcc tggagcagct ggagagcatc atcaacttcg   1380
agaagctgac cgagtgacaa agctccaatg tgatgcctat cctgtcccca ctgaccaagg   1440
gcatcctggg cttcgtgttt acctgacac tgccttctga gcggggcctg tcttgcatca   1500
gcgaggcaga cgcaaccaca ccagtccg ccaatctggg cgaggagatc ctgtctcagc   1560
tgtacctgtg gccccgggtg acatatcact ccccttctta cgcctatcac cagttcgagc   1620
ggagagccaa gtacaagaga cacttccag gctttgccca gtctctgctg ttcggctacc   1680
ccgtgtacgt gttcggcgat tgcgtgcagg gcgactggga tgccatccgg tttagatact   1740
```

-continued

```
gcgcaccacc tggatatgca ctgctgaggt gtaacgacac caattattcc gccctgctgg     1800
cagtgggcgc cctggagggc cctcgcaatc aggattggct gggcgtgcca aggcagctgg     1860
tgacacgcat gcaggccatc cagaacgcag gcctgtgcac cctggtggca atgctggagg     1920
agacaatctt ctggctgcag gcctttctga tggccctgac cgacagcggc cccaagacaa     1980
acatcatcgt ggattcccag tacgtgatgg gcatctccaa gccttctttc caggagtttg     2040
tggactggga gaacgtgagc ccagagctga attccaccga tcagccattc tggcaggcag     2100
gaatcctggc aaggaacctg gtgcctatgg tggccacagt gcaggccag aatctgaagt     2160
accagggcca gagcctggtc atcagcgcct ccatcatcgt gtttaacctg ctggagctgg     2220
agggcgacta tcgggacgat ggcaacgtgt gggtgcacac cccactgagc cccagaacac     2280
tgaacgcctg ggtgaaggcc gtggaggaga agaaggcat cccagtgcac ctggagctgg     2340
cctccatgac caatatggag ctgatgtcta gcatcgtgca ccagcaggtg aggacatacg     2400
gacccgtgtt catgtgcctg ggaggcctgc tgaccatggt ggcaggagcc gtgtggctga     2460
cagtgcgggt gctggagctg ttcagagccg cccagctggc caacgatgtg gtgctgcaga     2520
tcatggagct gtgcggagca gcctttcgcc aggtgtgcca caccacagtg ccatggccaa     2580
atgcctccct gaccccccaag tggaacaatg agacaacaca gcctcagatc gccaactgta     2640
gcgtgtacga cttcttcgtg tggctgcact actatagcgt gagggatacc ctgtggcccc     2700
gcgtgacata ccacatgaat aagtacgcct atcacatgct ggagaggcgc gccaagtata     2760
agagaggccc tggcccaggc gcaaagtttg tggcagcatg gaccctgaag gaccgccgcg     2820
gccccggccc cggccagtat atcaaggcta acagtaagtt cattggaatc acagagctgg     2880
gacccggacc tggataatga gtttaaactc ccatttaaat gtgagggtta atgcttcgag     2940
cagacatgat aagatacatt gatgagtttg gacaaaccac aactagaatg cagtgaaaaa     3000
aatgctttat ttgtgaaatt tgtgatgcta ttgctttatt tgtaaccatt ataagctgca     3060
ataaacaagt taacaacaac aattgcattc attttatgtt tcaggttcag ggggagatgt     3120
gggaggtttt ttaaagcaag taaaacctct acaaatgtgg taaataaact ataacggtcc     3180
taaggtagcg agtgagtagt gttctggggc ggggaggac ctgcatgagg gccagaataa     3240
ctgaaatctg tgcttttctg tgtgttgcag cagcatgagc ggaagcggct cctttgaggg     3300
aggggtattc agcccttatc tgacgggggcg tctcccctcc tgggcgggag tgcgtcagaa     3360
tgtgatggga tccacggtgg acggccggcc cgtgcagccc gcgaactctt caaccctgac     3420
ctatgcaacc ctgagctctt cgtcgttgga cgcagctgcc gccgcagctg ctgcatctgc     3480
cgccagcggc gtgcgcggaa tggccatggg cgccggctac tacggccactc tggtggccaa     3540
ctcgagttcc accaataatc ccgccagcct gaacgaggag aagctgttgc tgctgatggc     3600
ccagctcgag gccttgaccc agcgcctggg cgagctgacc cagcaggtgg ctcagctgca     3660
ggagcagacg cgggccgcgg ttgccacggt gaaatccaaa taaaaaatga atcaataaat     3720
aaacggagac ggttgttgat tttaacacag agtctgaatc tttatttgat ttttcgcgcg     3780
cggtaggccc tggaccaccg gtctcgatca ttgagcaccc ggtggatctt ttccaggacc     3840
cggtagaggt gggcttggat gttgaggtac atgggcatga gcccgtcccg ggggtggagg     3900
tagctccatt gcagggcctc gtgctcgggg gtggtgttgt aaatcaccca gtcatagcag     3960
gggcgcaggt catggtgttg cacaaatatct ttgaggagga gactgatggc cacgggcagc     4020
cctttggtgt aggtgtttac aaatctgttg agctgggagg gatgcatgcg ggggagatg     4080
aggtgcatct tggcctggat cttgagattg gcgatgttac cgcccagatc ccgcctgggg     4140
ttcatgttgt gcaggaccac cagcacgtg tatccggtgc acttgggaa tttatcatgc     4200
aacttggaag ggaaggcgtg aaagaatttg gcgacgcctt tgtgcccgcc caggtttttcc     4260
atgcactcat ccatgatgat ggcgatggc ccgtgggcgg cggcctggac aaagacgttt     4320
cggggggtcgg acacatcata gttgtggtcc tgggtgaggt catcataggc catttttaatg     4380
aatttgggggc ggaggtgcc ggactggggg acaaaggtac cctcgatccc gggggcgtag     4440
ttcccctcac agatctgcat ctcccaggct ttgagctcgg agggggggat catgtccacc     4500
tgcgggggga taaagaacac ggtttccggg gcggggagga tgagctggc cgaaagcaag     4560
ttccggagca gctgggactt gccgcagccg gtggggccgt agatgacccc gatgaccggc     4620
tgcaggtggt agttgaggga gagacagctg ccgtcctccc ggaggagggg ggccacctcg     4680
ttcatcatct cgcgcacgtg catgttctcg cgcaccagtt ccgccaggag gcgctctccc     4740
cccaggata ggagctcctg gagcgaggcg aagttttttca gcggcttgag tccgtcagca     4800
atgggcattt tggagagggt ttgttgcaag agttccaggc ggtcccagag ctcggtgatg     4860
tgctctacgg catctcgatc cagcagacct cctcgtttcg cggggttggga cggctgcggg     4920
agtagggcac cagacgatgg gcgtccagcg cagccagggt ccggtccttc cagggtcgca     4980
gcgtccgcgt cagggtggtc tccgtcacgg tgaagggcgg cgggccgggc tgggcgcttg     5040
cgagggtgcg cttcaggctc atccggctgg tcgaaaccg ctcccgatcg gcgccctgcc     5100
cgtcggccag gtagcaattg accatgagtt cgtagttgag cgcctcggcc gcgtggcctt     5160
tggcgcggag cttacctttg gaagtctgcc cgcaggcggg acagaggagg gacttgaggg     5220
cgtagagctt ggggggcgagg aagacggact cgggggggcgta ggcgtccgcg ccgcagtcgg     5280
cgcagacggt ctcgcactcc acgagccagg tgaggtcggg ctggtcgggg tcaaaaacca     5340
gtttcccgcc gttctttttg atgcgtttct tacctttggt ctccatgagc tcgtgtcccc     5400
gctgggtgac aaagaggctg tccgtgtccc cgtagaccga ctttatgggc cggtcctcga     5460
gcggtgtgcc gcggtcctcc tcgtagagga accccgccca ctccgagacg aaagcccggg     5520
tccaggccag cacgaaggag gccacgtggg acgggtacgg gtcgttgtcc accacgggct     5580
ccactttttc cagggtatgc aaacacatgt cccctcgtc cacatccagg aaggtgattg     5640
gcttgtaagt gtaggccacg tgaccggggg tcccggccgg gggggtataa aagggtgcgg     5700
gtccctgctc gtcctcactg tcttccggat cgctgtccag gagcgccagc tgttgggggta     5760
ggtattccct ctcgaaggcg ggcatgacct cggcactcag gttgtcagtt tctagaaacg     5820
aggaggattt gatattgacg gtgccggcgg agatgccttt caagagccct cgtccatct     5880
ggtcagaaaa gacgatcttt ttgttgtcga gcttggtggc gaaggagccg tagagggcgt     5940
tggagaggag cttggcgatg gagcgcatgg tctggttttt ttccttgtcg gcgcgctcct     6000
tggcggcgat gttgagctgc acgtactcgc gcgccacgca cttccattcg gggaagacgg     6060
tggtcagctc gtcgggcacg attctgacct gccagcccg attatgcagg gtgatgaggt     6120
ccacactggt ggccacctcg ccgcgcaggg gctcattagt ccagcagagg gtcctccgcct     6180
tgcgcgagca gaaggggggc aggggggtcca gcatgacctc gtcgggggggg tcggcatcga     6240
tggtgaagat gccgggcagg aggtcgggggt caaagtagct gatggaagtg gccagatcgt     6300
ccagggcagc ttgccattcg cgcacggcca gcgcgctctc gtagggactg agggggcgtgc     6360
cccagggcat gggatgggta agcgcggagg cgtacatgcc gcagatgtcg tagacgtaga     6420
ggggctcctc gaggatgccg atgtaggtgg ggtagcagcg ccccccgcgg atgctggcgc     6480
```

-continued

```
gcacgtagtc atacagctcg tgcgaggggg cgaggagccc cgggcccagg ttggtgcgac    6540
tgggcttttc ggcgcggtag acgatctggc ggaaaatggc atgcgagttg gaggagatgg    6600
tgggcctttg gaagatgttg aagtgggcgt ggggcagtcc gaccgagtcg cggatgaagt    6660
gggcgtagga gtcttgcagc ttggcgacga gctcggcggt gactaggacg tccagagcgc    6720
agtagtcgag ggtctcctgg atgatgtcat acttgagctg tcccttttgt ttccacagct    6780
cgcggttgag aaggaactct tcgcggtcct tccagtactc ttcgaggggg aacccgtcct    6840
gatctgcacg gtaagagcct agcatgtaga actggttgac ggccttgtag gcgcagcagc    6900
ccttctccac ggggagggcg taggcctggg cggccttgcg cagggaggtg tgcgtgaggg    6960
cgaaagtgtc cctgaccatg accttgagga actggtgctt gaagtcgata tcgtcgcagc    7020
cccctgctc ccagagctgg aagtccgtgc gcttcttgta ggcgggggttg ggcaaagcga    7080
aagtaacatc gttgaagagg atcttgcccg cgcggggcat aaagttgcga gtgatgcgga    7140
aaggttgggg cacctcggcc cggttgttga tgacctgggc ggcgagcacg atctcgtcga    7200
agccgttgat gttgtggccc acgatgtaga gttccacgaa tcgcggacgg cccttgacgt    7260
ggggcagttt cttgagctcc tcgtaggtga gctcgtcggg gtcgctgagc ccgtgctgct    7320
cgagcgccca gtcggcgaga tgggggttgg cgcggaggaa ggaagtccag agatccacgg    7380
ccagggcggt ttgcagacgg tcccggtact gacggaactg ctgcccgacg gccatttttt    7440
cggggggtgac gcagtagaag gtgcgggggt ccccgtgcca gcgatcccat ttgagctgga    7500
gggcgagatc gagggcgagc tcgacgagcc ggtcgtcccc ggagagtttc atgaccagca    7560
tgaaggggac gagctgcttg ccgaaggacc ccatccaggt gtaggtttcc acatcgtagg    7620
tgaggaagag cctttcggtg cgaggatgcg agccgatggg gaagaactgg atctcctgcc    7680
accaattgga ggaatggctg ttgatgtgat ggaagtagaa atgccgacgg cgcgccgaac    7740
actcgtgctt gtgtttatac aagcggccac agtgctcgca acgctgcacg ggatgcacgt    7800
gctgcacgag ctgtacctga gttccttttga cgaggaattt cagtgggaag tggagtcgtg    7860
gcgcctgcat ctcgtgctgt actacgtcgt ggtggtcggc ctggccctct tctgcctcga    7920
tggtggtcat gctgacgagc ccgcgcggga ggcaggtcca gacctcggcg cgagcgggtc    7980
ggagagcgag gacgagggcg cgcaggccgg agctgtccag ggtcctgaga cgctgcggga    8040
tcaggtcagt gggcagggc ggcgcgcggt tgacttgcag gagttttttcc agggcgcgcga    8100
ggaggtccag atggtacttg atctccaccg cgccattggt ggcgacgtcg atggcttgca    8160
gggtcccgtg cccctggggt gtgaccaccg tcccccgttt cttcttgggc ggctggggcg    8220
acgggggcgg tgcctcttcc atggttagaa gcggcggcga ggacgccgcc cgggcggcag    8280
gggcggctcg gggcccggag gcaggggcgg caggggcacg tcggcgccgc gcgcgggtag    8340
gttctggtac tgcgcccgga gaagactggc gtgagcgacg acgcgacggt tgacgtcctg    8400
gatctgacgc ctctgggtga aggccacggg acccgtgagt ttgaacctga aagagagttc    8460
gacagaatca atctcggtat cgttgacggc ggcctgccgc aggatctctt gcacgtcgcc    8520
cgagttgtcc tggtaggcga tctcggtcat gaactgctcg atctcctcct cttgaaggtc    8580
tccgcggccg gcgcgctcca cggtggccgc gaggtcgttg gagatgcggc ccatgagctg    8640
cgagaaggcg ttcatgcccg cctcgttcca gacgcggctg tagaccacga cgccctcggg    8700
atcgcgggcg cgcatgacca cctgggcgag gttgagctcc acgtggcgcg tgaagaccgc    8760
gtagttgcag aggcgctggt agaggtagtt gagcgtggtg ggcggtcgtc cggtgacgaa    8820
gaaatacatg atccagcggc ggagcggcat ctcgctgacg tcgcccagcg cctccaaacg    8880
ttccatggcc tcgtaaaagt ccacggcgaa gttgaaaaac tgggagttgc gcgccgagac    8940
ggtcaactcc tcctccagaa gacggatgag ctcggcgatg gtggcgcgca cctcgcgctc    9000
gaaggcccc gggagttcct ccacttcctc ttcttcctcc tccactaaca tctcttctac    9060
ttcctcctca ggcggcagtg gtggcggggg aggggggcctg cgtcgccggc ggcgcacggg    9120
cagacggtcg atgaagcgct cgatggtctc gccgcgccgg cgtcgcatgg tctcggtgac    9180
ggcgcgcccg tcctcgcggg gccgcagcgt gaagacgccg ccgcgcatct ccaggtggcc    9240
gggggggtcc ccgttgggca gggagagggc gctgacgatg catcttatca attgccccgt    9300
agggactccg cgcaaggacc tgagcgtctc gagatccacg ggatctgaaa accgctgaac    9360
gaaggcttcg agccagtcgc agtcgcaagg taggctgagc acggtttctt ctggcgggtc    9420
atgttggttg ggagcggggc gggcgatgct gctggtgatg aagttgaaat aggcggttct    9480
gagacggcgg atggtggcga ggagcaccag gtctttgggc ccggcttgct ggatgcgcag    9540
acggtcggcc atgccccagg cgtggtcctg acacctggcc aggtccttgt agtagtcctg    9600
catgagccgc tccacgggca cctcctcctc gcccgcgcgg ccgtgcatgc gcgtgagccc    9660
gaagccgcgc tggggctgga cgagcgccag gtcggcgacg acgcgctcgg cgaggatggc    9720
ttgctggatc tgggtgaggg tggtctggaa gtcatcaaag tcgacgaagc ggtggtaggc    9780
tccggtgttg atggtgtagg agcagttggc catgacggac cagttgacgg tctggtggcc    9840
cggacgcacg agctcgtggt acttgaggcg cgagtaggcg cgcgtgtcga agatgtagtc    9900
gttgcaggtg cgcaccaggt actggtagcc gatgaggaag tgcggcggcg gctggcggta    9960
gagcggccat cgctcggtgg cggggggccc gggcgcgagg tcctcgagca tggtgcggtg   10020
gtagccgtag atgtacctgg acatccaggt gatgccggcg gcggtggtgg aggcggcgag   10080
gaactgcgcg acgcggttcc agatgttgcg cagcggcagg aagtagttca tggtgggcac   10140
ggtcggcccc gtgaggcgcg cgcagtcgtg gatgctctat acgggcaaaa acgaaagcgg   10200
tcagcggctc gactccgtgg cctggaggct aagcgaacgg gttgggctgc gcgtgtaccc   10260
cggttcgaat ctcgaatcag gctggagccg cagctaacgt ggtattggca ctccgctctc   10320
gacccaagcc tgcaccaacc ctccaggata cggaggcggg tcgtttttgca acttttttttt   10380
ggaggccgga tgagactagt aagcgcggaa agcggccgac cgcgatggct cgctgccgta   10440
gtctggagaa gaatcgccag ggttgcgttg cggtgtgccc cggttcgagg ccggccggat   10500
tccgcggcta acgagggcgt ggctgccccg tcgtttccaa gaccccatag ccagccgact   10560
tctccagtta cggagcgagc ccctcttttg ttttgtttgt ttttgccaga tgcatcccgt   10620
actcggcag atgcgcccc accaccctcc accgcaacaa cagccccctc cacagccggc   10680
gcttctgccc ccgcccagc agcaacttcc agccacgacc gccgcggccg ccgtgagcgg   10740
ggctggacag agttatgatc accagctggc cttggaagag ggcgagggc tggcgcgcct   10800
gggggcgtcg tcgccggagc ggcacccgcg cgtgcagatg aaaagggacg ctcgcgaggc   10860
ctacgtgccc aagcagaacc tgttcagaga caggagcgg aggagatgcg   10920
cgcggcccgg ttccacgcgg ggcgggagct gcgcgcgcggc ctggaccgaa agagggtgct   10980
gagggacgag gatttcgagg cggacgagct gacggggatc agccccgcgc gcgcgcacgt   11040
ggccgcggcc aacctggtca cggcgtacga gcagaccgtg aaggaggaga gcaacttcca   11100
aaaatccttc aacaaccacg tgcgcaccct gatcgcgcgc gaggaggtga ccctgggcct   11160
gatgcacctg tgggacctgc tggaggccat cgtgcagaac cccaccagca agccgctgac   11220
```

-continued

```
ggcgcagctg ttcctggtgg tgcagcatag tcgggacaac gaagcgttca gggaggcgct 11280
gctgaatatc accgagcccg agggccgctg gctcctggac ctggtgaaca ttctgcagag 11340
catcgtggtg caggagcgcg ggctgccgct gtccgagaag ctggcggcca tcaacttctc 11400
ggtgctgagt ttgggcaagt actacgctag gaagatctac aagaccccgt acgtgcccat 11460
agacaaggag gtgaagatcg acgggtttta catgcgcatg accctgaaag tgctgaccct 11520
gagcgacgat ctggggggtgt accgcaacga caggatgcac cgtgcggtga gcgccagcag 11580
gcggcgcgag ctgagcgacc aggagctgat gcatagtctg cagcggggccc tgaccggggc 11640
cgggaccgag ggggagagct actttgacat gggcgcggac ctgcactggc agcccagccg 11700
ccgggccttg gaggcggcgg caggaccctta cgtagaagag gtggacgatg aggtggacga 11760
ggagggcgag tacctggaag actgatggcg cgaccgtatt tttgctagat gcaacaacaa 11820
cagccacctc ctgatcccgc gatgcggggcg gcgctgcaga gccagccgtc cggcattaac 11880
tcctcggacg attggaccca ggccatgcaa cgcatcatgg cgctgacgac ccgcaacccc 11940
gaagcctttta gacagcagcc ccaggccaac cggctctcgg ccatcctgga ggccgtggtg 12000
ccctcgcgct ccaaccccac gcacgagaag gtcctggcca tcgtgaacgc gctggtggag 12060
aacaaggcca tccgcggcga cgaggccggc ctggtgtaca acgcgctgct ggagcgcgtg 12120
gcccgctaca acagcaccaa cgtgcagacc aacctggacc gcatggtgac cgacgtgcgc 12180
gaggccgtgg cccagcgcga gcggttccac cgcgagtcca acctgggatc catggtggc 12240
ctgaacgcct tcctcagcac ccagcccgcc aacgtgcccc ggggccagga ggactacacc 12300
aacttcatca gcgccctgcg cctgatggtg accgaggtgc cccagagcga ggtgtaccag 12360
tccgggccgg actacttctt ccagaccagt cgccagggct tgcagaccgt gaacctgagc 12420
caggctttca agaacttgca gggcctgtgg ggcgtgcagg ccccggtcgg ggaccgcgcg 12480
acggtgtcga gcctgctgac cgcgaactcg cgcctgctgc tgctgctggt cgccccccttc 12540
acggacagcg gcagcatcaa ccgcaactcg tacctgggct acctgattaa cctgtaccgc 12600
gaggccatcg gccaggcgca cgtggacgag cagacctacc aggagatcac ccacgtgagc 12660
cgcgccctgg gccaggacga cccgggcaac ctggaagcca ccctgaactt tttgctgacc 12720
aaccggtcgc agaagatccc gccccagtac gcgctcaaga gcggggagga gcgcatcctg 12780
cgttacgtgc agcagagcgt gggcctgttc ctgatgcagg aggggggccac ccccagcgcc 12840
gcgctcgaca tgaccgcgcg caacatggag cccagcatgt acgccagcaa ccgcccgttc 12900
atcaataaac tgatgggacta cttgcatcgg gcggccgcca tgaactctga ctatttcacc 12960
aacgccatcc tgaatcccca ctggctcccg ccgcgggggt tctacacggg cgagtacgac 13020
atgcccgacc ccaatgacgg gttcctgtgg gacgatgtgg acagcagcgt gttctcccccc 13080
cgaccggggtg ctaacgagcg ccccttgtgg aagaaggaag gcagcgaccg acgcccgtcc 13140
tcggcgctgt ccgccgcgga gggtgctgcc gcggcggtgc ccgaggccgc cagtcctttc 13200
ccgagcttgc ccttctcgct gaacagtatc cgcagcagcg agctgggcag gatcacgcgc 13260
ccgcgcttgc tgggcgaaga ggagtacttg aatgactcgc tgttgagacc cgagcgggag 13320
aagaacttcc ccaataacgg gatagaaagc ctggtggaca agatgagccg ctggaagacg 13380
tatgcgcagg agcacaggga cgatccccgg gcgtcgcagg gggccacgag ccggggcagc 13440
gccgcccgta aacgccggtg gcacgacagg cagcggggac agatgtggga cgatgaggac 13500
tccgccgacg acagcagcgt gttggacttg ggtggggagtg gtaacccgtt cgctcacctg 13560
cgcccccgta tcgggcgcat gatgtaagag aaaccgaaaa taaatgatac tcaccaaggc 13620
catggcgacc agcgtgcgtt cgtttcttct ctgttgttgt tgtatctagt atgatgaggc 13680
gtgcgtaccc ggagggtcct cctccctcgt acgagagcgt gatgcagcag gcgatggcgg 13740
cggcggcgat gcagccccccg ctggaggctc cttacgtgcc cccgcggtac ctggcgccta 13800
cggaggggcg gaacagcatt cgttactcgg agctggcacc cttgtacgat accacccggt 13860
tgtacctggt ggacaacaag tcggcggaca tcgcctcgct gaactaccag aacgaccaca 13920
gcaacttcct gaccaccgtg gtgcagaaca atgacttcac ccccacggag gccagcaccc 13980
agaccatcaa cttttgacgag cgctcgcggt ggggcgggcca gctgaaaacc atcatgcaca 14040
ccaacatgcc caacgtgaac gagttcatgt acagcaacaa gttcaaggcg cgggtgatgg 14100
tctcccgcaa gaccccccaat ggggtgacag tgacagagga ttatgatggt agtcaggatg 14160
agctgaagta tgaatgggtg gaatttgagc tgcccgaagg caacttctcg gtgaccatga 14220
ccatcgacct gatgaacaac gccatcatcg acaattactt ggcgggtggg cggcagaacg 14280
gggtgctgga gagcgacatc ggcgtgaagt tcgacactag gaacttcagg ctgggctggg 14340
accccgtgac cgagctggtc atgcccggggg tgtacaccaa cgaggctttc catcccgata 14400
ttgtcttgct gcccggctgc ggggtggact tcaccgagag ccgcctcagc aacctgctgg 14460
gcattcgcaa gaggcagccc ttccaggaag gcttccagat catgtacgag gatctggagg 14520
ggggcaacat ccccgcgctc ctggatgtcg acgcctatga gaaaagcaag gaggatgcag 14580
cagctgaagc aactgcagcc gtagctaccg cctctaccga ggtcaggggc gataattttg 14640
caagcgccgc agcagtggca gcggccgagg cggctgaaac cgaaagtaag atagtcattc 14700
agccggtgga gaaggatagc aagaacagga gctacaacgt actaccggac aagataaaca 14760
ccgcctaccg cagctggtac ctagcctaca actatgcgca ccccgagaag ggcgtgcgct 14820
cctggacgct gctcaccacc tcggacgtca cctgcggcgt ggagcaagtc tactggtcgc 14880
tgcccgacat gatgcaagac ccggtcacct tccgctccac gcgtcaagtt agcaactacc 14940
cggtggtggg cgccgagctc ctgcccgtct actccaagag cttcttcaac gagcaggccg 15000
tctactcgca gcagctgcgc gccttcacct cgcttacgca cgtcttcaac gcgcttcaccg 15060
agaaccagat cctcgtccgc ccgcccgcgc ccaccattac caccgtcagt gaaaacgttc 15120
ctgctctcac agatcacggg accctgccgc tgcgcagcag tatccggggga gtccagcgcg 15180
tgaccgttac tgacgccaga cgccgcacct gcccctacgt ctacaaggcc ctgggcatag 15240
tcgcgccgcg cgtcctctcg agccgcacct tctaaatgtc cattctcatc tcgcccagta 15300
ataacaccgg ttggggcctg cgcgcgcgcccca gcaagatgta cggaggcgct cgccaacgct 15360
ccacgcaaca ccccgtcgc gtgcgcgggc acttccgcgc tccctggggc gccctcaagg 15420
gccgcgtgcg gtcgcgcacc accgtcgacg acgtgatcga ccaggtggtg gccgacgcgc 15480
gcaactacac ccccgcgcc gcgccgtct ccaccgtgga cgccgtcatc gacagcgtgg 15540
tggccgacgc gcgccggtac gcccgcgcca agagccggcg gcggcgcatc gcccggcggc 15600
accggagcac ccccgccatg cgccgggcgc gagccttgct ggcgagcgac aggcgcacg 15660
gacgcagggc catgctcagg gcggccagac gcgcggcttc aggcgccagc gccggcagga 15720
cccggagacg cgcggccacg gcggcggcag cggccatcgc cagcatgtcc cgcccgcggc 15780
gagggaacgt gtactgggtg cgcgacgccg ccaccggtgt gcgcgtgccc gtgcgcaccc 15840
gcccccctcg cacttgaaga tgttcacttc gcgatgttga tgtgtcccag cggcgaggag 15900
gatgtccaag cgcaaattca aggaagagat gctccaggtc atcgcgcctg agatctacgg 15960
```

-continued

```
ccctgcggtg gtgaaggagg aaagaaagcc ccgcaaaatc aagcgggtca aaaaggacaa   16020
aaaggaagaa gaaagtgatg tggacggatt ggtggagttt gtgcgcgagt tcgccccccg   16080
gcggcgcgtg cagtggcgcg ggcggaaggt gcaaccggtg ctgagacccg gcaccaccgt   16140
ggtcttcacg cccggcgagc gctccggcac cgcttccaag cgctcctacg acgaggtgta   16200
cggggatgat gatattctgg agcaggcggc cgagcgcgtg ggcgagtttg cttacggcaa   16260
gcgcagccgt tccgcaccga aggaagaggc ggtgtccatc ccgctggacc acggcaaccc   16320
cacgccgagc ctcaagcccg tgaccttgca gcaggtgctg ccgaccgcgg cgccgcgccg   16380
ggggttcaag cgcgagggcg aggatctgta ccccaccatg cagctgatgg tgcccaagcg   16440
ccagaagctg gaagacgtgc tggagaccat gaaggtggac ccggacgtgc agcccgaggt   16500
caaggtgcgg cccatcaagc aggtggcccc gggcctgggc gtgcagaccg tggacatcaa   16560
gattcccacg gagcccatgg aaacgcagac cgagcccatg atcaagccca gcaccagcac   16620
catggaggtg cagacggatc cctggatgcc atcggctcct agtcgaagac cccggcgcaa   16680
gtacggcgcg gccagcctgc tgatgcccaa ctacgcgctg catccttcca tcatccccac   16740
gccgggctac cgcgggcacg gcttctaccg cggtcatacc agcagccgcc gccgcaagac   16800
caccactcgc cgccgccgtc gccgcaccg cgctgcaacc accccgccg ccctggtgcg   16860
gagagtgtac cgccgcggcc gcgcacctct gaccctgccg cgcgcgcgct accacccgag   16920
catcgccatt taaactttcg cctgctttgc agatcaatgg ccctcacatg ccgccttcgc   16980
gttcccatta cgggctaccg aggaagaaaa ccgcgccgta gaaggctggc ggggaacggg   17040
atgcgtcgcc accaccaccg gcggcggcgc gccatcagca agcggttggg gggaggcttc   17100
ctgcccgcgc tgatccccat catcgccgcg gcgatcgggg cgatccccgg cattgcttcc   17160
gtggcggtgc aggcctctca gcgccactga gacacacttg gaaacatctt gtaataaacc   17220
aatggactct gacggctcctg gtcctgtgat gtgttttcgt agacagatgg aagacatcaa   17280
ttttgtcgtcc ctggctccgc gacacggcac gcggccgttc atgggcacct ggagcgacat   17340
cggcaccagc caactgaacg ggggcgcctt caattggagc agtctctgga gcgggcttaa   17400
gaatttcggg tccacgctta aaacctatgg cagcaaggcg tggaacagca ccacagggca   17460
ggcgctgagg gataagctga aagagcagaa cttccagcag aaggtggtcg atgggctcgc   17520
ctcgggcatc aacggggtgg tggacctggc caaccaggcc gtgcagcggc agatcaacag   17580
ccgcctggac ccggtgccgc ccgccggctc cgtggagatg ccgcaggtgg aggaggagct   17640
gcctcccctg gacaagcggg gcgagaagcg accccgcccc gatgcggagg agacgctgct   17700
gacgcacacg gacgagccgc cccgtacga ggaggcggtg aaactgggtc tgcccaccac   17760
gcggcccatc gcgcccctgg ccaccggggt gctgaaaccc gaaaagcccg cgaccctgga   17820
cttgcctcct ccccagcctt cccgcccctc tacagtggct aagccctgc cgccggtggc   17880
cgtggcccgc gcgcgacccg ggggcaccgc ccgccctcat gcgaactggc agagcactct   17940
gaacagcatc gtgggtctgg gagtgcagag tgtgaagcgc cgccgctgct attaaaccta   18000
ccgtagcgct taacttgctt gtctgtgtgt gtatgtatta tgtcgccgcc gccgctgtcc   18060
accagaagga ggagtgaaga ggcgcgtcgc cgagttgcaa gatggccacc ccatcgatgc   18120
tgcccagtg ggcgtacatg cacatcgccg gacaggacgc ttcggagtac ctgagtccgg   18180
gtctggtgca gtttgcccgc gccacagaca cctacttcag tctggggaac aagtttagga   18240
accccacggt ggcgcccacg cacgatgtga ccaccgaccg cagccagcgg ctgacgctgg   18300
gcttcgtgcc cgtggaccgc gaggacaaca cctactcgta caaagtgcgc tacacgctgg   18360
ccgtgggcga caaccgcgtg ctggacatgg ccagcaccta ctttgacatc cgcggcgtgc   18420
tggatcgggg ccctagcttc aaaccctact ccggcaccgc ctacaacagt ctggcccca   18480
agggagcacc caacacttgt cagtggacat ataaagccga tggtgaaact gccacagaaa   18540
aaacctatac atatggaaat gcacccgtgc agggcattaa catcacaaaa gatggtattc   18600
aacttggaac tgacaccgat gatcagccaa tctacgcaga taaaacctat cagcctgaac   18660
ctcaagtggg tgatgctgaa tggcatgaca tcactgtac tgatgaaaag tatggaggca   18720
gagctcttaa gcctgatacc aaaatgaagc cttgttatgg ttcttttgcc aagcctacta   18780
ataaagaagg aggtcaggca aatgtgaaaa caggaacagc cactactaaa gaatatgaca   18840
tagacatggc tttctttgac aacagaagtg cggctgctgc tggcctagct ccagaaattg   18900
ttttgtatac tgaaaatgtg gatttggaaa ctccagatac ccatattgta tacaaagcag   18960
gcacagatga cagcagctct tctattaatt tgggtcagca agccatgccc aacagacctta   19020
actacattgg tttcagagac aacttttatcg ggctcatgta ctacaacagc actggcaata   19080
tggggggtgct ggccggtcag gcttctcagc tgaatgctgt ggttgacttg caagacagaa   19140
acaccgagct gtcctaccag ctcttgcttg actctctggg tgacagaacc cggtatttca   19200
gtatgtggaa tcaggcggtg gacagctatg atcctgatgt gcgcattatt gaaaatcatg   19260
gtgtggagga tgaacttccc aactattgtt tccctctgga tgctgttggc agaacagata   19320
cttatcaggg aattaaggct aatggaactg atcaaaccac atggaccaaa gatgacagtg   19380
tcaatgatgc taatgagata ggcaagggta tccattcgc catggaaatc aacatccaag   19440
ccaacctgtg gaggaacttc ctctacgcca acgtggccct gtacctgccc gactcttaca   19500
agtacacgcc ggccaatgtt accctgcca ccaacaccaa cacctacgat tacatgaacg   19560
gccgggtggt ggcgccctcg ctggtggact cctacatcaa catcggggcg cgctggtcgc   19620
tggatcccat ggacaacgtg aacccccttca accaccaccg caatgcgggg ctgcgctacc   19680
gctccatgct cctgggcaac gggcgctacg tgcccttcca catccaggtg ccccagaaat   19740
ttttcgccat caagagcctc ctgctcctgc ccgggtccta cacctacgag tggaacttcc   19800
gcaaggacgt caacatgatc ctgcagagct ccctcggcaa cgacctgcgc acggacgggg   19860
cctccatctc cttcaccagc atcaacctct acgccacctt cttccccatg gcgcacaaca   19920
cggcctccac gctcgaggcc atgctgcgca acgacaccaa cgaccagtcc ttcaacgact   19980
acctctcggc ggccaacatg ctctaccca tcccggccaa cgccaccaac gtgcccatct   20040
ccatcccctc gcgcaactgg gccgccttcc gcggctggtc cttcacgcgt ctcaagacca   20100
aggagacgcc ctcgctgggc tccgggttcg accctactt cgtctactcg ggctccatcc   20160
cctacctcga cggcaccttc tacctcaacc acaccttcaa gaaggtctcc atcaccttcg   20220
actcctccgt cagctggccc ggcaacgacc ggctcctgac gcccaacgag ttcgaaatca   20280
agcgcaccgt cgacggcgag ggctacaacg tggcccagtg caacatgacc aaggactggt   20340
tcctggtcca gatgctgacc cactacaaca cggcttctac gtgcccgagg   20400
gctacaagga ccgcatgtac tccttcttcc gcaacttcca gcccatgagc cgccaggtgg   20460
tggacgaggc caactacaag gactaccagg ccgtcacccct ggctaccag cacaacaact   20520
cgggcttcgt cggctacctc gcgcccacca tgcgccaggg ccagccctac cccgccaact   20580
accccctaccc gctcatcggc aagagcgcg tcaccagcgt cacccagaaa aagttcctct   20640
gcgacagggt catgtggcgc atccccttct ccagcaactt catgtccatg ggcgcgctca   20700
```

-continued

```
ccgacctcgg ccagaacatg ctctatgcca actccgccca cgcgctagac atgaatttcg   20760
aagtcgaccc catggatgag tccacccttc tctatgttgt cttcgaagtc ttcgacgtcg   20820
tccgagtgca ccagccccac cgcggcgtca tcgaggccgt ctacctgcgc accccttct    20880
cggccggtaa cgccaccacc taagctcttg cttcttgcaa gccatggccg cgggctccgg   20940
cgagcaggag ctcagggcca tcatccgcga cctgggctgc gggccctact tcctgggcac   21000
cttcgataag cgcttccggg gattcatggc cccgcacaag ctggcctgcg ccatcgtcaa   21060
cacggccggc cgcgagaccg ggggcgagca ctggctggcc ttcgcctgga acccgcgctc   21120
gaacacctgc tacctcttcg accccttcgg gttctcggac gagcgcctca agcagatcta   21180
ccagttcgag tacgagggcc tgctgcgccg cagcgccctg gccaccgagg accgctgcgt   21240
caccctggaa aagtccaccc agaccgtgca gggtccgcgc tcggccgcct gcgggctctt   21300
ctgctgcatg ttcctgcacg ccttcgtgca ctggcccgac cgcccatgg acaagaaccc    21360
caccatgaac ttgctgacgg gggtgcccaa cggcatgctc cagtcgcccc aggtggaacc   21420
caccctgcgc cgcaaccagg aggcgctcta ccgcttcctc aactcccact ccgcctactt   21480
tcgctcccac cgcgcgcgca tcgagaaggc caccgccttc gaccgcatga atcaagacat   21540
gtaaaccgtg tgtgtatgtt aaatgtcttt aataaacagc actttcatgt tacacatgca   21600
tctgagatga tttatttaga aatcgaaagg gttctgccgg gtctcggcat ggcccgcggg   21660
cagggacacg ttgcggaact ggtacttggc cagccacttg aactcgggga tcagcagttt   21720
gggcagcggg gtgtcgggga aggagtcggt ccacagcttc cgcgtcagt gcagggcgcc    21780
cagcaggtcg ggcgcggaga tcttgaaatc gcagttggga cccgcgttct gcgcgcggga   21840
gttgcggtac acggggttgc agcactggaa caccatcagg gccgggtgct tcacgctcgc   21900
cagcaccgtc gcgtcggtga tgctctccac gtcgaggtcc tcggcgttgg ccatcccgaa   21960
ggggtcatc ttgcaggtct gccttcccat ggtgggcacg cacccgggct tgtggttgca    22020
atcgcagtgc aggggatca gcatcatctg ggcctggtcg gcgttcatcc ccgggtacat    22080
ggccttcatg aaagcctcca attgcctgaa cgcctgctgg gccttggctc cctcggtgaa    22140
gaagaccccg caggacttgc tagagaactg gttggtggcg cacccggcgt cgtgcacgca    22200
gcagcgcgcg tcgttgttgg ccagctgcac cacgctgcgc cccagcggt tctgggtgat     22260
cttggcccgg tcggggttct ccttcagcgc gcgctgcccg ttctcgctcg ccacatccat    22320
ctcgatcatg tgctccttct ggatcatggt ggtcccgtgc aggcaccgca gcttgccctc    22380
ggcctcggtg cacccgtgca gccacagcgc gcacccggtg cactccagt tcttgtgggc     22440
gatctgggaa tgcgcgtgca cgaagccctg caggaagcgg cccatcatgg tggtcagggt    22500
cttgttgcta gtgaaggtca gcggaatgcc gcggtgctcc tcgttgatgt acaggtggca    22560
gatgcggcgg tacacctcgc cctgctcggg catcagctgg aagttggctt tcaggtcggt    22620
ctccacgcgg tagcggtcca tcagcatagt catgatttcc ataccccttct cccaggccga   22680
gacgatgggc aggctcatag ggttcttcac catcatctta gcgctagcag cgcggccag     22740
ggggtcgctc tcgtccaggg tctcaaagct ccgcttgccg tccttctcgg tgatccgcac    22800
cgggggggtag ctgaagccca cggccgccag ctcctcctcg gcctgtcttt cgtcctcgct   22860
gtcctggctg acgtcctgca ggaccacatg cttggtcttg cggggtttct tcttgggcgg     22920
cagcggcggc ggagatgttg gagatggcga ggggggagcgc gagttctcgc tcaccactac    22980
tatctcttcc tcttcttggt ccgaggccac gcggcggtag gcgggtgtct tcggggcag     23040
aggcggaggc gacgggctct cgccgccgcg acttggcgga tggctggcag agccccttcc    23100
gcgttcgggg gtgcgctccc ggcggcgctc tgactgactt cctccgcggc cggccattgt     23160
gttctcctag ggaggaacaa caagcatgga gactcagcca tcgccaacct cgccatctgc    23220
ccccaccgcc gacgagaagc agcagcagca gaatgaaagc ttaaccgccc cgccgcccag    23280
ccccgccacc tccgacgcgg ccgtcccaga catgcaagag atggaggaat ccatcgagat   23340
tgacctgggc tatgtgacgc ccgcggagca cgaggaggag ctggcagtgc gcttttcaca    23400
agaagagata caccaagaac agccagagca ggaagcagag aatgagcaga gtcaggctgg   23460
gctcgagcat gacggcgact acctccacct gagcgggggag gacgagtcatcaagca        23520
tctggcccgg caggccacca tcgtcaagga tgcgctgctc gaccgcaccg aggtgccct    23580
cagcgtggag gagctcagcc gcgcctacga gttgaacctc ttctcgccgc gcgtgcccc    23640
caagcgccag cccaatggca cctgcgagcc caacccgcgc ctcaacttct acccggtctt    23700
cgcggtgccc gaggccctgg ccacctacca catctttttc aagaaccaaa agatcccgt     23760
ctcctgccgc gccaaccgca cccgcgccga cgcccttttc aacctgggtc ccggcgccg     23820
cctacctgat atcgcctcct tggaagaggt tcccaagatc ttcgagggtc tgggcagcga   23880
cgagactcgg gccgcgaacg ctctgcaagg agaaggagga gagcatgagc accacagcgc   23940
cctggtcgag ttggaaggcg acaacgcgcg gctggcggtg ctcaaacgca cggtcgagct   24000
gacccatttc gcctacccgg ctctgaacct gccccccaaa gtcatgagcg cggtcatgga   24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag   24180
tccccagagt ttggaagagc ggcgcaaact catgatggcc gtggtcctgg tgaccgtgga   24240
gctggagtgc ctgcgccgct tcttcgccga cgcggagacc ctgcgcaagg tcgaggagaa   24300
cctgcactac ctcttcaggc acgggttcgt gcgccaggcc tgcaagatct ccaacgtgga    24360
gctgaccaac ctggtctcct acatgggcat cttgcacgag aaccgcctgg ggcagaacgt    24420
gctgcacacc accctgcgcg gggaggcccg gcgcgactac atccgcgact gcgtctacct    24480
ctacctctgc cacacctggc agacgggcat gggcgtgtag cagcagtgtc tggaggagca    24540
gaacctgaaa gagctctgca agctcctgca gaagaacctc aagggtctgt ggaccgggtt    24600
cgacgagcgc accaccgcct cggacctggc cgacctcatt ttccccgagc gcctcaggct   24660
gacgctgcgc aacggcctgc ccgactttat gagccaaagc atgttgcaaa actttcgctc   24720
tttcatcctc gaacgctccg gaatcctgcc cgccacctgc tccgcgctgc cctcggactt   24780
cgtgccgctg accttccgcg agtgcccccc gccgctgtgg agccactgct acctgctgcg   24840
cctggccaac tacctggcct accactcgga cgtgatcgag gacgtcagcg gcgagggcct    24900
gctcgagtgc cactgccgct gcaacctctg cacgccgcac cgctccctgg cctgcaaccc    24960
ccagctgctg agcgagaccc agatcatcgg caccttcgag ttgcaagggc ccagcgaagg    25020
cgagggttca gccgccaagg ggggtctgaa actcaccccg gggctgtgga cctcggccta    25080
cttgcgcaag ttcgtgcccg aggactacca tccccttcga atcaggttct acgaggacca    25140
atccatccg cccaaggccg agctgtcggc ctgcgtcatc acccagggg cgatcctggc      25200
ccaattgcaa gccatccaga aatcccgcca agaattcttg ctgaaaaagg gccgcggggt    25260
ctacctcgac ccccagaccg gtgaggagct caaccccggc ttcccccagg atgccccgag    25320
gaaacaagaa gctgaaagtg gagctgccgc ccgtggagga tttggaggaa gactgggaga  25380
acagcagtca ggcagaggag gaggagatgg aggaagactg ggacagcact caggcagagg    25440
```

```
aggacagcct gcaagacagt ctggaggaag acgaggagga ggcagaggag gaggtggaag   25500
aagcagccgc cgccagaccg tcgtcctcgg cggggggagaa agcaagcagc acggatacca   25560
tctccgctcc gggtcggggt cccgctcgac cacacagtag atgggacgag accggacgat   25620
tcccgaaccc caccacccag accggtaaga aggagcggca gggatacaag tcctggcggg   25680
ggcacaaaaa cgccatcgtc tcctgcttgc aggcctgcgg gggcaacatc tccttcaccc   25740
ggcgctacct gctcttccac cgcgggggtga actttccccg caacatcttg cattactacc   25800
gtcacctcca cagcccctac tacttccaag aagaggcagc agcagcagaa aaagaccagc   25860
agaaaaccag cagctagaaa atccacacgc gcggcagcag gtggactgag gatcgcggcg   25920
aacgagccgg cgcaaacccg ggagctgagg aaccggatct ttcccaccct ctatgccatc   25980
ttccagcaga gtcgggggca ggagcaggaa ctgaaagtca agaaccgttc tctgcgctcg   26040
ctcacccgca gttgtctgta tcacaagagc gaagaccaac ttcagcgcac tctcgaggac   26100
gccgaggctc tcttcaacaa gtactgcgcg ctcactctta aagagtagcc cgcgcccgcc   26160
cagtcgcaga aaaaggcggg aattacgtca cctgtgccct tcgccctagc cgcctccacc   26220
catcatcatg agcaaagaga ttcccacgcc ttacatgtcg agctaccagc cccagatggg   26280
cctggccgcc ggtgccgccc aggactactc cacccgcatg aattggctca gcgccgggcc   26340
cgcgatgatc tcacgggtga atgacatccg cgcccaccga aaccagatac tcctagaaca   26400
gtcagcgctc accgccacgc cccgcaatca cctcaatccg cgtaattggc ccgccgccct   26460
ggtgtaccag gaaattcccc agcccacgac cgtactactt ccgcgagacg cccaggccga   26520
agtccagctg actaactcag gtgtccagct ggcgggcggc gccaccctgt gtcgtcaccg   26580
ccccgctcag ggtataaagc ggctggtgat ccggggcaga ggcacacagc tcaacgacga   26640
ggtggtgagc tcttcgctgg gtctgcgacc tgacggagtc ttccaactcg ccggatcggg   26700
gagatcttcc ttcacgcctc gtcaggccgt cctgactttg gagagttcgt cctcgcagcc   26760
ccgctcgggt ggcatcggca ctctccagtt cgtggaggag ttcactccct cggtctactt   26820
caaccccttc tccggctccc ccggccacta cccggacgag ttcatcccga acttcgacgc   26880
catcagcgag tcggtggacg gctacgattg aatgtcccat ggtggcgcag ctgacctagc   26940
tcggcttcga cacctggacc actgccgccg cttccgctgc ttcgctcggg atctcgccga   27000
gtttgcctac tttgagctgc ccgaggagca ccctcagggc ccggcccacg gagtgcggat   27060
cgtcgtcgaa gggggcctcg actcccacct gcttcggatc ttcagccagc gtccgatcct   27120
ggtcgagcgc gagcaaggac agacccttct gactctgtac tgcatctgca accacccggg   27180
cctgcagtaccag agtctttgtt gtctgctgtg tactgagtat aataaaagct gagatcagcg   27240
actactccgg acttccgtgt gttcctgaat ccatcaacca gtctttgttc ttcaccggga   27300
acgagaccga gctccagctc cagtgtaagc cccacaagaa gtacctcacc tggctgttcc   27360
agggctcccc gatcgccgtt gtcaaccact gcgacaacga cggagtcctg ctgagcggcc   27420
ctgccaacct tactttttcc acccgcagaa gcaagctcca gctcttccaa ccttcctcc    27480
ccgggaccta tcagtgcgtc tcgggaccct gccatcacac cttccacctg atcccgaata   27540
ccacagcgtc gctccccgct actaacaacc aaactaacct ccaccaacgc caccgtcgcg   27600
acggccacaa tacatgccca tattagacta tgaggccgag ccacagcgac ccatgctccc   27660
cgctattagt tacttcaatc taaccggcgg agatgactga cccactggcc aacaacaacg   27720
tcaacgacct tctcctggac atggacggcc gcgcctcgga gcagcgactc gcccaacttc   27780
gcattcgcca gcagcaggag agagccgtca aggagctgca ggatgcggtg gccatccacc   27840
agtgcaagag aggcatcttc tgcctggtga aacaggccaa gatctcctac gaggtcactc   27900
caaacgacca tcgcctctcc tacgagctcc tgcagcagcg ccagaagttc acctgcctgg   27960
tcggagtcaa ccccatcgtc atcacccagc agtctggcga taccaagggg tgcatccact   28020
gctcctgcga ctcccccgac tgcgtccaca ctctgatcaa gaccctctgc ggcctccgcg   28080
acctcctccc catgaactaa tcaccccctt atccagtgaa ataaagatca tattgatgat   28140
gattttacag aaataaaaaa taatcatttg atttgaaata aagatacaat catattgatg   28200
atttgagttt aacaaaaaaa taaagaatca cttacttgaa atctgatacc aggtctctgt   28260
ccatgttttc tgccaacacc acttcactcc cctcttccca gctctggtac tgcaggcccc   28320
ggcgggctgc aaacttcctc cacacgctga aggggatgtc aaattcctcc tgtccctcaa   28380
tcttcatttt atcttctatc agatgtccaa aaagcgcgtc cgggtggatg atgacttcga   28440
cccgctac ccctacgatg cagacaacgc accgaccgtg cccttcatca accccccctt   28500
cgtctcttca gatggattcc aagagaagcc cctgggggtg ttgtccctgc gactggccga   28560
ccccgtcacc accaagaacg gggaaatcac cctcaagctg ggagaggggg tggacctcga   28620
ttcctcggga aaactcatct ccaacacggc caccaaggcc gccgcccctc tcagttttc    28680
caacacacc atttcccta acatggatca cccctttcac actaaagatg gaaaattatc   28740
cttacaagtt tctccaccat taaatatact gagaacaagc attctaaaca cactagcttt   28800
aggtttggga tcaggtttag gactccgtgg ctctgccttg gcagtacagt tagtctctcc   28860
acttacattt gatactgatg gaaacataaa gcttaccttta gacagaggtt tgcatgttac   28920
aacaggagat gcaattgaaa gcaacataag ctgggctaaa ggtttaaaat ttgaagatgg   28980
agccatagca accaacattg gaaatgggtt agagtttgga agcagtagta cagaaacagg   29040
tgttgatgat gcttacccaa tccaagttaa acttggatct ggccttagct ttgacagtac   29100
aggagccata atggctggta acaaagaaga cgataaactc actttgtgga caacacctga   29160
tccatcacca aactgtcaaa tactcgcaga aaatgatgca aaactaacac tttgcttgac   29220
taaatgtggt agtcaaatac tggccactgt gtcagtctta gttgtaggaa gtggaaacct   29280
aaacccatt actggcaccg taagcagtgc tcaggtgttt ctacgtttg atgcaaacgg   29340
tgttctttta acagaacatt ctacactaaa aaaatactgg gggtataggc agggagatag   29400
catagatggc actccatata ccaatgctgt aggattcatg cccaatttaa aagcttatcc   29460
aaagtcacaa agttctacta ctaaaaataa tatagtaggg caagtataca tgatggagaa   29520
tgtttcaaaa cctatgcttc tcactataac cctcaatgt actgatgaca gcaacagtac   29580
atattcaatg tcatttttcat acacctggac taatgtgaagc tatgttggag caacatttgg   29640
ggctaactct tataccttct catacatcgc ccaagaatga acactgtatc ccaccctgca   29700
tgccaaccct tcccacccca ctctgtggaa caaactctga aacacaaaat aaaataaagt   29760
tcaagtgttt tattgattca acagttttac aggattcgag cagttatttt tcctccaccc   29820
tcccaggaca tggaatacac caccctctcc ccccgaccag ccttgaacat ctgaatgcca   29880
ttggtgatgg acatgctttt ggtctccacg ttcacacag tttcagacg agccagtctc   29940
gggtcggtca gggagatgaa accctccggg cactcccgca tctgcacctc acagctcaac   30000
agctgaggat tgtcctcggt ggtcgggatc acgttatct ggaagaagca gaagagcggc   30060
ggtgggaatc atagtccgcg aacgggatcg gccggtggtg tcgcatcagg ccccgcagca   30120
gtcgctgccg ccgccgctcc gtcaagctgc tgctcagggg gtccgggtcc agggactccc   30180
```

```
tcagcatgat gcccacggcc ctcagcatca gtcgtctggt gcggcgggcg cagcagcgca   30240
tgcggatctc gctcaggtcg ctgcagtacg tgcaacacag aaccaccagg ttgttcaaca   30300
gtccatagtt caacacgctc cagccgaaac tcatcgcggg aaggatgcta cccacgtggc   30360
cgtcgtacca gatcctcagg taaatcaagt ggtgcccct ccagaacacg ctgcccacgt    30420
acatgatctc cttgggcatg tggcggttca ccacctccg gtaccacatc accctctggt    30480
tgaacatgca gccccggatg atcctgcgga accacagggc cagcaccgcc ccgcccgcca   30540
tgcagcgaag agaccccggg tcccggcaat ggcaatggag gacccaccgc tcgtacccgt   30600
ggatcatctg ggagctgaac aagtctatgt tggcacagca caggcatatg ctcatgcatc   30660
tcttcagcac tctcaactcc tcgggggtca aaaccatatc ccagggcacg gggaactctt   30720
gcaggacagc gaaccccgca gaacagggca atcctcgcac agaacttaca ttgtgcatgg   30780
acagggtatc gcaatcaggc agcaccgggt gatcctccac cagagaagcg cgggtctcgg   30840
tctcctcaca gcgtggtaag ggggccggcc gatacgggtg atggcgggac gcggctgatc   30900
gtgttcgcga ccgtgtcatg atgcagttgc tttcggacat tttcgtactt gctgtagcag   30960
aacctggtcc gggcgctgca caccgatcgc cggcggcggt ctcggcgctt ggaacgctcg   31020
gtgttgaaat tgtaaaacag ccactctctc agaccgtgca gcagatctag ggcctcagga   31080
gtgatgaaga tcccatcatg cctgatggct ctgatcacat cgaccaccgt ggaatgggcc   31140
agacccagcc agatgatgca attttgttgg gtttcggtga cggcgggggga gggaagaaca   31200
ggaagaacca tgattaactt ttaatccaaa cggtctcgga gtacttcaaa atgaagatcg   31260
cggagatggc acctctcgcc cccgctgtgt tggtggaaaa taacagccag gtcaaaggtg   31320
atacggttct cgagatgttc cacggtggct tccagcaaag cctccacgcg cacatccaga   31380
aacaagacaa tagcgaaagc gggagggttc tctaattcct caatcatcat gttacactcc   31440
tgcaccatcc ccagataatt ttcattttc cagccttgaa tgattcgaac tagttcgtga   31500
ggtaaatcca agccagccat gataaagagc tcgcgcagag cgccctccac cggcattctt   31560
aagcacaccc tcataattcc aagatattct gctcctggtt cacctgcagc agattgacaa   31620
gcggaatatc aaaatctctg ccgcgatccc tgagctcctc cctcagcaat aactgtaagt   31680
actctttcat atcctctccg aaattttag ccataggacc accaggaata agattagggc    31740
aagccacagt acagataaac cgaagtcctc cccagtgagc attgccaaat gcaagactgc   31800
tataagcatg ctggctagac ccggtgatat cttccagata actggacaga aaatcgccca   31860
ggcaattttt aagaaaatca acaaaagaaa aatcctccag gtggacgttt agagcctcgg   31920
gaacaacgat gaagtaaatg caagcggtgc gttccagcat ggttagttag ctgatctgta   31980
gaaaaaacaa aaatgaacat taaaccatgc tagcctggcg aacaggtggg taaatcgttc   32040
tctccagcac caggcaggcc acggggtctc cggcgcgacc ctcgtaaaaa ttgtcgctat   32100
gattgaaaac catcacagag agacgttccc ggtggccggc gtgaatgatt cgacaagatg   32160
aatacacccc cggaacattg gcgtccgcga gtgaaaaaaa gcgcccgagg aagcaataag   32220
gcactacaat gctcagtctc aagtccagca aagcgatgcc atgcggatga agcacaaaat   32280
tctcaggtgc gtacaaaatg taattactcc cctcctgcac aggcagcaaa gcccccgatc   32340
cctccaggta cacatacaaa gcctcagcgt ccatagctta ccgagcagca gcacacaaca   32400
ggcgcaagag tcagagaaag gctgagctct aacctgtcca cccgctctct gctcaatata   32460
tagcccagat ctacactgac gtaaaggcca aagtctaaaa atacccgcca aataatcaca   32520
cacgcccagc acacgcccag aaaccggtga cacactcaaa aaaatacgcg cacttcctca   32580
aacgcccaaa actgccgtca tttccgggtt cccacgctac gtcatcaaaa cacgactttc   32640
aaattccgtc gaccgttaaa aacgtcaccc gccccgcccc taacggtcgc ccgtctctca   32700
gccaatcagc gccccgcatc cccaaattca aacacctcat ttgcatatta acgcgcacaa   32760
aaagtttgag gtatattatt gatgatgg                                      32788
```

```
SEQ ID NO: 13           moltype = DNA  length = 30684
FEATURE                 Location/Qualifiers
misc_feature           1..30684
                        note = Description of Artificial Sequence: Synthetic
                         polynucleotide
source                  1..30684
                        mol_type = other DNA
                        organism = synthetic construct
SEQUENCE: 13
ccatcttcaa taatatacct caaactttt gtgcgcgtta atatgcaaat gaggcgtttg     60
aatttgggga ggaagggcgg tgattggtcg agggatgagc gaccgttagg ggcggggcga   120
gtgacgtttt gatgacgtgg ttgcgaggag gagccagttt gcaagttctc gtgggaaaag   180
tgacgtcaaa cgaggtgtgg tttgaacacg gaaatactca attttcccgc gctctctgac   240
aggaaatgag gtgtttctgg gcggatgcaa gtgaaaacgg gccattttcg cgcgaaaact   300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cggtgtcaaa gtccggtgtt tttacgtagg tgtcagctga tcgccaggggt  480
atttaaacct gcgctctcca gtcaagaggc cactcttgag tgccagcgag aagagtttc    540
tcctccgcgc cgcgagtcag atctcacctt tgaaagtagg gataacaggg taatgacatt   600
gattattgac tagttgttaa tagtaatcaa ttacgggtc attagttcat agcccatata    660
tggagttccg cgttacataa cttacggtaa atggcccgcc tggctgaccg cccaacgacc   720
cccgcccatt gacgtcaata atgacgtatg ttcccatagt aacgccaata gggactttcc   780
attgacgtca atgggtggag tatttacggt aaactgccca cttggcagta catcaagtgt   840
atcatatgcc aagtccgccc cctattgacg tcaatgacgg taaatggccc gcctggcatt   900
atgcccagta catgacctta cgggactttc ctacttggca gtacatctac gtattagtca   960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc cccgttgacg caaatgggcg  1140
gtaggcgtgt acggtgggag gtctatataa gcagagctcg tttagtgaac cgtcagatcg  1200
cctggaacgc catccacgct gttttgacct ccatagaaga cagcggatcgc gccaccatgg  1260
tgagcaaggg cgaggagctg ttcaccgggg tggtgcccat cctggtcgag ctggacggcg  1320
acgtaaacgg ccacaagttc agcgtgtccg gcgaggcg gggcgatgcc acctacggca    1380
agctgaccct gaagttcatc tgcaccaccg gcaagctgcc cgtgccctgg cccaccctcg  1440
tgaccaccct gacctacggc gtgcagtgct tcagccgcta ccccgaccac atgaagcagc  1500
```

-continued

```
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacacccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg ggggaggacc tgcatgaggg ccagaataac tgaaatctgt gctttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
tctcgatcat tgagcacccg gtggatcttt tccaggaccc ggtagaggtg ggcttggatg   2940
ttgaggtaca tgggcatgag cccgtccggg gggtggaggt agctccattg cagggcctcg   3000
tgctcggggg tggtgttgta aatcacccag tcatagcagg ggcgcaggcc atggtgttgc   3060
acaatatctt tgaggaggag actgatggcc acgggcagcc ctttggtgta ggtgtttaca   3120
aatctgttga gctgggaggg atgcatgcg ggggagatga ggtgcatctt ggcctggatc   3180
ttgagattgg cgatgttacc gcccagatcc cgcctgggt tcatgttgtg caggaccacc   3240
agcacggtgt atccggtgca cttggggaat ttatcatgca acttggaagg gaaggccgtg   3300
aagaatttgg cgacgccttt gtgcccgccc aggttttcca tgcactcatc catgatgatg   3360
gcgatgggcc cgtgggcggc ggcctgggca aagacgtttc gggggtcgga cacatcatag   3420
ttgtggtcct gggtgaggtc atcataggcc attttaatga atttggggcg gagggtgccg   3480
gactggggga caaaggtacc ctcgatcccg ggggcgtagt tcccctcaca gatctgcatc   3540
tcccaggctt tgagctcgga ggggggggatc atgtccacct gcggggcgat aaagaaacacg   3600
gtttccgggg cgggggagat gagctgggcc gaaagcaagt tccggagcag ctgggacttg   3660
ccgcagccgg tggggccgta gatgaccccg atgaccggct gcaggtggta gttgaggag   3720
agacagctgc cgtcctcccg gaggaggggg gccacctcgt tcatcatctc gcgcacgtgc   3780
atgttctcgc gcaccagttc cgccaggagg cgctctcccc ccaggggatag gagctcctgg   3840
agcgaggcga agtttttcag cggcttgagt ccgtcggcca tgggcatttt ggagagggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagccg agccagggtc cggtccttcc agggtcgagc cgccgcgtc agggtggtct   4080
ccgtcacggt gaaggggtgc gcgccgggct gggcgcttgc gagggtgcgc ttcaggctca   4140
tccggctggt cgaaaaccgc tcccgatcgg cgccctgcgc gtcggccagg tagcaattga   4200
ccatgagttc gtagttgagc gcctcggccg cgtggccttt ggcgcggagc ttacctttgg   4260
aagtctgccc gcaggcggga cagaggaggg acttgaggga gtaagacttg ggggcgagga   4320
agacggactc gggggcgtag gcgtccgcgc cgcagtgggc gcagacggtc tcgcactcca   4380
cgagccaggt gaggtcgggc tggtcggggt caaaaaccag tttcccgccg ttctttttga   4440
tgcgtttctt acctttggtc tccatgagct cgtgtccccg ctgggtgaca aagaggctgt   4500
ccgtgtcccc gtagaccgac tttatggggc ggtcctcgga cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc cacctttccc agggtatgca   4680
aacacatgtc ccctcgtcc acatccagga aggtgattgg cttgtaagtg taggccacgt   4740
gaccggggtc cccggccggg ggggtataaa agggtgcagg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattgacgg   4920
tgccggcgga gatgcctttc aagagcccct cgtccatctg gtcagaaaag acgatctttt   4980
tgttgtcgag cttggtggcg aaggagccgt agagggcgtt ggagaggaac ttggcgatgg   5040
agcgcatggt ctggttttt tccttgtcgg cgcgctcctt ggcggcgatg ttgagctcga   5100
cgtactcgcg cgccacgcac ttccattcgg ggaagacggt ggtcagctcg tcgggcacga   5160
ttctgacctg ccagccccga ttatgcaggg tgatgaggtc cacactggtg gccacctcgc   5220
cgcgcagggg ctcattagtc cagcagaggc gtccgccctt gcgcgagcag aaggggggca   5280
ggggtccag catgacctcg tcggggggt cggcatcgat ggtgaagatg ccgggtccga   5340
ggtcggggtc aaagtagctg atggaagtgg ccagatcgtc cagggcagct tgccattcgc   5400
gcacggccag cgcgcgctcg tagggactga ggggcgtgcc ccagggcatg ggatgggtaa   5460
gcgcggaggc gtacatgccg cagatgtcgt agacgtagag gggctcctcg aggatgccga   5520
tgtaggtggg gtagcagcgc ccccgcgga tgctggcgcg cacgtagtca tacagctcgt   5580
gcgaggggggc gaggagcccc ggggccaggt tggtgcgaac ggcttttcg gcgcggtaga   5640
cgatctggcg gaaaatggca tgcgagtggg aggagatggt gggccttggg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt ccctttttgtt tccacagctc gcggttgaga aggaactctt   5880
cgcggtcctt ccagtactct tcgagggggga acccgtcctg atctgcacgg taagagcctg   5940
gcatgtagaa ctggttgacg gccttgtagg cgcagcagcc cttctccacg gggaggggcgt   6000
aggcctgggc ggccttgcgc agggaggtgt gcgtgaggggc gaaagtgtcc ctgaccatga   6060
ccttgaggaa ctggtgcttg aagtcgatat cgtcgcagcc ccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
```

-continued

```
ggttgttgat gacctgggcg gcgagcacga tctcgtcgaa gccgttgatg ttgtggccca   6300
cgatgtagag ttccacgaat cgcggacggc ccttgacgtg gggcagtttc ttgagctcct   6360
cgtaggtgag ctcgtcgggg tcgctgagcc cgtgctgctc gagcgcccag tcggcgagat   6420
gggggttggc gcgaggaag gaagtccaga gatccacggc cagggcggtt tgcagacggt    6480
cccggtactg acggaactgc tgcccgacgg ccattttttc gggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cggggcggt gcctcttcca    7320
tggttagaag cggcggcgag gacgcgcgcc gggcggcagg ggcggctcgg ggcccggagg    7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcggcggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgaacga gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtgccg ggggggtccc cgttgggcag    8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggcc ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
ggggcgccg ggcgcgaggt cctcgagcat ggtgcggtgg tagccgtaga tgtacctgga    9120
catccaggtg atgccggcgg cggtggtgga ggcgcgcggg aactcgcgga cgcggttcca   9180
gatgttcgcg agcggcagga agtagttcat ggtgggcacg gtctgccccg tgaggcgcgc   9240
gcagtcgtgg atgctctata cgggcaaaaa cgaaagcggt cagcggctcg actccgtggc   9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctctttgt tttgtttgtt tttgccagat gcatcccgta ctgcggcaga tgcgcccca    9720
ccaccttcca ccgcaacaac agcccctcc acagccggcg cttctgcccc cgccccagca    9780
gcaacttcca gccacgaccg ccgcggccgc cgtgagcggg gctggacaga gttatgatca   9840
ccagctggcc ttggaagagg gcgaggggct ggcgcgcctg ggggcgtcgt cgccggagcg   9900
gcacccgcgc gtgcagatga aaagggacg tcgcgaggcc tacgtgccca agcagaacct    9960
gttcagagac aggagcggcg aggagcccga ggagatgcgc gcggcccggt tccacgcggg  10020
gcgggagctg cggcgcggcc tggaccgaaa gagggtgcg agggacgagg atttcgcagg   10080
ggacgagctg acggggatca gccccgcgcg cgcgcacgtg gccgcggcca acctggtcac  10140
ggcgtacgag cagaccgtga aggaggagag caacttccaa aaatccttca caaccacgt   10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg cctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggtttttac atgcgcatga ccctgaaagt gctgaccctg agcgacgatc tggggtgtg   10620
ccgcaacgac aggatgcacc gtgcggtgag cgccgacggg gacggc tgacggc gacca   10680
ggagctgatg catagtctgc agcggggcct gaccgggggcc gggaccgagg gggagagcta  10740
ctttgacatg ggcgcggacc tgcactggca gcccagccgc cgggccttgg aggcggcggc   10800
aggaccctac gtagaagagg tggacgatga ggtggacgag gagggcgagt acctggaaga  10860
ctgatggcgc gaccgtattt ttgctagatg caacaacaac agccacctcc tgatcccgc    10920
atgcgggcgg cgctgcagag ccagccgtcc ggcattaact cctcggacga ttggacccag  10980
```

-continued

```
gccatgcaac gcatcatggc gctgacgacc cgcaaccccg aagcctttag acagcagccc 11040
caggccaacc ggctctcggc catcctggag gccgtggtgc cctcgcgctc caaccccacg 11100
cacgagaagg tcctggccat cgtgaacgcg ctggtggaga acaaggccat ccgcggcgac 11160
gaggccggcc tggtgtacaa cgcgctgctg gagcgcgtgg cccgctacaa cagcaccaac 11220
gtgcagacca acctggaccg catggtgacc gacgtgcgg aggccgtggc ccagcgcgag 11280
cggttccacc gcgagtccaa cctgggatcc atggtggcgc tgaacgcctt cctcagcacc 11340
cagcccgcca acgtgccccg gggccaggag gactacacca acttcatcag cgccctgcgc 11400
ctgatggtga ccgaggtgcc ccagagcgag gtgtaccagt ccgggccgga ctacttcttc 11460
cagaccagtc gccagggctt gcagaccgtg aacctgagcc aggctttcaa gaacttgcag 11520
ggcctgtggg gcgtgcaggc cccggtcggg gaccgcgcga cggtgtcgag cctgctgacg 11580
ccgaactcgc gcctgctgct gctgctggtg gcccccttca cggacagcgg cagcatcaac 11640
cgcaactcgt acctgggcta cctgattaac ctgtaccgcg aggccatcgg ccaggcgcac 11700
gtggacgagc agacctacca ggagatcacc cacgtgagcc gcgccctggg ccaggacgac 11760
ccgggcaacc tggaagccac cctgaacttt ttgctgacca accggtcgca gaagatcccg 11820
ccccagtacg cgctcagcac cgaggaggag cgcatcctgc gttacgtgca gcagagcgtg 11880
ggcctgttcc tgatgcagga gggggccacc cccagcgccg cgctcgacat gaccgcgcgc 11940
aacatggagc ccagcatgta cgccagcaac cgcccgttca tcaataaact gatggactac 12000
ttgcatcggg cggccgccat gaactctgac tatttcacca acgccatcct gaatccccac 12060
tggctcccgc cgccggggtt ctacacgggc gagtacgaca tgcccgaccc caatgacggg 12120
ttcctgtggg acgatgtgga cagcagcgtg ttctcccccc gaccgggtgc taacgagcgc 12180
cccttgtgga agaaggaagg cagcgaccga cgcccgtcct cggcgctgtc cggccgcgag 12240
ggtgctgccg cggcggtgcc cgaggccgcc agtccttttcc cgagcttgcc cttctcgctg 12300
aacagtatcc gcagcagcga gctgggcagg atcacgcgcc cgcgcttgct gggcgaagag 12360
gagtacttga atgactcgct gttgagaccc gagcgggaga agaacttccc caataacggg 12420
atagaaagcc tggtggacaa gatgagccgc tggaagacgt atgcgcagga gcacagggac 12480
gatccccgag cgtcgcaggg ggccacgagc cggggcaacg ccgcccgtaa acgccggtgg 12540
cacgacaggc agcggggaca gatgtgggac gatgaggact ccgccgacga cagcagcgtg 12600
ttggacttgg gtgggagtgg taacccgttc gctcacctgc gccccccgtat cgggcgcatg 12660
atgtaagaga aaccgaaaat aaatgatact caccaaggcc atggcgacca gcgtgcgttc 12720
gtttcttctc tgttgttgtt gtatctagta tgatgaggcg tgcgtacccg gagggtcctc 12780
ctccctcgta cgagagcgtg atgcagcagg cgatggcgcc ggcggcgatg cagccccgc 12840
tggaggctcc ttacgtgccc ccgcggtacc tggcgcctac ggaggggcgg aacagcattc 12900
gttactcgga gctggcaccc ttgtacgata ccacccggtt gtacctggtg gacaacaagt 12960
cggcggacat cgcctcgctg aactaccaga acgaccacag caacttcctg accaccgtgg 13020
tgcagaacaa tgacttcacc cccacggagg ccagcaccca gaccatcaac tttgacgagc 13080
gctcgcggtg gggcggccag ctgaaaacca tcatgcacac caacatgccc aacgtgaacg 13140
agttcatgta cagcaacaag ttcaaggcgc gggtgatggt ctcccgcaag acccccaatg 13200
gggtgacagt gacagaggat tatgatggta gtcaggatga gctgaagtat gaatgggtgg 13260
aatttgagct gcccgaaggc aacttctcgg tgaccatgac catcgacctg atgaacaacg 13320
ccatcatcga caattacttg gcggtggggc ggcagaacgg ggtgctggag agcgacatcg 13380
gcgtgaagtt cgacactagg aacttcaggc tgggctggga ccccgtgacc gagctggtca 13440
tgcccggggt gtacaccaac gaggctttcc atccccgatat tgtcttgctg cccggctgcg 13500
gggtgacttt caccgagagc cgcctcagca acctgctggg cattcgcaag ggcagccct 13560
tccaggaagg cttccagatc atgtacgagg atctggaggg gggcaacatc cccgcgctcc 13620
tggatgtcga cgcctatgag aaaagcaagg aggatgcagc agctgaagca actgcagccg 13680
tagctaccgc ctctaccgag gtcaggggcg ataattttgc aagcgccgca gcagtggcag 13740
cggccgaggc ggctgaaacc gaaagtaaga tagtcattca gccggtggag aaggatagca 13800
agaacaggag ctacaacgta ctaccggaca agataaacac cgcctaccgc agctggtacc 13860
tagcctacaa ctatggcgac cccgagaagg gcgtgcgctc ctggacgctg ctcaccacct 13920
cggacgtcac ctgcggcgtg gagcaagtct actggtcgct gcccgacatg atgcaagacc 13980
cggtcacctt ccgctccacg cgtcaagtta gcaactaccc ggtggtgggc gccgagctcc 14040
tgcccgtcta ctccaagagc ttcttcaacc agcaggccgt ctactcgcag cagctgcgcg 14100
ccttcacctc gcttacgcac gtcttcaacc gcttcccga gaaccagatc ctcgtccgcc 14160
cgccgcgcc caccattacc accgtcagtg aaaacgttcc tgctctcaca gatcacggga 14220
ccctgccgct gcgcagcagt atccgggag tccagccggt gaccgttact gacgccagac 14280
gccgcacctg cccctacgtc tacaaggccc tgggcatagt cgcgccgcgc gtcctctcga 14340
gccgcacctt ctaaatgtcc attctcatct cgcccagtaa taacaccggt tggggcctgc 14400
gcgcgcccag caagatgtac ggaggcgctc gccaacgctc cacgcaacac cccgtgcgcg 14460
tgcgcgggca cttccgcgct ccctgggcg ccctcaaggg ccgcgtgcgg tcgcgcacca 14520
ccgtcgacga cgtgatcgac caggtggtgg ccgacgcgcg caactacacc cccgccgccg 14580
cgcccgtctc caccgtggac gccgtcatcg acagcgtggt ggccgacgcg cgccggtacg 14640
cccgcgccaa gagccggcgg cggcgcatcg cccggcggca ccgagcacc cccgccatgc 14700
gcgcggcgcg agccttgctg cgcagggcca ggcgcacggg acgcagggcc atgctcaggg 14760
cggccagacg cgcggcttca ggcgccagcg ccggcacggc ccggagacgc ccggcgagcg 14820
cggcggcagc ggccatcgcc agcatgtccc gcccgcggcg agggaacgtg tactgggtgg 14880
gcgacgccgc caccggtgtg cgcgtgcccg tgcgcacccg cccccctcgc acttgaagat 14940
gttcacttcg cgatgttgat gtgtcccagc ggcgaggagg atgtccaagc gcaaattcaa 15000
ggaagagatg ctccaggtca tcgcgcctga gatctacgcc cctgcggtgg tgaaggagga 15060
aagaaagccc cgcaaaatca agcgggtcaa aaaggacaaa aaggaagaag aaagtgatgt 15120
ggacggattg gtggagtttg tgcgcgagtt cgccccccgg cggcgcgtgc agtggcgcgg 15180
gcggaaggtg caaccggtgc tgagacccgg caccaccgtg gtcttcacgc ccggcgagcg 15240
ctccggcacc gcttccaagc gctcctacga cgaggtgtac ggggatgatg atattctgga 15300
gcaggcggcc gagcgcctgg gcgagtttgc ttacggcaag cgcagccgtt ccgcaccgaa 15360
ggaagaggtg gtgtccatcc cgctggacca cggcaaccgc acgcgcaact ccaagcccgt 15420
gaccttgcag caggtgctgc cgaccgcggc gccgcgccgg gggttcaagc gcgagggcga 15480
ggatctgtac cccaccatgc agctgatggt gcccaagcgc cagaagctgg aagacgtgct 15540
ggagaccatg aaggtggacc cggacgtgca gcccgaggtc aaggtgcggc ccatcaagca 15600
ggtggccccg ggcctgggcg tgcagaccgt ggacatcaag attcccacgg agcccatgga 15660
aacgcagacc gagcccatga tcaagcccag caccagcacc atggaggtgc agacggatcc 15720
```

-continued

```
ctggatgcca tcggctccta gtcgaagacc ccggcgcaag tacgcgcgcg ccagcctgct   15780
gatgcccaac tacgcgctgc atccttccat catcccacg  ccgggctacc gcggcacgcg   15840
cttctaccgc ggtcatacca gcagccgccg ccgcaagacc accactcgcc gccgccgtcg   15900
ccgcaccgcc gctgcaacca cccctgccgc cctggtgcgg agagtgtacc gccgcggccg   15960
cgcacctctg accctgccgc gcgcgcgcta ccacccgagc atcgccattt aaactttcgc   16020
ctgctttgca gatcaatggc cctcacatgc cgccttcgcg ttcccattac gggctaccga   16080
ggaagaaaac cgcgccgtag aaggctggcg gggaacggga tgcgtcgcca ccaccaccgg   16140
cggcggcgcg ccatcagcaa gcggttgggg ggaggcttcc tgcccgcgct gatccccatc   16200
atcgccgcgg cgatcggggc gatccccggc attgcttccg tggcggtgca ggcctctcag   16260
cgccactgag acacacttgg aaacatcttg taataaacca atggactctg acgctcctgg   16320
tcctgtgatg tgtttcgta  dacagatgga agacatcaat ttttcgtccc tggctccgcg   16380
acacggcacg cggccgttca tgggcacctg gagcgacatc ggcaccagcc aactgaacgg   16440
gggcgccttc aattggagca gtctctggag cgggcttaag aatttcgggt ccacgcttaa   16500
aacctatggc agcaaggcgt ggaacagcac cacagggcag gcgctgaggg ataagctgaa   16560
agagcagaac ttccagcaga aggtggtcga tgggctcgcc tcgggcatca acggggtggt   16620
ggacctggcc aaccaggccg tgcagcggca gatcaacagc cgcctggacc cggtgccgcc   16680
cgccggctcc gtggagatgc cgcaggtgga ggaggagctg cctcccctgg acaagcgggg   16740
cgagaagcga ccccgccccg atgcggagga gacgctgctg acgcacacgg acgagccgcc   16800
cccgtacgag gaggcggtga aactgggtct gcccaccacg cggcccatcg cgcccctggc   16860
caccgggggtg ctgaaacccg aaaagcccgc gaccctggac ttgcctcctc cccagccttc   16920
ccgcccctct acagtggcta agccctgcc  gccggtggcc gtggcccgcg cgcgaccCgg   16980
gggcaccgcc cgccctcatg cgaactggca gagcactctg aacagcatcg tgggtctggg   17040
agtgcagagt gtgaagcgcc gccgctgcta ttaaacctac cgtagcgctt aacttgcttg   17100
tctgtgtgtg tatgtattat gtcgccgccg ccgctgtcca ccagaaggag gagtgaagag   17160
gcgcgtcgcc gagttgcaag atggccaccc catcgatgct gccccagtgg gcgtacatgc   17220
acatcgccgg acaggacgct tcggagtacc tgagtccggg tctggtgcag tttgcccgcg   17280
ccacagacac ctacttcagt ctggggaaca agtttaggga ccccacggtg gcgcccacgc   17340
acgatgtgac caccgaccgc agccagcggc tgacgctgcg cttcgtgccc gtggaccgcg   17400
aggacaacac ctactcgtac aaagtgcgct acacgctggc cgtgggcgac aaccgcgtgc   17460
tggacatggc cagcacctac tttgacatcc gcggcgtgct ggatcggggc cctagcttca   17520
aaccctactc cggcaccgcc tacaacagtc tggcccccaa gggagcaccc aacacttgtc   17580
agtggacata taaagccgat ggtgaaactg ccacagaaaa aacctataca tatggaaatg   17640
cacccgtgca gggcattaac atcacaaaag atggtattca acttggaact gacaccgatg   17700
atcagccaat ctacgcagat aaaacctatc agcctgaacc tcaagtgggt gatgctgaat   17760
ggcatgacat cactggtact gatgaaaagt atggaggcag agctcttaag cctgatacca   17820
aaatgaagcc ttgttatggt tctttttgcca agcctactaa taaagaagga ggtcaggcaa   17880
atgtgaaaac aggaacaggc actactaaag aatatgacat agacatggct ttctttgaca   17940
acagaagtgc ggctgctgct ggcctagctc cagaaattgt tttgtatact gaaaatgtgg   18000
atttggaaac tccagatacc catattgtat acaaagcagg cacagatgac agcagctctt   18060
ctattaattt gggtcagcaa gccatgcccca acagacctaa ctacattggt ttcagagaca   18120
actttatcgg gctcatgtac tacaacagca ctggcaatat ggggggtgctg gccggtcagg   18180
cttctcagct gaatgctgtg gttgacttgc aagacagaaa caccgagctg tcctaccagc   18240
tcttgcttga ctctctgggt gacagaaccc ggtatttcag tatgtggaat caggcggtgg   18300
acagctatga tcctgatgtg cgcattattg aaaatcatgg tgtggaggat gaacttccca   18360
actattgttt ccctctggat gctgttggca gaacagatac ttatcaggga attaaggcta   18420
atggaactga tcaaaccaca tggaccaaag atgacagtgt caatgatgct aatgagatag   18480
gcaaggtaa  tcattcgcc  atggaaatca acatccaagc caacctgtgg aggaacttcc   18540
tctacgccaa cgtggccctg tacctgcccg actcttacaa gtacacgccg gccaatgtta   18600
ccctgcccac caacaccaac acctacgatt acatgaacgg ccgggtggtg gcgccctcgc   18660
tggtggactc ctacatcaac atcggggcgc gctggtcgct ggatcccatg gacaacgtga   18720
acccecttcaa ccaccaccgc aatgcggggc tgcgctaccg ctccatgctc ctgggcaacg   18780
ggcgctacgt gccccttccac atccaggtgc cccagaaatt tttcgccatc aagagcctcc   18840
tgctcctgcc cggggtcctac acctacgagt ggaacttccg caaggacgtc aacatgatcc   18900
tgcagagctc cctcggcaac gacctgcgca cggacggggc ctccatctcc ttcaccagca   18960
tcaacctcta cgccaccttc ttccccatgg cgcacaacac ggcctccacg ctcgaggcca   19020
tgctgcgcaa cgacaccaac gaccagtcct tcaacgacta cctctcggcg gccaacatgc   19080
tctaccccat cccggccaac gccaccaacg tgcccatctc catcccctcg cgcaactggg   19140
ccgccttccg cggctggtcc ttcacgcgtc tcaagaccaa ggagacgccc tcgctgggct   19200
ccgggttcga ccccctcttc gtctactcgg gctccatccc ctacctcgac ggcacctttt   19260
acctcaacca cacctttaag aaggtctcca tcaccttcga ctcctcgtc agctggcccg   19320
gcaacgaccg gctcctgacg cccaacgagt tcgaaatcaa gcgcaccgtc gacggcgagg   19380
gctacaacgt ggcccagtgc aacatgacca aggactggtt cctggtccag atgctggccc   19440
actacaacat cggctaccag ggcttctacg tgcccgaggg ctacaaggac cgcatgtact   19500
ccttcttccg caacttccag cccatgagcc gccaggtggt ggacgaggtc aactacaagg   19560
actaccaggc cgtcacccctg gcctaccagc acaacaactc gggcttcgtc ggctacctcg   19620
cgcccaccat gcgccagggc cagccctacc ccgccaacta ccctacccg  ctcatcggca   19680
agagcgccgt caccagcgtc acccagaaaa agtcctctg  cgacagggtc atgtggcgca   19740
tccccttctc cagcaacttc atgtccatgg gcgcgctcac cgacctcggc cagaacatgc   19800
tctatgccaa ctcccgcccac gactacagaca tgaatttga  agtcgaccccc atggatgagt   19860
ccaccccttct ctatgttgtc ttcgaagtct tcgacgtcgt ccgagtgcac cagcccacc    19920
gcggcgtcat cgaggccgtc tacctgcgca cccccttctc ggccggtaac gccaccacct    19980
aagctcttgc ttcttgcaag ccatggccgc gggctccggc gagcaggagc tcagggccat   20040
catccgcgac ctgggctgcg ggccctactt cctgggcacc ttcgataagc gcttcccggg   20100
attcatggcc ccgcacaagc tggcgtcaac acggccggcc gcgagaccgg   20160
gggcgagcac tggctggcct tcgcctggaa cccgcgctcg aacacctgct acctcttcga   20220
ccccttcggg ttctcggacg agcgcctcaa gcagatctac cagttcgagt acgagggcct   20280
gctgcgccga agcgccctgg ccaccgagga ccgctgcgtc accctggaaa agtccaccca   20340
gaccgtgcag ggtccgcgct cggccgcctg cgggctcttc tgctgcatgt tcctgcacgc   20400
cttcgtgcac tggcccgacc gccccatgga caagaacccc accatgaact tgctgacggg   20460
```

-continued

```
ggtgcccaac ggcatgctcc agtcgcccca ggtggaaccc accctgcgcc gcaaccagga 20520
ggcgctctac cgcttcctca actcccactc cgcctacttt cgctcccacc gcgcgcgcat 20580
cgagaaggcc accgccttcg accgcatgaa tcaagacatg taaaccgtgt gtgtatgtta 20640
aatgtcttta ataaacagca ctttcatgtt acacatgcat ctgagatgat ttatttagaa 20700
atcgaaaggg ttctgccggg tctcgcgcatg gcccgcgggc agggacacgt tgcggaactg 20760
gtacttggcc agccacttga actcggggat cagcagtttg ggcagcgggg tgtcgggg aa 20820
ggagtcggtc cacagcttcc gcgtcagttg cagggcgccc agcaggtcgg gcgcggagat 20880
cttgaaatcg cagttgggac ccgcgttctg cgcgcgggag ttgcggtaca cggggttgca 20940
gcactggaac accatcaggg ccgggtgctt cacgctcgcc agcaccgtcg cgtcggtgat 21000
gctctccacg tcgaggtcct cggcgttggc catcccgaag ggggtcatct tgcaggtctg 21060
ccttcccatg gtgggcacgc acccgggctt gtggttgcaa tcgcagtgca gggggatcag 21120
catcatctgg gcctggtcgg cgttcatccc cgggtacatg gccttcatga aagcctccaa 21180
ttgcctgaac gcctgctggg ccttggctcc ctcggtgaag aagaccccgc aggacttgct 21240
agagaactgg ttggtggcgc aaccggcgtc gtgcacgcag agcggccgct cgttgttggc 21300
cagctgcacc acgctgcgcc cccagcggtt ctgggtgatc ttggcccggt cggggttctc 21360
cttcagcgcg cgctgcccgt tctcgctcgc cacatccatc tcgatcatgt gctccttctg 21420
gatcatggtc gtcccgtgca ggcaccgcag cttgccctcg gcctcggtgc acccgtgcag 21480
ccacagcgcg cacccggtgc actcccagtt cttgtgggcg atctgggaat gcgcgtgcac 21540
gaagccctgc aggaagcggc ccatcatggt ggtcagggtc ttgttgctag tgaaggtcag 21600
cggaatgccg cggtgctcct cgttgatgta caggtggcag atgcggcggt acacctcgcc 21660
ctgctcgggc atcagctgga agttggcttt caggtcggtc tccacgcggt agcggtccat 21720
cagcatagtc atgatttcca tacccttctc ccaggccgag acgatgggca ggctcatagg 21780
gttcttcacc atcatcttag cgctagcagc cgcggccagg gggtcgctct cgtccagggt 21840
ctcaaagctc cgcttgccgt ccttctcggt gatccgcacc gggggggtagc tgaagcccac 21900
ggccgccagc tcctcctcgg cctgtctttc gtcctcgctg tcctggctga cgtcctgcag 21960
gaccacatgc ttggtcttgc ggggtttctt cttgggcggc agcggcgggg gagatgttgg 22020
agatggcgag ggggagcgcg agttctcgct caccactact atctcttcct cttcttggtc 22080
cgaggccacg cggcggtagg tatgtctctt cgggggcaga ggcggaggcg acgggctctc 22140
gccgccgcga cttggcggat ggctggcaga gcccccttccg cgttcggggg tgcgctcccg 22200
gcggcgctct gactgacttc ctccgcgggc ggcattgtg ttctcctagg gaggaacaac 22260
aagcatggag actcagccat cgccaacctc gccatctgcc cccaccgccg acgagaagca 22320
gcagcagcag aatgaaagct taaccgcccc gccgcccagc cccgccacct ccgacgcggc 22380
cgtcccagac atgcaagaga tggaggaatc catcgagatt gacctgggct atgtgacgcc 22440
cgcggagcac gaggaggagc tggcagtgcg cttttcacaa gaagagatac accaagaaca 22500
gccagagcag gaagcagaga atgagcagag tcaggctggg ctcgagcatg acggcgacta 22560
cctccacctg agcgggggggg aggacgcgct catcaagcat ctggcccggc aggccaccat 22620
cgtcaaggat gcgctgctcg accgcaccga ggtgcccctc agcgtggagg agctcagccg 22680
cgcctacgag ttgaacctct tctcgccgcg cgtgcccccc aagcgccagc ccaatggcac 22740
ctgcgagccc aaccgcgcc tcaacttcta cccggtcttc gcggtgcccg aggccctggc 22800
cacctaccac atctttttca agaaccaaaa gatccccgtc tcctgccgcg ccaaccgcac 22860
ccgcgccgac gcccttttca acctgggtcc cggcgcccgc ctacctgata tcgcctcctt 22920
ggaagaggtt cccaagatct tcgagggtct gggcagcgac gagactcggg ccgcgaacgc 22980
tctgcaagga gaaggaggag agcatgagca ccacagcgcc ctggtcgagt tggaaggcga 23040
caacgcgcgg ctggcggtgc tcaaacgcac ggtcgagctg acccatttcg cctacccggc 23100
tctgaacctg cccccccaaag tcatgagcgc ggtcatggac caggtgctca tcaagcgcgc 23160
gtcgcccatc tccgaggacg agggcatgca agactccgag gagggcaagc ccgtggtcag 23220
cgacgacgag ttggcccggt ggctgggtcc taatgctagt ccccagagtt tggaagagcg 23280
gcgcaaactc atgatggccg tggtcctggt gaccgtggag ctggagtgcc tgcgccgctt 23340
cttcgccgac gcggagaccc tgcgcaaggt cgaggagaac ctgcactacc tcttcaggca 23400
cggggttcgtg cgccaggcct gcaagatctc caacgtggag ctgaccaacc tggtctccta 23460
catgggcagt ttgcacgaga accgcctggg gcagaacgtg ctgcacacca ccctgcgcgg 23520
ggaggcccgg cgcgactaca tccgcgactg cgtctacctc tacctctgcc acacctggca 23580
gacgggcatg ggcgtgtggc agcagtgtct ggaggagcag aacctgaaag agctctgcaa 23640
gctcctgcag aagaacctca agggtctgtg gaccgggttc gacgagcgca ccaccgcctc 23700
ggacctggcc gacctcattt tccccgagcg cctcaggctg acgctgacga aggcctgccc 23760
cgactttatg agccaaagca tgttgcaaaa cttttcgctct ttcatcctcg aacgctccga 23820
aatcctgccc gccacctgct ccgcgctgcc ctcggacttc gtgccgctga ccttccgcga 23880
gtgcccccccg ccgctgtgga gccactgcta cctgctgcgc ctggccaact acctggccta 23940
ccactcggac gtgatcgagg acgtcagcgg cgagggccctg ctcgagtgcc actgccggtg 24000
caacctctgc acgccgcacc gctccctggc ctgcaaccca cagctgctga gcgagaccca 24060
gatcatcggc accttcgagt tgcaagggcc cagcgaaggc gagggttcag ccgccaaggg 24120
gggtctgaaa ctcacccccgg ggctgtggac ctcggcctac ttgcgcaagt tcgtgcccga 24180
ggactaccat cccttcgaga tcaggttcta cgaggaccaa tcccatccgc ccaaggccga 24240
gctgtcgggc c tgcgtcatca ccagggggc gatcctggcc caattgcaag ctccagaa 24300
atcccgccaa gaattcttgc tgaaaaaggg ccgcgggggtc tacctcgacc cccagaccgg 24360
tgaggagctc aaccccggct tccccccagga tgccccgagg aaacaagaag ctgaaagtgg 24420
agctgccgcc cgtggaggat ttggaggaag actgggagaa cagcagtcag gcagaggagg 24480
aggagatgga ggaagactgg gacagcactc aggcagagga ggacagcctg caagacagtc 24540
tggaggaaga cgaggaggag gcagaggagg aggtggaaga cagccgcgcc gccagaccgt 24600
cgtcctcggc gggggagaaa gcaagcagca cggataccat ctccgctccg ggtcgggggtc 24660
ccgctcgacc acacagtaga tgggacgaga ccggacgatt cccgaacccc accacccaga 24720
ccggtaagaa ggagcggcag ggatacaagt cctggcgggg gcacaaaaac gccatcgtct 24780
cctgcttgca ggcctgcggg ggcaacatct ccttcacccg gcgctacctg ctcttccacc 24840
gcgggggtgaa cttttcccccgc aacatcttgc attactaccg tcacctccac agcccctact 24900
acttccaaga agaggcagca gcagcagaaa aagaccagca gaaaaccagc agctagaaaa 24960
tccacacgcgg cggcagcagg tggactgagg atcgcggcga acgagccggc gcaaaccccg 25020
gagctgagga accggatctt tcccaccctc tatgccatct tccagcagag tcgggggcag 25080
gagcaggaac tgaaagtcaa gaaccgttct ctgcgctcgc tcaccgcag ttgtctgtat 25140
cacaagagcg aagaccaact tcagcgcact ctcgaggacg ccgaggctct cttcaacaag 25200
```

```
tactgcgcgc tcactcttaa agagtagccc gcgcccgccc agtcgcagaa aaaggcggga   25260
attacgtcac ctgtgccctt cgccctagcc gcctccaccc atcatcatga gcaaagagat   25320
tcccacgcct tacatgtgga gctaccagcc ccagatgggc ctggccgccg gtgccgccca   25380
ggactactcc acccgcatga attggctcag cgccgggccc gcgatgatct cacgggtgaa   25440
tgacatccgc gcccaccgaa accagatact cctagaacag tcagcgctca ccgccacgcc   25500
ccgcaatcac ctcaatccgc gtaattggcc cgccgccctg gtgtaccagg aaattcccca   25560
gcccacgacc gtactacttc cgcgagacgc ccaggccgaa gtccagctga ctaactcagg   25620
tgtccagctg gcgggcggcg ccaccctgtg tcgtcaccgc cccgctcagg gtataaagcg   25680
gctggtgatc cggggcagag gcacacagct caacgacgag gtggtgagct cttcgctggg   25740
tctgcgacct gacggagtct tccaactcgc cggatcgggg agatcttcct tcacgcctcg   25800
tcaggccgtc ctgactttgg agagttcgtc ctcgcagccc cgctcgggtg gcatcggcac   25860
tctccagttc gtggaggagt tcactccctc ggtctacttc aacccccttct ccggctcccc   25920
cggccactac ccggacgagt tcatcccgaa cttcgacgcc atcagcgagt cggtggacgg   25980
ctacgattga aactaatcac ccccttatcc agtgaaataa agatcatatt gatgatgatt   26040
ttacagaaat aaaaaataat catttgattt gaaataaaga tacaatcata ttgatgattt   26100
gagtttaaca aaaaaataaa gaatcactta cttgaaatct gataccaggt ctctgtccat   26160
gtttctgcc aacaccactt cactcccctc ttcccagctc tggtactgca ggccccggcg   26220
ggctgcaaac ttcctccaca cgctgaaggg gatgtcaaat tcctcctgtc cctcaatctt   26280
cattttatct tctatcagat gtccaaaaag cgcgtccggg tggatgatga cttcgacccc   26340
gtctacccct acgatgcaga caacgcaccg accgtgccct tcatcaaccc cccettcgtc   26400
tcttcagatg gattccaaga gaagccctg ggggtgttgt ccctgcgact ggccgacccc   26460
gtcaccacca agaacgggga aatcaccctc aagctgggag aggggtgga cctcgattcc   26520
tcgggaaaac tcatctccaa cacggccacc aaggccgccg cccctctcag ttttccaac   26580
aacaccattt cccttaacat ggatcacccc ttttacacta aagatggaaa attatcctta   26640
caagtttctc caccattaaa tatactgaga acaagcattc taaacacact agctttaggt   26700
tttggatcag gtttaggact ccgtggctct gccttggcag tacagttagt ctctccactt   26760
acatttgata ctgatggaaa cataaagctt accttagaca gaggtttgca tgttacaaca   26820
ggagatgcaa ttgaaagcaa cataagctgg gctaaaggtt taaaatttga agatggagcc   26880
atagcaacca acattggaaa tgggttagag tttggaagca gtagtacaga aacaggtgtt   26940
gatgatgctt acccaatcca agttaaactt ggatctggcc ttagctttga cagtacagga   27000
gccataatgg ctggtaacaa agaagacgat aaactcactt tgtgtgacaac acctgatcca   27060
tcaccaaact gtcaaatact cgcagaaaat gatgcaaaac taacactttg cttgactaaa   27120
tgtggtagtc aaatactggc cactgtgtca gtcttagttg taggaagtgg aaacctaaac   27180
cccattactg gcaccgtaag cagtgctcag gtgtttctac gttttgatgc aaacggtgtt   27240
cttttaacag aacattctac actaaaaaaa tactgggggt ataggcaggg agatagcata   27300
gatggcactc catataccaa tgctgtagga ttcatgccca atttaaaagc ttatccaaag   27360
tcacaaagtt ctactactaa aaataatata gtagggcaag tatacatgaa tggagatgtt   27420
tcaaaaccta tgcttctcac tataacctc aatggtactg atgacagcaa cagtacatat   27480
tcaatgtcat tttcatacac ctggactaat ggaagctatg ttggagcaac atttggggct   27540
aactcttata ccttctcata catcgcccaa gaatgaacac tgtatcccac cctgcatgcc   27600
aacccttccc accccactct gtggaacaaa ctctgaaaca caaaataaaa taaagttcaa   27660
gtgttttatt gattcaacag ttttacagga ttcgagcagt tattttttcct ccaccctccc   27720
aggacatgga atacaccacc ctctcccccc gcacagcctt gaacatctga atgccattgg   27780
tgatggacat gcttttggtc tccacgttcc acacagtttc agagcgagcc agtctcgggt   27840
cggtcaggga gatgaaaccc tccgggcact cccgcatctg cacctcacag ctcaacagct   27900
gaggattgtc ctcggtggtc gggatcacgg ttatctggaa gaagcagaag agcggcggtg   27960
ggaatcatag tccgcgaacg ggatcggccg gtggtgtcga atcaggcccc gcagcagtcg   28020
ctgccgccgc cgctccgtca agctgctgct caggggtcc gggtccaggg actccctcag   28080
catgatgccc acggccctca gcatcagtcg tctggtgcgg cgggcgcagc agcgcatgcg   28140
gatctcgctc aggtcgctgc agtacgtgca acacagaacc accaggttgt tcaacagtcc   28200
atagttcaac acgctccagc cgaaactcat cgcgggaagg atgctaccca cgtggccgtc   28260
gtaccagatc ctcaggtaaa tcaagtggtg cccctccag aacacgctgc ccacgtacat   28320
gatctccttg ggcatgtggc ggttcaccac ctcccggtac cacatcaccc tctgttgaa   28380
catgcagccc cggatgatcc tgcggaacca cagggccagc accgccccgc ccgccatgca   28440
gcgaagagac cccgggtccc ggcaatggca atggaggacc caccgctcgt acccgtggat   28500
catctgggag ctgaacaagt ctatgttggc acagcacagg catatgctca tgcatctctt   28560
cagcactctc aactcctcgg gggtcaaaac catatcccag ggcacgggga actcttgcag   28620
gacagcgaac cccgcagaac agggcaatcc tcgcacagaa cttacattgt gcatggacag   28680
ggtatcgcaa tcaggcagca ccgggtgatc ctccaccaga gaagcgcggg tctcggtctc   28740
ctcacagcgt ggtaaggggg ccggccgata cgggtgatgg cgggacgcgg ctgatcgtgt   28800
tcgcgaccgt gtcatgatgc agttgctttc ggacattttc gtacttgctg tagcagaacc   28860
tggtccgggc gctgcacacc gatcgccggc ggcggtctcg gcgcttggaa cgctcggtgt   28920
tgaaattgta aaacagccac tctctcagac cgtgcagcag atctagggcc tcaggagtga   28980
tgaagatccc atcatgcctg atggctctga tcacatcgac caccgtggaa tgggccgagac   29040
ccagccagat gatgcaattt tgttgggttt cggtgacggc gggggaggga agaacaggaa   29100
gaaccatgat taacttttaa tccaaacggt ctcggagtac ttcaaaatga agatcgcgga   29160
gatggcacct ctcgccccg ctgtgttggt ggaaaataac agccaggtca aaggtgatac   29220
ggttctcgag atgttccacg gtggcttcca gcaaagcctc cacgcgcaca tccagaaaca   29280
agacaatagc gaaagcggga gggttctcta attcctcaat catcatgtta cactcctgca   29340
ccatccccag ataattttca tttttccagc cttgaatgat tcgaactagt tcctgaggta   29400
aatccaagcc agccatgata aagagctcgc gcagagcgcc ctccaccggc attcttaagc   29460
acaccctcat aattccaaga tattctgctc ctggttcacc tgcagcagat tgacaagcgg   29520
aatatcaaaa tctctgccgc gatccctgag ctcctccctc agcaataact gtaagtactc   29580
tttcatatcc tctccgaaat ttttagccat aggaccacca ggataagat tagggcaagc   29640
cacagtacag ataaaccgaa gtcctcccca gtgagcattg ccaaatgcaa gactgctata   29700
agcatgctgg ctagacccgg tgatatcttc cagataactg gacagaaaat cgcccaggca   29760
atttttaaga aaatcaacaa aagaaaaatc ctccaggtgg acgtttagag cctcgggaac   29820
aacgatgaag taaatgcaag cggtgcgttc cagcatggtt agttagctga tctgtagaaa   29880
aaacaaaaat gaacattaaa ccatgctagc ctggcgaaca ggtgggtaaa tcgttctctc   29940
```

-continued

```
cagcaccagg caggccacgg ggtctccggc gcgaccctcg taaaaattgt cgctatgatt  30000
gaaaaccatc acagagagac gttcccggtg gccggcgtga atgattcgac aagatgaata  30060
caccccgga acattggcgt ccgcgagtga aaaaaagcgc ccgaggaagc aataaggcac    30120
tacaatgctc agtctcaagt ccagcaaagc gatgccatgc ggatgaagca caaaattctc  30180
aggtgcgtac aaaatgtaat tactcccctc ctgcacaggc agcaaagccc ccgatccctc  30240
caggtacaca tacaaagcct cagcgtccat agcttaccga gcagcagcac acaacaggcg    30300
caagagtcag agaaaggctg agctctaacc tgtccacccg ctctctgctc aatatatagc    30360
ccagatctac actgacgtaa aggccaaagt ctaaaaatac ccgccaaata atcacacacg    30420
cccagcacac gcccagaaac cggtgcacaca ctcaaaaaaa tacgcgcact tcctcaaacg   30480
cccaaaactg ccgtcatttc cgggttccca cgctacgtca tcaaaacacg actttcaaat    30540
tccgtcgacc gttaaaaacg tcacccgccc cgcccctaac ggtcgcccgt ctctcagcca    30600
atcagcgccc cgcatcccca aattcaaaca cctcatttgc atattaacgc gcacaaaaag    30660
tttgaggtat attattgatg atgg                                          30684
```

```
SEQ ID NO: 14          moltype = DNA  length = 8602
FEATURE                Location/Qualifiers
misc_feature           1..8602
                       note = Description of Artificial Sequence: Synthetic
                        polynucleotide
source                 1..8602
                       mol_type = other DNA
                       organism = synthetic construct
SEQUENCE: 14
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccgagacg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatggaga gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccatg aggctaagga ggtgcgtgaa gccgaggagt    1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg    1860
tgccagaggga acatgcaata cccgtccagg actttcaagc tctgagtgaa agtgccacca  1920
ttgtgtacaa cgaacgtgag ttcgtaaaca ggtacctgga ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctcattac caagtaccaa ccataggggt gtatgcgtg ccaggatcag   2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata   2400
ttgacgaagc ttttgcttgt catgcaggta ctctcagagg gctcatcgac gctataaagac   2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg  2880
tcctactgac ccgcacggag accgcatcg tgtggaaaac actagccggc gacccatgga  2940
taaaaacact gactgccaag taccctggga atttcactgc cacgatagag gagtggcaag  3000
cagagcgtga tgccatcatg aggcacatct tggagagacc ggaccctacc gacgtcttcc    3060
agaataaggc aaacgtgtgt tggggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
```

-continued

```
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcggcac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag aagcagtgtg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaacttc tcatatttgg aagggaccaa gtttccaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gaacgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcgggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacagagca ggagtttgag gcgttcgtag cacaacaaca atgacggttt gagtcgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa gctacaacta gctagacgta  5940
ttctgcaagg cctagggcat tatttgaagg cagaagaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct cttttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgg  6900
tgacgctgat tgaggcggct tccggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat aatgtgctgtg gtgggaagt  7200
aagcgcctta tttctgtgga gggtttattt tgtgtgactc cgtcgaccggc acagcgtgcc  7260
gtgtggcaga cccccctaaaa aggctgttta gcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctcgagg  7500
gggcccctat aactctctac ggctaacctg aatggactac gactctagaa tagtctttaa  7560
ttaaagtccg ccatatgagg ccaccatgca gatcttcgtg aagaccctga ccggcaagac  7620
catcaccta gaggtggagc ccagtgacac catcgagaac gtgaaggcca agatccagga  7680
taaagagggc atcccccctg accagcagag gctgatcttt gccggcaagc agctggaaga  7740
tggccgcaac ctctctgatt acaacatcca gaaggagtca acccgcctcc tggtccttcg  7800
cctgagaggt ggcgctgctt acagtataat caactttgaa aaactggctg cttacggcat  7860
cctgggcttt gtgtttacac tggctgccta cctgctgttt ggctatcctg tgtacgtggc  7920
cgcttatgga ctgtgtaccc tggtggccat gctggctgct acaatctgg tgcctatggt  7980
ggccacagtg gccgccctatt gtcttggcgg actgctgaca atggtggcag cctacagccc  8040
gagctatgcg tatcatcagt ttgcagccta cggcccagga ccaggcgcta aatttgtggc  8100
```

```
tgcctggaca ctgaaagccg ccgctggacc aggtcctgga cagtacatca aggccaacag   8160
caagttcatc ggcatcaccg aactcggccc aggaccaggc tatccctacg atgtgcctga   8220
ttacgcctga tagtgatgat tcgaacggcc gtatcacgcc caaacattta cagccgcggt   8280
gtcaaaaacc gcgtggacgt ggttaacatc cctgctggga ggatcagccg taattattat   8340
aattggcttg gtgctggcta ctattgtggc catgtacgtg ctgaccaacc agaaacataa   8400
ttgaatacag cagcaattgg caagctgctt acatagaact cgcggcgatt ggcatgccgc   8460
cttaaaattt ttattttatt ttttcttttc ttttccgaat cggattttgt ttttaatatt   8520
tcaaaaaaaa aaaaaaaaaa aaaaaaaaaa aaaaaaaaaa aaaaaaaaaa aaaaaaaaaa   8580
aaaaaaaaaa aaaaaaaaaa aa                                            8602
```

```
SEQ ID NO: 15           moltype = DNA  length = 9595
FEATURE                 Location/Qualifiers
misc_feature            1..9595
                        note = Description of Artificial Sequence: Synthetic
                        polynucleotide
source                  1..9595
                        mol_type = other DNA
                        organism = synthetic construct
SEQUENCE: 15
atgggcggcg catgagagaa gcccagacca attacctacc caaaatggag aaagttcacg   60
ttgacatcga ggaagacagc ccattcctca gagctttgca gcggagcttc ccgcagtttg   120
aggtagaagc caagcaggtc actgataatg accatgctaa tgccgagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggacgt cgccgccgtc atgagcgacc   420
ctgacctgga aactgagact atgtgcctcc acgacgacga gtcgtgtcgc tacgaagggc   480
aagtcgctgt ttaccaggat gtatacgcgg ttgacggacc gacaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
cgatgcaccg cgagggattc ttgtgctgca aagtgacaga cacattgaac ggggagaggg   1020
tctctttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatgggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaaactgtaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca cccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcacccact gttccgttat tcattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttttcttc attcgtcagc aaattgaagg   3540
gcagaactgt cctggtggtc ggggaaaagt tgtccgtccc aggcaaaatg gttgactggt   3600
```

-continued

```
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcgggccaagg   4680
atatagcaga aattaatgcc atgtggcccg ttgcaacgag ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc    5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctgacgta    5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgg   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc    7260
gtgtggcaga cccccctaaaa aggctgttta gcttggcaa acctctggca gcagacgatg    7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaaagtccg ccatatgaga tggaagatgc caaaaacatt aagaagggcc cagcgccatt   7620
ctacccactc gaagacggga ccgccggcga gcagctgcac aaagccatga agcgctacgc   7680
cctggtgccc ggcaccatcg cctttaccga cgcacatatc gaggtggaca ttacctacgc   7740
cgagtacttc gagatgagcg ttcggctggc agaagctatg aagcgctatg gctgaatac    7800
aaaccatcgg atcgtggtgt gcagcgagaa tagcttgcag ttcttcatgc ccgtgttggg   7860
tgccctgttc atcggtgtgg ctgtggcccc agctaacgac atctacaacg agcgcgagct   7920
gctgaacagc atgggcatca gccagcccac cgtcgtattc gtgagcaaga aagggctgca   7980
aaagatcctc aacgtgcaaa agaagctacc gatcataaaa gatatcatca tcatggatag   8040
caagaccgac taccagggct tccaaagcat gtacaccttc gtgacttccc atttgccacc   8100
cggcttcaac gagtacgact tcgtgcccga gagcttcgac cgggacaaaa ccatcgccct   8160
gatcatgaac agtagtggca gtaccggatt gcccaagggc gtagccctac cgcaccgcac   8220
cgcttgtgtc cgattcagtc atgcccgcga ccccatcttc ggcaaccaga tcatccccga   8280
caccgctatc ctcagcgtgg tgccatttca ccacggcttc ggcatgttca ccacgctggg   8340
```

```
ctacttgatc tgcggctttc gggtcgtgct catgtaccgc ttcgaggagg agctattctt   8400
gcgcagcttg caagactata agattcaatc tgccctgctg gtgcccacac tatttagctt   8460
cttcgctaag agcactctca tcgacaagta cgacctaagc aacttgcacg agatcgccag   8520
cggcgggggcg ccgctcagca aggaggtagg tgaggccgtg gccaaacgct tccacctacc   8580
aggcatccgc cagggctacg gcctgacaga aacaaccagc gccattctga tcaccccga   8640
aggggacgac aagcctggcg cagtaggcaa ggtggtgccc ttcttcgagg ctaaggtggt   8700
ggacttggac accggtaaga cactgggtgt gaaccagcgc ggcgagctgt gcgtccgtgg   8760
ccccatgatc atgagcggct acgttaacaa ccccgaggct acaaacgctc tcatcgacaa   8820
ggacggctgg ctgcacagcg gcgacatcgc ctactgggac gaggacgagc acttcttcat   8880
cgtggaccgg ctgaagagcc tgatcaaata caagggctac caggtagccc cagccgaact   8940
ggagagcatc ctgctgcaac accccaacat cttcgacgcc ggggtcgccg gcctgcccga   9000
cgacgatgcc ggcgagctgc ccgccgcagt cgtcgtgctg gaacacggta aaaccatgac   9060
cgagaaggag atcgtggact atgtggccag ccaggttaca accgccaaga agctgcgcgg   9120
tggtgttgtg ttcgtggacg aggtgcctaa aggactgacc ggcaagttgg acgccgcaa   9180
gatccgcgag attctcatta aggccaagaa gggcggcaag atcgccgtgt aattcgaacg   9240
gccgtatcac gcccaaacat ttacagccgc ggtgtcaaaa accgcgtgga cgtggttaac   9300
atccctgctg ggaggatcag ccgtaattat tataattggc ttggtgctgg ctactattgt   9360
ggccatgtac gtgctgacca accagaaaca taattgaata cagcagcaat tggcaagctg   9420
cttacataga actcgcggcg attggcatgc cgccttaaaa ttttttatttt atttttttct   9480
ttcttttccg aatcggattt tgttttttaat atttcaaaaa aaaaaaaaaa aaaaaaaaaa   9540
aaaaaaaaaa aaaaaaaaaa aaaaaaaaaa aaaaaaaaaa aaaaaaaaaa aaaaa         9595
```

```
SEQ ID NO: 16               moltype = AA   length = 139
FEATURE                     Location/Qualifiers
REGION                      1..139
                            note = Description of Artificial Sequence: Synthetic
                             polypeptide
source                      1..139
                            mol_type = protein
                            organism = synthetic construct
SEQUENCE: 16
PSSLSASVGD RVTITCRASQ SINSYLDWYQ QKPGKAPKLL IYAASSLQSG VPSRFSGSGS   60
GTDFTLTISS LQPEDFATYY CQQYYSTPFT FGPGTKVEIK RTVAAPSVFI FPPSDEQLKS   120
GTASVVCLLN NFYPREAKV                                                 139
```

```
SEQ ID NO: 17               moltype = AA   length = 167
FEATURE                     Location/Qualifiers
REGION                      1..167
                            note = Description of Artificial Sequence: Synthetic
                             polypeptide
source                      1..167
                            mol_type = protein
                            organism = synthetic construct
SEQUENCE: 17
GVVQPGRSLR LSCAASGFTF SSYGMHWVRQ APGKGLEWVA VIWYDGSNKY YADSVKGRFT   60
ISRDNSKNTL YLQMNSLRAE DTAVYYCARD PRGATLYYYY GMDVWGQGT TVTVSSASTK   120
GPSVFPLAPC SRSTSESTAA LGCLVKDYFP EPVTVSWNSG ALTSGVH               167
```

```
SEQ ID NO: 18               moltype = AA   length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 18
GFTFSSYGMH                                                          10
```

```
SEQ ID NO: 19               moltype = AA   length = 15
FEATURE                     Location/Qualifiers
REGION                      1..15
                            note = Description of Artificial Sequence: Synthetic peptide
source                      1..15
                            mol_type = protein
                            organism = synthetic construct
SEQUENCE: 19
VIWYDGSNKY YADSV                                                    15
```

```
SEQ ID NO: 20               moltype = AA   length = 16
FEATURE                     Location/Qualifiers
REGION                      1..16
                            note = Description of Artificial Sequence: Synthetic peptide
source                      1..16
                            mol_type = protein
                            organism = synthetic construct
SEQUENCE: 20
DPRGATLYYY YYGMDV                                                   16
```

```
SEQ ID NO: 21               moltype = AA   length = 11
```

```
FEATURE              Location/Qualifiers
REGION               1..11
                     note = Description of Artificial Sequence: Synthetic peptide
source               1..11
                     mol_type = protein
                     organism = synthetic construct
SEQUENCE: 21
RASQSINSYL D                                                              11

SEQ ID NO: 22        moltype = AA   length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 22
AASSLQS                                                                   7

SEQ ID NO: 23        moltype = AA   length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 23
QQYYSTPFT                                                                 9

SEQ ID NO: 24        moltype = AA   length = 108
FEATURE              Location/Qualifiers
REGION               1..108
                     note = Description of Artificial Sequence: Synthetic
                      polypeptide
source               1..108
                     mol_type = protein
                     organism = synthetic construct
SEQUENCE: 24
EIVLTQSPGT LSLSPGERAT LSCRASQRVS SSYLAWYQQK PGQAPRLLIY DASSRATGIP 60
DRFSGSGSGT DFTLTISRLE PEDFAVYYCQ QYGSLPWTFG QGTKVEIK          108

SEQ ID NO: 25        moltype = AA   length = 121
FEATURE              Location/Qualifiers
REGION               1..121
                     note = Description of Artificial Sequence: Synthetic
                      polypeptide
source               1..121
                     mol_type = protein
                     organism = synthetic construct
SEQUENCE: 25
EVQLVESGGG LVQPGGSLRL SCAASGFTFS RYWMSWVRQA PGKGLEWVAN IKQDGSEKYY 60
VDSVKGRFTI SRDNAKNSLY LQMNSLRAED TAVYYCAREG GWFGELAFDY WGQGTLVTVS 120
S                                                            121

SEQ ID NO: 26        moltype = AA   length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 26
RYWMS                                                                     5

SEQ ID NO: 27        moltype = AA   length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 27
NIKQDGSEKY YVDSVKG                                                        17

SEQ ID NO: 28        moltype = AA   length = 12
FEATURE              Location/Qualifiers
REGION               1..12
                     note = Description of Artificial Sequence: Synthetic peptide
source               1..12
```

```
                              mol_type = protein
                              organism = synthetic construct
SEQUENCE: 28
EGGWFGELAF DY                                                    12

SEQ ID NO: 29      moltype = AA  length = 12
FEATURE            Location/Qualifiers
REGION             1..12
                   note = Description of Artificial Sequence: Synthetic peptide
source             1..12
                   mol_type = protein
                   organism = synthetic construct
SEQUENCE: 29
RASQRVSSSY LA                                                    12

SEQ ID NO: 30      moltype = AA  length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 30
DASSRAT                                                           7

SEQ ID NO: 31      moltype = AA  length = 9
FEATURE            Location/Qualifiers
REGION             1..9
                   note = Description of Artificial Sequence: Synthetic peptide
source             1..9
                   mol_type = protein
                   organism = synthetic construct
SEQUENCE: 31
QQYGSLPWT                                                         9

SEQ ID NO: 32      moltype = DNA  length = 2019
FEATURE            Location/Qualifiers
misc_feature       1..2019
                   note = Description of Artificial Sequence: Synthetic
                    polynucleotide
source             1..2019
                   mol_type = other DNA
                   organism = synthetic construct
SEQUENCE: 32
gcccgggcat ttaaatgcga tcgcatcgat tacgactcta gaatagtcta gtccgcaggc  60
caccatgcag atcttcgtga agaccctgac cggcaagacc atcaccctag aggtggagcc  120
cagtgacacc atcgagaacg tgaaggccaa gatccaggat aaagagggca tccccctga  180
ccagcagagg ctgatctttg ccggcaagca gctggaagat ggccgcaccc tctctgatta  240
caacatccag aaggagtcaa ccctgcacct ggtccttcgc ctgagaggtg ccatgtttca  300
ggcgctgagc gaaggctgca ccccgtatga tattaaccag atgctgaacg tgctgggcga  360
tcatcaggtc tcaggccttg agcagcttga gagtataatc aactttgaaa aactgactga  420
atggaccagt tctaatgtta tgcctatcct gtctcctctg acaaagggca tcctgggctt  480
cgtgtttacc ctgaccgtgc cttctgagag aggacttagc tgcattagcg aagcggatgc  540
gaccaccccg gaaagcgcga acctgggcga agaaattctg agccagctgt atctttggcc  600
aaggtgacc taccattccc ctagttatgc ttaccaccaa tttgaaagac gagccaaata  660
taaaagacac ttccccggct ttggccagag cctgctgttt ggctaccctg tgtacgtgtt  720
cggcgattgc gtgcagggcg attgggatgc gattcgcttt cgctattgcg cgccgccggg  780
ctatgcgctg ctgcgctgca acgataccaa ctatagcgct ctgctggctg tggggggccct  840
agaaggaccc aggaatcagg actggcttgg tgtcccaaga caacttgtaa ctcggatgca  900
ggctattcag aatgccggcc tgtgtaccct ggtggccatg ctggaagaga caatcttctg  960
gctgcaagcg tttctgatgg cgctgaccga tagcggcccg aaaaccaaca ttattgtgga  1020
tagccagtat gtgatgggca ttagcaaacc gagctttcag gaatttgtgg attgggaaaa  1080
cgtgagcccg gaactgaaca gcaccgatca gccgtttttgg caagccggaa tcctggccag  1140
aaatctggtg cctatggtgg ccacagtgca gggccagaac ctgaagtacc agggtcagtc  1200
actagtcatc tctgcttcta tcattgtctt caacctgctg gaactggaag gtgattatcg  1260
agatgatggc aacgtgtggg tgcataccccc gctgagcccg cgcaccctga cgcgtgggt  1320
gaaagcggtg gaagaaaaaa aaggtattcc agttcaccta gagctggcca gtatgaccaa  1380
catggagctc atgagcagta ttgtgcatca gcaggtcaga acatacggcc ccgtgttcat  1440
gtgtctcggc ggactgctta caatggtggc tggtgctgtg tggctgacag tgcgagtgct  1500
cgagctgttc cgggccgcgc agctggccaa cgacgtggtc ctccagatca tggagctttg  1560
tggtgcagcg tttcgccagg tgtgccatac caccgtgccg tggccgaacg cgagcctgac  1620
cccgaaatgg aacaacgaaa ccacccagcc ccagatcgcc aactgcagcg tgtatgactt  1680
ttttgtgtgg ctccattatt attctgttcg agacacactt tggccaaggg tgacctacca  1740
tatgaacaaa tatgcgtatc atatgctgga aagacgagcc aaatataaaa gaggaccagg  1800
acctggcgct aaatttgtgg ccgcctggac actgaaagcc gctgctgtc ctggacctgg  1860
ccagtacatc aaggccaaca gcaagttcat cggcatcacc gaactcggac ccggaccagg  1920
ctgatgattt cgaaatttaa ataagcttgc ggccgctagg gataacaggg taattatcac  1980
gcccaaacat ttacagccgc ggtgtcaaaa accgcgtgg                        2019
```

```
SEQ ID NO: 33          moltype = AA   length = 619
FEATURE                Location/Qualifiers
REGION                 1..619
                       note = Description of Artificial Sequence: Synthetic
                        polypeptide
source                 1..619
                       mol_type = protein
                       organism = synthetic construct
SEQUENCE: 33
MQIFVKTLTG KTITLEVEPS DTIENVKAKI QDKEGIPPDQ QRLIFAGKQL EDGRTLSDYN   60
IQKESTLHLV LRLRGAMFQA LSEGCTPYDI NQMLNVLGDH QVSGLEQLES IINFEKLTEW  120
TSSNVMPILS PLTKGILGFV FTLTVPSERG LSCISEADAT TPESANLGEE ILSQLYLWPR  180
VTYHSPSYAY HQFERRAKYK RHFPGFGQSL LFGYPVYVFG DCVQGDWDAI RFRYCAPPGY  240
ALLRCNDTNY SALLAVGALE GPRNQDWLGV PRQLVTRMQA IQNAGLCTLV AMLEETIFWL  300
QAFLMALTDS GPKTNIIVDS QYVMGISKPS FQEFVDWENV SPELNSTDQP FWQAGILARN  360
LVPMVATVQG QNLKYQGQSL VISASIIVFN LLELEGDYRD DGNVWVHTPL SPRTLNAWVK  420
AVEEKKGIPV HLELASMTNM ELMSSIVHQQ VRTYGPVFMC LGGLLTMVAG AVWLTVRVLE  480
LFRAAQLAND VVLQIMELCG AAFRQVCHTT VPWPNASLTP KWNNETTQPQ IANCSVYDFF  540
VWLHYYSVRD TLWPRVTYHM NKYAYHMLER RAKYKRGPGP GAKFVAAWTL KAAAGPGPGQ  600
YIKANSKFIG ITELGPGPG                                               619

SEQ ID NO: 34          moltype = DNA   length = 1638
FEATURE                Location/Qualifiers
misc_feature           1..1638
                       note = Description of Artificial Sequence: Synthetic
                        polynucleotide
source                 1..1638
                       mol_type = other DNA
                       organism = synthetic construct
SEQUENCE: 34
atggccggga tgttccaggc actgtccgaa ggctgcacac cctatgatat taaccagatg   60
ctgaatgtcc tgggagacca ccaggtctct ggcctggagc agctggagag catcatcaac  120
ttcgagaagc tgaccgagtg gacaagctcc aatgtgatgc ctatcctgtc cccactgacc  180
aagggcatcc tgggcttcgt gtttaccctg acagtgcctt ctgagcgggg cctgtcttgc  240
atcagcgagg cagacgcaac cacaccagag tccgccaatc tgggcgagga gatcctgtct  300
cagctgtacc tgtggccccg ggtgacatat cactcccctt cttacgccta tcaccagttc  360
gagcggagag ccaagtacaa gagacacttc ccaggctttg gccagtctct gctgttcggc  420
taccccgtgt acgtgttcgg cgattgcgtg cagggcgact gggatgccat ccggtttaga  480
tactgcgcac cacctggata tgcactgctg aggtgtaacg acaccaatta ttccgccctg  540
ctggcagtgg gcgccctgga gggccctcgc aatcaggatt ggctgggcgt gccaaggcag  600
ctggtgacac gcatgcaggc catccagaac gcaggcctgt gcaccctggt ggcaatgctg  660
gaggagacaa tcttctggct gcaggccttt ctgatggccc tgaccgacag cggccccaag  720
acaaacatca tcgtggattc ccagtacgtg atgggcatct ccaagccttc tttccaggag  780
tttgtggact gggagaacgt gagcccagag ctgaattcca ccgatcagcc attctggcag  840
gcaggaatcc tggcaaggaa cctggtgcct atggtggcca cagtgcaggg ccagaatctg  900
aagtaccagg gccagagcct ggtcatcagc gcctccatca tcgtgtttaa cctgctggag  960
ctggagggcg actatcggga cgatggcaac gtgtgggtgc acacccccag cagccccaag 1020
acactgaacg cctgggtgaa ggccgtggag gagaagaagg gcatcccagt gcacctggag 1080
ctggcctcca tgaccaatat ggagctgatg tctagcatcg tgcaccagca ggtgaggaca 1140
tacgacccctg tgttcatgtg cctggaggc ctgctgacca tggtggcagg agccgtgtgg 1200
ctgacagtgc gggtgctgga gctgttcaga gccgcccagc tggccaacga tgtggtgctg 1260
cagatcatgg agctgtgcgg agcagccttt cgccaggtgt gccacaccac agtgccatgg 1320
cccaatgcct ccctgacccc caagtggaac aatgagacaa cacagcctca gatcgccaac 1380
tgtagcgtgt acgacttctt cgtgtggctg cactactata gcgtgaggga taccctgtgg 1440
ccccgcgtga cataccacat gaataagtac gcctatcaca tgctggagag gcgcgccaag 1500
tataagagag ccctggcccc aggcgcaaag tttgtggcag catggaccct gaaggccgcc 1560
gccggcccccg gccccggcca gtatatcaag gctaacagta agttcattgg aatcacagag 1620
ctgggacccg gacctgga                                                1638

SEQ ID NO: 35          moltype = AA   length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 35
MAGMFQALSE GCTPYDINQM LNVLGDHQVS GLEQLESIIN FEKLTEWTSS NVMPILSPLT   60
KGILGFVFTL TVPSERGLSC ISEADATTPE SANLGEEILS QLYLWPRVTY HSPSYAYHQF  120
ERRAKYKRHF PGFGQSLLFG YPVYVFGDCV QGDWDAIRFR YCAPPGYALL RCNDTNYSAL  180
LAVGALEGPR NQDWLGVPRQ LVTRMQAIQN AGLCTLVAML EETIFWLQAF LMALTDSGPK  240
TNIIVDSQYV MGISKPSFQE FVDWENVSPE LNSTDQPFWQ AGILARNLVP MVATVQGQNL  300
KYQGQSLVIS ASIIVFNLLE LEGDYRDDGN VWVHTPLSPR TLNAWVKAVE EKKGIPVHLE  360
LASMTNMELM SSIVHQQVRT YGPVFMCLGG LLTMVAGAVW LTVRVLELFR AAQLANDVVL  420
QIMELCGAAF RQVCHTTVPW PNASLTPKWN NETTQPQIAN CSVYDFFVWL HYYSVRDTLW  480
PRVTYHMNKY AYHMLERRAK YKRGPGPGAK FVAAWTLKAA AGPGPGQYIK ANSKFIGITE  540
LGPGPG                                                             546
```

```
SEQ ID NO: 36          moltype = DNA   length = 2019
FEATURE                Location/Qualifiers
misc_feature           1..2019
                       note = Description of Artificial Sequence: Synthetic
                       polynucleotide
source                 1..2019
                       mol_type = other DNA
                       organism = synthetic construct
SEQUENCE: 36
gcccgggcat ttaaatgcga tcgcatcgat tacgactcta gaatagtcta gtccgcaggc    60
caccatgcag atcttcgtga agaccctgac cggcaagacc atcaccctag aggtggagcc   120
cagtgacacc atcgagaacg tgaaggccaa gatccaggat aaagagggca tcccccctga   180
ccagcagagg ctgatctttg ccggcaagca gctggaagat ggccgcaccc tctctgatta   240
caacatccag aaggagtcaa ccctgcacct ggtccttcgc ctgagaggtg ccatgtttca   300
ggcgctgagc gaaggctgca ccccgtatga tattaaccag atgctgaacg tgctgggcga   360
tcatcagttt aagcacatca aagcctttga ccggacattt gctaacaacc caggtcccat   420
ggttgtgttt gccacacctg ggcctatcct gtctcctctg acaaagggca tcctgggctt   480
cgtgtttacc ctgaccgtgc cttctgagag aggacttagc tgcattagcg aagcggatgc   540
gaccacccccg gaaagcgcga acctgggcga agaaattctg agccagctgt atctttggcc   600
aagggtgacc taccattccc ctagttatgc ttaccaccaa tttgaaagac gagccaaata   660
taaaagacac ttccccggct ttggccagag cctgctgttt ggctaccctg tgtacgtgtt   720
cggcgattgc gtgcagggcg attgggatgc gattcgcttt cgctattgcg cgccgccggg   780
ctatcgcgctg ctgcgctgca acgataccaa ctatagcgct ctgctggctg tggggggccct   840
agaaggaccc aggaatcagg actggcttgg tgtcccaaga caacttgtaa ctcggatgca   900
ggctattcag aatgccggcc tgtgtaccct ggtggccatg ctggaagaga caatcttctg   960
gctgcaagcg tttctgatgg cgctgaccga tagcggcccg aaaaccaaca ttattgtgga  1020
tagccagtat gtgatgggca ttagcaaacc gagctttcag gaatttgtgg attgggaaaa  1080
cgtgagcccg gaactgaaca gcaccgatca gccgtttttgg caagccggaa tcctggccag  1140
aaatctggtg cctatggtgg ccacagtgca gggccagaac ctgaagtacc agggtcagtc  1200
actagtcatc tctgcttcta tcattgtctt caacctgctg gacatggaag gtgattatcg  1260
agatgatggc aacgtgtggg tgcataccCC gctgagcccg cgcacccctga acgcgtgggt  1320
gaaagcggtg gaagaaaaaa aaggtattcc agttcaccta gagctggcca gtatgaccaa  1380
catggagctc atgagcagta ttgtgcatca gcaggtcaga acatacggcc ccgtgttcat  1440
gtgtctcggc ggactgctta caatggtggc tggtgctgtg tggctgacag tgcgagtgct  1500
cgagctgctc cgggccgcgc agctggccaa cgacgtgggtc ctccagatca tggagctttg  1560
tggtgcagcg tttcgccagg tgtgccatac caccgtgccg tggccgaacg cgagcctgac  1620
cccgaaatgg aacaacgaaa ccacccagcc ccagatcgcc aactgcagcg tgtatgactt  1680
ttttgtgtgg ctccattatt attctgttcg agacacactt tggccaaggg tgacctacca  1740
tatgaacaaa tatgcgtatc atatgctgga agacgagcc aaatataaaa gaggaccagg  1800
acctggcgct aaatttgtgg ccgcctggac actgaaagcc gctgctgtc ctggacctgg  1860
ccagtacatc aaggccaaca gcaagttcat cggcatcacc gaactcggac ccggaccagg  1920
ctgatgattt cgaaatttaa ataagcttgc ggccgctagg gataacaggg taattatcac  1980
gcccaaacat ttacagccgc ggtgtcaaaa accgcgtgg                         2019

SEQ ID NO: 37          moltype = AA   length = 619
FEATURE                Location/Qualifiers
REGION                 1..619
                       note = Description of Artificial Sequence: Synthetic
                       polypeptide
source                 1..619
                       mol_type = protein
                       organism = synthetic construct
SEQUENCE: 37
MQIFVKTLTG KTITLEVEPS DTIENVKAKI QDKEGIPPDQ QRLIFAGKQL EDGRTLSDYN    60
IQKESTLHLV LRLRGAMFQA LSEGCTPYDI NQMLNVLGDH QFKHIKAFDR TFANNPGPMV   120
VFATPGPILS PLTKGILGFV FTLTVPSERG LSCISEADAT TPESANLGEE ILSQLYLWPR   180
VTYHSPSYAY HQFERRAKYK RHFPGFGQSL LFGYPVYVFG DCVQGDWDAI RFRYCAPPGY   240
ALLRCNDTNY SALLAVGALE GPRNQDWLGV PRQLVTRMQA IQNAGLCTLV AMLEETIFWL   300
QAFLMALTDS GPKTNIIVDS QYVMGISKPS FQEFVDWENV SPELNSTDQP FWQAGILARN   360
LVPMVATVQG QNLKYQGQSL VISASIIVFN LLELEGDYRD DGNVWVHTPL SPRTLNAWVK   420
AVEEKKGIPV HLELASMTNM ELMSSIVHQQ VRTYGPVFMC LGGLLTMVAG AVWLTVRVLE   480
LFRAAQLAND VVLQIMELCG AAFRQVCHTT VPWPNASLTP KWNNETTQPQ IANCSVYDFF   540
VWLHYYSVRD TLWPRVTYHM NKYAYHMLER RAKYKRGPGP GAKFVAAWTL KAAAGPGPGQ   600
YIKANSKFIG ITELGPGPG                                                619

SEQ ID NO: 38          moltype = DNA   length = 228
FEATURE                Location/Qualifiers
misc_feature           1..228
                       note = Description of Artificial Sequence: Synthetic
                       polynucleotide
source                 1..228
                       mol_type = other DNA
                       organism = synthetic construct
SEQUENCE: 38
atgcagatct tcgtgaagac cctgaccggc aagaccatca ccctagaggt ggagcccagt    60
gacaccatcg agaacgtgaa ggccaagatc caggataaag agggcatccc cctgaccag   120
cagaggctga tctttgccgg caagcagctg gaagatggcc gcaccctctc tgattacaac   180
atccagaagg agtcaaccct gcacctggtc cttcgcctga gaggtggc                228
```

```
SEQ ID NO: 39          moltype = DNA   length = 228
FEATURE                Location/Qualifiers
misc_feature           1..228
                       note = Description of Artificial Sequence: Synthetic
                        polynucleotide
source                 1..228
                       mol_type = other DNA
                       organism = synthetic construct
SEQUENCE: 39
atgcagatct tcgtgaagac cctgaccggc aagaccatca ccctagaggt ggagcccagt   60
gacaccatcg agaacgtgaa ggccaagatc caggataaag agggcatccc ccctgaccag  120
cagaggctga tctttgccgg caagcagctg gaagatggcc gcaccctctc tgattacaac  180
atccagaagg agtcaacccct gcacctggtc cttcgcctga gaggtgcc              228

SEQ ID NO: 40          moltype = DNA   length = 78
FEATURE                Location/Qualifiers
source                 1..78
                       mol_type = other DNA
                       organism = Homo sapiens
SEQUENCE: 40
atggccgtca tggcgccccg aaccctcgtc ctgctactct cggggctct ggccctgacc    60
cagacctggg cgggctct                                               78

SEQ ID NO: 41          moltype = DNA   length = 201
FEATURE                Location/Qualifiers
source                 1..201
                       mol_type = other DNA
                       organism = Homo sapiens
SEQUENCE: 41
ccgtcttccc agcccaccat ccccatcgtg ggcatcattg ctggcctggt tctctttgga   60
gctgtgatca ctggagctgt ggtcgctgct gtgatgtgga ggaggaagag ctcagataga  120
aaaggaggga gctactctca ggctgcaagc agtgacagtg cccagggctc tgatgtgtct  180
ctcacagctt gtaaagtgtg a                                           201

SEQ ID NO: 42          moltype = DNA   length = 60
FEATURE                Location/Qualifiers
misc_feature           1..60
                       note = Description of Artificial Sequence: Synthetic
                        oligonucleotide
source                 1..60
                       mol_type = other DNA
                       organism = synthetic construct
SEQUENCE: 42
atggagaccg atacactgct gctgtgggtg ctgctcctgt gggtgccagg aagcacaggc   60

SEQ ID NO: 43          moltype = DNA   length = 3178
FEATURE                Location/Qualifiers
source                 1..3178
                       mol_type = other DNA
                       organism = Homo sapiens
SEQUENCE: 43
ggcaccgatt cggggcctgc ccggacttcg ccgcacgctg cagaacctcg cccagcgccc   60
accatgcccc ggcagctcag cgcggcggcc gcgctcttcg cgtccctggc cgtaattttg  120
cacgatggca gtcaaatgag agcaaaagca tttccagaaa ccagagatta ttctcaacct  180
actgcagcag caacagtaca ggacataaaa aaacctgtcc agcaaccagc taagcaagca  240
cctcaccaaa ctttagcagc aagattcatg gatggtcata tcacctttca aacagcggcc  300
acagtaaaaa ttccaacaac taccccagca actacaaaaa acactgcaac caccagccca  360
attacctaca ccctggtcac aacccaggcc acacccaaca actcacacac agctcctcca  420
gttactgaag ttacagtcgg ccctagctta gcccttatt cactgccacc caccatcacc  480
ccaccagctc atacagctgg aaccagttca tcaaccgtca gccacacaac tgggaacacc  540
actcaaccca gtaaccagac caccccttcca gcaactttat cgatagcact gcacaaaagc  600
acaaccggtc agaagcctga tcaaacccacc catgcccccag gaacaacggc agctgcccac  660
aataccaccc gcacagctgc acctgcctcc acggttcctg ggcccaccct tgcacctcag  720
ccatccgtcag tcaagactgg aatttatcag gttctaaaac gagcagact ctgtataaaa  780
gcagagatgg ggatacagct gattgttcaa gacaaggagt cggttttttc acctcggaga  840
tacttcaaca tcgaccccaa cgcaacgcaa gcctctggga actgtggcac ccgaaaatcc  900
aaccttctgt tgaattttca gggcggattt gtgaatctca catttaccaa ggatgaagaa  960
tcatattata tcagtgaagt gggagcctat ttgaccgtct cagatccaga gacagtttac 1020
caaggaatca aacatgcggt ggtgatgttc cagacacgcag tcgggcattc cttcaagtgc 1080
gtgagtgaac agagcctcca gttgtcagcc cacctgcagg tgaaaacaac cgatgtccaa 1140
cttcaagcct ttgattttga agatgaccac tttggaaatg tggatgagtg ctcgtctgac 1200
tacacaattg tgcttcctgt gattggggcc atcgtggttg tgtctctgcct tatggggtatg 1260
ggtgtctata aaatccgcct aaggtgtcaa tcatctggat accagagaat ctaattgttg 1320
cccggggga atgaaaataa tggaatttag agaactcttt catccctccc aggatggatg 1380
ttgggaaatt ccctcagagt gtgggtcctt caaacaatgt aaaccaccat cttctattca 1440
aatgaagtga tcatgtgtg atttaagttc aggcagcaca tcaatttcta aatacttttt 1500
gtttatttta tgaaagatat agtgagctgt ttattttcta gtttcctttta gaatattttta 1560
gccactcaaa gtcaacattt gagatatgtt gaattaacat aatatatgta aagtagaata 1620
agccttcaaa ttataaacca agggtcaatt gtaactaata ctactgtgtg tgcattgaag 1680
```

```
attttatttt acccttgatc ttaacaaagc ctttgctttg ttatcaaatg gactttcagt    1740
gcttttacta tctgtgtttt atggtttcat gtaacataca tattcctggt gtagcactta    1800
actccttttc cactttaaat ttgttttttgt tttttgagac ggagtttcac tcttgtcacc    1860
caggctggag tacagtggca cgatctcggc ttatggcaac ctccgcctcc cgggttcaag    1920
tgattctcct gcttcagctt cccgagtagc tgggattaca ggcacacact accacgcctg    1980
gctaattttt gtattttat tatagacggg tttcaccatg ttggccagac tggtcttgaa    2040
ctcttgacct caggtgatcc acccacctca gcctcccaaa gtgctgggat tacaggcatg    2100
agccattgcg cccggcctta aatgtttttt ttaatcatca aaaagaacaa catatctcag    2160
gttgtctaag tgttttttatg taaaaccaac aaaaagaaca aatcagctta tatttttat    2220
cttgatgact cctgctccag aattgctaga ctaagaatta ggtggctaca gatggtagaa    2280
ctaaacaata agcaagagac aataataatg gcccttaatt attaacaaag tgccagagtc    2340
taggctaagc actttatcta tatctcattt cattctcaca acttataagt gaatgagtaa    2400
actgagactt aagggaactg aatcacttaa atgtcacctg gctaactgat ggcagagcca    2460
gagcttgaat tcatgttggt ctgacatcaa ggtctttgct cttctcccta caccaagtta    2520
cctacaagaa caatgacacc acactctgcc tgaaggctca cacctcatac cagcatacgc    2580
tcaccttaca gggaaatggg tttatccagg atcatgagac attagggtag atgaaaggag    2640
agctttgcag ataacaaaat agcctatcct taatacatcc tccactctct ggaaggagac    2700
tgaggggctt tgtaaaacat tagtcagttg ctcattttta tgggattgct tagctgggct    2760
gtaaagatga aggcatcaaa taaactcaaa gtattttaa attttttga taatagagaa    2820
acttcgctaa ccaactgttc tttcttgagt gtatagcccc atcttgtggt aacttgctgc    2880
ttctgcactt catatccata tttcctattg ttcactttat tctgtagagc agcctgccaa    2940
gaatttttatt tctgctgttt tttttgctgc taaagaaagt aactaagtca ggatgttaac    3000
agaaaagtcc acataaccct agaattctta gtcaaggaat aattcaagtc agcctagaga    3060
ccatgttgac tttcctcatg tgtttcctta tgactcagta agttggcaag gtcctgactt    3120
tagtcttaat aaaacattga attgtagtaa aggttttttgc aataaaaact tactttggg    3178
```

```
SEQ ID NO: 44          moltype = DNA  length = 1858
FEATURE                Location/Qualifiers
source                 1..1858
                       mol_type = other DNA
                       organism = Mus sp.
SEQUENCE: 44
attccggagg tgaaaaacaa tggcacaacg tgtataatgg ccagcttctc tgcctccttt    60
ctgaccacct acgagactgc gaatggttct cagatcgtga acatttccct gccagcctct    120
gcagaagtac tgaaaaatgg cagttcttgt ggtaaagaaa atgtttctga ccccagcctc    180
acaattactt ttggaagagg atatttactg acactcaact tcacaaaaaa tacaacacgt    240
tacagtgtcc agcatatgta tttttacatat aacttgtcag atacagaaca ttttcccaat    300
gccatcagca aagagatcta caccatggat tccacaactg acatcaaggc agacatcaac    360
aaagcatacc ggtgtgtcag tgatatccgg gtctacatga agaatgtgac cgttgtgctc    420
cgggatgcca ctatccaggc ctacctgtcg agtggcaact tcagcaagga agagacacac    480
tgcacacagg atggaccttc cccaaccact gggccaccca gccctcacc accacttgtg    540
cccacaaacc ccactgtatc caagtacaat gttactggta acaacggaac ctgcctgctg    600
gcctctatgg cactgcaact gaatatcacc tacctgaaca aggacaacaa gacggtgacc    660
agagcgttca acatcagccc aaatgacaca tctagtggga gttgcggtat caacttggtg    720
accctgaaag tggagaacaa gaacagagcc ctggaattgc agtttgggat gaatgccagc    780
tctagcctgt ttttcttgca aggagtgcgc ttgaatatga ctcttcctga tgccctagtg    840
cccacattca gcatctccaa ccattcactg aaagctcttc aggccactgt gggaaactca    900
tacaagtgca acactgagga acacatcttt gtcagcaaga tgctctccct caatgtcttc    960
agtgtgcagg tccaggcttt caaggtggac agtgacaggt ttgggtctgt ggaagagtgt    1020
gttcaggatg gtaacaacat gttgatcccc attgctgtgg gcggtgccct ggcagggctg    1080
atcctcatcg tcctcattgc ctacctcatt ggcaggaaga ggagtcacgc cggctatcag    1140
accatctagc ctggtgggca ggtgcaccag agatgcacag gggcctgttc tcacatcccc    1200
aagcttagat aggtgtggaa gggaggcaca ctttctggca aactgttta aaatctgctt    1260
tatcaaatgt gaagttcatc ttgcaacatt tactatgcac aaaggaataa ctattgaaat    1320
gacggtgtta attttgctaa ctgggttaaa tattgatgag aaggctccac tgatttgact    1380
tttaagactt ggtgtttggt tcttcattct tttactcaga tttaagccta tcaaagggat    1440
actctggtcc agaccttggc ctggcaaggg tggctgatgg ttaggctgca cacacttaag    1500
aagcaacggg agcagggaag gcttgcacac aggcacgcac agggtcaacc tctggacact    1560
tggcttgggc tacctggcct tgggggggct gaactctggc atctggctgg gtacacaccc    1620
ccccaatttc tgtgctctgc caccgtgag ctgccactt cctaaataga aaatggcatt    1680
atttttattt acttttttgt aaagtgattt ccagtcttgt gttggcgttc agggtggccc    1740
tgtctctgca ctgtgtacaa taatagattc acactgctga cgtgtcttgc agcgtaggtg    1800
ggttgtacac tgggcatcag ctcacgtaat gcattgcctg taacgatgct aataaaaa    1858
```

```
SEQ ID NO: 45          moltype = DNA  length = 2339
FEATURE                Location/Qualifiers
source                 1..2339
                       mol_type = other DNA
                       organism = Homo sapiens
SEQUENCE: 45
ggcccaaccg ccgcccgcgc ccccgctctc cgcaccgtac ccggccgcct cgcgccatgg    60
cggccccgg cagcgcccgg cgaccctgc tgctgctact gctgttgctg ctgctcggcc    120
tcatgcattg tgcgtcagca gcaatgttta tggtgaaaaa tggcaacggg accgcgtgca    180
taatggccaa cttctctgct gccttctcag tgaactacga caccaagagt ggccctaaga    240
acatgacctt tgacctgcca tcagatgcca cagtggtgct caaccgcagc tcctgtggaa    300
aagagaacac ttctgacccc agtctcgtga ttgcttttgg aagaggacat acactcactc    360
tcaatttcac gagaaatgca acacgttaca gcgtccagct catgagtttt gtttataact    420
tgtcagacac acaccttttc cccaatgcga gctccaaaga aatcaagact gtggaatcta    480
taactgacat cagggcagat atagataaaa aatacagatg tgttagtggc acccaggtcc    540
```

```
acatgaacaa cgtgaccgta acgctccatg atgccaccat ccaggcgtac ctttccaaca   600
gcagcttcag caggggagag acacgctgtg aacaagacag gccttcccca accacacgc   660
cccctgcgcc acccagcccc tcgccctcac ccgtgcccaa gagcccctct gtggacaagt   720
acaacgtgag cggcaccaac gggacctgcc tgctggccag catggggctg cagctgaacc   780
tcacctatga gaggaaggac aacacgacgg tgacaaggct tctcaacatc aaccccaaca   840
agacctcggc cagcgggagc tgcggcgccc acctggtgac tctggagctg cacagcgagg   900
gcaccaccgt cctgctcttc cagttcggga tgaatgcaag ttctagccgg ttttttcctac   960
aaggaatcca gttgaataca attcttcctg acgccagaga ccctgccttt aaagctgcca  1020
acggctccct gcgagcgctg caggccacag tcggcaattc ctacaagtgc aacgcggagg  1080
agcacgtccg tgtcacgaag gcgttttcag tcaatatatt caaagtgtgg gtccaggctt  1140
tcaaggtgga aggtggccag tttggctctg tggaggagtg tctgctggac gagaacagca  1200
tgctgatccc catcgctgtg ggtggtgccc tggcgggggct ggtcctcatc gtcctcatcg  1260
cctacctcgt cggcaggaag aggagtcacg caggctacca gactatctag cctggtgcac  1320
gcaggcacag cagctgcagg ggcctctgtt cctttctctg ggcttagggt cctgtcgaag  1380
gggaggcaca ctttctggca aacgtttctc aaatctgctt catccaatgt gaagttcatc  1440
ttgcagcatt tactatgcac aacagagtaa ctatcgaaat gacggtgtta attttgctaa  1500
ctgggttaaa tattttgcta actggttaaa cattaatatt taccaaagta ggattttgag  1560
ggtggggtg ctctctctga gggggtgggg gtgccgctgt ctctgagggg tggggggtgcc  1620
gctgtctctg aggggtgggg gtgccgctct ctctgagggg gtgggggtgc cgctttctct  1680
gaggggtgg gggtgccgct ctctctgagg gggtgggggt gctgctctct ccgaggggtg  1740
gaatgccgct gtctctgagg ggtgggggtg ccgctctaaa ttggctccat atcatttgag  1800
tttagggttc tggtgtttgg tttcttcatt ctttactgca ctcagattta agccttacaa  1860
agggaaagcc tctggccgtc acacgtagga cgcatgaagg tcactcgtgg tgaggctgac  1920
atgctcacac attacaacag tagagaggga aaatcctaag acagaggaac tccagagatg  1980
agtgtctgga gcgcttcagt tcagctttaa aggccaggac gggccacacg tggctggcgg  2040
cctcgttcca gtggcggcac gtccttgggc gtctctaatg tctgcagctc aagggctggc  2100
actttttaa atataaaaat gggtgttatt tttattttt tttgtaaagt gattttggt  2160
cttctgttga cattcggggt gatcctgttc tgcgctgtgt acaatgtgag atcggtgcgt  2220
tctcctgatg ttttgccgtg gcttgggat tgtacacggg accagctcac gtaatgcatt  2280
gcctgtaaca atgtaataaa aagcctcttt cttttaaaaa aaaaaaaaa aaaaaaaa   2339
```

```
SEQ ID NO: 46          moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 46
cagtacatca aggccaacag caagttcatc ggcatcaccg aactc                    45

SEQ ID NO: 47          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 47
QYIKANSKFI GITEL                                                      15

SEQ ID NO: 48          moltype = DNA  length = 39
FEATURE                Location/Qualifiers
misc_feature           1..39
                       note = Description of Artificial Sequence: Synthetic
                        oligonucleotide
source                 1..39
                       mol_type = other DNA
                       organism = synthetic construct
SEQUENCE: 48
gctaaatttg tggctgcctg gacactgaaa gccgccgct                           39

SEQ ID NO: 49          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 49
AKFVAAWTLK AAA                                                        13

SEQ ID NO: 50          moltype = DNA  length = 593
FEATURE                Location/Qualifiers
source                 1..593
                       mol_type = other DNA
                       organism = Woodchuck hepatitis virus
SEQUENCE: 50
```

```
aatcaacctc tggattacaa aatttgtgaa agattgactg gtattcttaa ctatgttgct   60
cctttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact  240
ggttggggca ttgccaccac ctgtcagctc ctttccggga ctttcgcttt cccctccct  300
attgccacgg cggaactcat cgccgcctgc cttgcccgct gctggacagg ggctcggctg  360
ttgggcactg acaattccgt ggtgttgtcg gggaagctga cgtcctttcc atggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tgt          593
```

```
SEQ ID NO: 51          moltype = DNA   length = 589
FEATURE                Location/Qualifiers
misc_feature           1..589
                       note = Description of Artificial Sequence: Synthetic
                        polynucleotide
source                 1..589
                       mol_type = other DNA
                       organism = synthetic construct
SEQUENCE: 51
tctcccccccc cccctctcc ctcccccccc cctaacgtta ctggccgaag ccgcttggaa   60
taaggccggt gtgcgtttgt ctatatgtta ttttccacca tattgccgtc ttttggcaat  120
gtgagggccc ggaaacctgg ccctgtcttc ttgacgagca ttcctagggg tctttcccct  180
ctcgccaaag gaatgcaagg tctgttgaat gtcgtgaagg aagcagttcc tctggaagct  240
tcttgaagac aaacaacgtc tgtagcgacc cttttgcaggc agcggaaccc cccacctggc  300
gacaggtgcc tctgcggcca aaagccacgt gtataagata cacctgcaaa ggcggcacaa  360
ccccagtgcc acgttgtgag ttggatagtt gtggaaagag tcaaatggct ctcctcaagc  420
gtattcaaca aggggctgaa ggatgcccag aaggtacccc attgtatggg atctgatctg  480
gggcctcggt gcacatgctt tacatgtgtt tagtcgaggt taaaaaaacg tctaggcccc  540
ccgaaccacg gggacgtggt tttcctttga aaaacacgat gataatatg              589
```

```
SEQ ID NO: 52          moltype = DNA   length = 720
FEATURE                Location/Qualifiers
misc_feature           1..720
                       note = Description of Artificial Sequence: Synthetic
                        polynucleotide
source                 1..720
                       mol_type = other DNA
                       organism = synthetic construct
SEQUENCE: 52
atggtgagca agggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctacccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtag  720
```

```
SEQ ID NO: 53          moltype = DNA   length = 1563
FEATURE                Location/Qualifiers
misc_feature           1..1563
                       note = Description of Artificial Sequence: Synthetic
                        polynucleotide
source                 1..1563
                       mol_type = other DNA
                       organism = synthetic construct
SEQUENCE: 53
atgctgctgc tgctgctgct gctgggcctg aggctacagc tctccctggg catcatccca   60
gttgaggagg agaacccgga cttctggaac cgcgaggcag cgcgaggcag gggtgccgcc  120
aagaagctgc agcctgcaca gacagccgcc aagaacctca tcatcttcct gggcgatggg  180
atgggggtgt ctacggtgac agctgccagg atcctaaaag ggcagaagaa ggacaaactg  240
gggcctgaga taccctggc catggaccgc ttcccatatg tggctctgtc caagacatac  300
aatgtagaca aacatgtgcc agacagtgga gccacagcca cggccctacct gtgcgggtc  360
aagggcaact tccagaccat tggcttgagt gcagccgccc gctttaacca gtgcaacacg  420
acacgcggca acgaggtcat ctccgtgatg aatcgggcca agaaagcagg gaagtcagtg  480
ggagtggtaa ccaccacacg agtgcagcac gcctcgccag ccggcacccta cgcccacacg  540
gtgaaccgca actggtactc ggacgccgac gtgcctgcct cggcccgcca ggagggggtgc  600
caggacatcg ctacgcagct catctccaac atggacattg acgtgatcct aggtggaggc  660
cgaaagtaca tgtttcgcat gggaaccca gaccctgaat accagatga ctacagccaa  720
ggtgggacca ggctggacgg gaagaatctg gtgcaggaat ggctggcgaa gcgccagggt  780
gcccggtatg tgtggaaccg cactgagctc atgcaggctt ccctggaccc gtctgtgacc  840
catctcatgg gtctctttga gcctggagac atgaaatacg agatccaccg agactccaca  900
ctggacccct ccctgatgga gatgacagag gctgccctgc gctgctgag caggaaccccc  960
cgcggcttct tcctcttcgt ggagggtggt cgcatcgacc atggtcatca tgaaagcagg  1020
```

```
gcttaccggg cactgactga gacgatcatg ttcgacgacg ccattgagag ggcgggccag  1080
ctcaccagcg aggaggacac gctgagcctc gtcactgccg accactccca cgtcttctcc  1140
ttcggaggct accccctgcg agggagctcc atcttcgggc tggccctctg caaggcccgg  1200
gacaggaagg cctacacggt cctcctatac ggaaacggtc caggctatgt gctcaaggac  1260
ggcgcccggc cggatgttac cgagagcgag agcgggacg ccgagtatcg gcagcagtca  1320
gcagtgcccc tggacgaaga gacccacgca ggcgaggacg tggcggtgtt cgcgcgcggc  1380
ccgcaggcgc acctggttca cggcgtgcag gagcagacct tcatagcgca cgtcatggcc  1440
ttcgccgcct gcctggagcc ctacaccgcc tgcgacctgg cgcccccgc cggcaccacc  1500
gacgccgcg accgggttta ctctagagtc ggggcggccg gccgcttcga gcagacatga  1560
taa  1563
```

```
SEQ ID NO: 54           moltype = DNA   length = 1653
FEATURE                 Location/Qualifiers
misc_feature            1..1653
                        note = Description of Artificial Sequence: Synthetic
                         polynucleotide
source                  1..1653
                        mol_type = other DNA
                        organism = synthetic construct
SEQUENCE: 54
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg ccagggctac  1020
ggcctgacag aaacaaccag cgccattctg atcaccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg tggtgttgt gttcgtggac  1560
gaggtgccta aggactgac cggcaagttg gacgcccgca agatccgcga gattctcatt  1620
aaggccaaga agggcggcaa gatcgccgtg taa  1653
```

```
SEQ ID NO: 55           moltype = DNA   length = 66
FEATURE                 Location/Qualifiers
source                  1..66
                        mol_type = other DNA
                        organism = Foot-and-mouth disease virus
SEQUENCE: 55
gtaaagcaaa cactgaactt tgaccttctc aagttggctg agacgttga gtccaatcct  60
gggccc  66
```

```
SEQ ID NO: 56           moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 56
GPGPG  5
```

```
SEQ ID NO: 57           moltype = AA   length = 100
FEATURE                 Location/Qualifiers
source                  1..100
                        mol_type = protein
                        organism = synthetic construct
SEQUENCE: 57
VTNTEMFVTA PDNLGYMYEV QWPGQTQPQI ANCSVYDFFV WLHYYSVRDT VTNTEMFVTA  60
PDNLGYMYEV QWPGQTQPQI ANCSVYDFFV WLHYYSVRDT  100
```

```
SEQ ID NO: 58           moltype = AA   length = 25
FEATURE                 Location/Qualifiers
```

-continued

```
source                  1..25
                        mol_type = protein
                        organism = synthetic construct
SEQUENCE: 58
VTNTEMFVTA PDNLGYMYEV QWPGQ                                      25

SEQ ID NO: 59           moltype = AA   length = 25
FEATURE                 Location/Qualifiers
source                  1..25
                        mol_type = protein
                        organism = synthetic construct
SEQUENCE: 59
TQPQIANCSV YDFFVWLHYY SVRDT                                      25

SEQ ID NO: 60           moltype = DNA   length = 19
FEATURE                 Location/Qualifiers
source                  1..19
                        mol_type = other DNA
                        organism = synthetic construct
SEQUENCE: 60
taatacgact cactatagg                                            19

SEQ ID NO: 61           moltype = DNA   length = 20
FEATURE                 Location/Qualifiers
source                  1..20
                        mol_type = other DNA
                        organism = synthetic construct
SEQUENCE: 61
taatacgact cactataggn                                           20

SEQ ID NO: 62           moltype = DNA   length = 17
FEATURE                 Location/Qualifiers
source                  1..17
                        mol_type = other DNA
                        organism = synthetic construct
SEQUENCE: 62
taatacgact cactata                                              17

SEQ ID NO: 63           moltype = DNA   length = 18
FEATURE                 Location/Qualifiers
source                  1..18
                        mol_type = other DNA
                        organism = synthetic construct
SEQUENCE: 63
taatacgact cactatan                                             18

SEQ ID NO: 64           moltype = DNA   length = 17
FEATURE                 Location/Qualifiers
source                  1..17
                        mol_type = other DNA
                        organism = synthetic construct
SEQUENCE: 64
atttaggtga cactata                                              17

SEQ ID NO: 65           moltype = AA   length = 448
FEATURE                 Location/Qualifiers
source                  1..448
                        mol_type = protein
                        organism = synthetic construct
SEQUENCE: 65
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                   448

SEQ ID NO: 66           moltype = AA   length = 215
FEATURE                 Location/Qualifiers
source                  1..215
                        mol_type = protein
                        organism = synthetic construct
SEQUENCE: 66
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                           215
```

-continued

```
SEQ ID NO: 67               moltype = AA   length = 440
FEATURE                     Location/Qualifiers
source                      1..440
                            mol_type = protein
                            organism = synthetic construct
SEQUENCE: 67
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLGK                                               440

SEQ ID NO: 68               moltype = AA   length = 214
FEATURE                     Location/Qualifiers
source                      1..214
                            mol_type = protein
                            organism = synthetic construct
SEQUENCE: 68
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 69               moltype = AA   length = 1701
FEATURE                     Location/Qualifiers
source                      1..1701
                            mol_type = protein
                            organism = synthetic construct
SEQUENCE: 69
ATGAAAGCTA TCCTTGTAGT CCTTCTCTAT ACTTTTGCCA CAGCTAACGC GGATACGCTG   60
TGCATCGGGT ATCACGCAAA TAACTCCACC GATACGGTGG ACACGGTGCT TGAGAAGAAT   120
GTAACTGTAA CTCATTCCGT GAACTTGCTG GAGGACAAAC ACAACGGGAA GTTGTGCAAG   180
CTCAGGGGGG TCGCGCCGTT GCATTTGGGA AAATGTAATA TCGCTGGATG GATCTTGGGT   240
AATCCCGAGT GCGAAAGCCT CAGCACCGCC AGCAGCTGGA GCTACATTGT GGAAACTCCC   300
TCAAGCGATA ACGGGACCTG TTACCCAGGG GATTTCATCG ACTATGAGGA ATTGCGGGAA   360
CAGTTGAGTT CTGTGTCTTC ATTTGAACGA TTTGAAATTT TCCCCAAGAC CAGTTCTTGG   420
CCTAATCACG ACTCTAACAA GGGTGTTACG GCAGCATGCC CGCATGCCGG AGCAAAGAGT   480
TTCTACAAAA ATTTGATCTG GTTGGTGAAG AAGGGCAACT CATACCCTAA GCTCAGTAAG   540
TCTTATATCA ATGACAAAGG AAAAGAAGTA CTGGTTTTGT GGGGAATCCA CCATCCGTCC   600
ACATCTGCAG ACCAACAGTC ACTCTACCAG AACGCGGATG CCTACGTTTT TGTGGGAAGC   660
TCAAGATATT CCAAAAAATT CAAGCCTGAG ATTGCTATTC GCCCAAAGGT CCGCGACCAA   720
GAAGGCAGGA TGAATTACTA CTGGACCTTG GTCGAGCCTG GTGATAAGAT TACATTTGAA   780
GCCACCGGTA ACCTTGTTGT CCCGAGGTGC GCCTTCGCGA TGGAGCGGAA TGCAGGGTCA   840
GGGATTATTA TATCGACAC CCCAGTACAC GACTGCAACA CAACTTGTCA GACCCCTAAG   900
GGTGCCATCA ATACATCCCT GCCGTTTCAG AATATCCATC CGATCACTAT AGGCAAGTGT   960
CCAAAATATG TGAAGAGCAC GAAGCTTAGG CTGGCGACCG GATTGCGGAA CATACCTTCT   1020
ATCCAGAGTC GCGGGCTCTT CGGAGCTATC GCGGGCTTCA TAGAGGGAGG ATGGACTGGA   1080
ATGGTAGATG GATGGTATGG TTACCACCAT CAGAACGAAC AGGGATCCGG GTACGCAGCA   1140
GATTTGAAAT CAACACAGAA CGCCATCGAC GAGATCACCA ATAAGGTGAA CTCTGTAATT   1200
GAAAAAATGA ATACGCAATT CACTGCAGTG GGGAAGGAAT TCAACCATCT GGAGAAACGA   1260
ATTGAAAACC TTAACAAGAA GGTAGATGAC GGTTTCCTCG ATATCTGGAC ATATAATGCA   1320
GAACTTTTGG TATTGCTGGA AAATGAACGG ACCCTGGATT ATCACGATTC AAACGTTAAA   1380
AATCTCTATG AGAAGGTTCG ATCTCAACTG AAGAACAACG CCAAGGAAAT AGGAAACGGA   1440
TGTTTCGAGT TCTATCATAA ATGCGATAAC ACATGCATGG AGAGCGTCAA GAACGGTACC   1500
TACGACTATC CTAAGTATAG TGAGGAAGCC AAACTCAATA GGGAAGAGAT CGACGGAGTC   1560
AAATTGGAAT CAACGCGAAT ATATCAGATT CTTGCAATTT ACAGCACTGT CGCGAGTAGC   1620
CTTGTGTTGG TTGTGAGCCT CGGTGCTATT TCCTTTTGGA TGTGCTCAAA CGGCTCTCTC   1680
CAGTGTAGAA TCTGCATTTG A                                             1701

SEQ ID NO: 70               moltype = AA   length = 1683
FEATURE                     Location/Qualifiers
source                      1..1683
                            mol_type = protein
                            organism = synthetic construct
SEQUENCE: 70
ATGAATACCC AAATATTGGT ATTCGCTCTG ATTGCAATTA TTCCGACTAA CGCAGATAAG   60
ATTTGCCTTG GCACCATGC TGTGAGTAAT GGAACTAAAG TTAACACACT TACCGAACGG   120
GGCGTTGAAG TCGTGAACGC CACAGAGACA GTCGAGAGAA CAAACATTCC ACGAATATGC   180
AGCAAAGGCA AACGAACTGT AGACCTCGGG CAATGCGGTC TCCTCGGTAC CATTACCGGT   240
CCTCCGCAGT GTGACCAGTT TCTGGAGTTT CAGCCGACC TCATCATTGA GCGACGGGAC   300
GGAAGCGACG TCTGCTACCC TGGGAAGTTC GTGAACGAAG AAGCGCTGCG GCAGATTTTG   360
AGAGAAAGTG GTGGTATAGA TAAAGAGGCG ATGGGCTTCA CGTATTCCGG TATAAGGACA   420
AATGGTGCCA CGTCTGCATG CAGGCGGAGC GGCAGCTCTT TTTACGCAGA GATGAAATGG   480
CTGTTGTCAA ACACCGATGA TGCGGCTTTT CCTCAAATGA CCAAAAGCTA TAAGAACACC   540
AGGAAATCCC CCGCACTCAT AGTCTGGGGT ATACATCACT CAGTGTCCAC AGCAGAACAA   600
```

-continued

```
ACGAAACTTT ATGGGTCTGG CAACAAACTG GTGACAGTGG GGTCCTCTAA CTATCAACAA  660
AGCTTTGTGC CATCACCAGG GGCTCGACCA CAAGTAAACG GACTCAGTGG GCGGATCGAC  720
TTCCACTGGT TGATGCTCAA TCCTAACGAT ACCGTTACCT TCTCTTTCAA CGGAGCCTTC  780
ATAGCGCCTG ACAGGGCCAG CTTTCTCAGG GGTAAATCCA TGGGGATACA GTCAGGGGTC  840
CAGGTGGATG CCAATTGCGA AGGCGATTGC TATCACTCTG GCGGAACAAT AATCTCCAAT  900
CTCCCGTTCC AGAATATTGA CTCACGGGCA GTAGGGAAAT GTCCCCGCTA TGTCAAACAG  960
AGGAGCTTGC TGCTTGCAAC CGGCATGAAG AACGTGCCTG AAATACCCAA AGGTAGGGGC  1020
CTTTTCGGGG CTATCGCGGG ATTTATCGAA AACGGGTGGG AGGGACTCAT CGACGGCTGG  1080
TACGGCTTTA GGCATCAAAA CGCGCAAGGT GAAGGCACGG CAGCTGACTA CAAGAGCACG  1140
CAGTCTGCCA TCGATCAGAT AACCGGGAAA CTTAATCGCC TGATCGAAAA GACAAATCAG  1200
CAATTTGAAC TCATCGACAA TGAATTTAAC GAAGTGGAGA AGCAAATTGG CAATGTCATC  1260
AACTGGACAA GAGACTCAAT TACGGAAGTT TGGAGCTACA ATGCTGAATT GCTTGTAGCA  1320
ATGGAAAACC AGCATACGAT AGACCTGGCT GATTCTGAGA TGGACAAGCT CTATGAGCGG  1380
GTAAAAAGGC AGCTCCGAGA AAACGCCGAG GAGGACGGTA CGGGATGCTT CGAGATTTTC  1440
CATAAGTGTG ACGACGACTG TATGGCAAGT ATCCGAAATA ACACTTACGA TCATTCAAAA  1500
TACCGGGAGG AAGCTATGCA AAACAGAATA CAGATTGACC CGGTTAAATT GAGCAGCGGC  1560
TATAAAGATG TGATCCTGTG GTTTAGCTTC GGAGCTTCCT GTTTCATTCT TCTGGCAATA  1620
GTTATGGGTC TTGTATTTAT TTGTGTAAAA AACGGGAATA TGCGATGCAC GATCTGTATC  1680
TGA                                                                 1683
```

INFECTIOUS DISEASE ANTIGENS AND VACCINES

CROSS REFERENCE TO RELATED APPLICATIONS

This application is continuation of International Application No. PCT/US2021/025828, filed Apr. 5, 2021, which claims the benefit of U.S. Provisional Application No. 63/005,160 filed Apr. 3, 2020, which is hereby incorporated in its entirety by reference for all purposes.

SEQUENCE LISTING

The instant application contains a Sequence Listing which has been submitted electronically and is hereby incorporated by reference in its entirety. The accompanying sequence listing .XML file name GSO-090WOC1, was created on Oct. 31, 2022, and is 381 kb in size.

BACKGROUND

One question for antigen vaccine design is which of the many coding mutations present generate the "best" therapeutic antigens, e.g., antigens that can elicit immunity.

In addition to the challenges of current antigen prediction methods, certain challenges also exist with the available vector systems that can be used for antigen delivery in humans, many of which are derived from humans. For example, many humans have pre-existing immunity to human viruses as a result of previous natural exposure, and this immunity can be a major obstacle to the use of recombinant human viruses for antigen delivery for vaccination, such as infectious disease vaccines.

SUMMARY

Disclosed herein is a composition for delivery of a self-replicating alphavirus-based expression system, wherein the composition for delivery of the self-replicating alphavirus-based expression system comprises: (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, b. optionally a 5' linker sequence, and c. optionally a 3' linker sequence; (ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, and (B) a lipid-nanoparticle (LNP), wherein the LNP encapsulates the self-replicating alphavirus-based expression system.

Also disclosed herein is a composition for delivery of a self-replicating alphavirus-based expression system, wherein the composition for delivery of the self-replicating alphavirus-based expression system comprises: (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises the nucleic acid sequence set forth in SEQ ID NO:6, wherein the RNA alphavirus backbone sequence comprises a 26S promoter nucleotide sequence and a poly(A) sequence, wherein the 26S promoter sequence is endogenous to the RNA alphavirus backbone, and wherein the poly(A) sequence is endogenous to the RNA alphavirus backbone; and (b) a cassette integrated between the 26S promoter nucleotide sequence and the poly(A) sequence, wherein the cassette is operably linked to the 26S promoter nucleotide sequence, and wherein the cassette comprises at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and (B) a lipid-nanoparticle (LNP), wherein the LNP encapsulates the self-replicating alphavirus-based expression system.

In some aspects, the nucleic acid sequence encoding the peptide comprises an epitope-encoding nucleic acid sequence. In some aspects, the nucleic acid sequence encoding the peptide comprises two or more distinct epitope-encoding nucleic acid sequences. In some aspects, the nucleic acid sequence encoding the peptide comprises two or more distinct epitope-encoding nucleic acid sequences. In some aspects, the nucleic acid sequence encoding the peptide comprises between 1-10, between 1-20, between 1-30, between 1-40, between 1-50, between 1-100, between 1-200, between 1-300, between 1-400, or between 1-500 distinct epitope-encoding nucleic acid sequences distinct epitope-encoding nucleic acid sequences. In some aspects, the nucleic acid sequence encoding the peptide comprises between 2-10, between 2-20, between 2-30, between 2-40, between 2-50, between 2-100, between 2-200, between 2-300, between 2-400, or between 2-500 distinct epitope-encoding nucleic acid sequences distinct epitope-encoding nucleic acid sequences. In some aspects, the nucleic acid sequence encoding the peptide comprises a nucleic acid sequence encoding a full-length protein expressed in the infectious disease organism. In some aspects, the nucleic acid sequence encoding the peptide comprises a nucleic acid sequence encoding a protein domain of the protein expressed in the infectious disease organism. In some aspects, the nucleic acid sequence encoding the peptide comprises a nucleic acid sequence encoding a protein subunit of the protein expressed in the infectious disease organism. In some aspects, the nucleic acid sequence encoding the peptide comprises two or more distinct nucleic acid sequences encoding a peptide selected from: an epitope, a full-length protein, a protein subunit, a protein domain, and combinations thereof of the protein expressed in the infectious disease organism.

In some aspects, the encoded peptide or peptides is capable of stimulating an immune response when expressed in a subject. In some aspects, the encoded peptide or peptides is capable of stimulating a T cell response when expressed in a subject. In some aspects, the encoded peptide or peptides is capable of stimulating a B cell response when expressed in a subject. In some aspects, the encoded peptide or peptides is capable of stimulating a T cell response and a B cell response when expressed in a subject.

In some aspects, the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

In some aspects, an ordered sequence of each element of the cassette in the composition for delivery of the self-replicating alphavirus-based expression system is described in the formula, from 5' to 3', comprising $P_a$-$(L5_b$-$N_c$-$L3_d)_X$-$(G5_e$-$U_f)_Y$-$G3_g$ wherein P comprises the second promoter nucleotide sequence, where a=0 or 1, N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1, G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an MHC class I epitope-encoding nucleic acid sequence, and Y=0, 1, or 2, where for each Y the corresponding $U_f$ is an MHC class II epitope-encoding nucleic acid sequence. In some aspects, for each X the corresponding $N_c$ is a distinct MHC class I epitope-encoding nucleic acid sequence. In some aspects, for each Y the corresponding $U_f$ is a distinct MHC class II epitope-encoding nucleic acid sequence. In some aspects, wherein a=0, b=1, d=1, e=1, g=1, h=1, X=20, Y=2, the at least one promoter nucleotide sequence is a single 26S promoter nucleotide sequence provided by the RNA alphavirus backbone, the at least one polyadenylation poly(A) sequence is a poly(A) sequence of at least 100 consecutive A nucleotides provided by the RNA alphavirus backbone, the cassette is integrated between the 26S promoter nucleotide sequence and the poly(A) sequence, wherein the cassette is operably linked to the 26S promoter nucleotide sequence and the poly(A) sequence, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native C-terminal amino acid sequence of the MHC I epitope, and wherein the 3' linker sequence encodes a peptide that is at least 3 amino acids in length, U is each of a PADRE class II sequence and a Tetanus toxoid MHC class II sequence, the RNA alphavirus backbone is the sequence set forth in SEQ ID NO:6, and each of the MHC class I epitope-encoding nucleic acid sequences encodes a polypeptide that is between 13 and 25 amino acids in length.

In some aspects, the LNP comprises a lipid selected from the group consisting of: an ionizable amino lipid, a phosphatidylcholine, cholesterol, a PEG-based coat lipid, or a combination thereof. In some aspects, the LNP comprises an ionizable amino lipid, a phosphatidylcholine, cholesterol, and a PEG-based coat lipid. In some aspects, the ionizable amino lipids comprise MC3-like (dilinoleylmethyl-4-dimethylaminobutyrate) molecules. In some aspects, the LNP-encapsulated expression system has a diameter of about 100 nm.

In some aspects, the composition for delivery of the self-replicating alphavirus-based expression system is formulated for intramuscular (IM), intradermal (ID), subcutaneous (SC), or intravenous (IV) administration. In some aspects, the composition for delivery of the self-replicating alphavirus-based expression system is formulated for intramuscular (IM) administration.

In some aspects, the cassette is integrated between the at least one promoter nucleotide sequence and the at least one poly(A) sequence. In some aspects, the at least one promoter nucleotide sequence is operably linked to the cassette.

In some aspects, the one or more vectors comprise one or more +-stranded RNA vectors. In some aspects, the one or more +-stranded RNA vectors comprise a 5' 7-methyl-guanosine (m7g) cap. In some aspects, the one or more +-stranded RNA vectors are produced by in vitro transcription. In some aspects, the one or more vectors are self-replicating within a mammalian cell. In some aspects, the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the RNA alphavirus backbone comprises at least one nucleotide sequence of a Venezuelan equine encephalitis virus. In some aspects, the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the RNA alphavirus backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof. In some aspects, the RNA alphavirus backbone does not encode structural virion proteins capsid, E2 and E1. In some aspects, the cassette is inserted in place of structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the Venezuelan equine encephalitis virus comprises the sequence of SEQ ID NO:3 or SEQ ID NO:5. In some aspects, the Venezuelan equine encephalitis virus comprises the sequence of SEQ ID NO:3 or SEQ ID NO:5 further comprising a deletion between base pair 7544 and 11175. In some aspects, the RNA alphavirus backbone comprises the sequence set forth in SEQ ID NO:6 or SEQ ID NO:7. In some aspects, the cassette is inserted at position 7544 to replace the deletion between base pairs 7544 and 11175 as set forth in the sequence of SEQ ID NO:3 or SEQ ID NO:5. In some aspects, the insertion of the cassette provides for transcription of a polycistronic RNA comprising the nsP1-4 genes and the at least one nucleic acid sequence, wherein the nsP1-4 genes and the at least one nucleic acid sequence are in separate open reading frames.

In some aspects, the at least one promoter nucleotide sequence is the native 26S promoter nucleotide sequence encoded by the RNA alphavirus backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more vectors are each at least 300 nt in size. In some aspects, the one or more vectors are each at least 1 kb in size. In some aspects, the one or more vectors are each 2 kb in size. In some aspects, the one or more vectors are each less than 5 kb in size.

In some aspects, the at least one antigen-encoding nucleic acid sequence comprises two or more antigen-encoding nucleic acid sequences. In some aspects, each antigen-encoding nucleic acid sequence is linked directly to one another. In some aspects, each antigen-encoding nucleic acid sequence is linked to a distinct antigen-encoding nucleic acid sequence with a nucleic acid sequence encoding a linker. In some aspects, the linker links two MHC class I epitope-encoding nucleic acid sequences or an MHC class I epitope-encoding nucleic acid sequence to an MHC class II epitope-encoding nucleic acid sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II epitope-encoding nucleic acid sequences or an MHC class II sequence to an MHC class I epitope-encoding nucleic acid sequence. In some aspects, the linker comprises the sequence GPGPG.

In some aspects, the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the at least one antigen-encoding nucleic acid sequence comprises at least 2-10, 2, 3, 4, 5, 6, 7, 8, 9, or 10 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one antigen-encoding nucleic acid sequence comprises at least 2-400 antigen-encoding nucleic acid sequences and wherein at least two of the antigen-encoding nucleic acid sequences encode epitope sequences or portions thereof that are presented by MHC class I on a cell surface. In some aspects, the MHC class I epitopes are presented by MHC class I on the infected cell surface.

In some aspects, the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence. In some aspects, the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length. In some aspects, the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible.

In some aspects, the at least one poly(A) sequence comprises a poly(A) sequence native to the alphavirus. In some aspects, the at least one poly(A) sequence comprises a poly(A) sequence exogenous to the alphavirus. In some aspects, the at least one poly(A) sequence is operably linked to at least one of the at least one nucleic acid sequences. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the epitope-encoding nucleic acid sequence comprises a MHC class I epitope-encoding nucleic acid sequence, and wherein the MHC class I epitope-encoding nucleic acid sequence is selected by performing the steps of: (a) obtaining at least one of exome, transcriptome, or whole genome nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence. In some aspects, each of the MHC class I epitope-encoding nucleic acid sequences is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and; and (c) selecting a subset of the set of epitopes based on the set of numerical likelihoods to generate a set of selected epitopes which are used to generate the at least 20 MHC class I epitope-encoding nucleic acid sequences. In some aspects, a number of the set of selected epitopes is 2-20. In some aspects, the presentation model represents dependence between: (a) presence of a pair of a particular one of the MHC alleles and a particular amino acid at a particular position of a peptide sequence; and (b) likelihood of presentation on the infected cell surface, by the particular one of the MHC alleles of the pair, of such a peptide sequence comprising the particular amino acid at the particular position. In some aspects, selecting the set of selected epitopes comprises selecting epitopes that have an increased likelihood of being presented on the infected cell surface relative to unselected epitopes based on the presentation model. In some aspects, selecting the set of selected epitopes comprises selecting epitopes that have an increased likelihood of being capable of inducing a infectious disease organism-specific immune response in the subject relative to unselected epitopes based on the presentation model. In some aspects, selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC). In some aspects, selecting the set of selected epitopes comprises selecting epitopes that have a decreased likelihood of being subject to inhibition via central or peripheral tolerance relative to unselected epitopes based on the presentation model. In some aspects, selecting the set of selected epitopes comprises selecting epitopes that have a decreased likelihood of being capable of inducing an autoimmune response to normal tissue in the subject relative to unselected epitopes based on the presentation model. In some aspects, exome or transcriptome nucleotide sequencing data is obtained by performing sequencing on the infected tissue. In some aspects, the sequencing is next generation sequencing (NGS) or any massively parallel sequencing approach.

Also disclosed herein is a composition for delivery of a chimpanzee adenovirus (ChAdV)-based expression system, wherein the composition for delivery of the ChAdV-based expression system comprises: the ChAdV-based expression system, wherein the ChAdV-based expression system comprises a viral particle comprising a ChAdV vector, wherein the ChAdV vector comprises: (a) a ChAdV backbone, wherein the ChAdV backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and wherein the cassette is operably linked to the at least one promoter nucleotide sequence and the at least one poly(A) sequence.

Also disclosed herein is a composition for delivery of a ChAdV-based expression system, wherein the composition for delivery of the ChAdV-based expression system comprises: the ChAdV-based expression system, wherein the ChAdV-based expression system comprises a viral particle comprising a ChAdV vector, wherein the ChAdV vector comprises: (a) a ChAdV backbone, wherein the ChAdV backbone comprises: (i) a modified ChAdV68 sequence comprising at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion; (2) nucleotides 27,125 to 31,825 of the sequence shown in SEQ ID NO:1 corresponding to an E3 deletion; and optionally (3) nucleotides 34,916 to 35,642 of the sequence shown in SEQ ID NO:1 corresponding to a partial E4 deletion; (ii) a CMV promoter nucleotide sequence; and (iii) an SV40 polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and wherein the cassette is inserted within the E1 deletion and the cassette is operably linked to the CMV promoter nucleotide sequence and the SV40 poly(A) sequence.

In some aspects, the nucleic acid sequence encoding the peptide comprises an epitope-encoding nucleic acid sequence. In some aspects, the nucleic acid sequence encoding the peptide comprises two or more distinct epitope-encoding nucleic acid sequences. In some aspects, the nucleic acid sequence encoding the peptide comprises two or more distinct epitope-encoding nucleic acid sequences. In some aspects, the nucleic acid sequence encoding the peptide comprises between 1-10, between 1-20, between 1-30, between 1-40, between 1-50, between 1-100, between 1-200, between 1-300, between 1-400, or between 1-500 distinct epitope-encoding nucleic acid sequences distinct epitope-encoding nucleic acid sequences. In some aspects, the nucleic acid sequence encoding the peptide comprises between 2-10, between 2-20, between 2-30, between 2-40, between 2-50, between 2-100, between 2-200, between 2-300, between 2-400, or between 2-500 distinct epitope-encoding nucleic acid sequences distinct epitope-encoding nucleic acid sequences. In some aspects, the nucleic acid sequence encoding the peptide comprises a nucleic acid sequence encoding a full-length protein expressed in the infectious disease organism. In some aspects, the nucleic acid sequence encoding the peptide comprises a nucleic acid sequence encoding a protein domain of the protein expressed in the infectious disease organism. In some aspects, the nucleic acid sequence encoding the peptide comprises a nucleic acid sequence encoding a protein subunit of the protein expressed in the infectious disease organism. In some aspects, the nucleic acid sequence encoding the peptide comprises two or more distinct nucleic acid sequences encoding a peptide selected from: an epitope, a full-length protein, a protein subunit, a protein domain, and combinations thereof of the protein expressed in the infectious disease organism.

In some aspects, the encoded peptide or peptides is capable of stimulating an immune response when expressed in a subject. In some aspects, the encoded peptide or peptides is capable of stimulating a T cell response when expressed in a subject. In some aspects, the encoded peptide or peptides is capable of stimulating a B cell response when expressed in a subject. In some aspects, the encoded peptide or peptides is capable of stimulating a T cell response and a B cell response when expressed in a subject.

In some aspects, the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

In some aspects, the epitope-encoding nucleic acid sequence encodes an epitope known or suspected to be presented by MHC class I on a surface of a cell, optionally wherein the surface of the cell is an infected cell surface, and optionally wherein the cell is a subject's cell. In some aspects, the cell is an infected cell selected from the group consisting of: a pathogen infected cell, a virally infected cell, a bacterially infected cell, an fungally infected cell, and a parasitically infected cell. In some aspects, the virally infected cell is selected from the group consisting of: an HIV infected cell, an HPV infected cell, a SARS infected cell, a SARS-CoV-2 infected cell, an Ebola infected cell, a HBV infected cell, an influenza infected cell, a HCV infected cell, a CMV infected cell, a Chikungunya virus infected cell, a RSV infected cell, a Dengue virus infected cell, a orthymyxoviridae family virus infected cell, and a tuberculosis infected cell.

In some aspects, an ordered sequence of each element of the cassette in the composition for delivery of the ChAdV-based expression system is described in the formula, from 5' to 3', comprising $P_a$-$(L5_b$-$N_c$-$L3_d)_X$-$(G5_e$-$U_f)_Y$-$G3_g$ wherein P comprises the at least one promoter sequence operably linked to at least one of the at least one antigen-encoding nucleic acid sequences, where a=1, N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1. G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an MHC class I epitope-encoding nucleic acid sequence, and Y=0, 1, or 2, where for each Y the corresponding $U_f$ is an MHC class II epitope-encoding nucleic acid sequence. In some aspects, for each X the corresponding $N_c$ is a distinct MHC class I epitope-encoding nucleic acid sequence. In some aspects, for each Y the corresponding $U_f$ is a distinct MHC class II epitope-encoding nucleic acid sequence. In some aspects, b=1, d=1, e=1, g=1, h=1, X=10, Y=2, P is a CMV promoter sequence, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native C-terminal amino acid sequence of the MHC I epitope, and wherein the 3' linker sequence encodes a peptide that is at least 3 amino acids in length, U is each of a PADRE class II sequence and a Tetanus toxoid MHC class II sequence, the ChAdV vector comprises a modified ChAdV68 sequence comprising at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion; (2) nucleotides 27,125 to 31,825 of the sequence shown in SEQ ID NO:1 corresponding to an E3 deletion; and optionally (3) nucleotides 34,916 to 35,642 of the sequence shown in SEQ ID NO:1 corresponding to a partial E4 deletion, and the antigen cassette is inserted within the E1 deletion, and each of the MHC class I antigen-encoding nucleic acid sequences encodes a polypeptide that is 25 amino acids in length.

In some aspects, the composition for delivery of the ChAdV-based expression system is formulated for intramuscular (IM), intradermal (ID), subcutaneous (SC), or intravenous (IV) administration. In some aspects, the composition for delivery of the ChAdV-based expression system is formulated for intramuscular (IM) administration.

In some aspects, the cassette is integrated between the at least one promoter nucleotide sequence and the at least one poly(A) sequence. In some aspects, the at least one promoter nucleotide sequence is operably linked to the cassette.

In some aspects, the ChAdV backbone comprises a ChAdV68 vector backbone. In some aspects, the ChAdV68 vector backbone comprises the sequence set forth in SEQ ID NO:1. In some aspects, the ChAdV68 vector backbone comprises a functional deletion in at least one gene selected from the group consisting of an adenovirus E1A, E1B, E2A, E2B, E3, L1, L2, L3, L4, and L5 gene with reference to a ChAdV68 genome or with reference to the sequence shown in SEQ ID NO:1, optionally wherein the adenoviral backbone or modified ChAdV68 sequence is fully deleted or functionally deleted in: (1) E1A and E1B; or (2) E1A, E1B, and E3 with reference to the adenovirus genome or with reference to the sequence shown in SEQ ID NO:1, optionally wherein the E1 gene is functionally deleted through an E1 deletion of at least nucleotides 577 to 3403 with reference to the sequence shown in SEQ ID NO:1 and optionally wherein the E3 gene is functionally deleted through an E3 deletion of at least nucleotides 27,125 to 31,825 with reference to the sequence shown in SEQ ID NO:1. In some aspects, the ChAdV68 vector backbone comprises one or more deletions between base pair number 577 and 3403 or between base pair 456 and 3014, and optionally wherein the vector further comprises one or more deletions between base pair 27,125 and 31,825 or between base pair 27,816 and 31,333 of the sequence set forth in SEQ ID NO:1. In some aspects, the ChAdV68 vector backbone comprises at least nucleotides 2 to 36,518 of the sequence set forth in SEQ ID NO:1, wherein the nucleotides 2 to 36,518 lack: A. nucleotides 577 to 3403 of the sequence shown in SEQ ID NO:1 corresponding to an E1 deletion; B. nucleotides 27,125 to 31,825 of the sequence shown in SEQ ID NO:1 corresponding to an E3 deletion; C. nucleotides 34,916 to 35,642 of the sequence shown in SEQ ID NO:1 corresponding to a partial E4 deletion; D. nucleotides 456 to 3014 of the sequence shown in SEQ ID NO:1; E. nucleotides 27,816 to 31,333 of the sequence shown in SEQ ID NO:1; F. nucleotides 3957 to 10346 of the sequence shown in SEQ ID NO:1; G. nucleotides 21787 to 23370 of the sequence shown in SEQ ID NO:1; H. nucleotides 33486 to 36193 of the sequence shown in SEQ ID NO:1; or combinations thereof.

In some aspects, the ChAdV68 vector backbone comprises a partially deleted E4 gene. In some aspects, the partially deleted E4 gene comprises: A. the E4 gene sequence shown in SEQ ID NO:1 and that lacks at least nucleotides 34,916 to 35,642 of the sequence shown in SEQ ID NO:1, B. the E4 gene sequence shown in SEQ ID NO:1 and that lacks at least nucleotides 34,916 to 34,942, nucleotides 34,952 to 35,305 of the sequence shown in SEQ ID NO:1, nucleotides 35,302 to 35,642 of the sequence shown in SEQ ID NO:1, and wherein the vector comprises at least nucleotides 2 to 36,518 of the sequence shown in SEQ ID NO:1, C. the E4 gene sequence shown in SEQ ID NO:1 and that lacks at least nucleotides 34,980 to 36,516 of the sequence shown in SEQ ID NO:1, and wherein the vector comprises at least nucleotides 2 to 36,518 of the sequence shown in SEQ ID NO:1, D. the E4 gene sequence shown in SEQ ID NO:1 and that lacks at least nucleotides 34,979 to 35,642 of the sequence shown in SEQ ID NO:1, and wherein the vector comprises at least nucleotides 2 to 36,518 of the sequence shown in SEQ ID NO:1, E. an E4 deletion of at least a partial deletion of E4Orf2, a fully deleted E4Orf3, and at least a partial deletion of E4Orf4, F. an E4 deletion of at least a partial deletion of E4Orf2, at least a partial deletion of E4Orf3, and at least a partial deletion of E4Orf4, G. an E4 deletion of at least a partial deletion of E4Orf1, a fully deleted E4Orf2, and at least a partial deletion of E4Orf3, or H. an E4 deletion of at least a partial deletion of E4Orf2 and at least a partial deletion of E4Orf3.

In some aspects, the cassette is inserted in the ChAdV backbone at the E1 region, E3 region, and/or any deleted AdV region that allows incorporation of the cassette. In some aspects, the ChAdV backbone is generated from one of a first generation, a second generation, or a helper-dependent adenoviral vector.

In some aspects, the at least one promoter nucleotide sequence is selected from the group consisting of: a CMV, a SV40, an EF-1, a RSV, a PGK, a HSA, a MCK, and a EBV promoter sequence. In some aspects, the at least one promoter nucleotide sequence is a CMV promoter sequence.

In some aspects, at least one of the epitope-encoding nucleic acid sequences encodes an epitope that, when expressed and translated, is capable of being presented by MHC class I on a cell of a subject. In some aspects, at least one of the epitope-encoding nucleic acid sequences encodes an epitope that, when expressed and translated, is capable of being presented by MHC class II on a cell of a subject.

In some aspects, the at least one antigen-encoding nucleic acid sequence comprises two or more antigen-encoding nucleic acid sequences. In some aspects, each antigen-encoding nucleic acid sequence is linked directly to one another. In some aspects, each antigen-encoding nucleic acid sequence is linked to a distinct antigen-encoding nucleic acid sequence encoding a linker. In some aspects, the linker links two MHC class I epitope-encoding nucleic acid sequences or an MHC class I epitope-encoding nucleic acid sequence to an MHC class II epitope-encoding nucleic acid sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II epitope-encoding nucleic acid sequences or an MHC class II sequence to an MHC class I epitope-encoding nucleic acid sequence. In some aspects, the linker comprises the sequence GPGPG.

In some aspects, the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the epitope-encoding nucleic acid sequence comprises at least one alteration that makes the encoded epitope have increased binding affinity to its corresponding MHC allele relative to the translated, corresponding wild-type nucleic acid sequence. In some aspects, the epitope-encoding nucleic acid sequence comprises at least one alteration that makes the encoded epitope have increased binding stability to its corresponding MHC allele relative to the translated, corresponding wild-type nucleic acid sequence. In some aspects, the epitope-encoding nucleic acid sequence comprises at least one alteration that makes the encoded epitope have an increased likelihood of presentation on its corresponding MHC allele relative to the translated, corresponding wild-type nucleic acid sequence. In some aspects, the at least one alteration comprises a point mutation, a frameshift mutation, a non-frameshift mutation, a deletion mutation, an insertion mutation, a splice variant, a genomic rearrangement, or a proteasome-generated spliced antigen. In some aspects, the epitope-encoding nucleic acid sequence encodes an epitope known or suspected to be expressed in a subject known or suspected to have an infection. In some aspects, the infection is selected from the group consisting of: a pathogen infection, a viral infection, a bacterial infection, an fungal infection, and a parasitic infection. In some aspects, the viral infection is selected from the group consisting of: an HIV infection, an HPV infection, a SARS infection, a SARS-CoV-2 infection, an Ebola infection, a HBV infection, an influenza infection, a HCV infection, a CMV infection, a Chikungunya virus infection, a RSV infection, a Dengue virus infection, a orthymyxoviridae family virus infection, and a tuberculosis infection. In some aspects, the bacterial infection is a tuberculosis infection.

In some aspects, the at least one antigen-encoding nucleic acid sequence comprises at least 2-10, 2, 3, 4, 5, 6, 7, 8, 9, or 10 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one antigen-encoding nucleic acid sequence comprises at least 2-400 antigen-encoding nucleic acid sequences and wherein at least two of the antigen-encoding nucleic acid sequences encode epitope sequences or portions thereof that are presented by MHC class I on a cell surface. In some aspects, at least two of the MHC class I epitopes are presented by MHC class I on the infected cell surface. In some aspects, the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence. In some aspects, the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length. In some aspects, the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE.

In some aspects, the at least one promoter nucleotide sequence is inducible. In some aspects, the at least one promoter nucleotide sequence is non-inducible.

In some aspects, the at least one poly(A) sequence comprises a Bovine Growth Hormone (BGH) SV40 polyA sequence. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the cassette further comprises at least one of: an intron sequence, a woodchuck hepatitis virus post-transcriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one antigen-encoding nucleic acid sequences. In some aspects, the cassette further comprises a reporter gene, including but not limited to, green fluorescent protein (GFP), a GFP variant, secreted alkaline phosphatase, luciferase, a luciferase variant, or a detectable peptide or epitope. In some aspects, the detectable peptide or epitope is selected from the group consisting of an HA tag, a Flag tag, a His-tag, or a V5 tag.

In some aspects, the one or more vectors further comprises one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES; or the heavy and light chain sequences of the antibody are linked by a flexible linker such as consecutive glycine residues. In some aspects, the immune modulator is a cytokine. In some aspects, the cytokine is at least one of IL-2, IL-7, IL-12, IL-15, or IL-21 or variants thereof of each.

In some aspects, the epitope-encoding nucleic acid sequence comprises a MHC class I epitope-encoding nucleic acid sequence, and wherein the MHC class I epitope-encoding nucleic acid sequence is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence. In some aspects, each of the MHC class I epitope-encoding nucleic acid sequences is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the at least 20 MHC class I epitope-encoding nucleic acid sequences. In some aspects, a number of the set of selected epitopes is 2-20. In some aspects, the presentation model represents dependence between: (a) presence of a pair of a particular one of the MHC alleles and a particular amino acid at a particular position of a peptide sequence; and (b) likelihood of presentation on the infected cell surface, by the particular one of the MHC alleles of the pair, of such a peptide sequence comprising the particular amino acid at the particular position. In some aspects, selecting the set of selected epitopes comprises selecting epitopes that have an increased likelihood of being presented on the infected cell surface relative to unselected epitopes based on the presentation model. In some aspects, selecting the set of selected epitopes comprises selecting epitopes that have an increased likelihood of being capable of inducing a infectious disease organism-specific immune response in the subject relative to unselected epitopes based on the presentation model. In some aspects, selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC). In some aspects, selecting the set of selected epitopes comprises selecting epitopes that have a decreased likelihood of being subject to inhibition via central or peripheral tolerance relative to unselected epitopes based on the presentation model. In some aspects, selecting the set of selected epitopes comprises selecting epitopes that have a decreased likelihood of being capable of inducing an autoimmune response to normal tissue in the subject relative to unselected epitopes based on the presentation model. In some aspects, exome or transcriptome nucleotide sequencing data is obtained by performing sequencing on the infected tissue. In some aspects, the sequencing is next generation sequencing (NGS) or any massively parallel sequencing approach.

In some aspects, the cassette comprises junctional epitope sequences formed by adjacent sequences in the cassette. In some aspects, at least one or each junctional epitope sequence has an affinity of greater than 500 nM for MHC. In some aspects, each junctional epitope sequence is non-self. In some aspects, the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the cassette. In some aspects, the prediction is based on presentation likelihoods generated by inputting sequences of the non-therapeutic epitopes into a presentation model. In some aspects, an order of the antigen-encoding nucleic acid sequences in the cassette is determined by a series of steps comprising: (a) generating a set of candidate cassette sequences corresponding to different orders of the antigen-encoding nucleic acid sequences; (b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine.

In some aspects, the composition for delivery of the ChAdV-based expression system is formulated in a pharmaceutical composition comprising a pharmaceutically acceptable carrier.

In some aspects, one or more of the epitope-encoding nucleic acid sequences are derived from an infection in or an infected cell of a subject. In some aspects, each of the epitope-encoding nucleic acid sequences are derived from an infection in or an infected cell of a subject. In some aspects, one or more of the epitope-encoding nucleic acid sequences are not derived from an infection in or an infected cell of a subject. In some aspects, each of the epitope-encoding nucleic acid sequences are not derived from an infection in or an infected cell of a subject.

In some aspects, the at least one antigen-encoding nucleic acid sequence comprises at least 10, 11, 12, 13, 14, 15, 16, 17, 18, 19, or 20 infectious disease organism-specific MHC class I antigen-encoding nucleic acid sequences linearly linked to each other. In some aspects, the at least one epitope-encoding nucleic acid sequence comprises at least 10, 11, 12, 13, 14, 15, 16, 17, 18, 19, or 20 infectious disease organism-specific MHC class I epitope-encoding nucleic acid sequences linearly linked to each other.

Also provided for herein is a kit comprising any of the compositions for delivery of the ChAdV-based expression system described herein, and instructions for use.

Also provided for herein is a composition for delivery of a self-replicating alphavirus-based expression system, wherein the composition for delivery of the self-replicating alphavirus-based expression system comprises: (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, wherein the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis; b. optionally a 5' linker sequence, and c. optionally a 3' linker sequence; (ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, and (B) a lipid-nanoparticle (LNP), wherein the LNP encapsulates the self-replicating alphavirus-based expression system.

Also provided for herein is a composition for delivery of a chimpanzee adenovirus (ChAdV)-based expression system, wherein the composition for delivery of the ChAdV-based expression system comprises: the ChAdV-based expression system, wherein the ChAdV-based expression system comprises a viral particle comprising a ChAdV vector, wherein the ChAdV vector comprises: (a) a ChAdV backbone, wherein the ChAdV backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, wherein the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis; b. optionally a 5' linker sequence, and c. optionally a 3' linker sequence; and wherein the cassette is operably linked to the at least one promoter nucleotide sequence and the at least one poly(A) sequence.

In some aspects the self-replicating alphavirus-based expression system or the ChAdV-based expression system comprise any of the features of any one of the above claims.

In some aspects, the cassette of the composition for delivery of the ChAdV-based expression system is identical to the cassette of the composition for delivery of the self-replicating alphavirus-based expression system.

Also disclosed herein is method for stimulating an immune response in a subject, the method comprising administering to the subject a composition for delivery of a self-replicating alphavirus-based expression system and/or administering to the subject a composition for delivery of a chimpanzee adenovirus (ChAdV)-based expression system, and wherein either: a. the composition for delivery of the ChAdV-based expression system comprises the ChAdV-based expression system, b, wherein the composition for delivery of the self-replicating alphavirus-based expression system comprises the self-replicating alphavirus-based expression system, or c. the composition for delivery of the ChAdV-based expression system comprises the ChAdV-based expression system, and wherein the composition for delivery of the self-replicating alphavirus-based expression system comprises the self-replicating alphavirus-based expression system.

In some aspects, the composition for delivery of the ChAdV-based expression system is administered as a priming dose and either the composition for delivery of the ChAdV-based expression system or the composition for delivery of the self-replicating alphavirus-based expression system is administered as one or more boosting doses. In some aspects, the composition for delivery of the self-replicating alphavirus-based expression system is administered as a priming dose either the composition for delivery of the ChAdV-based expression system or the composition for delivery of the self-replicating alphavirus-based expression system is administered as one or more boosting doses. In some aspects, two or more boosting doses are administered. In some aspects, 1, 2, 3, 4, 5, 6, 7, or 8 boosting doses are administered.

In some aspects, the composition for delivery of the ChAdV-based expression system is administered intramuscularly (IM), intradermally (ID), subcutaneously (SC), or intravenously (IV). In some aspects, the composition for delivery of the ChAdV-based expression system is administered (IM). In some aspects, the IM administration is administered at separate injection sites. In some aspects, the separate injection sites are in opposing deltoid muscles. In some aspects, the separate injection sites are in gluteus or rectus femoris sites on each side.

In some aspects, the composition for delivery of the self-replicating alphavirus-based expression system is administered intramuscularly (IM), intradermally (ID), subcutaneously (SC), or intravenously (IV). In some aspects, the composition for delivery of the self-replicating alphavirus-based expression system is administered (IM). In some aspects, the IM administration is administered at separate injection sites. In some aspects, the separate injection sites are in opposing deltoid muscles. In some aspects, the separate injection sites are in gluteus or rectus femoris sites on each side. In some aspects, the injection site of the one or more boosting doses is as close as possible to the injection site of the priming dose.

In some aspects, the method further comprises determining or having determined the HLA-haplotype of the subject.

In some aspects, the method further comprises administering nivolumab. In some aspects, nivolumab is administered as an intravenous (IV) infusion. In some aspects, nivolumab is administered at a dose of 480 mg. In some aspects, nivolumab is administered on day 1. In some aspects, nivolumab is on administered day 1 and administered every 4 weeks (Q4W) following the priming dose. In some aspects, nivolumab is on administered on the same day as the priming dose or on the same day as the one or more boosting doses. In some aspects, nivolumab is formulated in solution at 10 mg/mL.

In some aspects, the method further comprises administering ipilimumab. In some aspects, ipilimumab is administered an intravenous (IV) infusion. In some aspects, ipilimumab is administered subcutaneously (SC). In some aspects, the SC administration is injected proximally (within ~2 cm) to one or more of the priming dose injection site or the one or more boosting dose injection sites. In some aspects, the SC administration is administered as 4 separate injections or administered as 6 separate injections. In some aspects, ipilimumab is administered at a dose of 30 mg. In some aspects, ipilimumab is administered on day 1. In some aspects, ipilimumab is on administered day 1 and administered every 4 weeks (Q4W) following the priming dose. In some aspects, ipilimumab is on administered on the same day as the priming dose or on the same day as the one or more boosting doses. In some aspects, ipilimumab is formulated in solution at 5 mg/mL.

In some aspects, the composition for delivery of the self-replicating alphavirus-based expression system comprises: (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; (ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, and (B) a lipid-nanoparticle (LNP), wherein the LNP encapsulates the self-replicating alphavirus-based expression system.

In some aspects, the composition for delivery of the self-replicating alphavirus-based expression system comprises. (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises the nucleic acid sequence set forth in SEQ ID NO:6, wherein the RNA alphavirus backbone sequence comprises a 26S promoter nucleotide sequence and a poly(A) sequence, wherein the 26S promoter sequence is endogenous to the RNA alphavirus backbone, and wherein the poly(A) sequence is endogenous to the RNA alphavirus backbone; and (b) a cassette integrated between the 26S promoter nucleotide sequence and the poly(A) sequence, wherein the cassette is operably linked to the 26S promoter nucleotide sequence, and wherein the cassette comprises at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and (B) a lipid-nanoparticle (LNP), wherein the LNP encapsulates the self-replicating alphavirus-based expression system.

In some aspects, the composition for delivery of the self-replicating alphavirus-based expression system comprises at least 30 µg of each of the one or more vectors. In some aspects, the composition for delivery of the self-replicating alphavirus-based expression system comprises at least 100 µg of each of the one or more vectors. In some aspects, the composition for delivery of the self-replicating alphavirus-based expression system comprises at least 300 µg of each of the one or more vectors. In some aspects, the composition for delivery of the self-replicating alphavirus-based expression system comprises at least 400 µg, at least 500 µg, at least 600 µg, at least 700 µg, at least 800 µg, at least 900 µg, at least 1000 µg of each of the one or more vectors. In some aspects, the composition for delivery of the self-replicating alphavirus-based expression system comprises between 10-30 µg, 10-100 µg, 10-300 µg, 30-100 µg, 30-300 µg, or 100-300 µg of each of the one or more vectors. In some aspects, the composition for delivery of the self-replicating alphavirus-based expression system comprises between 10-500 µg, 10-1000 µg, 30-500 µg, 30-1000 µg, or 500-1000 µg of each of the one or more vectors. In some aspects, the composition for delivery of the self-replicating alphavirus-based expression system comprises 400 µg, 500 µg, 600 µg, 700 µg, 800 µg, 900 µg, or 1000 µg of each of the one or more vectors In some aspects, the composition for delivery of the self-replicating alphavirus-based expression system comprises 10 µg, 30 µg, 100 µg, or 300 µg of each of the one or more vectors. In some aspects, the composition for delivery of the self-replicating alphavirus-based expression system comprises less than or equal to 300 µg of each of the one or more vectors.

In some aspects, the weight to weight ratio of the LNP to total weight of the one or more vectors is between 10-40 to 1. In some aspects, the weight to weight ratio of the LNP to total weight of the one or more vectors is between 16-32 to 1. In some aspects, the weight to weight ratio of the LNP to total weight of the one or more vectors is about 24 to 1. In some aspects, the weight to weight ratio of the LNP to total weight of the one or more vectors is 24 to 1.

In some aspects, the one or more vectors is at a concentration of 1 mg/mL.

In some aspects, an ordered sequence of each element of the cassette in the composition for delivery of the self-replicating alphavirus-based expression system is described in the formula, from 5' to 3', comprising $P_a\text{-}(L5_b\text{-}N_c\text{-}L3_d)_X\text{-}(G5_e\text{-}U_f)_Y\text{-}G3_g$ wherein P comprises the second promoter nucleotide sequence, where a=0 or 1, N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1, G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an MHC class I epitope-encoding nucleic acid sequence, and Y=0, 1, or 2, where for each Y the corresponding $U_f$ is an MHC class II epitope-encoding nucleic acid sequence. In some aspects, for each X the corresponding $N_c$ is a distinct MHC class I epitope-encoding nucleic acid sequence. In some aspects, for each Y the corresponding $U_f$ is a distinct MHC class II epitope-encoding nucleic acid sequence. In some aspects, a=0, b=1, d=1, e=1, g=1, h=1, X=20, Y=2, the at least one promoter nucleotide sequence is a single 26S promoter nucleotide sequence provided by the RNA alphavirus backbone, the at least one polyadenylation poly(A) sequence is a poly(A) sequence of at least 100 consecutive A nucleotides provided by the RNA alphavirus backbone, the cassette is integrated between the 26S promoter nucleotide sequence and the poly(A) sequence, wherein the cassette is operably linked to the 26S promoter nucleotide sequence and the poly(A) sequence, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native C-terminal amino acid sequence of the MHC I epitope, and wherein the 3' linker sequence encodes a peptide that is at least 3 amino acids in length, U is each of a PADRE class II sequence and a Tetanus toxoid MHC class II sequence, the RNA alphavirus backbone is the sequence set forth in SEQ ID NO:6, and each of the MHC class I epitope-encoding nucleic acid sequences encodes a polypeptide that is between 13 and 25 amino acids in length.

In some aspects, the LNP comprises a lipid selected from the group consisting of: an ionizable amino lipid, a phosphatidylcholine, cholesterol, a PEG-based coat lipid, or a combination thereof. In some aspects, the LNP comprises an ionizable amino lipid, a phosphatidylcholine, cholesterol, and a PEG-based coat lipid. In some aspects, the ionizable amino lipids comprise MC3-like (dilinoleylmethyl-4-dimethylaminobutyrate) molecules. In some aspects, the LNP-encapsulated expression system has a diameter of about 100 nm.

In some aspects, the cassette is integrated between the at least one promoter nucleotide sequence and the at least one poly(A) sequence.

In some aspects, the at least one promoter nucleotide sequence is operably linked to the cassette.

In some aspects, the one or more vectors comprise one or more +-stranded RNA vectors. In some aspects, the one or more +-stranded RNA vectors comprise a 5' 7-methyl-guanosine (m7g) cap. In some aspects, the one or more +-stranded RNA vectors are produced by in vitro transcription. In some aspects, the one or more vectors are self-replicating within a mammalian cell. In some aspects, the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the RNA alphavirus backbone comprises at least one nucleotide sequence of a Venezuelan equine encephalitis virus. In some aspects, the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the RNA alphavirus backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof. In some aspects, the RNA alphavirus backbone does not encode structural virion proteins capsid, E2 and E1. In some aspects, the cassette is inserted in place of structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the Venezuelan equine encephalitis virus comprises the sequence of SEQ ID NO:3 or SEQ ID NO:5. In some aspects, the Venezuelan equine encephalitis virus comprises the sequence of SEQ ID NO:3 or SEQ ID NO:5 further comprising a deletion between base pair 7544 and 11175. In some aspects, the RNA alphavirus backbone comprises the sequence set forth in SEQ ID NO:6 or SEQ ID NO:7. In some aspects, the cassette is inserted at position 7544 to replace the deletion between base pairs 7544 and 11175 as set forth in the sequence of SEQ ID NO:3 or SEQ ID NO:5. In some aspects, the insertion of the cassette provides for transcription of a polycistronic RNA comprising the nsP1-4 genes and the at least one nucleic acid sequence, wherein the nsP1-4 genes and the at least one nucleic acid sequence are in separate open reading frames.

In some aspects, the at least one promoter nucleotide sequence is the native 26S promoter nucleotide sequence encoded by the RNA alphavirus backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more vectors are each at least 300 nt in size. In some aspects, the one or more vectors are each at least 1 kb in size. In some aspects, the one or more vectors are each 2 kb in size. In some aspects, the one or more vectors are each less than 5 kb in size.

In some aspects, the at least one antigen-encoding nucleic acid sequence comprises two or more antigen-encoding nucleic acid sequences. In some aspects, each antigen-encoding nucleic acid sequence is linked directly to one another. In some aspects, each antigen-encoding nucleic acid sequence is linked to a distinct antigen-encoding nucleic acid sequence with a nucleic acid sequence encoding a linker. In some aspects, the linker links two MHC class I epitope-encoding nucleic acid sequences or an MHC class I epitope-encoding nucleic acid sequence to an MHC class II epitope-encoding nucleic acid sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II epitope-encoding nucleic acid sequences or an MHC class II sequence to an MHC class I epitope-encoding nucleic acid sequence. In some aspects, the linker comprises the sequence GPGPG.

In some aspects, the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the at least one antigen-encoding nucleic acid sequence comprises at least 2-10, 2, 3, 4, 5, 6, 7, 8, 9, or 10 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one antigen-encoding nucleic acid sequence comprises at least 2-400 antigen-encoding nucleic acid sequences and wherein at least two of the antigen-encoding nucleic acid sequences encode epitope sequences or portions thereof that are presented by MHC class I on a cell surface. In some aspects, at least two of the MHC class I epitopes are presented by MHC class I on the infected cell surface.

In some aspects, the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence. In some aspects, the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length. In some aspects, the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible. In some aspects, the at least one poly(A) sequence comprises a poly(A) sequence native to the alphavirus. In some aspects, the at least In some aspects, the at least one poly(A) sequence is operably linked to at least one of the at least one nucleic acid sequences. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the epitope-encoding nucleic acid sequence comprises a MHC class I epitope-encoding nucleic acid sequence, and wherein the MHC class I epitope-encoding nucleic acid sequence is selected by performing the steps of: (a) obtaining at least one of exome, transcriptome, or whole genome nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence. In some aspects, each of the MHC class I epitope-encoding nucleic acid sequences is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the at least 20 MHC class I epitope-encoding nucleic acid sequences. In some aspects, a number of the set of selected epitopes is 2-20. In some aspects, the presentation model represents dependence between: (a) presence of a pair of a particular one of the MHC alleles and a particular amino acid at a particular position of a peptide sequence; and (b) likelihood of presentation on the infected cell surface, by the particular one of the MHC alleles of the pair, of such a peptide sequence comprising the particular amino acid at the particular position. In some aspects, selecting the set of selected epitopes comprises selecting epitopes that have an increased likelihood of being presented on the infected cell surface relative to unselected epitopes based on the presentation model. In some aspects, selecting the set of selected epitopes comprises selecting epitopes that have an increased likelihood of being capable of inducing a infectious disease organism-specific immune response in the subject relative to unselected epitopes based on the presentation model. In some aspects, selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC). In some aspects, selecting the set of selected epitopes comprises selecting epitopes that have a decreased likelihood of being subject to inhibition via central or peripheral tolerance relative to unselected epitopes based on the presentation model. In some aspects, selecting the set of selected epitopes comprises selecting epitopes that have a decreased likelihood of being capable of inducing an autoimmune response to normal tissue in the subject relative to unselected epitopes based on the presentation model. In some aspects, exome or transcriptome nucleotide sequencing data is obtained by performing sequencing on the infected tissue. In some aspects, the sequencing is next generation sequencing (NGS) or any massively parallel sequencing approach.

In some aspects, the ChAdV vector comprises: (a) a ChAdV backbone, wherein the ChAdV backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and wherein the cassette is operably linked to the at least one promoter nucleotide sequence and the at least one poly(A) sequence.

In some aspects, the ChAdV vector comprises: (a) a ChAdV backbone, wherein the ChAdV backbone comprises: (i) a modified ChAdV68 sequence comprising at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion; (2) nucleotides 27,125 to 31,825 of the sequence shown in SEQ ID NO:1 corresponding to an E3 deletion; and optionally (3) nucleotides 34,916 to 35,642 of the sequence shown in SEQ ID NO:1 corresponding to a partial E4 deletion; (ii) a CMV promoter nucleotide sequence; and (iii) an SV40 polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide b. optionally a 5' linker sequence, and c. optionally a 3' linker sequence; and wherein the cassette is inserted within the E1 deletion and the cassette is operably linked to the CMV promoter nucleotide sequence and the SV40 poly(A) sequence.

In some aspects, the nucleic acid sequence encoding the peptide comprises an epitope-encoding nucleic acid sequence, optionally wherein the nucleic acid sequence encoding the peptide comprises two or more distinct epitope-encoding nucleic acid sequences. In some aspects, the nucleic acid sequence encoding the peptide comprises between 1-10, between 1-20, between 1-30, between 1-40, between 1-50, between 1-100, between 1-200, between 1-300, between 1-400, or between 1-500 distinct epitope-encoding nucleic acid sequences distinct epitope-encoding nucleic acid sequences, optionally wherein the nucleic acid sequence encoding the peptide comprises between 2-10, between 2-20, between 2-30, between 2-40, between 2-50, between 2-100, between 2-200, between 2-300, between 2-400, or between 2-500 distinct epitope-encoding nucleic acid sequences distinct epitope-encoding nucleic acid sequences. In some aspects, the nucleic acid sequence encoding the peptide comprises a nucleic acid sequence encoding a peptide selected from: an epitope, a full-length protein, a protein subunit, a protein domain, of the protein expressed in the infectious disease organism, optionally wherein the infectious disease organism comprises two or more distinct nucleic acid sequences encoding a peptide selected from: an epitope, a full-length protein, a protein subunit, a protein domain, and combinations thereof of the protein expressed in the infectious disease organism. In some aspects, the encoded peptide or peptides is capable of stimulating an immune response when expressed in a subject, optionally wherein the immune response is a T cell response and/or a B cell response. In some aspects, the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

In some aspects, the epitope-encoding nucleic acid sequence encodes an epitope known or suspected to be presented by MHC class I on a surface of a cell, optionally wherein the surface of the cell is an infected cell surface, and optionally wherein the cell is the subject's cell. In some aspects, the cell is an infected cell selected from the group consisting of: a pathogen infected cell, a virally infected cell, a bacterially infected cell, an fungally infected cell, and a parasitically infected cell. In some aspects, the virally infected cell is selected from the group consisting of: an HIV infected cell, an HPV infected cell, a SARS infected cell, a SARS-CoV-2 infected cell, an Ebola infected cell, a HBV infected cell, an influenza infected cell, a HCV infected cell, a CMV infected cell, a Chikungunya virus infected cell, a RSV infected cell, a Dengue virus infected cell, a orthymyxoviridae family virus infected cell, and a tuberculosis infected cell.

In some aspects, an ordered sequence of each element of the cassette in the composition for delivery of the ChAdV-based expression system is described in the formula, from 5' to 3', comprising $P_a\text{-}(L5_b\text{-}N_c\text{-}L3_d)_X\text{-}(G5_e\text{-}U_f)_Y\text{-}G3_g$ wherein P comprises the at least one promoter sequence operably linked to at least one of the at least one antigen-encoding nucleic acid sequences, where a=1, N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1, G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an MHC class I epitope-encoding nucleic acid sequence, and Y=0, 1, or 2, where for each Y the corresponding $U_f$ is an MHC class II epitope-encoding nucleic acid sequence. In some aspects, for each X the corresponding $N_c$ is a distinct MHC class I epitope-encoding nucleic acid sequence. In some aspects, for each Y the corresponding $U_f$ is a distinct MHC class II epitope-encoding nucleic acid sequence. In some aspects, b=1, d=1, e=1, g=1, h=1, X=10, Y=2, P is a CMV promoter sequence, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native C-terminal amino acid sequence of the MHC I epitope, and wherein the 3' linker sequence encodes a peptide that is at least 3 amino acids in length, U is each of a PADRE class II sequence and a Tetanus toxoid MHC class II sequence, the ChAdV vector comprises a modified ChAdV68 sequence comprising at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion; (2) nucleotides 27,125 to 31,825 of the sequence shown in SEQ ID NO:1 corresponding to an E3 deletion; and optionally (3) nucleotides 34,916 to 35,642 of the sequence shown in SEQ ID NO:1 corresponding to a partial E4 deletion, and the antigen cassette is inserted within the E1 deletion, and each of the MHC class I antigen-encoding nucleic acid sequences encodes a polypeptide that is 25 amino acids in length.

In some aspects, the cassette is integrated between the at least one promoter nucleotide sequence and the at least one poly(A) sequence. In some aspects, the at least one promoter nucleotide sequence is operably linked to the cassette.

In some aspects, the ChAdV backbone comprises a ChAdV68 vector backbone. In some aspects, the ChAdV68 vector backbone comprises the sequence set forth in SEQ ID NO:1. In some aspects, the ChAdV68 vector backbone comprises a functional deletion in at least one gene selected from the group consisting of an adenovirus E1A, E1B, E2A, E2B, E3, L1, L2, L3, L4, and L5 gene with reference to a ChAdV68 genome or with reference to the sequence shown in SEQ ID NO:1, optionally wherein the adenoviral backbone or modified ChAdV68 sequence is fully deleted or functionally deleted in: (1) E1A and E1B; or (2) E1A, E1B, and E3 with reference to the adenovirus genome or with reference to the sequence shown in SEQ ID NO:1, optionally wherein the E1 gene is functionally deleted through an E1 deletion of at least nucleotides 577 to 3403 with reference to the sequence shown in SEQ ID NO:1 and optionally wherein the E3 gene is functionally deleted through an E3 deletion of at least nucleotides 27,125 to 31,825 with reference to the sequence shown in SEQ ID NO:1. In some aspects, the ChAdV68 vector backbone comprises one or more genes or regulatory sequences with reference to a ChAdV68 genome or with reference to the sequence shown in SEQ ID NO:1, optionally wherein the one or more genes or regulatory sequences are selected from the group consisting of the chimpanzee adenovirus inverted terminal repeat (ITR), E1A, E1B, E2A, E2B, E3, E4, L1, L2, L3, L4, and L5 genes.

In some aspects, the ChAdV68 vector backbone comprises a partially deleted E4 gene. In some aspects, the partially deleted E4 gene comprises: A. the E4 gene sequence shown in SEQ ID NO:1 and that lacks at least nucleotides 34,916 to 35,642 of the sequence shown in SEQ ID NO:1, B. the E4 gene sequence shown in SEQ ID NO:1 and that lacks at least nucleotides 34,916 to 34,942, nucleotides 34,952 to 35,305 of the sequence shown in SEQ ID NO:1, nucleotides 35,302 to 35,642 of the sequence shown in SEQ ID NO:1, and wherein the vector comprises at least nucleotides 2 to 36,518 of the sequence shown in SEQ ID NO:1. C. the E4 gene sequence shown in SEQ ID NO:1 and that lacks at least nucleotides 34,980 to 36,516 of the sequence shown in SEQ ID NO:1, and wherein the vector comprises at least nucleotides 2 to 36,518 of the sequence shown in SEQ ID NO:1, D. the E4 gene sequence shown in SEQ ID NO:1 and that lacks at least nucleotides 34,979 to 35,642 of the sequence shown in SEQ ID NO:1, and wherein the vector comprises at least nucleotides 2 to 36,518 of the sequence shown in SEQ ID NO:1, E. an E4 deletion of at least a partial deletion of E4Orf2, a fully deleted E4Orf3, and at least a partial deletion of E4Orf4, F. an E4 deletion of at least a partial deletion of E4Orf2, at least a partial deletion of E4Orf3, and at least a partial deletion of E4Orf4, G. an E4 deletion of at least a partial deletion of E4Orf1, a fully deleted E4Orf2, and at least a partial deletion of E4Orf3, or H. an E4 deletion of at least a partial deletion of E4Orf2 and at least a partial deletion of E4Orf3. In some aspects, the ChAdV68 vector backbone comprises at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion; (2) nucleotides 27,125 to 31,825 of the sequence shown in SEQ ID NO:1 corresponding to an E3 deletion; and (3) nucleotides 34,916 to 35,642 of the sequence shown in SEQ ID NO:1 corresponding to a partial E4 deletion; optionally wherein the antigen cassette is inserted within the E1 deletion. In some aspects, the ChAdV68 vector backbone comprises the sequence set forth in SEQ ID NO:29369, optionally wherein the antigen cassette is inserted within the E1 deletion. In some aspects, the ChAdV68 vector backbone comprises at least nucleotides 2 to 36,518 of the sequence set forth in SEQ ID NO:1, wherein the nucleotides 2 to 36,518 lack: A. nucleotides 577 to 3403 of the sequence shown in SEQ ID NO:1 corresponding to an E1 deletion; B. nucleotides 27,125 to 31,825 of the sequence shown in SEQ ID NO:1 corresponding to an E3 deletion; C. nucleotides 34,916 to 35,642 of the sequence shown in SEQ ID NO:1 corresponding to a partial E4 deletion; D. nucleotides 456 to 3014 of the sequence shown in SEQ ID NO:1; E. nucleotides 27,816 to 31,333 of the sequence shown in SEQ ID NO:1; F. nucleotides 3957 to 10346 of the sequence shown in SEQ ID NO:1; G. nucleotides 21787 to 23370 of the sequence shown in SEQ ID NO:1; H. nucleotides 33486 to 36193 of the sequence shown in SEQ ID NO:1; or combinations thereof. In some aspects, the ChAdV68 vector backbone comprises at least nucleotides 2 to 36,518 of the sequence set forth in SEQ ID NO:1, wherein the nucleotides 2 to 36,518 lack: (1) nucleotides 577 to 3403 of the sequence shown in SEQ ID NO:1 corresponding to an E1 deletion and (2) nucleotides 27,125 to 31,825 of the sequence shown in SEQ ID NO:1 corresponding to an E3 deletion.

In some aspects, the ChAdV68 vector backbone comprises the sequence set forth in SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence set forth in SEQ ID NO:1, optionally wherein the sequence is fully deleted or functionally deleted in: (1) E1A and E1B; (2) E1A, E1B, and E3; or (3) E1A, E1B, E3, and E4 of the sequence set forth in SEQ ID NO: 1. In some aspects, the ChAdV68 vector backbone comprises a gene or regulatory sequence obtained from the sequence of SEQ ID NO: 1, optionally wherein the gene is selected from the group consisting of the chimpanzee adenovirus inverted terminal repeat (ITR), E1A, E1B, E2A, E2B, E3, E4, L1, L2, L3, L4, and L5 genes of the sequence set forth in SEQ ID NO: 1 In some aspects, the ChAdV68 vector backbone comprises one or more deletions between base pair number 577 and 3403 or between base pair 456 and 3014, and optionally wherein the vector further comprises one or more deletions between base pair 27,125 and 31,825 or between base pair 27,816 and 31,333 of the sequence set forth in SEQ ID NO:1. In some aspects, the ChAdV68 vector backbone comprises one or more deletions between base pair number 3957 and 10346, base pair number 21787 and 23370, and base pair number 33486 and 36193 of the sequence set forth in SEQ ID NO:1.

In some aspects, the cassette is inserted in the ChAdV backbone at the E1 region, E3 region, and/or any deleted AdV region that allows incorporation of the cassette. In some aspects, the ChAdV backbone is generated from one of a first generation, a second generation, or a helper-dependent adenoviral vector.

In some aspects, the at least one promoter nucleotide sequence is selected from the group consisting of: a CMV, a SV40, an EF-1, a RSV, a PGK, a HSA, a MCK, and a EBV promoter sequence. In some aspects, the at least one promoter nucleotide sequence is a CMV promoter sequence.

In some aspects, at least one of the epitope-encoding nucleic acid sequences encodes an epitope that, when expressed and translated, is capable of being presented by MHC class I on a cell of the subject. In some aspects, at least one of the epitope-encoding nucleic acid sequences encodes an epitope that, when expressed and translated, is capable of being presented by MHC class II on a cell of the subject.

In some aspects, the at least one antigen-encoding nucleic acid sequence comprises two or more antigen-encoding nucleic acid sequences. In some aspects, each antigen-encoding nucleic acid sequence is linked directly to one another.

In some aspects, each antigen-encoding nucleic acid sequence is linked to a distinct antigen-encoding nucleic acid sequence with a nucleic acid sequence encoding a linker. In some aspects, the linker links two MHC class I epitope-encoding nucleic acid sequences or an MHC class I epitope-encoding nucleic acid sequence to an MHC class II epitope-encoding nucleic acid sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II epitope-encoding nucleic acid sequences or an MHC class II sequence to an MHC class I epitope-encoding nucleic acid sequence. In some aspects, the linker comprises the sequence GPGPG.

In some aspects, the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the epitope-encoding nucleic acid sequence comprises at least one alteration that makes the encoded epitope have increased binding affinity to its corresponding MHC allele relative to the translated, corresponding wild-type nucleic acid sequence. In some aspects, the epitope-encoding nucleic acid sequence comprises at least one alteration that makes the encoded epitope have increased binding stability to its corresponding MHC allele relative to the translated, corresponding wild-type nucleic acid sequence. In some aspects, the epitope-encoding nucleic acid sequence comprises at least one alteration that makes the encoded epitope have an increased likelihood of presentation on its corresponding MHC allele relative to the translated, corresponding wild-type nucleic acid sequence. In some aspects, the at least one alteration comprises a point mutation, a frameshift mutation, a non-frameshift mutation, a deletion mutation, an insertion mutation, a splice variant, a genomic rearrangement, or a proteasome-generated spliced antigen.

In some aspects, the epitope-encoding nucleic acid sequence encodes an epitope known or suspected to be expressed in the subject known or suspected to have an infection. In some aspects, the infection is selected from the group consisting of: a pathogen infection, a viral infection, a bacterial infection, a fungal infection, and a parasitic infection. In some aspects, the viral infection is selected from the group consisting of: an HIV infection, an HPV infection, a SARS infection, a SARS-CoV-2 infection, an Ebola infection, a HBV infection, an influenza infection, a HCV infection, a CMV infection, a Chikungunya virus infection, a RSV infection, a Dengue virus infection, a orthymyxoviridae family virus infection, and a tuberculosis infection.

In some aspects, the at least one antigen-encoding nucleic acid sequence comprises at least 2-10, 2, 3, 4, 5, 6, 7, 8, 9, or 10 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences, optionally wherein each antigen-encoding nucleic acid sequence encodes a distinct antigen-encoding nucleic acid sequence. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one antigen-encoding nucleic acid sequence comprises at least 2-400 antigen-encoding nucleic acid sequences and wherein at least two of the antigen-encoding nucleic acid sequences encode epitope sequences or portions thereof that are presented by MHC class I on a cell surface. In some aspects, at least two of the MHC class I epitopes are presented by MHC class I on the infected cell surface.

In some aspects, the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence. In some aspects, the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length. In some aspects, the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE.

In some aspects, the at least one promoter nucleotide sequence is inducible. In some aspects, wherein the at least one promoter nucleotide sequence is non-inducible. In some aspects, the at least one poly(A) sequence comprises a Bovine Growth Hormone (BGH) SV40 polyA sequence. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the cassette further comprises at least one of: an intron sequence, a woodchuck hepatitis virus post-transcriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one antigen-encoding nucleic acid sequences. In some aspects, the cassette further comprises a reporter gene, including but not limited to, green fluorescent protein (GFP), a GFP variant, secreted alkaline phosphatase, luciferase, a luciferase variant, or a detectable peptide or epitope. In some aspects, the detectable peptide or epitope is selected from the group consisting of an HA tag, a Flag tag, a His-tag, or a V5 tag.

In some aspects, the one or more vectors further comprises one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES: or the heavy and light chain sequences of the antibody are linked by a flexible linker such as consecutive glycine residues. In some aspects, the immune modulator is a cytokine. In some aspects, the cytokine is at least one of IL-2, IL-7, IL-12, IL-15, or IL-21 or variants thereof of each.

In some aspects, the epitope-encoding nucleic acid sequence comprises a MHC class I epitope-encoding nucleic acid sequence, and wherein the MHC class I epitope-encoding nucleic acid sequence is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence. In some aspects, each of the MHC class I epitope-encoding nucleic acid sequences is selected by performing the steps of: (a) obtaining at least one of exome, transcriptome, or whole genome infectious disease organism nucleotide sequencing data from the infectious disease organism, wherein the infectious disease organism nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the at least 20 MHC class I epitope-encoding nucleic acid sequences. In some aspects, a number of the set of selected epitopes is 2-20. In some aspects, the presentation model represents dependence between: (a) presence of a pair of a particular one of the MHC alleles and a particular amino acid at a particular position of a peptide sequence; and (b) likelihood of presentation on the infected cell surface, by the particular one of the MHC alleles of the pair, of such a peptide sequence comprising the particular amino acid at the particular position. In some aspects, selecting the set of selected epitopes comprises selecting epitopes that have an increased likelihood of being presented on the infected cell surface relative to unselected epitopes based on the presentation model. In some aspects, selecting the set of selected epitopes comprises selecting epitopes that have an increased likelihood of being capable of inducing a infectious disease organism-specific immune response in the subject relative to unselected epitopes based on the presentation model. In some aspects, selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC). In some aspects, selecting the set of selected epitopes comprises selecting epitopes that have a decreased likelihood of being subject to inhibition via central or peripheral tolerance relative to unselected epitopes based on the presentation model. In some aspects, selecting the set of selected epitopes comprises selecting epitopes that have a decreased likelihood of being capable of inducing an autoimmune response to normal tissue in the subject relative to unselected epitopes based on the presentation model. In some aspects, exome or transcriptome nucleotide sequencing data is obtained by performing sequencing on the infected tissue. In some aspects, the sequencing is next generation sequencing (NGS) or any massively parallel sequencing approach.

In some aspects, the cassette comprises junctional epitope sequences formed by adjacent sequences in the cassette. In some aspects, at least one or each junctional epitope sequence has an affinity of greater than 500 nM for MHC. In some aspects, each junctional epitope sequence is non-self.

In some aspects, the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the cassette. In some aspects, the prediction is based on presentation likelihoods generated by inputting sequences of the non-therapeutic epitopes into a presentation model. In some aspects, an order of the antigen-encoding nucleic acid sequences in the cassette is determined by a series of steps comprising: (a) generating a set of candidate cassette sequences corresponding to different orders of the antigen-encoding nucleic acid sequences; (b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine.

In some aspects, the composition for delivery of the ChAdV-based expression system is formulated in a pharmaceutical composition comprising a pharmaceutically acceptable carrier.

In some aspects, one or more of the epitope-encoding nucleic acid sequences are derived from an infection in or an infected cell of a subject. In some aspects, each of the epitope-encoding nucleic acid sequences are derived from an infection in or an infected cell of a subject. In some aspects, one or more of the epitope-encoding nucleic acid sequences are not derived from an infection in or an infected cell of a subject. In some aspects, each of the epitope-encoding nucleic acid sequences are not derived from an infection in or an infected cell of a subject.

Also provided for herein is a method for stimulating an immune response in a subject, the method comprising administering to the subject a composition for delivery of a self-replicating alphavirus-based expression system: wherein the composition for delivery of the self-replicating alphavirus-based expression system comprises: (A) the self-replicating alphavirus-based expression system, wherein the self-replicating alphavirus-based expression system comprises one or more vectors, wherein the one or more vectors comprises: (a) an RNA alphavirus backbone, wherein the RNA alphavirus backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, wherein the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis; b. optionally a 5' linker sequence, and c. optionally a 3' linker sequence; (ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, and (B) a lipid-nanoparticle (LNP), wherein the LNP encapsulates the self-replicating alphavirus-based expression system.

Also provided for herein is a method for stimulating an immune response in a subject, the method comprising administering to the subject a composition for delivery of a chimpanzee adenovirus (ChAdV)-based expression system, wherein the composition for delivery of the ChAdV-based expression system comprises: the ChAdV-based expression system, wherein the ChAdV-based expression system comprises a viral particle comprising a ChAdV vector, wherein the ChAdV vector comprises: (a) a ChAdV backbone, wherein the ChAdV backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence comprising: a. a nucleic acid sequence encoding an infectious disease organism peptide selected from the group consisting of: a pathogen-derived peptide, a virus-derived peptide, a bacteria-derived peptide, a fungus-derived peptide, and/or a parasite-derived peptide, wherein the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis; b. optionally a 5' linker sequence, and c. optionally a 3' linker sequence; and wherein the cassette is operably linked to the at least one promoter nucleotide sequence and the at least one poly(A) sequence.

In some aspects, the self-replicating alphavirus-based expression system or the ChAdV-based expression system comprise any of the features of any one of the above claims.

The method of any of the above claims, wherein the cassette of the composition for delivery of the ChAdV-based expression system is identical to the cassette of the composition for delivery of the self-replicating alphavirus-based expression system.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 7 shows a time course of CD8+ anti-epitope responses in *Rhesus macaques* dosed with chAd-MAG plus anti-CTLA4 antibody (Ipilimumab) delivered IV. (Group 5). Mean SFC/1e6 splenocytes is shown.

I. DEFINITIONS

Figure 1A:
FIG. 1A, FIG. 1B, FIG. 1C AND FIG. 1D illustrates antigen-specific cellular immune responses measured using ELISpot. Antigen-specific IFN-gamma production to six different mamu A01 restricted epitopes was measured in PBMCs for the VEE-MAG25mer srRNA-LNP1 (30 µg) (FIG. 1A), VEE-MAG25mer srRNA-LNP1 (100 µg) (FIG. 1B), or VEE-MAG25mer srRNA-LNP2 (100 µg) (FIG. 1C) homologous prime/boost or the ChAdV68.5WTnt.MAG25mer/VEE-MAG25mer srRNA heterologous prime/boost group (FIG. 1D) using ELISpot 1, 2, 3, 4, 5, 6, 8, 9, or 10 weeks after the first boost immunization (6 rhesus macaques per group). Results are presented as mean spot forming cells (SFC) per $10^6$ PBMCs for each epitope in a stacked bar graph format. Values for each animal were normalized to the levels at pre-bleed (week 0).
Figure 1A:
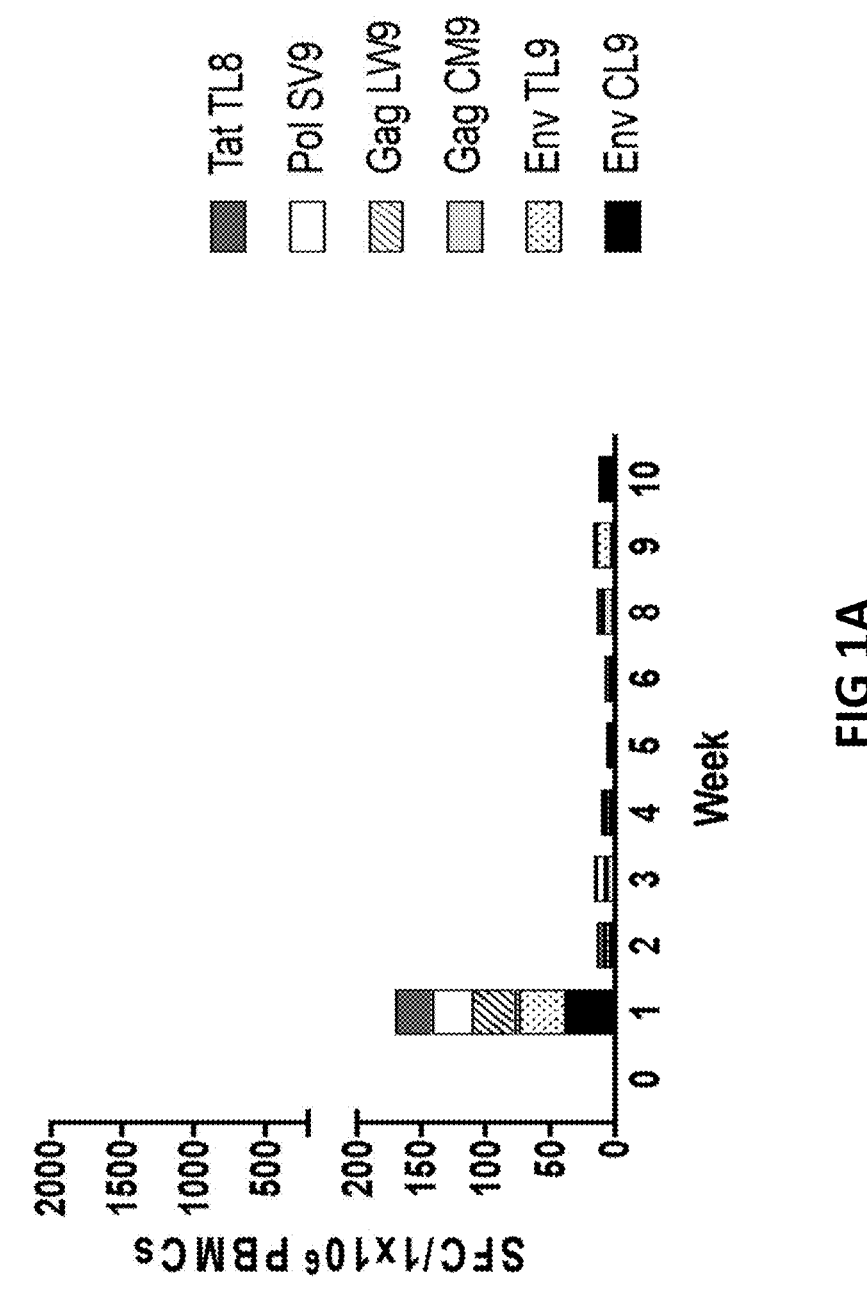

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response. An antigen can be a neoantigen. An antigen can be a "shared antigen" that is an antigen found among a specific population, e.g., a specific population of patients infected with or at risk of infection for an infectious disease.

an antigen As used herein the term "antigen-based vaccine" is a vaccine composition based on one or more antigens, e.g., a plurality of antigens. The vaccines can be nucleotide-based (e.g., virally based, RNA based, or DNA based), protein-based (e.g., peptide based), or a combination thereof.

As used herein the term "candidate antigen" is a mutation or other aberration giving rise to a sequence that may represent an antigen.

As used herein the term "coding region" is the portion(s) of a gene that encode protein.

As used herein the term "coding mutation" is a mutation occurring in a coding region.

As used herein the term "ORF" means open reading frame.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the infectious disease peptidome, meaning the union of the peptidomes of all cells that are infected by the infectious disease).

As used herein the term "ELISpot" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include infection type, infection sub-type, and smoking history.

The term "antigen-encoding nucleic acid sequences derived from an infection" refers to nucleic acid sequences obtained from infected cells or a infectious disease organism, e.g. via RT-PCR; or sequence data obtained by sequencing the infected cell or infectious disease organism and then synthesizing the nucleic acid sequences using the sequencing data, e.g., via various synthetic or PCR-based methods known in the art. Derived sequences can include nucleic acid sequence variants, such as sequence-optimized nucleic acid sequence variants (e.g., codon-optimized and/or otherwise optimized for expression), that encode the same polypeptide sequence as the corresponding native infectious disease organism nucleic acid sequence. Derived sequences can include nucleic acid sequence variants that encode a modified infectious disease organism polypeptide sequence having one or more (e.g., 1, 2, 3, 4, or 5) mutations relative to a native infectious disease organism polypeptide sequence. For example, a modified polypeptide sequence can have one or more missense mutations relative to the native polypeptide sequence of an infectious disease organism protein.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a 26S promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, or other 26S subgenomic promoter sequence, a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value: TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. ANTIGEN IDENTIFICATION

Research methods for NGS analysis of tumor and normal exome and transcriptomes have been described and applied in the antigen identification space.[6,14,15] Certain optimizations for greater sensitivity and specificity for antigen identification in the clinical setting can be considered. These optimizations can be grouped into two areas, those related to laboratory processes and those related to the NGS data analysis. The research methods described can also be applied to identification of antigens in other settings, such as identification of identifying antigens from an infectious disease organism, an infection in a subject, or an infected cell of a subject. Examples of optimizations are known to those skilled in the art, for example the methods described in more detail in U.S. Pat. No. 10,055,540, US Application Pub. No. US20200010849A1, international patent application publications WO/2018/195357 and WO/2018/208856, U.S. application Ser. No. 16/606,577, and international patent application PCT/US2020/021508, each herein incorporated by reference, in their entirety, for all purposes.

Methods for identifying antigens (e.g., antigens derived from an infectious disease organism) include identifying antigens that are likely to be presented on a cell surface (e.g., presented by MHC on an infected cell or an immune cell, including professional antigen presenting cells such as dendritic cells), and/or are likely to be immunogenic. As an example, one such method may comprise the steps of: obtaining at least one of exome, transcriptome or whole genome nucleotide sequencing and/or expression data from an infected cell or an infectious disease organism, wherein the nucleotide sequencing data and/or expression data from the an infected cell of the subject, wherein the infectious disease organism nucleotide sequencing and/or expression data is used to obtain data representing peptide sequences of each of a set of antigens (e.g., antigens derived from an infectious disease organism); inputting the peptide sequence of each antigen into one or more presentation models to generate a set of numerical likelihoods that each of the antigens is presented by one or more MHC alleles on the cell surface of an infected cell of the subject or cells present in the subject, the set of numerical likelihoods having been identified at least based on received mass spectrometry data; and selecting a subset of the set of antigens based on the set of numerical likelihoods to generate a set of selected antigens.

The presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have an infection, and wherein the set of reference data comprises at least one of: data representing exome nucleotide sequences from infected tissue, data representing exome nucleotide sequences from normal tissue, data representing transcriptome nucleotide sequences from infected tissue, data representing proteome sequences from infected tissue, and data representing MHC peptidome sequences from infected tissue, and data representing MHC peptidome sequences from normal tissue. The reference data can further comprise mass spectrometry data, sequencing data, RNA sequencing data, expression profiling data, and proteomics data for single-allele cell lines engineered to express a predetermined MHC allele that are subsequently exposed to synthetic protein, normal and tumor human cell lines, and fresh and frozen primary samples, and T cell assays (e.g., ELISpot). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Methods for identifying shared antigens also include generating an output for constructing a personalized cancer vaccine by identifying one or more antigens from one or more cells of a subject that are likely to be presented on a surface of infected cells. As an example, one such method may comprise the steps of: obtaining at least one of exome, transcriptome, or whole genome nucleotide sequencing and/or expression data from the infected cells and normal cells of the subject, wherein the nucleotide sequencing and/or expression data is used to obtain data representing peptide sequences of each of a set of antigens identified by comparing the nucleotide sequencing and/or expression data from the infected cells and the nucleotide sequencing and/or expression data from the normal cells, peptide sequence identified from the normal cells of the subject; encoding the peptide sequences of each of the antigens into a corresponding numerical vector, each numerical vector including information regarding a plurality of amino acids that make up the peptide sequence and a set of positions of the amino acids in the peptide sequence; inputting the numerical vectors, using a computer processor, into a deep learning presentation model to generate a set of presentation likelihoods for the set of antigens, each presentation likelihood in the set representing the likelihood that a corresponding antigen is presented by one or more class II MHC alleles on the surface of the infected cells of the subject, the deep learning presentation model; selecting a subset of the set of antigens based on the set of presentation likelihoods to generate a set of selected antigens; and generating the output for constructing the personalized cancer vaccine based on the set of selected antigens.

Specific methods for identifying antigens (e.g., infectious disease organism derived antigens) are known to those skilled in the art, for example the methods described in more detail in international patent application publications WO/2017/106638, WO/2018/195357, and WO/2018/208856, each herein incorporated by reference, in their entirety, for all purposes.

A method of treating a subject having an infection is disclosed herein, comprising performing the steps of any of the antigen identification methods described herein, and further comprising obtaining a infectious disease vaccine comprising the set of selected antigens, and administering the infectious disease vaccine to the subject.

A method disclosed herein can also include identifying one or more T cells that are antigen-specific for at least one of the antigens in the subset. In some embodiments, the identification comprises co-culturing the one or more T cells with one or more of the antigens in the subset under conditions that expand the one or more antigen-specific T cells. In further embodiments, the identification comprises contacting the one or more T cells with a tetramer comprising one or more of the antigens in the subset under conditions that allow binding between the T cell and the tetramer. In even further embodiments, the method disclosed herein can also include identifying one or more T cell receptors (TCR) of the one or more identified T cells. In certain embodiments, identifying the one or more T cell receptors comprises sequencing the T cell receptor sequences of the one or more identified T cells. The method disclosed herein can further comprise genetically engineering a plurality of T cells to express at least one of the one or more identified T cell receptors; culturing the plurality of T cells under conditions that expand the plurality of T cells; and infusing the expanded T cells into the subject. In some embodiments, genetically engineering the plurality of T cells to express at least one of the one or more identified T cell receptors comprises cloning the T cell receptor sequences of the one or more identified T cells into an expression vector; and transfecting each of the plurality of T cells with the expression vector. In some embodiments, the method disclosed herein further comprises culturing the one or more identified T cells under conditions that expand the one or more identified T cells; and infusing the expanded T cells into the subject.

Also disclosed herein is an isolated T cell that is antigen-specific for at least one selected antigen in the subset.

Also disclosed herein is a methods for manufacturing an infectious disease vaccine, comprising the steps of: obtaining at least one of exome, transcriptome or whole genome infectious disease organism nucleotide sequencing and/or expression data from the infected cell of the subject, wherein the infectious disease organism nucleotide sequencing and/or expression data is used to obtain data representing peptide sequences of each of a set of antigens (e.g., where peptides are derived from any polypeptide known to or have been found to have altered expression in a infected cell or infected tissue in comparison to a normal cell or tissue); inputting the peptide sequence of each antigen into one or more presentation models to generate a set of numerical likelihoods that each of the antigens is presented by one or more MHC alleles on the cell surface of the infected cell of the subject, the set of numerical likelihoods having been identified at least based on received mass spectrometry data; and selecting a subset of the set of antigens based on the set of numerical likelihoods to generate a set of selected antigens; and producing or having produced a infectious disease vaccine comprising the set of selected antigens.

Also disclosed herein is an infectious disease vaccine including a set of selected antigens selected by performing the method comprising the steps of: obtaining at least one of exome, transcriptome or whole genome infectious disease organism nucleotide sequencing and/or expression data from the infected cell of the subject, wherein the infectious disease organism nucleotide sequencing and/or expression data is used to obtain data representing peptide sequences of each of a set of antigens, and wherein the peptide sequence of each antigen (e.g., derived from any polypeptide known to or have been found to have altered expression in a infected cell or infected tissue in comparison to a normal cell or tissue); inputting the peptide sequence of each antigen into one or more presentation models to generate a set of numerical likelihoods that each of the antigens is presented by one or more MHC alleles on the cell surface of the infected cell of the subject, the set of numerical likelihoods having been identified at least based on received mass spectrometry data; and selecting a subset of the set of antigens based on the set of numerical likelihoods to generate a set of selected antigens; and producing or having produced an infectious disease vaccine comprising the set of selected antigens.

The vaccine may include one or more of a nucleotide sequence, a polypeptide sequence, RNA, DNA, a cell, a plasmid, or a vector.

The vaccine may include one or more antigens presented on the infected cell surface.

The infectious disease vaccine may include one or more antigens that is immunogenic in the subject.

The infectious disease vaccine may not include one or more antigens that induce an autoimmune response against normal tissue in the subject.

The infectious disease vaccine may include an adjuvant.
The infectious disease vaccine may include an excipient.

A method disclosed herein may also include selecting antigens that have an increased likelihood of being presented on the infected cell surface relative to unselected antigens based on the presentation model.

A method disclosed herein may also include selecting antigens that have an increased likelihood of being capable of inducing a infectious disease organism-specific immune response in the subject relative to unselected antigens based on the presentation model.

A method disclosed herein may also include selecting antigens that have an increased likelihood of being capable of being presented to naïve T cells by professional antigen presenting cells (APCs) relative to unselected antigens based on the presentation model, optionally wherein the APC is a dendritic cell (DC).

A method disclosed herein may also include selecting antigens that have a decreased likelihood of being subject to inhibition via central or peripheral tolerance relative to unselected antigens based on the presentation model.

A method disclosed herein may also include selecting antigens that have a decreased likelihood of being capable of inducing an autoimmune response to normal tissue in the subject relative to unselected antigens based on the presentation model.

The exome or transcriptome nucleotide sequencing and/or expression data may be obtained by performing sequencing on the infected tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the antigen encoded peptide bind; the predicted stability of the antigen encoded peptide-MHC complex; the sequence and length of the antigen encoded peptide; the probability of presentation of antigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall antigen encoded peptide-sequence-independent probability of presentation by the particular MHC allele in other distinct subjects who express the particular MHC allele; the overall antigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the antigen encoded peptide within its source protein sequence; the presence of protease cleavage motifs in the antigen encoded peptide, optionally weighted according to the expression of corresponding proteases in the infected cells (as measured by RNA-seq or mass spectrometry); the turn-over rate of the source protein as measured in the appropriate cell type; the length of the source protein, optionally considering the specific splice variants ("isoforms") most highly expressed in the infected cells as measured by RNA-seq or proteome mass spectrometry, or as predicted from the annotation of germline or somatic splicing mutations detected in DNA or RNA sequence data; the level of expression of the proteasome, immunoproteasome, thymoproteasome, or other proteases in the infected cells (which may be measured by RNA-seq, proteome mass spectrometry, or immunohistochemistry); the expression of the source gene of the antigen encoded peptide (e.g., as measured by RNA-seq or mass spectrometry); the typical tissue-specific expression of the source gene of the antigen encoded peptide during various stages of the cell cycle; a comprehensive catalog of features of the source protein and/or its domains as can be found in e.g. uniProt or PDB www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the antigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the infected cells, stroma, or infected tissue; the copy number of the source gene of the antigen encoded peptide in the infected cells; the probability that the peptide binds to the TAP or the measured or predicted binding affinity of the peptide to the TAP; the expression level of TAP in the infected cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); infection type (e.g., a pathogen infection, a viral infection, a bacterial infection, an fungal infection, and a parasitic infection); clinical infection subtype (e.g., an HIV infection, an HPV infection, a SARS infection, a SARS-CoV-2 infection, an Ebola infection, a HBV infection, an influenza infection, a HCV infection, a CMV infection, a Chikungunya virus infection, a RSV infection, a Dengue virus infection, a orthymyxoviridae family virus infection, and a tuberculosis infection); smoking history; the typical expression of the source gene of the peptide in the relevant infection type or clinical subtype.

A method disclosed herein may also include obtaining a infectious disease vaccine comprising the set of selected antigens (e.g., infectious disease organism derived antigens) or a subset thereof, optionally further comprising administering the infectious disease vaccine to the subject.

At least one of the antigens (e.g., infectious disease organism derived antigens) in the set of selected antigens, when in polypeptide form, may include at least one of: a binding affinity with MHC with an IC50 value of less than 1000 nM, for MHC Class I polypeptides a length of 8-15, 8, 9, 10, 11, 12, 13, 14, or 15 amino acids, for MHC Class II polypeptides a length of 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the polypeptide in the parent protein sequence promoting proteasome cleavage, and presence of sequence motifs promoting TAP transport. For MHC Class II, presence of sequence motifs within or near the peptide promoting cleavage by extracellular or lysosomal proteases (e.g., cathepsins) or HLA-DM catalyzed HLA binding.

Disclosed herein is are methods for identifying one or more antigens (e.g., infectious disease organism derived antigens) that are likely to be presented on a cell surface of an infected cell, comprising executing the steps of: receiving mass spectrometry data comprising data associated with a plurality of isolated peptides eluted from major histocompatibility complex (MHC) derived from a plurality of fresh or frozen samples; obtaining a training data set by at least identifying a set of training peptide sequences present in the samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the infected cell are presented by one or more MHC alleles on the infected cell surface.

The presentation model may represent dependence between: presence of a pair of a particular one of the MHC alleles and a particular amino acid at a particular position of a peptide sequence; and likelihood of presentation on the infected cell surface, by the particular one of the MHC alleles of the pair, of such a peptide sequence comprising the particular amino acid at the particular position.

A method disclosed herein can also include selecting a subset of antigens (e.g., infectious disease organism derived antigens), wherein the subset of antigens is selected because each has an increased likelihood that it is presented on the cell surface of the infected cell relative to one or more distinct antigens.

A method disclosed herein can also include selecting a subset of antigens (e.g., infectious disease organism derived antigens), wherein the subset of antigens is selected because each has an increased likelihood that it is capable of inducing a disease-specific immune response in the subject relative to one or more distinct antigens.

A method disclosed herein can also include selecting a subset of antigens (e.g., infectious disease organism derived antigens), wherein the subset of antigens is selected because each has an increased likelihood that it is capable of being presented to naïve T cells by professional antigen presenting cells (APCs) relative to one or more distinct antigens, optionally wherein the APC is a dendritic cell (DC).

A method disclosed herein can also include selecting a subset of antigens (e.g., infectious disease organism derived antigens), wherein the subset of antigens is selected because each has a decreased likelihood that it is subject to inhibition via central or peripheral tolerance relative to one or more distinct antigens.

A method disclosed herein can also include selecting a subset of antigens (e.g., infectious disease organism derived antigens), wherein the subset of antigens is selected because each has a decreased likelihood that it is capable of inducing an autoimmune response to normal tissue in the subject relative to one or more distinct antigens.

A method disclosed herein can also include selecting a subset of antigens (e.g., infectious disease organism derived antigens), wherein the subset of antigens is selected because each has a decreased likelihood that it will be differentially post-translationally modified in infected cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3$^{rd}$ *Ed.* (Plenum Press) Vols A and B (1992).

III. ANTIGENS

Antigens can include nucleotides or polypeptides. For example, an antigen can be an RNA sequence that encodes for a polypeptide sequence. Antigens useful in vaccines can therefore include nucleotide sequences or polypeptide sequences. Antigens can be derived from nucleotide sequences or polypeptide sequences of an infectious disease organism. Polypeptide sequences of an infectious disease organism include, but are not limited to, a pathogen-derived peptide, a virus-derived peptide, a bacteria-derived peptide, a fungus-derived peptide, and/or a parasite-derived peptide. Infectious disease organism include, but are not limited to, Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

Disclosed herein are isolated peptides that comprise infectious disease organism specific antigens or epitopes identified by the methods disclosed herein, peptides that comprise known infectious disease organism specific antigens or epitopes, and mutant polypeptides or fragments thereof identified by methods disclosed herein. Antigen peptides can be described in the context of their coding sequence where an antigen includes the nucleotide sequence (e.g., DNA or RNA) that codes for the related polypeptide sequence.

Antigens that can be incorporated into a vaccine (e.g., encoded in a cassette) include immunogens which are useful to immunize a human or non-human animal against viruses, such as pathogenic viruses which infect human and non-human vertebrates. Antigens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The Flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (e.g., the glyco-(G) protein and the fusion (F) protein, for which sequences are available from GenBank). Influenza virus is classified within the family orthomyxovirus and can be suitable source of antigens (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the subfamily oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. Nos. 5,891,994 and 6,193, 981.] See, also, the HIV and SIV proteins described in D. H. Barouch et al, J. Virol., 75(5):2462-2467 (March 2001), and R. R. Amara, et al, *Science*, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (Human CMV), muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Antigens that can be incorporated into a vaccine (e.g., encoded in a cassette) also include immunogens which are useful to immunize a human or non-human animal against pathogens including bacteria, fungi, parasitic microorganisms or multicellular parasites which infect human and non-human vertebrates. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae: *Pseudomonas*, acinetobacteria and *Eikenella*; melioidosis; *Salmonella; Shigella; Haemophilus (Haemophilus influenzae, Haemophilus somnus); Moraxella; H. ducreyi* (which causes chancroid); *Brucella; Franisella tularensis* (which causes tularemia); *Yersinia (Pasteurella); Streptobacillus moniliformis* and spirillum. Gram-positive bacilli include *Listeria monocytogenes; Erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Examples of specific bacterium species are, without limitation, *Streptococcus pneumoniae, Streptococcus pyogenes, Streptococcus agalactiae, Streptococcus faecalis, Moraxella catarrhalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium, Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis (*Cryptococcus*), blastomycosis (*Blastomyces*), histoplasmosis (*Histoplasma*) and coccidioidomycosis (Coccidiodes); candidiasis (*Candida*), aspergillosis (*Aspergillis*), and mucormycosis; sporotrichosis: paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *Mycoplasma* and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis (e.g., caused by *Leishmania major*); trypanosomiasis; toxoplasmosis (e.g., caused by *Toxoplasma gondii*); *Pneumocystis carinii*; Trichans; *Toxoplasma gondii*; babesiosis; giardiasis (e.g., caused by *Giardia*); trichinosis (e.g., caused by *Trichomonas*); filariasis; schistosomiasis (e.g., caused by *Schistosoma*); nematodes; trematodes or flukes; and cestode (tapeworm) infections. Other parasitic infections may be caused by *Ascaris, Trichuris, Cryptosporidium*, and *Pneumocystis carinii*, among others.

Also disclosed herein are peptides derived from any polypeptide associated with an infectious disease organism, an infection in a subject, or an infected cell of a subject. Antigens can be derived from nucleic acid sequences or polypeptide sequences of an infectious disease organism. Polypeptide sequences of an infectious disease organism include, but are not limited to, a pathogen-derived peptide, a virus-derived peptide, a bacteria-derived peptide, a fungus-derived peptide, and/or a parasite-derived peptide. Infectious disease organism include, but are not limited to, Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

Antigens can be selected that are predicted to be presented on the cell surface of a cell, such as an infected cell or an immune cell, including professional antigen presenting cells such as dendritic cells. Antigens can be selected that are predicted to be immunogenic.

One or more polypeptides encoded by an antigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more antigens can be presented on the surface of an infected cell.

One or more antigens can be immunogenic in a subject having or suspected to have an infection, e.g., capable of eliciting a T cell response and/or a B cell response in the subject. One or more antigens can be immunogenic in a subject at risk of an infection, e.g., capable of eliciting a T cell response and/or a B cell response in the subject that provides immunological protection (i.e., immunity) against the infection, e.g., such as stimulating the production of memory T cells, memory B cells, and/or antibodies specific to the infection.

One or more antigens can be capable of eliciting a B cell response, such as the production of antibodies that recognize the one or more antigens (e.g., antibodies that recognize an infectious disease antigens). Antibodies can recognize linear polypeptide sequences or recognize secondary and tertiary structures. Accordingly, B cell antigens can include linear polypeptide sequences or polypeptides having secondary and tertiary structures, including, but not limited to, full-length proteins, protein subunits, protein domains, or any polypeptide sequence known or predicted to have secondary and tertiary structures. In general, antigens capable of eliciting a B cell response to an infection are antigens found on the surface of an infectious disease organism.

One or more antigens can include a combination of antigens capable of eliciting a T cell response (e.g., peptides including predicted T cell epitope sequences) and distinct antigens capable of eliciting a T cell response (e.g., full-length proteins, protein subunits, protein domains).

One or more antigens that induce an autoimmune response in a subject can be excluded from consideration in the context of vaccine generation for a subject.

The size of at least one antigenic peptide molecule (e.g., an epitope sequence) can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the antigenic peptide molecules are equal to or less than 50 amino acids.

Antigenic peptides and polypeptides can be: for MHC Class I 15 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) epitope sequence present, a longer peptide would consist of: (3) the entire stretch of novel infectious disease-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses. Longer peptides can also a full-length protein, a protein subunit, a protein domain, and combinations thereof of a peptide expressed in an infectious disease organism.

Antigenic peptides and polypeptides can be presented on an HLA protein. In some aspects antigenic peptides and polypeptides are presented on an HLA protein with greater affinity than a wild-type peptide. In some aspects, an antigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, antigenic peptides and polypeptides do not induce an autoimmune response and/or invoke immunological tolerance when administered to a subject.

Also provided are compositions comprising at least two or more antigenic peptides. In some embodiments the composition contains at least two distinct peptides. At least two distinct peptides can be derived from the same polypeptide. By distinct polypeptides is meant that the peptide vary by length, amino acid sequence, or both. The peptides can be derived from any polypeptide known to or suspected to be associated with an infectious disease organism, or peptides derived from any polypeptide known to or have been found to have altered expression in an infected cell in comparison to a normal cell or tissue (e.g., an infectious disease polynucleotide or polypeptide, including infectious disease polynucleotides or polypeptides with expression restricted to a host cell).

Antigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, antigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A antigenic peptide can be linked to the T helper peptide either directly or via a spacer either at the amino or carboxy terminus of the peptide. The amino terminus of either the antigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect an antigen includes a nucleic acid (e.g. polynucleotide) that encodes an antigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. The polynucleotide sequence encoding an antigen can be sequence-optimized to improve expression, such as through improving transcription, translation, post-transcriptional processing, and/or RNA stability. For example, poly-nucleotide sequence encoding an antigen can be codon-optimized. "Codon-optimization" herein refers to replacing infrequently used codons, with respect to codon bias of a given organism, with frequently used synonymous codons. Polynucleotide sequences can be optimized to improve post-transcriptional processing, for example optimized to reduce unintended splicing, such as through removal of splicing motifs (e.g., canonical and/or cryptic/non-canonical splice donor, branch, and/or acceptor sequences) and/or introduction of exogenous splicing motifs (e.g., splice donor, branch, and/or acceptor sequences) to bias favored splicing events. Exogenous intron sequences include, but are not limited to, those derived from SV40 (e.g., an SV40 mini-intron) and derived from immunoglobulins (e.g., human β-globin gene). Exogenous intron sequences can be incorporated between a promoter/enhancer sequence and the antigen(s) sequence. Exogenous intron sequences for use in expression vectors are described in more detail in Callendret et al. (Virology. 2007 Jul. 5; 363(2): 288-302), herein incorporated by reference for all purposes. Polynucleotide sequences can be optimized to improve transcript stability, for example through removal of RNA instability motifs (e.g., AU-rich elements and 3' UTR motifs) and/or repetitive nucleotide sequences. Polynucleotide sequences can be optimized to improve accurate transcription, for example through removal of cryptic transcriptional initiators and/or terminators. Polynucleotide sequences can be optimized to improve translation and translational accuracy, for example through removal of cryptic AUG start codons, premature polyA sequences, and/or secondary structure motifs. Polynucleotide sequences can be optimized to improve nuclear export of transcripts, such as through addition of a Constitutive Transport Element (CTE), RNA Transport Element (RTE), or Woodchuck Posttranscriptional Regulatory Element (WPRE). Nuclear export signals for use in expression vectors are described in more detail in Callendret et al. (Virology. 2007 Jul. 5; 363(2): 288-302), herein incorporated by reference for all purposes. Polynucleotide sequences can be optimized with respect to GC content, for example to reflect the average GC content of a given organism. Sequence optimization can balance one or more sequence properties, such as transcription, translation, post-transcriptional processing, and/or RNA stability. Sequence optimization can generate an optimal sequence balancing each of transcription, translation, post-transcriptional processing, and RNA stability. Sequence optimization algorithms are known to those of skill in the art, such as GeneArt (Thermo Fisher), Codon Optimization Tool (IDT), Cool Tool (University of Singapore), SGI-DNA (La Jolla California). One or more regions of an antigen-encoding protein can be sequence-optimized separately.

A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

IV. VACCINE COMPOSITIONS

Also disclosed herein is an immunogenic composition, e.g., a vaccine composition, capable of raising a specific immune response, e.g., a infectious disease organism-specific immune response. Vaccine compositions typically comprise one or a plurality of antigens, e.g., selected using a method described herein or selected from a pathogen-derived peptide, a virus-derived peptide, a bacteria-derived peptide, a fungus-derived peptide, and/or a parasite-derived peptide. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 antigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen sequences, 6, 7, 8, 9, 10 11, 12, 13, or 14 different antigen sequences, or 12, 13 or 14 different antigen sequences.

A vaccine can contain between 1 and 30 antigen-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen-encoding nucleic acid sequences, 6, 7, 8, 9, 10 11, 12, 13, or 14 different antigen-encoding nucleic acid sequences, or 12, 13 or 14 different antigen-encoding nucleic acid sequences. Antigen-encoding nucleic acid sequences can refer to the antigen encoding portion of an antigen "cassette." Features of an antigen cassette are described herein. An antigen-encoding nucleic acid sequence can contain one or more epitope-encoding nucleic acid sequences (e.g., an antigen-encoding nucleic acid sequence encoding concatenated T cell epitopes).

A vaccine can contain between 1 and 30 distinct epitope-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more distinct epitope-encoding nucleic acid sequences, 6, 7, 8, 9, 10 11, 12, 13, or 14 distinct epitope-encoding nucleic acid sequences, or 12, 13 or 14 distinct epitope-encoding nucleic acid sequences. Epitope-encoding nucleic acid sequences can refer to sequences for individual epitope sequences, such as each of the T cell epitopes in an antigen-encoding nucleic acid sequence encoding concatenated T cell epitopes.

A vaccine can contain at least two repeats of an epitope-encoding nucleic acid sequence. A used herein, a "repeat" refers to two or more iterations of an identical nucleic acid epitope-encoding nucleic acid sequence (inclusive of the optional 5' linker sequence and/or the optional 3' linker sequences described herein) within an antigen-encoding nucleic acid sequence. In one example, the antigen-encoding nucleic acid sequence portion of a cassette encodes at least two repeats of an epitope-encoding nucleic acid sequence. In further non-limiting examples, the antigen-encoding nucleic acid sequence portion of a cassette encodes more than one distinct epitope, and at least one of the distinct epitopes is encoded by at least two repeats of the nucleic acid sequence encoding the distinct epitope (i.e., at least two distinct epitope-encoding nucleic acid sequences). In illustrative non-limiting examples, an antigen-encoding nucleic acid sequence encodes epitopes A, B, and C encoded by epitope-encoding nucleic acid sequences epitope-encoding sequence A ($E_A$), epitope-encoding sequence B ($E_B$), and epitope-encoding sequence C ($E_C$), and exemplary antigen-encoding nucleic acid sequences having repeats of at least one of the distinct epitopes are illustrated by, but is not limited to, the formulas below:

Repeat of One Distinct Epitope (Repeat of Epitope A):

$$E_A\text{-}E_B\text{-}E_C\text{-}E_A;\ \text{or}$$

$$E_A\text{-}E_A\text{-}E_B\text{-}E_C$$

Repeat of Multiple Distinct Epitopes (Repeats of Epitopes a, B, and C):

$$E_A\text{-}E_B\text{-}E_C\text{-}E_A\text{-}E_B\text{-}E_C;\ \text{or}$$

$$E_A\text{-}E_A\text{-}E_B\text{-}E_B\text{-}E_C\text{-}E_C$$

Multiple Repeats of Multiple Distinct Epitopes (Repeats of Epitopes a, B, and C):

$$E_A\text{-}E_B\text{-}E_C\text{-}E_A\text{-}E_B\text{-}E_C\text{-}E_A\text{-}E_B\text{-}E_C;\ \text{or}$$

$$E_A\text{-}E_A\text{-}E_A\text{-}E_B\text{-}E_B\text{-}E_B\text{-}E_C\text{-}E_C\text{-}E_C$$

The above examples are not limiting and the antigen-encoding nucleic acid sequences having repeats of at least one of the distinct epitopes can encode each of the distinct epitopes in any order or frequency. For example, the order and frequency can be a random arrangement of the distinct epitopes, e.g., in an example with epitopes A, B, and C, by the formula $E_A\text{-}E_B\text{-}E_C\text{-}E_C\text{-}E_A\text{-}E_B\text{-}E_A\text{-}E_C\text{-}E_A\text{-}E_C\text{-}E_C\text{-}E_B$.

Also provided for herein is an antigen-encoding cassette, the antigen-encoding cassette having at least one antigen-encoding nucleic acid sequence described, from 5' to 3', by the formula:

$$(E_x\text{-}(E^N_n)_y)_z$$

where E represents a nucleotide sequence comprising at least one of the at least one distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof.

Each E or $E^N$ can independently comprise any epitope-encoding nucleic acid sequence described herein (e.g., a peptide encoding an infectious disease T cell epitope). For example, Each E or $E^N$ can independently comprises a nucleotide sequence described, from 5' to 3', by the formula $(L5_b$-$N_c$-$L3_d)$, where N comprises the distinct epitope-encoding nucleic acid sequence associated with each E or $E^N$, where c=1, L5 comprises a 5' linker sequence, where b=0 or 1, and L3 comprises a 3' linker sequence, where d=0 or 1. Epitopes and linkers that can be used are further described herein.

Repeats of an epitope-encoding nucleic acid sequences (inclusive of optional 5' linker sequence and/or the optional 3' linker sequences) can be linearly linked directly to one another (e.g., $E_A$-$E_A$ . . . as illustrated above). Repeats of an epitope-encoding nucleic acid sequences can be separated by one or more additional nucleotides sequences. In general, repeats of an epitope-encoding nucleic acid sequences can be separated by any size nucleotide sequence applicable for the compositions described herein. In one example, repeats of an epitope-encoding nucleic acid sequences can be separated by a separate distinct epitope-encoding nucleic acid sequence (e.g., $E_A$-$E_B$-$E_C$-$E_A$ . . . , as illustrated above). In examples where repeats are separated by a single separate distinct epitope-encoding nucleic acid sequence, and each epitope-encoding nucleic acid sequences (inclusive of optional 5' linker sequence and/or the optional 3' linker sequences) encodes a peptide 25 amino acids in length, the repeats can be separated by 75 nucleotides, such as in antigen-encoding nucleic acid represented by $E_A$-$E_B$-$E_A$ . . . $E_A$ is separated by 75 nucleotides. In an illustrative example, an antigen-encoding nucleic acid having the sequence VTNTEMFVTAPDNLGYMYEVQWPGQTQPQIANC-SVY- DFFVWLHYYSVRDTVTNTEM FVTAPDNLGY-MYEVQWPGQTQPQIANCSVYDFFVWLHYYSVRDT (SEQ ID NO: 57) encoding repeats of 25mer antigens Trp1 (VTNTEMFVTAPDNLGYMYEVQWPGQ) (SEQ ID NO: 58) and Trp2 (TQPQIANCSVYDFFVWLHYYSVRDT) (SEQ ID NO: 59), the repeats of Trp1 are separated by the 25mer Trp2 and thus the repreats of the Trp1 epitope-encoding nucleic acid sequences are separated the 75 nucleotide Trp2 epitope-encoding nucleic acid sequence. In examples where repeats are separated by 2, 3, 4, 5, 6, 7, 8, or 9 separate distinct epitope-encoding nucleic acid sequence, and each epitope-encoding nucleic acid sequences (inclusive of optional 5' linker sequence and/or the optional 3' linker sequences) encodes a peptide 25 amino acids in length, the repeats can be separated by 150, 225, 300, 375, 450, 525, 600, or 675 nucleotides, respectively.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of raising a specific cytotoxic T-cells response and/or a specific helper T-cell response.

The vaccine composition can be capable of raising a specific B-cell response (e.g., an antibody response).

The vaccine composition can be capable of raising a specific cytotoxic T-cells response, a specific helper T-cell response, and/or a specific B-cell response (e.g., an antibody response. The vaccine composition can be capable of raising a specific cytotoxic T-cells response, a specific helper T-cell response, and a specific B-cell response (e.g., an antibody response.

A vaccine composition can further comprise an adjuvant and/or a carrier. Examples of useful adjuvants and carriers are given herein below. A composition can be associated with a carrier such as e.g. a protein or an antigen-presenting cell such as a dendritic cell (DC) capable of presenting the peptide to a T-cell.

Adjuvants are any substance whose admixture into a vaccine composition increases or otherwise modifies the immune response to an antigen. Carriers can be scaffold structures, for example a polypeptide or a polysaccharide, to which an antigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, Lipo Vac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7. TLR 8 and/or TLR 9 may also be used.

Other examples of useful adjuvants include, but are not limited to, chemically modified CpGs (e.g. CpR, Idera), Poly(I:C) (e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41. Lu et al., Efficient identification of mutated cancer antigens recognized by T cells associated with durable tumor regressions, *Clin Cancer Res.* (2014) 20(13): 3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

IV.A. Antigen Cassette

The methods employed for the selection of one or more antigens, the cloning and construction of a "cassette" and its insertion into a viral vector are within the skill in the art given the teachings provided herein. By "antigen cassette" or "cassette" is meant the combination of a selected antigen or plurality of antigens (e.g., antigen-encoding nucleic acid sequences) and the other regulatory elements necessary to transcribe the antigen(s) and express the transcribed product. The selected antigen or plurality of antigens can refer to distinct epitope sequences, e.g., an antigen-encoding nucleic acid sequence in the cassette can encode an epitope-encoding nucleic acid sequence (or plurality of epitope-encoding nucleic acid sequences) such that the epitopes are transcribed and expressed. An antigen or plurality of antigens can be operatively linked to regulatory components in a manner which permits transcription. Such components include conventional regulatory elements that can drive expression of the antigen(s) in a cell transfected with the viral vector. Thus the antigen cassette can also contain a selected promoter which is linked to the antigen(s) and located, with other, optional regulatory elements, within the selected viral sequences of the recombinant vector. Cassettes can include one or more antigens, such as one or more pathogen-derived peptides, a virus-derived peptides, bacteria-derived peptides, fungus-derived peptides, and/or parasite-derived peptides. A cassette can have one or more antigen-encoding nucleic acid sequences, such as a cassette containing multiple antigen-encoding nucleic acid sequences each independently operably linked to separate promoters and/or linked together using other multicistonic systems, such as 2A ribosome skipping sequence elements (e.g., E2A, P2A, F2A, or T2A sequences) or Internal Ribosome Entry Site (IRES) sequence elements. A linker can also have a cleavage site, such as a TEV or furin cleavage site. Linkers with cleavage sites can be used in combination with other elements, such as those in a multicistronic system. In a non-limiting illustrative example, a furin protease cleavage site can be used in conjunction with a 2A ribosome skipping sequence element such that the furin protease cleavage site is configured to facilitate removal of the 2A sequence following translation. In a cassette containing more than one antigen-encoding nucleic acid sequences, each antigen-encoding nucleic acid sequence can contain one or more epitope-encoding nucleic acid sequences (e.g., an antigen-encoding nucleic acid sequence encoding concatenated T cell epitopes).

Useful promoters can be constitutive promoters or regulated (inducible) promoters, which will enable control of the amount of antigen(s) to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art.

The antigen cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the antigen-based sequences and before the viral vector sequences. A common intron sequence can also be derived from SV-40, and is referred to as the SV-40 T intron sequence. an antigen cassette can also contain such an intron, located between the promoter/enhancer sequence and the antigen(s). Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

A antigen cassette can have one or more antigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more antigens. Antigens can be linked directly to one another. Antigens can also be linked to one another with linkers. Antigens can be in any orientation relative to one another including N to C or C to N.

As described elsewhere, the antigen cassette can be located in the site of any selected deletion in the viral vector backbone, such as the site of the E1 gene region deletion or E3 gene region deletion of a ChAd-based vector or the deleted structural proteins of a VEE backbone, among others which may be selected.

The antigen cassette can be described using the following formula to describe the ordered sequence of each element, from 5' to 3':

$$(P_a\text{-}(L5_b\text{-}N_c\text{-}L3_d)_X)_Z\text{---}(P2_h\text{-}(G5_e\text{-}U_f)_Y)_W\text{-}G3_g$$

wherein P and P2 comprise promoter nucleotide sequences, N comprises an MHC class I epitope encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding $N_c$ is a epitope encoding nucleic acid sequence, where for each Y the corresponding $U_f$ is a universal MHC class II epitope-encoding nucleic acid sequence, optionally wherein the at least one universal sequence comprises at least one of Tetanus toxoid and PADRE. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (e.g., only the promoter nucleotide sequence provided by the vector backbone, such as an RNA alphavirus backbone, is present), 10 MHC class I epitope are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to the vectorbackbone. Examples of linking the 3' end of the antigen cassette to the vectorbackbone include linking directly to the 3' UTR elements provided by the vectorbackbone, such as a 3' 19-nt CSE. Examples of linking the 5' end of the antigen cassette to the vector backbone include linking directly to a promoter or 5' UTR element of the vector backbone, such as a 26S promoter sequence, an alphavirus 5' UTR, a 51-nt CSE, or a 24-nt CSE.

Other examples include: where a=1 describing where a promoter other than the promoter nucleotide sequence provided by the vector backbone is present; where a=1 and Z is greater than 1 where multiple promoters other than the promoter nucleotide sequence provided by the vector backbone are present each driving expression of 1 or more distinct MHC class I epitope encoding nucleic acid sequences; where h=1 describing where a separate promoter is present to drive expression of the MHC class II epitope-encoding nucleic acid sequences; and where g=0 describing the MHC class II epitope-encoding nucleic acid sequence, if present, is directly linked to the vector backbone.

Other examples include where each MHC class I epitope that is present can have a 5' linker, a 3' linker, neither, or both. In examples where more than one MHC class I epitope is present in the same antigen cassette, some MHC class I epitopes may have both a 5' linker and a 3' linker, while other MHC class I epitopes may have either a 5' linker, a 3' linker, or neither. In other examples where more than one MHC class I epitope is present in the same antigen cassette, some MHC class I epitopes may have either a 5' linker or a 3' linker, while other MHC class I epitopes may have either a 5' linker, a 3' linker, or neither.

Other examples include where each antigen that is present can have a 5' linker, a 3' linker, neither, or both. In examples where more than one antigen is present in the same antigen cassette, some antigens may have both a 5' linker and a 3' linker, while other antigens may have either a 5' linker, a 3' linker, or neither. In other examples where more than one antigen is present in the same antigen cassette, some antigens may have either a 5' linker or a 3' linker, while other antigens may have either a 5' linker, a 3' linker, or neither.

In examples where more than one MHC class II epitope is present in the same antigen cassette, some MHC class II epitopes may have both a 5' linker and a 3' linker, while other MHC class II epitopes may have either a 5' linker, a 3' linker, or neither. In other examples where more than one MHC class II epitope is present in the same antigen cassette, some MHC class II epitopes may have either a 5' linker or a 3' linker, while other MHC class II epitopes may have either a 5' linker, a 3' linker, or neither.

The promoter nucleotide sequences P and/or P2 can be the same as a promoter nucleotide sequence provided by the vector backbone, such as a RNA alphavirus backbone. For example, the promoter sequence provided by the vector backbone, Pn and P2, can each comprise a 26S subgenomic promoter or a CMV promoter. The promoter nucleotide sequences P and/or P2 can be different from the promoter nucleotide sequence provided by the vector backbone, as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encode a MHC class I epitope, a MHC class II epitope, an epitope capable of stimulating a B cell response, or a combination thereof. For each X, N can encode a combination of a MHC class I epitope, a MHC class II epitope, and an epitope capable of stimulating a B cell response. For each X, N can encode a combination of a MHC class I epitope and a MHC class II epitope. For each X, N can encode a combination of a MHC class I epitope and an epitope capable of stimulating a B cell response. For each X, N can encode a combination of a MHC class II epitope and an epitope capable of stimulating a B cell response. For each X, each N can encode a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length. For each X, each N can encode a MHC class II epitope. For each X, each N can encode an epitope capable of stimulating a B cell response.

The cassette encoding the one or more antigens can be 700 nucleotides or less. The cassette encoding the one or more antigens can be 700 nucleotides or less and encode 2 distinct epitope-encoding nucleic acid sequences (e.g., encode 2 distinct SARS-CoV-2 derived nucleic acid sequence encoding an immunogenic polypeptide). The cassette encoding the one or more antigens can be 700 nucleotides or less and encode at least 2 distinct epitope-encoding nucleic acid sequences. The cassette encoding the one or more antigens can be 700 nucleotides or less and encode 3 distinct epitope-encoding nucleic acid sequences. The cassette encoding the one or more antigens can be 700 nucleotides or less and encode at least 3 distinct epitope-encoding nucleic acid sequences. The cassette encoding the one or more antigens can be 700 nucleotides or less and include 1-10, 1-5, 1, 2, 3, 4, 5, 6, 7, 8, 9, 10, or more antigens.

The cassette encoding the one or more antigens can be between 375-700 nucleotides in length. The cassette encoding the one or more antigens can be between 375-700 nucleotides in length and encode 2 distinct epitope-encoding nucleic acid sequences. The cassette encoding the one or more antigens can be between 375-700 nucleotides in length and encode at least 2 distinct epitope-encoding nucleic acid sequences. The cassette encoding the one or more antigens can be between 375-700 nucleotides in length and encode 3 distinct epitope-encoding nucleic acid sequences. The cassette encoding the one or more antigens be between 375-700 nucleotides in length and encode at least 3 distinct epitope-encoding nucleic acid sequences. The cassette encoding the one or more antigens can be between 375-700 nucleotides in length and include 1-10, 1-5, 1, 2, 3, 4, 5, 6, 7, 8, 9, 10, or more antigens.

The cassette encoding the one or more antigens can be 600, 500, 400, 300, 200, or 100 nucleotides in length or less. The cassette encoding the one or more antigens can be 600, 500, 400, 300, 200, or 100 nucleotides in length or less and encode 2 distinct epitope-encoding nucleic acid sequences. The cassette encoding the one or more antigens can be 600, 500, 400, 300, 200, or 100 nucleotides in length or less and encode at least 2 distinct epitope-encoding nucleic acid sequences. The cassette encoding the one or more antigens can be 600, 500, 400, 300, 200, or 100 nucleotides in length or less and encode 3 distinct epitope-encoding nucleic acid sequences. The cassette encoding the one or more antigens can be 600, 500, 400, 300, 200, or 100 nucleotides in length or less and encode at least 3 distinct epitope-encoding nucleic acid sequences. The cassette encoding the one or more antigens can be 600, 500, 400, 300, 200, or 100 nucleotides in length or less and include 1-10, 1-5, 1, 2, 3, 4, 5, 6, 7, 8, 9, 10, or more antigens.

The cassette encoding the one or more antigens can be between 375-600, between 375-500, or between 375-400 nucleotides in length. The cassette encoding the one or more antigens can be between 375-600, between 375-500, or between 375-400 nucleotides in length and encode 2 distinct epitope-encoding nucleic acid sequences. The cassette encoding the one or more antigens can be between 375-600, between 375-500, or between 375-400 nucleotides in length and encode at least 2 distinct epitope-encoding nucleic acid sequences. The cassette encoding the one or more antigens can be between 375-600, between 375-500, or between 375-400 nucleotides in length and encode 3 distinct epitope-encoding nucleic acid sequences. The cassette encoding the one or more antigens can be between 375-600, between 375-500, or between 375-400 nucleotides in length and encode at least 3 distinct epitope-encoding nucleic acid sequences. The cassette encoding the one or more antigens can be between 375-600, between 375-500, or between 375-400 nucleotides in length and include 1-10, 1-5, 1, 2, 3, 4, 5, 6, 7, 8, 9, 10, or more antigens.

IV.B. Immune Checkpoints

Vectors described herein, such as C68 vectors described herein or alphavirus vectors described herein, can comprise a nucleic acid which encodes at least one antigen and the same or a separate vector can comprise a nucleic acid which encodes at least one immune modulator (e.g., an antibody such as an scFv) which binds to and blocks the activity of an immune checkpoint molecule. Vectors can comprise an antigen cassette and one or more nucleic acid molecules encoding a checkpoint inhibitor.

Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. *Nat Biotechnol.* 2005 May; 23(5):584-90. Epub 2005 Apr. 17; herein incorporated by reference for all purposes.

IV.C. Additional Considerations for Vaccine Design and Manufacture

IV.C.1. Determination of a Set of Peptides that Cover all Tumor Subclones

Truncal peptides, meaning those presented by all or most subclones, can be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of subclones and choosing peptides so as to maximize the number of subclones covered by the vaccine.[54]

IV.C.2. Antigen Prioritization

After all of the above antigen filters are applied, more candidate antigens may still be available for vaccine inclusion than the vaccine technology can support. Additionally, uncertainty about various aspects of the antigen analysis may remain and tradeoffs may exist between different properties of candidate vaccine antigens. Thus, in place of predetermined filters at each step of the selection process, an integrated multi-dimensional model can be considered that places candidate antigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of antigens may lower the probability that an infected cell will escape immune attack via downregulation or mutation of HLA molecules)
7. Coverage of HLA classes (covering both HLA-I and HLA-II may increase the probability of therapeutic response and decrease the probability of infectious disease escape)

Additionally, optionally, antigens can be deprioritized (e.g., excluded) from the vaccination if they are predicted to be presented by HLA alleles lost or inactivated in either all or part of the patient's infected cell. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010). Antigens can also be deprioritized if mass-spectrometry data indicates a predicted antigen is not presented by a predicted HLA allele.

IV.D. Self-Amplifying RNA Vectors

In general, all self-amplifying RNA (SAM) vectors contain a self-amplifying backbone derived from a self-replicating virus. The term "self-amplifying backbone" refers to minimal sequence(s) of a self-replicating virus that allows for self-replication of the viral genome. For example, minimal sequences that allow for self-replication of an alphavirus can include conserved sequences for nonstructural protein-mediated amplification (e.g., a nonstructural protein 1 (nsP1) gene, a nsP2 gene, a nsP3 gene, a nsP4 gene, and/or a polyA sequence). A self-amplifying backbone can also include sequences for expression of subgenomic viral RNA (e.g., a 26S promoter element for an alphavirus). SAM vectors can be positive-sense RNA polynucleotides or negative-sense RNA polynucleotides, such as vectors with backbones derived from positive-sense or negative-sense self-replicating viruses. Self-replicating viruses include, but are not limited to, alphaviruses, flaviviruses (e.g., Kunjin virus), measles viruses, and rhabdoviruses (e.g., rabies virus and vesicular stomatitis virus). Examples of SAM vector systems derived from self-replicating viruses are described in Lundstrom (Molecules. 2018 Dec. 13; 23(12). pii: E3310. doi: 10.3390/molecules23123310), herein incorporated by reference for all purposes.

IV.D.1. Alphavirus Biology

Alphaviruses are members of the family Togaviridae, and are positive-sense single stranded RNA viruses. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbrial Review 1994). A natural alphavirus genome is typically around 12 kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' poly A tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

IV.D.2. Alphavirus as a Delivery Vector

Alphaviruses (including alphavirus sequences, features, and other elements) can be used to generate alphavirus-based delivery vectors (also be referred to as alphavirus vectors, alphavirus viral vectors, alphavirus vaccine vectors, self-replicating RNA (srRNA) vectors, or self-amplifying RNA (samRNA) vectors). Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly illicit an immune response to the heterologous antigen expressed. However, the degree of desired cytotoxicity can be a balancing act, and thus several attenuated alphaviruses have been developed, including the TC-83 strain of VEE. Thus, an example of an antigen expression vector described herein can utilize an alphavirus backbone that allows for a high level of antigen expression, elicits a robust immune response to antigen, does not elicit an immune response to the vector itself, and can be used in a safe manner. Furthermore, the antigen expression cassette can be designed to elicit different levels of an immune response through optimization of which alphavirus sequences the vector uses, including, but not limited to, sequences derived from VEE or its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of an antigen expression vector described herein can utilize an alphavirus backbone wherein the structural proteins are replaced by an antigen cassette, the resulting vector both reducing biosafety concerns, while at the same time promoting efficient expression due to the reduction in overall expression vector size.

IV.D.3. Self-Amplifying Virus Production In Vitro

A convenient technique well-known in the art for RNA production is in vitro transcription (IVT). In this technique, a DNA template of the desired vector is first produced by techniques well-known to those in the art, including standard molecular biology techniques such as cloning, restriction digestion, ligation, gene synthesis, and polymerase chain reaction (PCR).

The DNA template contains a RNA polymerase promoter at the 5' end of the sequence desired to be transcribed into RNA (e.g., SAM). Promoters include, but are not limited to, bacteriophage polymerase promoters such as T3, T7, K11, or SP6. Depending on the specific RNA polymerase promoter sequence chosen, additional 5' nucleotides can transcribed in addition to the desired sequence. For example, the canonical T7 promoter can be referred to by the sequence TAATACGACTCACTATAGG (SEQ ID NO: 60), in which an IVT reaction using the DNA template TAATACGACT-CACTATAGGN (SEQ ID NO: 61) for the production of desired sequence N will result in the mRNA sequence GG-N. In general, and without wishing to be bound by theory, T7 polymerase more efficiently transcribes RNA transcripts beginning with guanosine. In instances where additional 5' nucleotides are not desired (e.g., no additional GG), the RNA polymerase promoter contained in the DNA template can be a sequence the results in transcripts containing only the 5' nucleotides of the desired sequence, e.g., a SAM having the native 5' sequence of the self-replicating virus from which the SAM vector is derived. For example, a minimal T7 promoter can be referred to by the sequence TAATACGACTCACTATA (SEQ ID NO: 62), in which an IVT reaction using the DNA template TAATACGACTCAC-TATAN (SEQ ID NO: 63) for the production of desired sequence N will result in the mRNA sequence N. Likewise, a minimal SP6 promoter referred to by the sequence ATT-TAGGTGACACTATA (SEQ ID NO: 64) can be used to generate transcripts without additional 5' nucleotides. In a typical IVT reaction, the DNA template is incubated with the appropriate RNA polymerase enzyme, buffer agents, and nucleotides (NTPs).

The resulting RNA polynucleotide can optionally be further modified including, but limited to, addition of a 5' cap structure such as 7-methylguanosine or a related structure, and optionally modifying the 3' end to include a polyadenylate (polyA) tail. In a modified IVT reaction, RNA is capped with a 5' cap structure co-transcriptionally through the addition of cap analogues during IVT. Cap analogues can include dinucleotide ($m^7G$-ppp-N) cap analogues or trinucleotide ($m^7G$-ppp-N—N) cap analogues, where N represents a nucleotide or modified nucleotide (e.g., ribonucleosides including, but not limited to, adenosine, guanosine, cytidine, and uradine). Exemplary cap analogues and their use in IVT reactions are also described in U.S. Pat. No. 10,519,189, herein incorporated by reference for all purposes. As discussed, T7 polymerase more efficiently transcribes RNA transcripts beginning with guanosine. To improve transcription efficiency in templates that do not begin with guanosine, a trinucleotide cap analogue ($m^7G$-ppp-N—N) can be used. The trinucleotide cap analogue can increase transcription efficiency 2, 3, 4, 5, 6, 7, 8, 9, 10, 11, 12, 13, 14, 15, 16, 17, 18, 19, 20-fold or more relative to an IVT reaction using a dinucleotide cap analogue ($m^7G$-ppp-N).

A 5' cap structure can also be added following transcription, such as using a vaccinia capping system (e.g., NEB Cat. No. M2080) containing mRNA 2'-O-methyltransferase and S-Adenosyl methionine.

The resulting RNA polynucleotide can optionally be further modified separately from or in addition to the capping techniques described including, but limited to, modifying the 3' end to include a polyadenylate (polyA) tail.

The RNxA can then be purified using techniques well-known in the field, such as phenol-chloroform extraction.

IV.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different antigen cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver antigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soluable vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

IV.E. Chimpanzee Adenovirus (ChAd)

IV.E.1. Viral Delivery with Chimpanzee Adenovirus

Vaccine compositions for delivery of one or more antigens (e.g., via an antigen cassette and including pathogen-derived peptides, a virally-derived peptides, a bacterially-derived peptides, a fungally-derived peptides, and a parasitically-derived peptides) can be created by providing adenovirus nucleotide sequences of chimpanzee origin, a variety of novel vectors, and cell lines expressing chimpanzee adenovirus genes. A nucleotide sequence of a chimpanzee C68 adenovirus (also referred to herein as ChAdV68) can be used in a vaccine composition for antigen delivery (See SEQ ID NO: 1). Use of C68 adenovirus derived vectors is described in further detail in U.S. Pat. No. 6,083,716, which is herein incorporated by reference in its entirety, for all purposes.

In a further aspect, provided herein is a recombinant adenovirus comprising the DNA sequence of a chimpanzee adenovirus such as C68 and an antigen cassette operatively linked to regulatory sequences directing its expression. The recombinant virus is capable of infecting a mammalian, preferably a human, cell and capable of expressing the antigen cassette product in the cell. In this vector, the native chimpanzee E1 gene, and/or E3 gene, and/or E4 gene can be deleted. an antigen cassette can be inserted into any of these sites of gene deletion. The antigen cassette can include an antigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering an antigen cassette into a mammalian cell comprising the step of introducing into the cell an effective amount of a chimpanzee adenovirus, such as C68, that has been engineered to express the antigen cassette.

Still another aspect provides a method for eliciting an immune response in a mammalian host. The method can comprise the step of administering to the host an effective amount of a recombinant chimpanzee adenovirus, such as C68, comprising an antigen cassette that encodes one or more antigens from the infection against which the immune response is targeted.

Still another aspect provides a method for eliciting an immune response in a mammalian host to treat or prevent a disease in a subject, such as an infectious disease. The method can comprise the step of administering to the host an effective amount of a recombinant chimpanzee adenovirus, such as C68, comprising an antigen cassette that encodes one or more antigens, such as from the infectious disease against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and an antigen cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the antigen cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a adenovirus vector comprising: a partially deleted E4 gene comprising a deleted or partially-deleted E4orf2 region and a deleted or partially-deleted E4orf3 region, and optionally a deleted or partially-deleted E4orf4 region. The partially deleted E4 can comprise an E4 deletion of at least nucleotides 34,916 to 35,642 of the sequence shown in SEQ ID NO:1, and wherein the vector comprises at least nucleotides 2 to 36,518 of the sequence set forth in SEQ ID NO:1. The partially deleted E4 can comprise an E4 deletion of at least a partial deletion of nucleotides 34,916 to 34,942 of the sequence shown in SEQ ID NO:1, at least a partial deletion of nucleotides 34,952 to 35,305 of the sequence shown in SEQ ID NO:1, and at least a partial deletion of nucleotides 35,302 to 35,642 of the sequence shown in SEQ ID NO:1, and wherein the vector comprises at least nucleotides 2 to 36,518 of the sequence set forth in SEQ ID NO:1 The partially deleted E4 can comprise an E4 deletion of at least nucleotides 34,980 to 36,516 of the sequence shown in SEQ ID NO:1, and wherein the vector comprises at least nucleotides 2 to 36,518 of the sequence set forth in SEQ ID NO:1. The partially deleted E4 can comprise an E4 deletion of at least nucleotides 34,979 to 35,642 of the sequence shown in SEQ ID NO:1, and wherein the vector comprises at least nucleotides 2 to 36,518 of the sequence set forth in SEQ ID NO:1. The partially deleted E4 can comprise an E4 deletion of at least a partial deletion of E4Orf2, a fully deleted E4Orf3, and at least a partial deletion of E4Orf4. The partially deleted E4 can comprise an E4 deletion of at least a partial deletion of E4Orf2, at least a partial deletion of E4Orf3, and at least a partial deletion of E4Orf4. The partially deleted E4 can comprise an E4 deletion of at least a partial deletion of E4Orf1, a fully deleted E4Orf2, and at least a partial deletion of E4Orf3. The partially deleted E4 can comprise an E4 deletion of at least a partial deletion of E4Orf2 and at least a partial deletion of E4Orf3. The partially deleted E4 can comprise an E4 deletion between the start site of E4Orf1 to the start site of E4Orf5. The partially deleted E4 can be an E4 deletion adjacent to the start site of E4Orf1. The partially deleted E4 can be an E4 deletion adjacent to the start site of E4Orf2. The partially deleted E4 can be an E4 deletion adjacent to the start site of E4Orf3. The partially deleted E4 can be an E4 deletion adjacent to the start site of E4Orf4. The E4 deletion can be at least 50, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 nucleotides. The E4 deletion can be at least 700 nucleotides. The E4 deletion can be at least 1500 nucleotides. The E4 deletion can be 50 or less, 100 or less, 200 or less, 300 or less, 400 or less, 500 or less, 600 or less, 700 or less, 800 or less, 900 or less, 1000 or less, 1100 or less, 1200 or less, 1300 or less, 1400 or less, 1500 or less, 1600 or less, 1700 or less, 1800 or less, 1900 or less, or 2000 or less nucleotides. The E4 deletion can be 750 nucleotides or less. The E4 deletion can be at least 1550 nucleotides or less.

The partially deleted E4 gene can be the E4 gene sequence shown in SEQ ID NO:1 that lacks at least nucleotides 34,916 to 35,642 of the sequence shown in SEQ ID NO:1. The partially deleted E4 gene can be the E4 gene sequence shown in SEQ ID NO:1 that lacks the E4 gene sequence shown in SEQ ID NO:1 and that lacks at least nucleotides 34,916 to 34,942, nucleotides 34,952 to 35,305 of the sequence shown in SEQ ID NO:1, and nucleotides 35,302 to 35,642 of the sequence shown in SEQ ID NO:1. The partially deleted E4 gene can be the E4 gene sequence shown in SEQ ID NO:1 and that lacks at least nucleotides 34,980 to 36,516 of the sequence shown in SEQ ID NO:1. The partially deleted E4 gene can be the E4 gene sequence shown in SEQ ID NO:1 and that lacks at least nucleotides 34,979 to 35,642 of the sequence shown in SEQ ID NO:1. The adenovirus vector having the partially deleted E4 gene can have a cassette, wherein the cassette comprises at least one payload nucleic acid sequence, and wherein the cassette comprises at least one promoter sequence operably linked to the at least one payload nucleic acid sequence. The adenovirus vector having the partially deleted E4 gene can have one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion. The adenovirus vector having the partially deleted E4 gene can have nucleotides 35,643 to 36,518 of the sequence shown in SEQ ID NO:1, and wherein the partially deleted E4 gene is 5' of the nucleotides 35,643 to 36,518. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

The partially deleted E4 gene can be the E4 gene sequence shown in SEQ ID NO:1 that lacks at least nucleotides 34,916 to 35,642 of the sequence shown in SEQ ID NO:1, nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

Also disclosed herein is a host cell transfected with a vector disclosed herein such as a C68 vector engineered to expression an antigen cassette. Also disclosed herein is a human cell that expresses a selected gene introduced therein through introduction of a vector disclosed herein into the cell.

Also disclosed herein is a method for delivering an antigen cassette to a mammalian cell comprising introducing into said cell an effective amount of a vector disclosed herein such as a C68 vector engineered to expression the antigen cassette.

Also disclosed herein is a method for producing an antigen comprising introducing a vector disclosed herein into a mammalian cell, culturing the cell under suitable conditions and producing the antigen.

IV.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38 [CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

IV.E.3. Recombinant Viral Particles as Vectors

The compositions disclosed herein can comprise viral vectors, that deliver at least one antigen to cells. Such vectors comprise a chimpanzee adenovirus DNA sequence such as C68 and an antigen cassette operatively linked to regulatory sequences which direct expression of the cassette. The C68 vector is capable of expressing the cassette in an infected mammalian cell. The C68 vector can be functionally deleted in one or more viral genes. an antigen cassette comprises at least one antigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

IV.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of an antigen cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

IV.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

IV.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene Ela and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express antigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising antigen(s) be inserted optionally into any deleted region of the chimpanzee C68 Ad virus. Alternatively, the cassette can be inserted into an existing gene region to disrupt the function of that region, if desired.

IV.E.7. Helper Viruses

Depending upon the chimpanzee adenovirus gene content of the viral vectors employed to carry the antigen cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the "helper" virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the antigen cassette on the adenovirus vector allows both the Ad vector and the helper virus to be independently monitored. This second reporter is used to enable separation between the resulting recombinant virus and the helper virus upon purification.

IV.E.8. Assembly of Viral Particle and Infection of a Cell Line

Assembly of the selected DNA sequences of the adenovirus, the antigen cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleotide sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired antigen cassette-containing viral vector, the vector can be transfected in vitro in the presence of a helper virus into the packaging cell line. Homologous recombination occurs between the helper and the vector sequences, which permits the adenovirus-antigen sequences in the vector to be replicated and packaged into virion capsids, resulting in the recombinant viral vector particles.

The resulting recombinant chimpanzee C68 adenoviruses are useful in transferring an antigen cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

IV.E.9. Use of the Recombinant Virus Vectors

The resulting recombinant chimpanzee C68 adenovirus containing the antigen cassette (produced by cooperation of the adenovirus vector and helper virus or adenoviral vector and packaging cell line, as described above) thus provides an efficient gene transfer vehicle which can deliver antigen(s) to a subject in vivo or ex vivo.

The above-described recombinant vectors are administered to humans according to published methods for gene therapy. A chimpanzee viral vector bearing an antigen cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of antigen transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of antigen(s) can be monitored to determine the frequency of dosage administration.

Recombinant, replication defective adenoviruses can be administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising an antigen cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to antigen(s) can be monitored to determine the need, if any, for boosters. Following an assessment of antibody titers in the serum, for example, optional booster immunizations may be desired

V. THERAPEUTIC AND MANUFACTURING METHODS

Also provided is a method of inducing a infectious disease organism-specific immune response in a subject, vaccinating against a infectious disease organism, treating and or alleviating a symptom of an infection associated with an infectious disease organism in a subject by administering to the subject one or more antigens such as a plurality of antigens identified using methods disclosed herein.

In some aspects, a subject has been diagnosed with an infection or is at risk of an infection, such as age, geographical/travel, and/or work-related increased risk of or predisposition to an infection, or at risk to a seasonal and/or novel disease infection.

A antigen can be administered in an amount sufficient to induce a CTL response. an antigen can be administered in an amount sufficient to induce a T cell response. an antigen can be administered in an amount sufficient to induce a B cell response.

A antigen can be administered alone or in combination with other therapeutic agents. Therapeutic agents can include those that target an infectious disease organism, such as an anti-viral or antibiotic agent.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each antigen to be included in a vaccine composition and the optimum dosing regimen can be determined. For example, an antigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of antigens present in the composition is/are tissue, infectious disease, and/or patient-specific. For instance, the exact selection of peptides can be guided by expression patterns of the parent proteins in a given tissue or guided by mutation or disease status of a patient. The selection can be dependent on the specific infectious disease (e.g. the specific SARS-CoV-2 isolate the subject is infected with or at risk for infection by), the status of the disease, the goal of the vaccination (e.g., preventative or targeting an ongoing disease), earlier treatment regimens, the immune status of the patient, and, of course, the HLA-haplotype of the patient. Furthermore, a vaccine can contain individualized components, according to personal needs of the particular patient. Examples include varying the selection of antigens according to the expression of the antigen in the particular patient or adjustments for secondary treatments following a first round or scheme of treatment.

A patient can be identified for administration of an antigen vaccine through the use of various diagnostic methods, e.g., patient selection methods described further below. Patient selection can involve identifying mutations in, or expression patterns of, one or more genes. Patient selection can involve identifying the infectious disease of an ongoing infection. Patient selection can involve identifying risk of an infection by an infectious disease. In some cases, patient selection involves identifying the haplotype of the patient. The various patient selection methods can be performed in parallel, e.g., a sequencing diagnostic can identify both the mutations and the haplotype of a patient. The various patient selection methods can be performed sequentially, e.g., one diagnostic test identifies the mutations and separate diagnostic test identifies the haplotype of a patient, and where each test can be the same (e.g., both high-throughput sequencing) or different (e.g., one high-throughput sequencing and the other Sanger sequencing) diagnostic methods.

For a composition to be used as a vaccine for an infectious disease, antigens with similar normal self-peptides that are expressed in high amounts in normal tissues can be avoided or be present in low amounts in a composition described herein. On the other hand, if it is known that the infected cell of a patient expresses high amounts of a certain antigen, the respective pharmaceutical composition for treatment of this infection can be present in high amounts and/or more than one antigen specific for this particularly antigen or pathway of this antigen can be included.

Compositions comprising an antigen can be administered to an individual already suffering from an infection. In therapeutic applications, compositions are administered to a patient in an amount sufficient to elicit an effective CTL response to the infectious disease organism antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the infectious disease organism has induced organ damage and/or other immune pathology. In such cases, in view of the minimization of extraneous substances and the relative nontoxic nature of an antigen, it is possible and can be felt desirable by the treating physician to administer substantial excesses of these compositions.

For therapeutic use, administration can begin at the detection or treatment of an infection. This can be followed by boosting doses until at least symptoms are substantially abated and for a period thereafter or immunity is considered to be provided (e.g., a memory B cell or T cell population, or antigen specific B cells or antibodies are produced).

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered to target specific infected tissues and/or cells of a subject. Disclosed herein are compositions for parenteral administration which comprise a solution of the antigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Antigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the antigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired antigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6 (7): 682-691 (1988); U.S. Pat. No. 5,279,833 Rose U.S. Pat. Nos. 5,279, 833; 9,106,309WOAWO 91/06309; and Felgner et al., Proc. Natl. Acad. Sci. USA 84:7413-7414 (1987).

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev*. (2011) 239(1): 45-61, Sakuma et al., Lentiviral vectors: basic to translational, *Biochem J*. (2012) 443(3):603-18, Cooper et al., Rescue of splicing-mediated intron loss maximizes expression in lentiviral vectors containing the human ubiquitin C promoter, *Nucl. Acids Res*. (2015) 43 (1): 682-690, Zufferey et al., Self-Inactivating Lentivirus Vector for Safe and Efficient In Vivo Gene Delivery, *J. Virol*. (1998) 72 (12): 9873-9880). Dependent on the packaging capacity of the above mentioned viral vector-based vaccine platforms, this approach can deliver one or more nucleotide sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med*. (2016) 22 (4): 433-8, Stronen et al., Targeting of cancer neoantigens with donor-derived T cell receptor repertoires, *Science*. (2016) 352 (6291): 1337-41. Lu et al., Efficient identification of mutated cancer antigens recognized by T cells associated with durable tumor regressions, *Clin Cancer Res*. (2014) 20(13): 3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing an infectious disease vaccine, comprising performing the steps of a method disclosed herein; and producing a infectious disease vaccine comprising a plurality of antigens or a subset of the plurality of antigens.

Antigens disclosed herein can be manufactured using methods known in the art. For example, a method of producing an antigen or a vector (e.g., a vector including at least one sequence encoding one or more antigens) disclosed herein can include culturing a host cell under conditions suitable for expressing the antigen or vector wherein the host cell comprises at least one polynucleotide encoding the antigen or vector, and purifying the antigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NS0 cell, yeast, or a HEK293 cell. Host cells can be transformed with one or more polynucleotides comprising at least one nucleic acid sequence that encodes an antigen or vector disclosed herein, optionally wherein the isolated polynucleotide further comprises a promoter sequence operably linked to the at least one nucleic acid sequence that encodes the antigen or vector. In certain embodiments the isolated polynucleotide can be cDNA.

VI. ANTIGEN USE AND ADMINISTRATION

A vaccination protocol can be used to dose a subject with one or more antigens. A priming vaccine and a boosting vaccine can be used to dose the subject. The priming vaccine can be based on C68 (e.g., the sequences shown in SEQ ID NO:1 or 2) or srRNA (e.g., the sequences shown in SEQ ID NO:3 or 4) and the boosting vaccine can be based on C68 (e.g., the sequences shown in SEQ ID NO:1 or 2) or srRNA (e.g., the sequences shown in SEQ ID NO:3 or 4). Each vector typically includes a cassette that includes antigens. Cassettes can include about 20 antigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab.

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

Anti-CTLA-4 (e.g., tremelimumab) can also be administered to the subject. For example, anti-CTLA4 can be administered subcutaneously near the site of the intramuscular vaccine injection (ChAdV68 prime or srRNA low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

Immune response, such as T cell responses and B cell responses, can be assessed as part of an immune monitoring protocol. For example, the ability of a vaccine composition described herein to stimulate an immune response can be monitored and/or assessed. As used herein, "stimulate an immune response" refers to any increase in a immune response, such as initiating an immune response (e.g., a priming vaccine stimulating the initiation of an immune response in a naïve subject) or enhancement of an immune response (e.g., a boosting vaccine stimulating the enhancement of an immune response in a subject having a pre-existing immune response to an antigen, such as a pre-existing immune response initiated by a priming vaccine).

T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELIS-pot assay. Specific CD4 or CD8 T cell responses to epitopes encoded in vaccines can be monitored from PBMCs by measuring induction of cytokines captured intracellularly or extracellularly, such as IFN-gamma, using flow cytometry.

Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluoresceine-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

B cell responses can be measured using one or more methods known in the art such as assays used to determine B cell differentiation (e.g., differentiation into plasma cells), B cell or plasma cell proliferation, B cell or plasma cell activation (e.g., upregulation of costimulatory markers such as CD80 or CD86), antibody class switching, and/or antibody production (e.g., an ELISA).

VII. ANTIGEN IDENTIFICATION

VII.A. Antigen Candidate Identification

Research methods for NGS analysis transcriptomes have been described and applied in the antigen identification space.[6,14,15] Certain optimizations for greater sensitivity and specificity for antigen identification in the clinical setting can be considered. These optimizations can be grouped into two areas, those related to laboratory processes and those related to the NGS data analysis. Examples of optimizations are known to those skilled in the art, for example the methods described in more detail in international patent application publications WO/2017/106638, WO/2018/195357, and WO/2018/208856, each herein incorporated by reference, in their entirety, for all purposes.

VII.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II-HLA-DR |
| Tu36 | Class II-HLA-DR |
| LN3 | Class II-HLA-DR |
| Tu39 | Class II-HLA-DR, DP, DQ |
| SPVL3 | Class II-HLA-DQ |
| B7/21 | Class II-HLA-DP |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20 C prior to MS analysis. HLA IPs can also be performed in 96 well plate format using plates that contain filter bottoms. Use of the plates allows for multiple IPs to be performed in tandem.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97).

VIII. PRESENTATION MODEL

Presentation models can be used to identify likelihoods of peptide presentation in patients. Various presentation models are known to those skilled in the art, for example the presentation models described in more detail in U.S. Pat. No. 10,055,540, US Application Pub. No. US20200010849A1 and US20110293637, and international patent application publications WO/2018/195357, WO/2018/208856, WO2016187508, each herein incorporated by reference, in their entirety, for all purposes.

IX. TRAINING MODULE

Training modules can be used to construct one or more presentation models based on training data sets that generate likelihoods of whether peptide sequences will be presented by MHC alleles associated with the peptide sequences. Various training modules are known to those skilled in the art, for example the presentation models described in more detail in U.S. Pat. No. 10,055,540, US Application Pub. No. US20200010849A1, and international patent application publication WO/2018/195357, and WO/2018/208856, each herein incorporated by reference, in their entirety, for all purposes. A training module can construct a presentation model to predict presentation likelihoods of peptides on a per-allele basis. A training module can also construct a presentation model to predict presentation likelihoods of peptides in a multiple-allele setting where two or more MHC alleles are present.

X. PREDICTION MODULE

A prediction module can be used to receive sequence data and select candidate antigens in the sequence data using a presentation model. Specifically, the sequence data may be DNA sequences, RNA sequences, and/or protein sequences extracted from infected cells of patients. A prediction module may identify candidate antigens that are pathogen-derived peptides, a virally-derived peptides, a bacterially-derived peptides, a fungally-derived peptides, and a parasitically-derived peptides by comparing sequence data extracted from normal tissue cells of a patient with the sequence data extracted from infected cells of the patient to identify portions containing one or more infectious disease organism associated antigens. A prediction module may identify candidate antigens that have altered expression in an infected cell or infected tissue in comparison to a normal cell or tissue by comparing sequence data extracted from normal tissue cells of a patient with the sequence data extracted from infected tissue cells of the patient to identify improperly expressed candidate antigens (e.g., identifying expressed polynucleotides and/or polypeptides specific to an infectious disease).

A presentation module can apply one or more presentation model to processed peptide sequences to estimate presentation likelihoods of the peptide sequences. Specifically, the prediction module may select one or more candidate antigen peptide sequences that are likely to be presented on infected cell HLA molecules by applying presentation models to the candidate antigens. In one implementation, the presentation module selects candidate antigen sequences that have estimated presentation likelihoods above a predetermined threshold. In another implementation, the presentation model selects the N candidate antigen sequences that have the highest estimated presentation likelihoods (where N is generally the maximum number of epitopes that can be delivered in a vaccine). A vaccine including the selected candidate antigens for a given patient can be injected into the patient to induce immune responses.

XI.B. Cassette Design Module

XI.B.1 Overview

A cassette design module can be used to generate a vaccine cassette sequence based on selected candidate peptides for injection into a patient. For example, a cassette design module can be used to generate a sequence encoding concatenated epitope sequences, such as concatenated T cell epitopes. Various cassette design modules are known to those skilled in the art, for example the cassette design modules described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

A set of therapeutic epitopes may be generated based on the selected peptides determined by a prediction module associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

Therapeutic epitopes may correspond to selected peptides themselves. Therapeutic epitopes may also include C- and/or N-terminal flanking sequences in addition to the selected peptides. N- and C-terminal flanking sequences can be the native N- and C-terminal flanking sequences of the therapeutic vaccine epitope in the context of its source protein.

Therapeutic epitopes can represent a fixed-length epitope Therapeutic epitopes can represent a variable-length epitope, in which the length of the epitope can be varied depending on, for example, the length of the C- or N-flanking sequence. For example, the C-terminal flanking sequence and the N-terminal flanking sequence can each have varying lengths of 2-5 residues, resulting in 16 possible choices for the epitope.

A cassette design module can also generate cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves.

A cassette design module can generate a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

A cassette design module can iterate through one or more candidate cassettes, and determine a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, a cassette design module may determine a cassette sequence associated with the lowest junction epitope presentation score among the candidate cassette sequences.

A cassette design module may iterate through one or more candidate cassette sequences, determine the junction epitope presentation score for the candidate cassettes, and identify an optimal cassette sequence associated with a junction epitope presentation score below the threshold.

A cassette design module may further check the one or more candidate cassette sequences to identify if any of the junction epitopes in the candidate cassette sequences are self-epitopes for a given patient for whom the vaccine is being designed. To accomplish this, the cassette design module checks the junction epitopes against a known database such as BLAST. In one embodiment, the cassette design module may be configured to design cassettes that avoid junction self-epitopes.

A cassette design module can perform a brute force approach and iterate through all or most possible candidate cassette sequences to select the sequence with the smallest junction epitope presentation score. However, the number of such candidate cassettes can be prohibitively large as the capacity of the vaccine increases. For example, for a vaccine capacity of 20 epitopes, the cassette design module has to iterate through $\sim 10^{18}$ possible candidate cassettes to determine the cassette with the lowest junction epitope presentation score. This determination may be computationally burdensome (in terms of computational processing resources required), and sometimes intractable, for the cassette design module to complete within a reasonable amount of time to generate the vaccine for the patient. Moreover, accounting for the possible junction epitopes for each candidate cassette can be even more burdensome. Thus, a cassette design module may select a cassette sequence based on ways of iterating through a number of candidate cassette sequences that are significantly smaller than the number of candidate cassette sequences for the brute force approach.

A cassette design module can generate a subset of randomly or at least pseudo-randomly generated candidate cassettes, and selects the candidate cassette associated with a junction epitope presentation score below a predetermined threshold as the cassette sequence. Additionally, the cassette design module may select the candidate cassette from the subset with the lowest junction epitope presentation score as the cassette sequence. For example, the cassette design module may generate a subset of ~1 million candidate cassettes for a set of 20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective. A cassette design module can determine an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the "distance" for traveling from node A to node B may be different from the "distance" for traveling from node B to node A. By solving for an improved optimal cassette using an asymmetric TSP, the cassette design module can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. A cassette sequence determined through this approach can result in a sequence with significantly less presentation of junction epitopes while potentially requiring significantly less computational resources than the random sampling approach, especially when the number of generated candidate cassette sequences is large. Illustrative examples of different computational approaches and comparisons for optimizing cassette design are described in more detail in U.S. Pat. No. 10,055,540, US Application Pub. No. US20200010849A1, and international patent application publications WO/2018/195357, and WO/2018/208856, each herein incorporated by reference, in their entirety, for all purposes.

A cassette design module can also generate cassette sequences by taking into account additional protein sequences encoded in the vaccine. For example, a cassette design module used to generate a sequence encoding concatenated T cell epitopes can take into account T cell epitopes already encoded by additional protein sequences present in the vaccine (e.g., full-length protein sequences), such as by removing T cell epitopes already encoded by the additional protein sequences from the list of candidate sequences.

A cassette design module can also generate cassette sequences by taking into account the size of the sequences. Without wishing to be bound by theory, in general, increased cassette size can negatively impact vaccine aspects, such as vaccine production and/or vaccine efficacy. In one example, the cassette design module can take into account overlapping sequences, such as overlapping T cell epitope sequences. In general, a single sequence containing overlapping T cell epitope sequences (also referred to as a "frame") is more efficient than separately linking individual T cell epitope sequences as it reduces the sequence size needed to encode the multiple peptides. Accordingly, in an illustrative example, a cassette design module used to generate a sequence encoding concatenated T cell epitopes can take into account the cost/benefit of extending a candidate T cell epitope to encode one or more additional T cell epitopes, such as determining the benefit gained in additional population coverage for an MHC presenting the additional T cell epitope versus the cost of increasing the size of the sequence.

A cassette design module can also generate cassette sequences by taking into account other aspects that improve potential safety, such as limiting encoding or the potential to encode a functional protein, functional protein domain, functional protein subunit, or functional protein fragment potentially presentially presenting a safety risk. In some cases, a cassette design module can limit sequence size of encoded peptides such that the are less than 50%, less than 49%, less than 48%, less than 47%, less than 46%, less than 45%, less than 45%, less than 43%, less than 42%, less than 41%, less than 40%, less than 39%, less than 38%, less than 37%, less than 36%, less than 35%, less than 34%, or less than 33% of the translated, corresponding full-length protein. In some cases, a cassette design module can limit sequence size of encoded peptides such that a single contiguous sequence is less than 50% of the translated, corresponding full-length protein, but more than one sequence may be derived from the same translated, corresponding full-length protein and together encode more than 50%. In an illustrative example, if a single sequence containing overlapping T cell epitope sequences ("frame") is larger than 50% of the translated, corresponding full-length protein, the frame can be split into multiple frames (e.g., f1, f2 etc.) such that each frame is less than 50% of the translated, corresponding full-length protein. A cassette design module can also limit sequence size of encoded peptides such that a single contiguous sequence is less than 49%, less than 48%, less than 47%, less than 46%, less than 45%, less than 45%, less than 43%, less than 42%, less than 41%, less than 40%, less than 39%, less than 38%, less than 37%, less than 36%, less than 35%, less than 34%, or less than 33% of the translated, corresponding full-length protein. Where multiple frames from the same gene are encoded, the multiple frames can have overlapping sequences with each other, in other words each separately encode the same sequence. Where multiple frames from the same gene are encoded, the two or more nucleic acid sequences derived from the same gene can be ordered such that a first nucleic acid sequence cannot be immediately followed by or linked to a second nucleic acid sequence if the second nucleic acid sequence follows, immediately or not, the first nucleic acid sequence in the corresponding gene. For example, if there are 3 frames within the same gene (f1,f2,f3 in increasing order of amino acid position):

The following cassette orderings are not allowed:
    f1 immediately followed by f2
    f2 immediately followed by f3
    f1 immediately followed by f3
The following cassette orderings are allowed:
    f3 immediately followed by f2
    f2 immediately followed by f1

XII. EXAMPLE COMPUTER

A computer can be used for any of the computational methods described herein. One skilled in the art will recognize a computer can have different architectures. Examples of computers are known to those skilled in the art, for example the computers described in more detail in U.S. Pat. No. 10,055,540, US Application Pub. No. US20200010849A1, and international patent application publications WO/2018/195357, and WO/2018/208856, each herein incorporated by reference, in their entirety, for all purposes.

XIII. ANTIGEN DELIVERY VECTOR EXAMPLE

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3$^{rd}$ *Ed.* (Plenum Press) Vols A and B (1992).

XIII.A. Antigen Cassette Design

Through vaccination, multiple class I MHC restricted antigens that stimulate the corresponding cellular immune response(s) can be delivered. In one example, a vaccine cassette was engineered to encode multiple epitopes as a single gene product where the epitopes were either embedded within their natural, surrounding peptide sequence or spaced by non-natural linker sequences. Several design parameters were identified that could potentially impact antigen processing and presentation and therefore the magnitude and breadth of the antigen specific CD8 T cell responses. In the present example, several model cassettes were designed and constructed to evaluate: (1) whether robust T cell responses could be generated to multiple epitopes incorporated in a single expression cassette; (2)

what makes an optimal linker placed between the antigens within the expression cassette—that leads to optimal processing and presentation of all epitopes; (3) if the relative position of the epitopes within the cassette impact T cell responses; (4) whether the number of epitopes within a cassette influences the magnitude or quality of the T cell responses to individual epitopes; (5) if the addition of cellular targeting sequences improves T cell responses.

Two readouts were developed to evaluate antigen presentation and T cell responses specific for marker epitopes within the model cassettes: (1) an in vitro cell-based screen which allowed assessment of antigen presentation as gauged by the activation of specially engineered reporter T cells (Aarnoudse et al., 2002; Nagai et al., 2012); and (2) an in vivo assay that used HLA-A2 transgenic mice (Vitiello et al., 1991) to assess post-vaccination immunogenicity of cassette-derived epitopes of human origin by their corresponding epitope-specific T cell responses (Cornet et al., 2006: Depla et al., 2008; Ishioka et al., 1999).

XIV. CHAD ANTIGEN CASSETTE DELIVERY VECTOR

XIV.A. ChAd Antigen Cassette Delivery Vector Construction

In one example, Chimpanzee adenovirus (ChAd) was engineered to be a delivery vector for antigen cassettes. In a further example, a full-length ChAdV68 vector was synthesized based on AC_000011.1 (sequence 2 from U.S. Pat. No. 6,083,716) with E1 (nt 457 to 3014) and E3 (nt 27,816-31,332) sequences deleted. Reporter genes under the control of the CMV promoter/enhancer were inserted in place of the deleted E1 sequences. Transfection of this clone into HEK293 cells did not yield infectious virus. To confirm the sequence of the wild-type C68 virus, isolate VR-594 was obtained from the ATCC, passaged, and then independently sequenced (SEQ ID NO:10). When comparing the AC_000011.1 sequence to the ATCC VR-594 sequence (SEQ ID NO:10) of wild-type ChAdV68 virus, 6 nucleotide differences were identified. In one example, a modified ChAdV68 vector was generated based on AC_000011.1, with the corresponding ATCC VR-594 nucleotides substituted at five positions (ChAdV68.5WTnt SEQ ID NO:1).

In another example, a modified ChAdV68 vector was generated based on AC_000011.1 with E1 (nt 577 to 3403) and E3 (nt 27,816-31,332) sequences deleted and the corresponding ATCC VR-594 nucleotides substituted at four positions. A GFP reporter (ChAdV68.4WTnt.GFP; SEQ ID NO:11) or model neoantigen cassette (ChAdV68.4WTnt.MAG25mer; SEQ ID NO:12) under the control of the CMV promoter/enhancer was inserted in place of deleted E1 sequences.

In another example, a modified ChAdV68 vector was generated based on AC_000011.1 with E1 (nt 577 to 3403) and E3 (nt 27,125-31,825) sequences deleted and the corresponding ATCC VR-594 nucleotides substituted at five positions. A GFP reporter (ChAdV68.5WTnt.GFP; SEQ ID NO:13) or model neoantigen cassette (ChAdV68.5WTnt.MAG25mer; SEQ ID NO:2) under the control of the CMV promoter/enhancer was inserted in place of deleted E1 sequences.

Relevant Vectors are Described Below:
    Full-Length ChAdVC68 sequence "ChAdV68.5WTnt" (SEQ ID NO:1); AC_000011.1 sequence with corresponding ATCC VR-594 nucleotides substituted at five positions.

ATCC VR-594 C68 (SEQ ID NO:10); Independently sequenced; Full-Length C68

ChAdV68.4WTnt.GFP (SEQ ID NO:11); AC_000011.1 with E1 (nt 577 to 3403) and E3 (nt 27,816-31,332) sequences deleted; corresponding ATCC VR-594 nucleotides substituted at four positions; GFP reporter under the control of the CMV promoter/enhancer inserted in place of deleted E1

ChAdV68.4WTnt.MAG25mer (SEQ ID NO:12); AC_000011.1 with E1 (nt 577 to 3403) and E3 (nt 27,816-31,332) sequences deleted; corresponding ATCC VR-594 nucleotides substituted at four positions; model neoantigen cassette under the control of the CMV promoter/enhancer inserted in place of deleted E1

ChAdV68.5WTnt.GFP (SEQ ID NO:13); AC_000011.1 with E1 (nt 577 to 3403) and E3 (nt 27,125-31,825) sequences deleted; corresponding ATCC VR-594 nucleotides substituted at five positions; GFP reporter under the control of the CMV promoter/enhancer inserted in place of deleted E1

XV. ALPHAVIRUS ANTIGEN CASSETTE DELIVERY VECTOR

XV.B. Alphavirus Vector

In one implementation of the present invention, a RNA alphavirus backbone for the antigen expression system was generated from a Venezuelan Equine Encephalitis (VEE) (Kinney, 1986, Virology 152:400-413) based self-replicating RNA (srRNA) vector. In one example, the sequences encoding the structural proteins of VEE located 3' of the 26S sub-genomic promoter were deleted (VEE sequences 7544 to 11,175 deleted; numbering based on Kinney et al 1986; SEQ ID NO:6) and replaced by antigen sequences (SEQ ID NO:14 and SEQ ID NO:4) or a luciferase reporter (e.g., VEE-Luciferase, SEQ ID NO:15).

XVI. NON-HUMAN PRIMATE STUDIES

Various dosing protocols using ChAdV68 and self-replicating RNA (srRNA) were evaluated in non-human primates (NHP).

Materials and Methods

A priming vaccine was injected intramuscularly (IM) in each NHP to initiate the study (vaccine prime). One or more boosting vaccines (vaccine boost) were also injected intramuscularly in each NHP. Bilateral injections per dose were administered according to groups outlined in tables and summarized below.

Immunizations

Mamu-A*01 Indian rhesus macaques were immunized bilaterally with $1\times10^{12}$ viral particles ($5\times10^{11}$ viral particles per injection) of ChAdV68.5WTnt.MAG25mer, 30 µg of VEE-MAG25MER srRNA, 100 µg of VEE-MAG25mer srRNA or 300 µg of VEE-MAG25mer srRNA formulated in LNP-1 or LNP-2. Vaccine boosts of 30 µg, 100 µg or 300 µg VEE-MAG25mer srRNA were administered intramuscularly at the indicated time after prime vaccination.

Immune Monitoring

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune NxT flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISpot harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISpot analysis, wells with saturation >50% were recorded as "too numerous to count". Samples with deviation of replicate wells >10% were excluded from analysis. Spot counts were then corrected for well confluency using the formula: spot count+ 2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Specific CD4 and CD8 T cell responses to 6 different rhesus macaque Mamu-A*01 class I epitopes encoded in the vaccines were monitored from PBMCs by measuring induction of intracellular cytokines, such as IFN-gamma, using flow cytometry. The results from both methods indicate that cytokines were induced in an antigen-specific manner to epitopes.

Immunogenicity in *Rhesus macaques*

This study was designed to (a) evaluate the immunogenicity and preliminary safety of VEE-MAG25mer srRNA 30 µg and 100 µg doses as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2; (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Select antigens used in this study are only recognized in *Rhesus macaques*, specifically those with a Mamu-A*01 MHC class I haplotype. Mamu-A*01 Indian rhesus macaques were randomized to the different study arms (6 macaques per group) and administered an IM injection bilaterally with either ChAdV68.5WTnt.MAG25mer or VEE-MAG25mer srRNA vector encoding model antigens that includes multiple Mamu-A*01 restricted epitopes. The study arms were as described below.

TABLE A

| Non-GLP immunogenicity study in Indian Rhesus Macaques | | | |
|---|---|---|---|
| Group | Prime | Boost 1 | Boost 2 |
| 1 | VEE-MAG25mer srRNA-LNP1(30 µg) | VEE-MAG25mer srRNA-LNP1 (30 µg) | VEE-MAG25mer srRNA-LNP1 (30 µg) |

TABLE A-continued

Non-GLP immunogenicity study in Indian Rhesus Macaques

| Group | Prime | Boost 1 | Boost 2 |
|---|---|---|---|
| 2 | VEE-MAG25mer srRNA-LNP1 (100 µg) | VEE-MAG25mer srRNA-LNP1 (100 µg) | VEE-MAG25mer srRNA-LNP1 (100 µg) |
| 3 | VEE-MAG25mer srRNA-LNP2 (100 µg) | VEE-MAG25mer srRNA-LNP2 (100 µg) | VEE-MAG25mer srRNA-LNP2 (100 µg) |
| 4 | ChAdV68.5WTnt. MAG25mer | VEE-MAG25mer srRNA-LNP1 (100 µg) | VEE-MAG25mer srRNA-LNP1 (100 µg) |

PBMCs were collected prior to immunization and on weeks 1, 2, 3, 4, 5, 6, 8, 9, and 10 after the initial immunization for immune monitoring.

Results

Antigen-specific cellular immune responses in peripheral blood mononuclear cells (PBMCs) were measured to six different Mamu-A*01 restricted epitopes prior to immunization and 1, 2, 3, 4, 5, 6, 8, 9, and 10 weeks after the initial immunization. Animals received a boost immunization with VEE-MAG25mer srRNA on weeks 4 and 8 with either 30 µg or 100 µg doses, and either formulated with LNP1 or LNP2, as described in Table A. Combined immune responses to all six epitopes were plotted for each immune monitoring timepoint (FIG. 1A-D and Tables B-E).

Combined antigen-specific immune responses were observed at all measurements with 170, 14, 15, 11, 7, 8, 14, 17, 12 SFCs per $10^6$ PBMCs (six epitopes combined) 1, 2, 3, 4, 5, 6, 8, 9, or 10 weeks after an initial VEE-MAG25mer srRNA-LNP1 (30 µg) prime immunization, respectively (FIG. 1A). Combined antigen-specific immune responses were observed at all measurements with 108, −3, 14, 1, 37, 4, 105, 17, 25 SFCs per $10^6$ PBMCs (six epitopes combined)

Figure 1B:
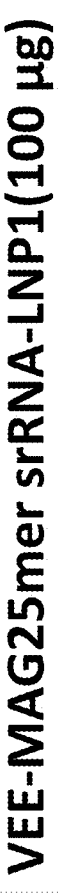
Figure 1B:
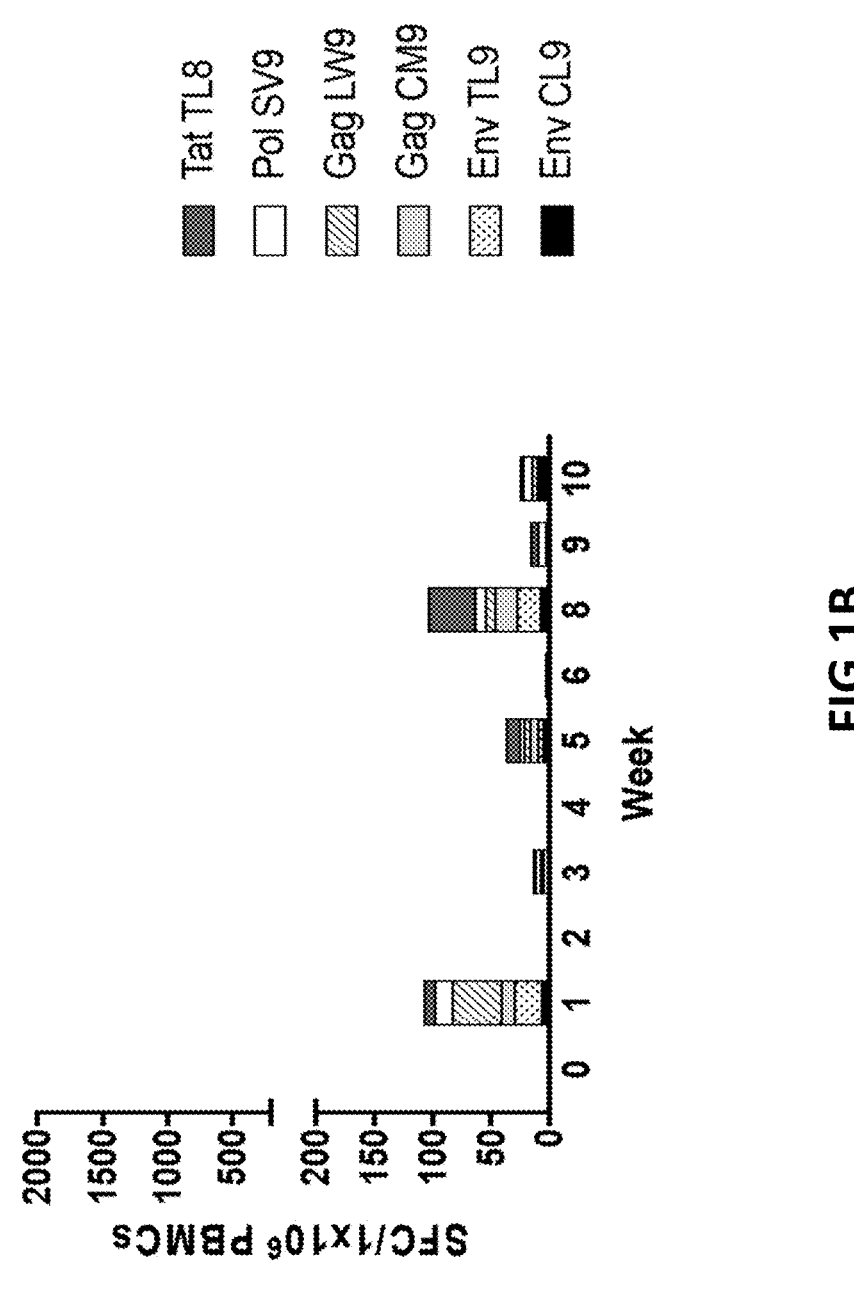
Figure 1C:
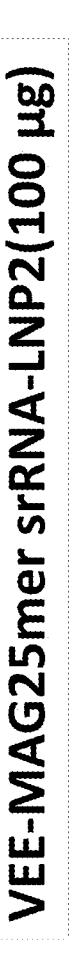
Figure 1C:
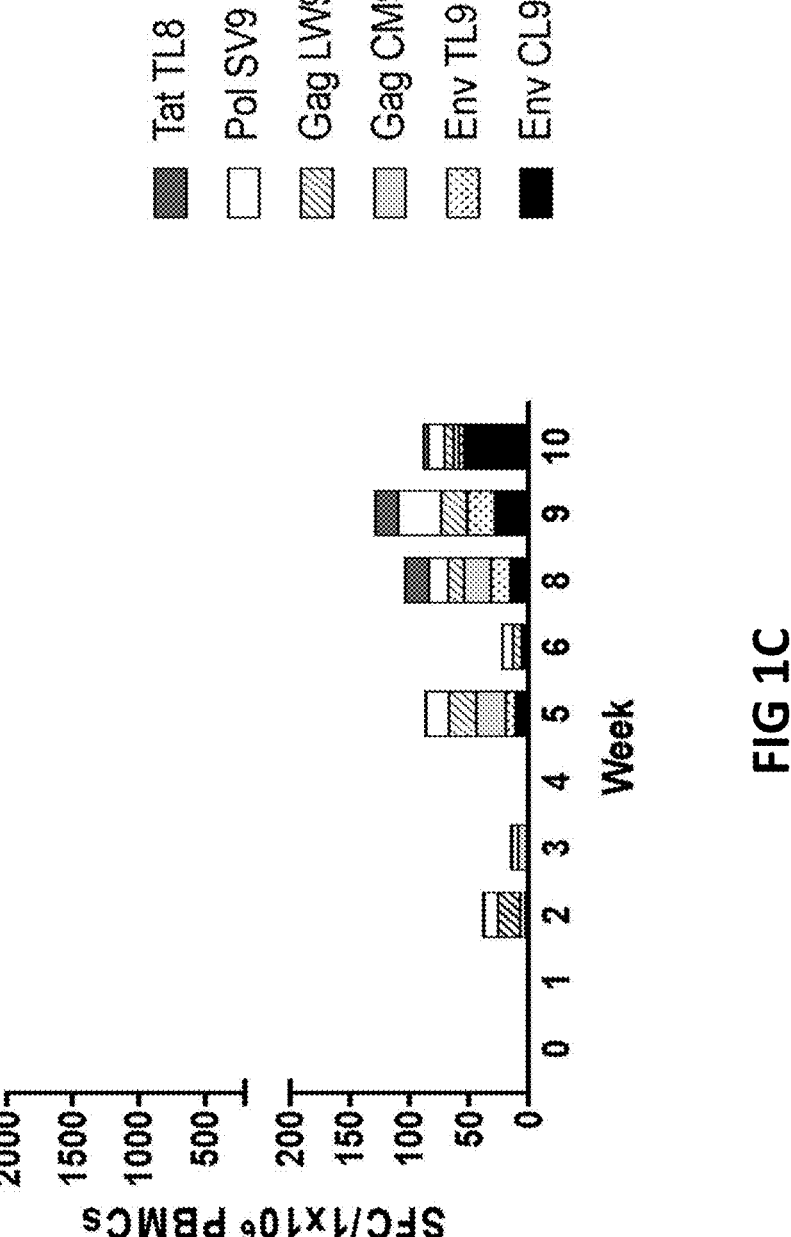

1, 2, 3, 4, 5, 6, 8, 9, or 10 weeks after an initial VEE-MAG25mer srRNA-LNP1 (100 µg) prime immunization, respectively (FIG. 1B). Combined antigen-specific immune responses were observed at all measurements with −17, 38, 14, −2, 87, 21, 104, 129, 89 SFCs per $10^6$ PBMCs (six epitopes combined) 1, 2, 3, 4, 5, 6, 8, 9, or 10 weeks after an initial VEE-MAG25mer srRNA-LNP2 (100 µg) prime immunization, respectively (FIG. 1C).

Negative values are a result of normalization to pre-bleed values for each epitope/animal.

Figure 1D:
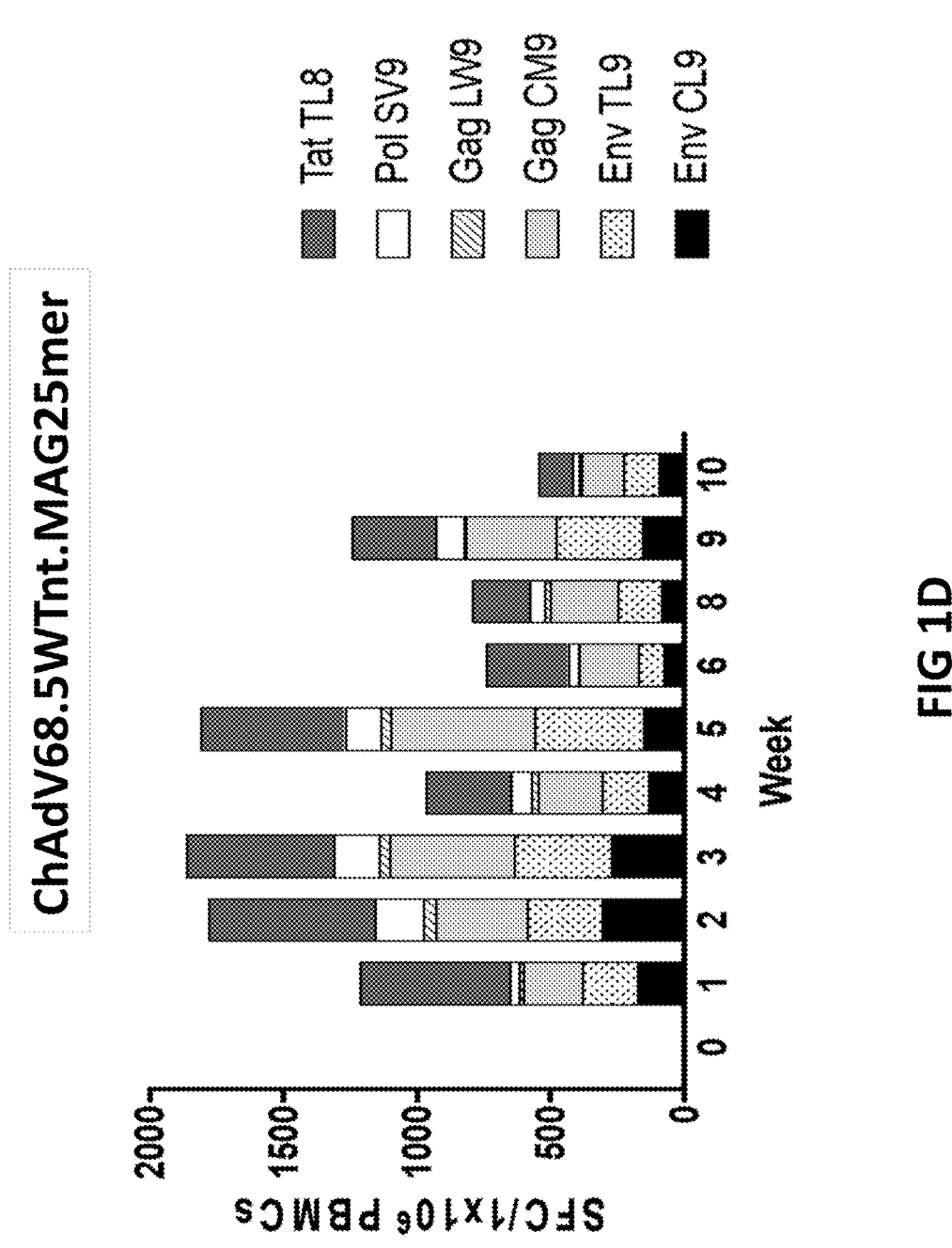

Combined antigen-specific immune responses were observed at all measurements with 1218, 1784, 1866, 973, 1813, 747, 797, 1249, and 547 SFCs per $10^6$ PBMCs (six epitopes combined) 1, 2, 3, 4, 5, 6, 8, 9, or 10 weeks after an initial ChAdV68.5WTnt.MAG25mer prime immunization, respectively (FIG. 1D). The immune response showed the expected profile with peak immune responses measured ~2-3 weeks after the prime immunization followed by a contraction in the immune response after 4 weeks. Combined antigen-specific cellular immune responses of 1813 SFCs per $10^6$ PBMCs (six epitopes combined) were measured 5 weeks after the initial immunization with ChAdV68.5WTnt.MAG25mer (i.e., 1 week after the first boost with VEE-MAG25mer srRNA). The immune response measured 1 week after the first boost with VEE-MAG25mer srRNA (week 5) was comparable to the peak immune response measured for the ChAdV68. 5WTnt.MAG25mer prime immunization (week 3) (FIG. 20D). Combined antigen-specific cellular immune responses of 1249 SFCs per $10^6$ PBMCs (six epitopes combined) was measured 9 weeks after the initial immunization with ChAdV68.5WTnt.MAG25mer, respectively (i.e., 1 week after the second boost with VEE-MAG25mer srRNA). The immune responses measured 1 week after the second boost with VEE-MAG25mer srRNA (week 9) was ~2-fold higher than that measured just before the boost immunization (FIG. 1D).

TABLE B

Mean spot forming cells (SFC) per $10^6$ PBMCs for each epitope ± SEM for VEE-MAG25mer srRNA-LNP1(30 µg) (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 39.7 ± 22.7 | 35.4 ± 25.1 | 3.2 ± 3.6 | 33 ± 28.1 | 30.9 ± 20.3 | 28.3 ± 17.5 |
| 3 | 2 ± 2.4 | 0.2 ± 1.8 | 1.8 ± 2.4 | 3.7 ± 1.9 | 1.7 ± 2.8 | 4.9 ± 2.3 |
| 4 | 1 ± 1.8 | 0.3 ± 1.2 | 5.5 ± 3.6 | 2.3 ± 2.2 | 5.7 ± 2.7 | 0.8 ± 0.8 |
| 5 | 0.5 ± 0.9 | 1.4 ± 3.8 | 3.1 ± 1.6 | 2.3 ± 2.7 | 1.9 ± 2 | 1.4 ± 1.2 |
| 6 | 1.9 ± 1.8 | −0.3 ± 3 | 1.7 ± 1.2 | 1.4 ± 1.4 | 0.8 ± 1.1 | 1.1 ± 1 |
| 8 | −0.4 ± 0.8 | −0.9 ± 2.9 | 0.5 ± 1.3 | 3 ± 1.1 | 2.2 ± 2.1 | 3.7 ± 2 |
| 9 | 1 ± 1.7 | 1.2 ± 4.2 | 7.2 ± 3.9 | 0.5 ± 0.7 | 1.6 ± 3 | 3 ± 1 |
| 10 | 3.8 ± 1.8 | 11 ± 5 | −1.1 ± 1.1 | 1.9 ± 0.9 | 1.3 ± 1.6 | 0.2 ± 0.5 |

TABLE C

Mean spot forming cells (SFC) per $10^6$ PBMCs for each epitope ± SEM for VEE-MAG25mer srRNA-LNP1(100 µg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 7.9 ± 17.2 | 23.2 ± 17.4 | 11.4 ± 4.9 | 41.7 ± 16.5 | 15 ± 13.5 | 8.9 ± 6.2 |
| 3 | −3.1 ± 4.6 | −7.2 ± 6.5 | 2.3 ± 2.3 | −0.3 ± 2.7 | 2.7 ± 5.1 | 2.2 ± 1.4 |

TABLE C-continued

| | Mean spot forming cells (SFC) per $10^6$ PBMCs for each epitope ± SEM for VEE-MAG25mer srRNA-LNP1(100 µg) (Group 2) | | | | | |
|---|---|---|---|---|---|---|
| | | | Antigen | | | |
| Wk | Env CL9 | Env TL9 | Gag CM9 | Gag LW9 | Pol SV9 | Tat TL8 |
| 4 | 1.9 ± 3.8 | −6.2 ± 7.6 | 10.5 ± 4.1 | 1.2 ± 2.9 | 5.6 ± 4.9 | 1.1 ± 0.8 |
| 5 | −2.6 ± 7 | −8 ± 5.9 | 1.5 ± 1.7 | 6.4 ± 2.3 | 0.7 ± 4.3 | 3.3 ± 1.3 |
| 6 | 6.3 ± 6.3 | 4.4 ± 8.3 | 6.6 ± 4.4 | 5.2 ± 5.2 | 3.9 ± 5 | 10.8 ± 6.9 |
| 8 | −3.6 ± 7.2 | −6.8 ± 7.3 | −0.8 ± 1.2 | 3.4 ± 4.2 | 6.4 ± 7.5 | 5.7 ± 2.7 |
| 9 | 8.1 ± 2.4 | 20.6 ± 23.4 | 18.9 ± 5.7 | 8.1 ± 8.9 | 9 ± 11.2 | 40 ± 17.6 |
| 10 | 3.1 ± 8 | −3.9 ± 8.5 | 3.3 ± 1.8 | 0.6 ± 2.9 | 7.4 ± 6.4 | 6.1 ± 2.5 |

TABLE D

| | Mean spot forming cells (SFC) per $10^6$ PBMCs for each epitope ± SEM for VEE-MAG25mer srRNA-LNP2(100 µg) (Group 3) | | | | | |
|---|---|---|---|---|---|---|
| | | | Antigen | | | |
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | −5.9 ± 3.8 | −0.3 ± 0.5 | −0.5 ± 1.5 | −5.7 ± 6.1 | −1 ± 1.3 | −3.2 ± 5.5 |
| 3 | 0.7 ± 5.2 | 3.4 ± 2.4 | 4.2 ± 4.6 | 18.3 ± 15.5 | 11.9 ± 5.1 | −0.4 ± 8.2 |
| 4 | −3.8 ± 5.5 | 2.3 ± 1.8 | 11.3 ± 6.1 | −3.1 ± 5.6 | 8.5 ± 4 | −1.5 ± 6.1 |
| 5 | −3.7 ± 5.7 | −0.1 ± 0.7 | −0.2 ± 1.6 | 3.4 ± 8.5 | 3 ± 3.1 | −4.6 ± 5 |
| 6 | 12.3 ± 15 | 7.8 ± 4.9 | 24.7 ± 19.8 | 23.2 ± 22.5 | 18.7 ± 15.8 | 0.5 ± 6.2 |
| 8 | 5.9 ± 12.3 | −0.1 ± 0.7 | −0.5 ± 1.3 | 8.8 ± 14.4 | 8.7 ± 8 | −1.3 ± 4 |
| 9 | 16.1 ± 13.4 | 16.5 ± 4 | 22.9 ± 4.2 | 13 ± 13.2 | 16.4 ± 7.8 | 19.6 ± 9.2 |
| 10 | 29.9 ± 21.8 | 22 ± 19.5 | 0.5 ± 2.6 | 22.2 ± 22.6 | 35.3 ± 15.8 | 19.4 ± 17.3 |

TABLE E

| | Mean spot forming cells (SFC) per $10^6$ PBMCs for each epitope ± SEM for ChAdV68.5WTnt.MAG25mer prime | | | | | |
|---|---|---|---|---|---|---|
| | | | Antigen | | | |
| Wk | Env CL9 | Env TL9 | Gag CM9 | Gag LW9 | Pol SV9 | Tat TL8 |
| 1 | 178 ± 68.7 | 206.5 ± 94.8 | 221.2 ± 120 | 15.4 ± 16.7 | 33.3 ± 25.9 | 563.5 ± 174.4 |
| 2 | 311.2 ± 165.5 | 278.8 ± 100.9 | 344.6 ± 110.8 | 46.3 ± 13.5 | 181.6 ± 76.8 | 621.4 ± 220.9 |
| 3 | 277.3 ± 101.1 | 359.6 ± 90.5 | 468.2 ± 106.6 | 41.7 ± 11.1 | 169.8 ± 57.8 | 549.4 ± 115.7 |
| 4 | 140 ± 46.5 | 169.6 ± 46.8 | 239.4 ± 37 | 26.5 ± 11.4 | 75 ± 31.6 | 322.2 ± 50.7 |
| 5 | 155.6 ± 62.1 | 406.7 ± 96.4 | 542.7 ± 143.3 | 35.1 ± 16.6 | 134.2 ± 53.7 | 538.5 ± 91.9 |
| 6 | 78.9 ± 42.5 | 95.5 ± 29.4 | 220.9 ± 75.3 | −1.4 ± 5.3 | 43.4 ± 19.6 | 308.1 ± 42.6 |
| 8 | 88.4 ± 30.4 | 162.1 ± 30.3 | 253.4 ± 78.6 | 21.4 ± 11.2 | 53.7 ± 22.3 | 217.8 ± 45.2 |
| 9 | 158.5 ± 69 | 322.3 ± 87.2 | 338.2 ± 137.1 | 5.6 ± 12.4 | 109.2 ± 17.9 | 314.8 ± 43.4 |
| 10 | 97.3 ± 32.5 | 133.2 ± 27 | 154.9 ± 59.2 | 10 ± 6 | 26 ± 16.7 | 125.5 ± 27.7 |

Non-GLP RNA Dose Ranging Study (Higher Doses) in Indian *Rhesus macaques*

This study was designed to (a) evaluate the immunogenicity of VEE-MAG25mer srRNAat a dose of 300 µg as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2 at the 300 µg dose; and (c) evaluate the kinetics of T-cell responses to VEE-MAG25mer srRNA and ChAdV68.5WTnt.-MAG25mer immunizations.

The study arm was conducted in Mamu-A*01 Indian rhesus macaques to demonstrate immunogenicity. Vaccine immunogenicity in nonhuman primate species, such as *Rhesus*, is the best predictor of vaccine potency in humans.

Furthermore, select antigens used in this study are only recognized in *Rhesus macaques*, specifically those with a Mamu-A*01 MHC class I haplotype. Mamu-A*01 Indian rhesus macaques were randomized to the different study arms (6 macaques per group) and administered an IM injection bilaterally with either ChAdV68.5-WTnt.MAG25mer or VEE-MAG25mer srRNA encoding model antigens that includes multiple Mamu-A*01 restricted antigens. The study arms were as described below.

PBMCs were collected prior to immunization and 4, 5, 6, 7, 8, 10, 11, 12, 13, 14, 15, 16, 17, 18, 19, 20, 21, 22, 23 or 24 weeks after the initial immunization for immune monitoring for group 1 (heterologous prime/boost). PBMCs were collected prior to immunization and 4, 5, 7, 8, 10, 11, 12, 13, 14, or 15 weeks after the initial immunization for immune monitoring for groups 2 and 3 (homologous prime/boost).

TABLE F

| Non-GLP immunogenicity study in Indian Rhesus Macaques | | | |
| --- | --- | --- | --- |
| Group Prime | Boost 1 | Boost 2 | Boost 3 |
| 1    ChAdV68.5WTnt. MAG25mer | VEE-MAG25mer srRNA-LNP2 (300 µg) | VEE-MAG25mer srRNA-LNP2 (300 µg) | VEE-MAG25mer srRNA-LNP2 (300 µg) |
| 2    VEE-MAG25mer srRNA-LNP2 (300 µg) | VEE-MAG25mer srRNA-LNP2 (300 µg) | VEE-MAG25mer srRNA-LNP2 (300 µg) | |
| 3    VEE-MAG25mer srRNA-LNP1 (300 µg) | VEE-MAG25mer srRNA-LNP1 (300 µg) | VEE-MAG25mer srRNA-LNP1 (300 µg) | |

Results

Figure 2:
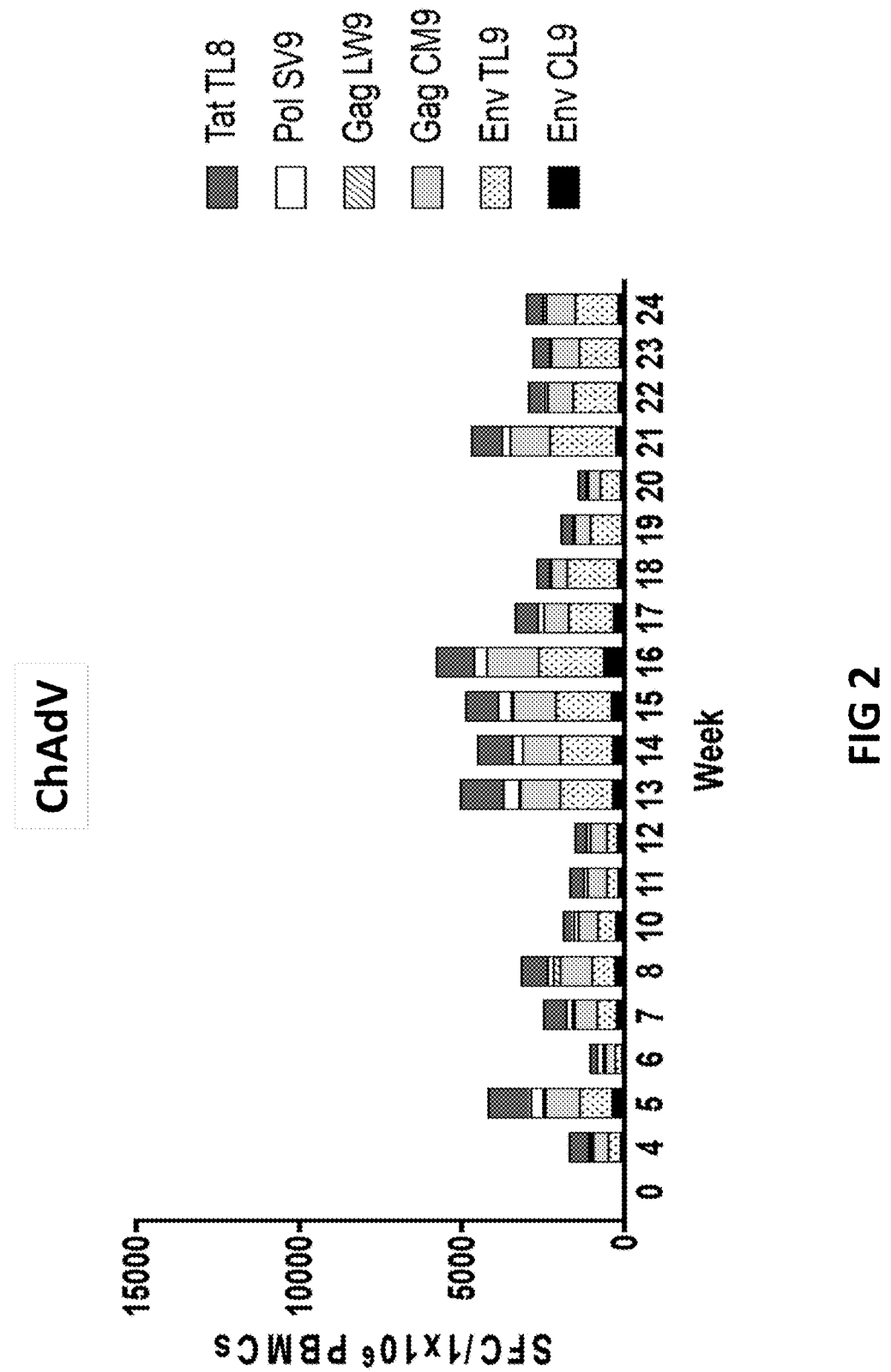
FIG. 2 shows antigen-specific cellular immune response measured using ELISpot. Antigen-specific IFN-gamma production to six different mamu A01 restricted epitopes was measured in PBMCs after immunization with the ChAdV68.5WTnt.MAG25mer/VEE-MAG25mer srRNA heterologous prime/boost regimen using ELISpot prior to immunization and 4, 5, 6, 7, 8, 10, 11, 12, 13, 14, 15, 16, 17, 18, 19, 20, 21, 22, 23 or 24 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were immunized with ChAdV68.5-WTnt.MAG25mer. Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, 15, 16, 17, 18, 19, 20, 21, 22, 23 or 24 weeks after the initial immunization (FIG. 2 and Table G). Animals received boost immunizations with VEE-MAG25mer srRNA using the LNP2 formulation on weeks 4, 12, and 20. Combined antigen-specific immune responses of 1750, 4225, 1100, 2529, 3218, 1915, 1708, 1561, 5077, 4543, 4920, 5820, 3395, 2728, 1996, 1465, 4730, 2984, 2828, or 3043 SFCs per $10^6$ PBMCs (six epitopes combined) were measured 4, 5, 6, 7, 8, 10, 11, 12, 13, 14, 15, 16, 17, 18, 19, 20, 21, 22, 23 or 24 weeks after the initial immunization with ChAdV68.5WTnt.MAG25mer (FIG. 2). Immune responses measured 1 week after the second boost immunization (week 13) with VEE-MAG25mer srRNA were ~3-fold higher than that measured just before the boost immunization (week 12). Immune responses measured 1 week after the third boost immunization (week 21) with VEE-MAG25mer srRNA, were ~3-fold higher than that measured just before the boost immunization (week 20), similar to the response observed for the second boost.

Figure 3:
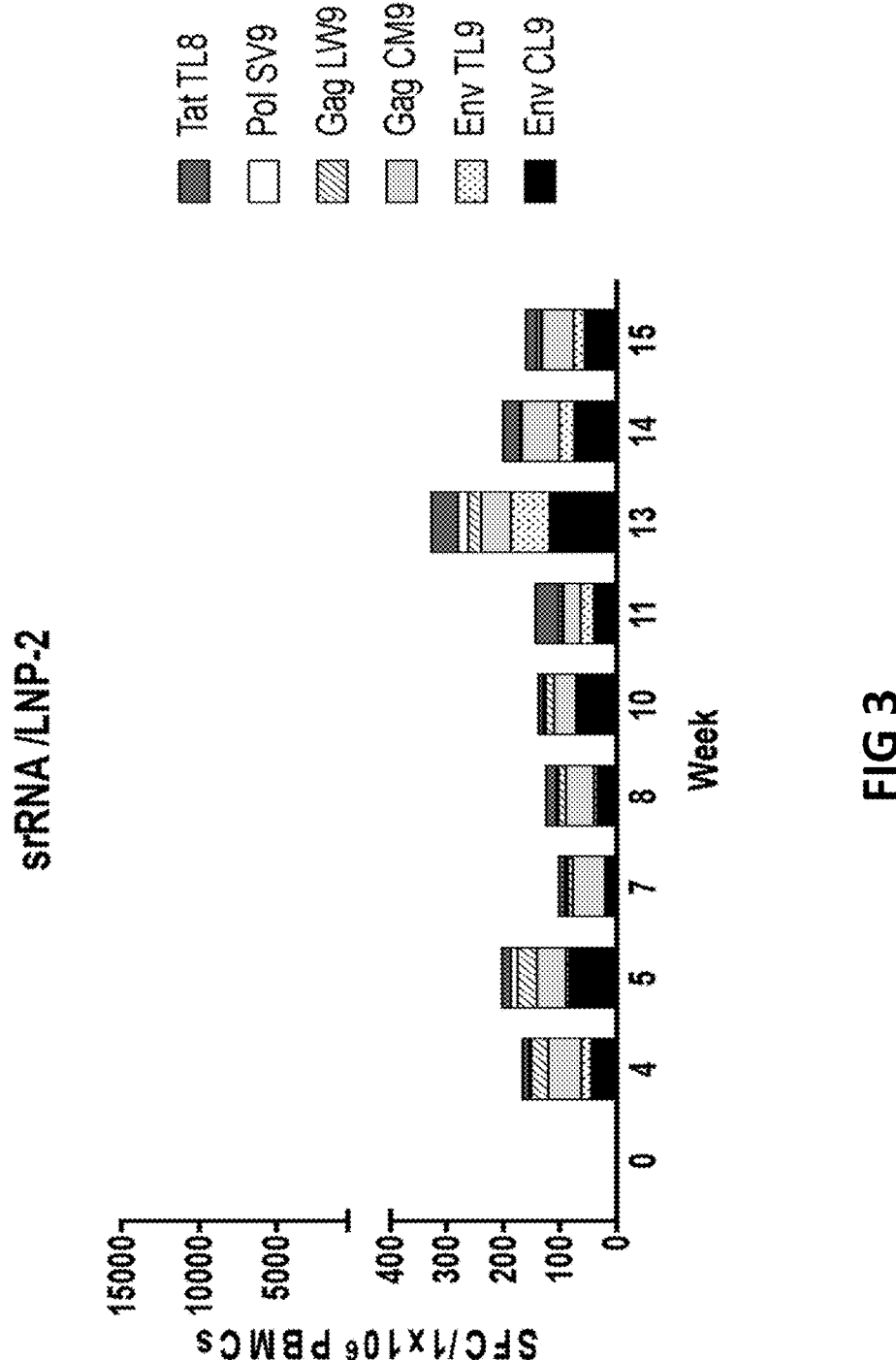
FIG. 3 shows antigen-specific cellular immune response measured using ELISpot. Antigen-specific IFN-gamma production to six different mamu A01 restricted epitopes was measured in PBMCs after immunization with the VEE- MAG25mer srRNA LNP2 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.
Figure 4:
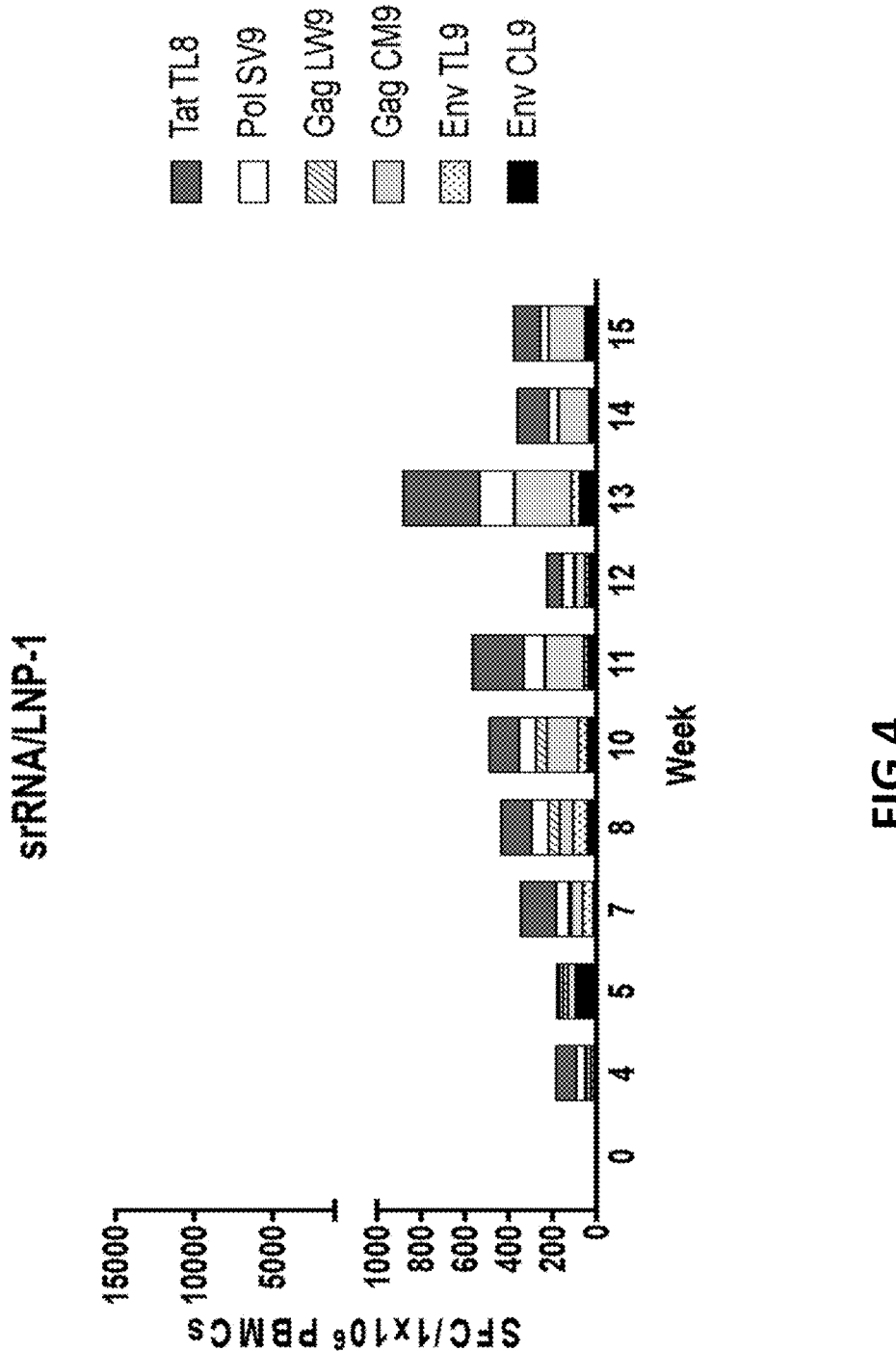
FIG. 4 shows antigen-specific cellular immune response measured using ELISpot. Antigen-specific IFN-gamma production to six different mamu A01 restricted epitopes was measured in PBMCs after immunization with the VEE-MAG25mer srRNA LNP1 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were also immunized with VEE-MAG25mer srRNA using two different LNP formulations (LNP1 and LNP2). Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, or 15 weeks after the initial immunization (FIGS. 3 and 4, Tables H and I). Animals received boost immunizations with VEE-MAG25mer srRNA using the respective LNP1 or LNP2 formulation on weeks 4 and 12. Combined antigen-specific immune responses of 168, 204, 103, 126, 140, 145, 330, 203, and 162 SFCs per $10^6$ PBMCs (six epitopes combined) were measured 4, 5, 7, 8, 10, 11, 13, 14, 15 weeks after the immunization with VEE-MAG25mer srRNA-LNP2 (FIG. 3). Combined antigen-specific immune responses of 189, 185, 349, 437, 492, 570, 233, 886, 369, and 381 SFCs per $10^6$ PBMCs (six epitopes combined) were measured 4, 5, 7, 8, 10, 11, 12, 13, 14, 15 weeks after the immunization with VEE-MAG25mer srRNA-LNP1 (FIG. 4).

TABLE G

| Mean spot forming cells (SFC) per $10^6$ PBMCs for each epitope ± SEM for priming vaccination with ChAdV68.5WTnt.MAG25mer (Group 1) | | | | | | |
| --- | --- | --- | --- | --- | --- | --- |
| | Antigen | | | | | |
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |

TABLE H

Mean spot forming cells (SFC) per $10^6$ PBMCs for each epitope ± SEM for priming vaccination with VEE-MAG25mer srRNA-LNP2 (300 μg) (Group 2)

| | Antigen | | | | | |
| Wk | Env CL9 | Env TL9 | Gag CM9 | Gag LW9 | Pol SV9 | Tat TL8 |
|---|---|---|---|---|---|---|
| 4 | 46 ± 27.1 | 18.4 ± 6.8 | 58.3 ± 45.8 | 29.9 ± 20.8 | 4.9 ± 2.3 | 10.7 ± 4 |
| 5 | 85.4 ± 54 | 5.2 ± 5.8 | 52.4 ± 51.2 | 34.5 ± 35 | 11.8 ± 12.2 | 14.4 ± 7.9 |
| 7 | 18.6 ± 32.5 | 1.9 ± 1.7 | 59.4 ± 55.7 | 9.3 ± 10.7 | 3.3 ± 3 | 10.7 ± 6.1 |
| 8 | 36.6 ± 39.4 | 6.3 ± 3.9 | 48.7 ± 39.9 | 13.5 ± 8.8 | 3.8 ± 3.6 | 17.2 ± 9.7 |
| 10 | 69.1 ± 59.1 | 4.4 ± 1.9 | 39.3 ± 38 | 14.7 ± 10.8 | 4.4 ± 5.3 | 8.5 ± 5.3 |
| 11 | 43 ± 38.8 | 22.6 ± 21.1 | 30.2 ± 26.2 | 3.3 ± 2.2 | 5.8 ± 3.5 | 40.3 ± 25.5 |
| 13 | 120.4 ± 78.3 | 68.2 ± 43.9 | 54.2 ± 36.8 | 21.8 ± 7.4 | 17.7 ± 6.1 | 47.4 ± 27.3 |
| 14 | 76 ± 44.8 | 28 ± 19.5 | 65.9 ± 64.3 | −0.3 ± 1.3 | 2.5 ± 2 | 31.1 ± 26.5 |
| 15 | 58.9 ± 41.4 | 19.5 ± 15.1 | 55.4 ± 51 | 2.5 ± 2 | 5.5 ± 3.6 | 20.1 ± 15.7 |

TABLE I

Mean spot forming cells (SFC) per $10^6$ PBMCs for each epitope ± SEM for priming vaccination with VEE-MAG25mer srRNA-LNP1 (300 μg) (Group 3)

| | Antigen | | | | | |
| Wk | Env CL9 | Env TL9 | Gag CM9 | Gag LW9 | Pol SV9 | Tat TL8 |
|---|---|---|---|---|---|---|
| 4 | 19.5 ± 8.7 | 13.3 ± 13.1 | 16.5 ± 15.3 | 10.5 ± 7.3 | 35.9 ± 24.8 | 92.9 ± 91.6 |
| 5 | 87.9 ± 43.9 | 12.7 ± 11.7 | 37.2 ± 31.9 | 21.1 ± 23.8 | 13.2 ± 13.7 | 12.6 ± 13.7 |
| 7 | 21.1 ± 13.3 | 48.8 ± 48.4 | 51.7 ± 39.5 | 9.1 ± 10.5 | 58.6 ± 55.8 | 159.4 ± 159 |
| 8 | 47.7 ± 21.7 | 66.4 ± 52.2 | 59.8 ± 57.4 | 49.4 ± 28 | 79.4 ± 63 | 133.8 ± 132.1 |
| 10 | 49 ± 30.2 | 42.2 ± 41.1 | 139.3 ± 139.3 | 51.6 ± 51.2 | 78.2 ± 75.8 | 131.7 ± 131.6 |
| 11 | 42 ± 26.8 | 20.9 ± 21.4 | 177.1 ± 162 | −6.3 ± 4.3 | 104.3 ± 104.1 | 231.5 ± 230.1 |
| 12 | 40.2 ± 19 | 20.3 ± 11.9 | 42.2 ± 46.7 | 3.7 ± 6.7 | 57 ± 44.7 | 70 ± 69.2 |
| 13 | 81.2 ± 48.9 | 38.2 ± 37.6 | 259.4 ± 222.2 | −4 ± 4.1 | 164.1 ± 159.3 | 347.3 ± 343.5 |
| 14 | 34.5 ± 31.8 | 5.3 ± 11.6 | 138.6 ± 137.3 | −4.7 ± 5.2 | 52.3 ± 52.9 | 142.6 ± 142.6 |
| 15 | 49 ± 24 | 6.7 ± 9.8 | 167.1 ± 163.8 | −6.4 ± 4.2 | 47.8 ± 42.3 | 116.6 ± 114.5 | srRNA Dose Ranging Study

In one implementation of the present invention, an srRNA dose ranging study can be conducted in mamu A01 Indian rhesus macaques to identify which srRNA dose to progress to NHP immunogenicity studies. In one example, Mamu A01 Indian rhesus macaques can be administered with an srRNA vector encoding model antigens that includes multiple mamu A01 restricted epitopes by IM injection. In another example, an anti-CTLA-4 monoclonal antibody can be administered SC proximal to the site of IM vaccine injection to target the vaccine draining lymph node in one group of animals. PBMCs can be collected every 2 weeks after the initial vaccination for immune monitoring. The study arms are described in below (Table J).

TABLE J

Non-GLP RNA dose ranging study in Indian Rhesus Macaques

| Group | Prime | Boost 1 | Boost 2 |
|---|---|---|---|
| 1 | srRNA-LNP (Low Dose) | srRNA-LNP (Low Dose) | srRNA-LNP (Low Dose) |
| 2 | srRNA-LNP (Mid Dose) | srRNA-LNP (Mid Dose) | srRNA-LNP (Mid Dose) |
| 3 | srRNA-LNP (High Dose) | srRNA-LNP (High Dose) | srRNA-LNP (High Dose) |
| 4 | srRNA-LNP (High Dose) + anti-CTLA-4 | srRNA-LNP (High Dose) + anti-CTLA-4 | srRNA-LNP (High Dose) + anti-CTLA-4 |

* Dose range of srRNA to be determined with the high dose ≤300 μg.

Immunogenicity Study in Indian *Rhesus macaques*

Figure 5:
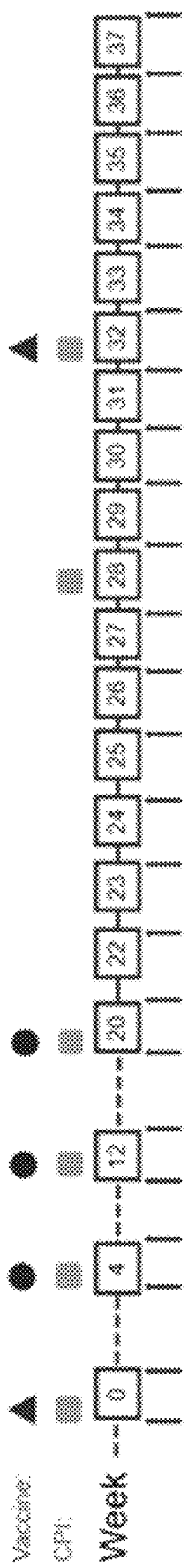
FIG. 5 illustrates the vaccination strategy used to evaluate immunogenicity of the antigen-cassette containing vectors in rhesus macaques. Triangles indicate chAd68 vaccination (1e12 vp/animal) at weeks 0 & 32. Circles represent alphavirus vaccination at weeks 0, 4, 12, 20, 28 & 32. Squares represent administration of an anti-CTLA4 antibody.

Vaccine studies were conducted in mamu A01 Indian rhesus macaques (NHPs) to demonstrate immunogenicity using the antigen vectors. FIG. 5 illustrates the vaccination strategy. Three groups of NHPs were immunized with ChAdV68.5-WTnt.MAG25mer and either with the checkpoint inhibitor anti-CTLA-4 antibody Ipilimumab (Groups 5 & 6) or without the checkpoint inhibitor (Group 4). The antibody was administered either intravenously (group 5) or subcutaneously (group 6). Triangles indicate chAd68 vaccination (1e12 vp/animal) at weeks 0 & 32. Circles represent alphavirus vaccination at weeks 0, 4, 12, 20, 28 and 32.

Figure 6:
FIG. 6 shows a time course of CD8+ anti-epitope responses in *Rhesus macaques* dosed with chAd-MAG alone (Group 4). Mean SFC/1e6 splenocytes is shown.
Figure 7:
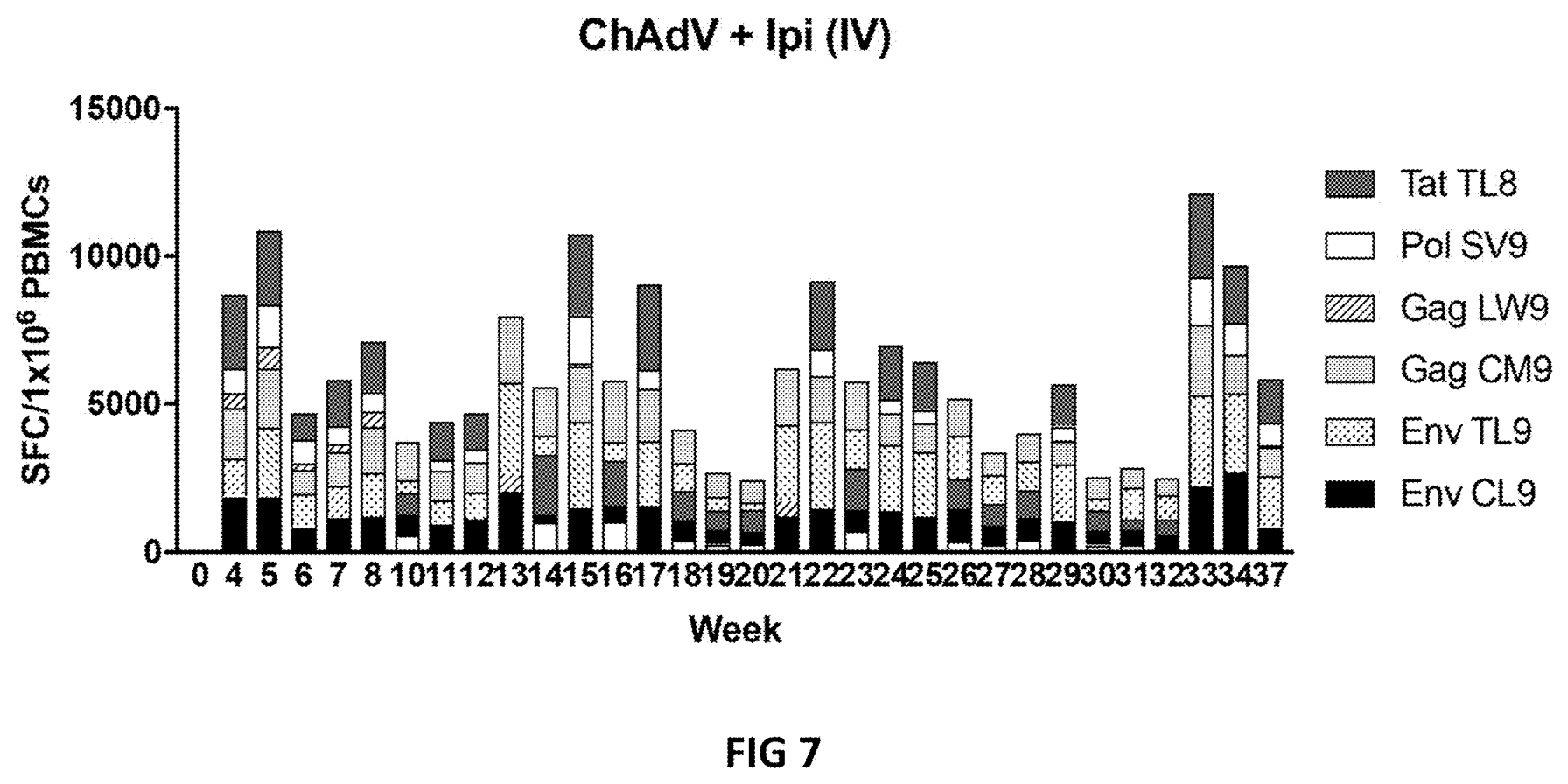
Figure 8:
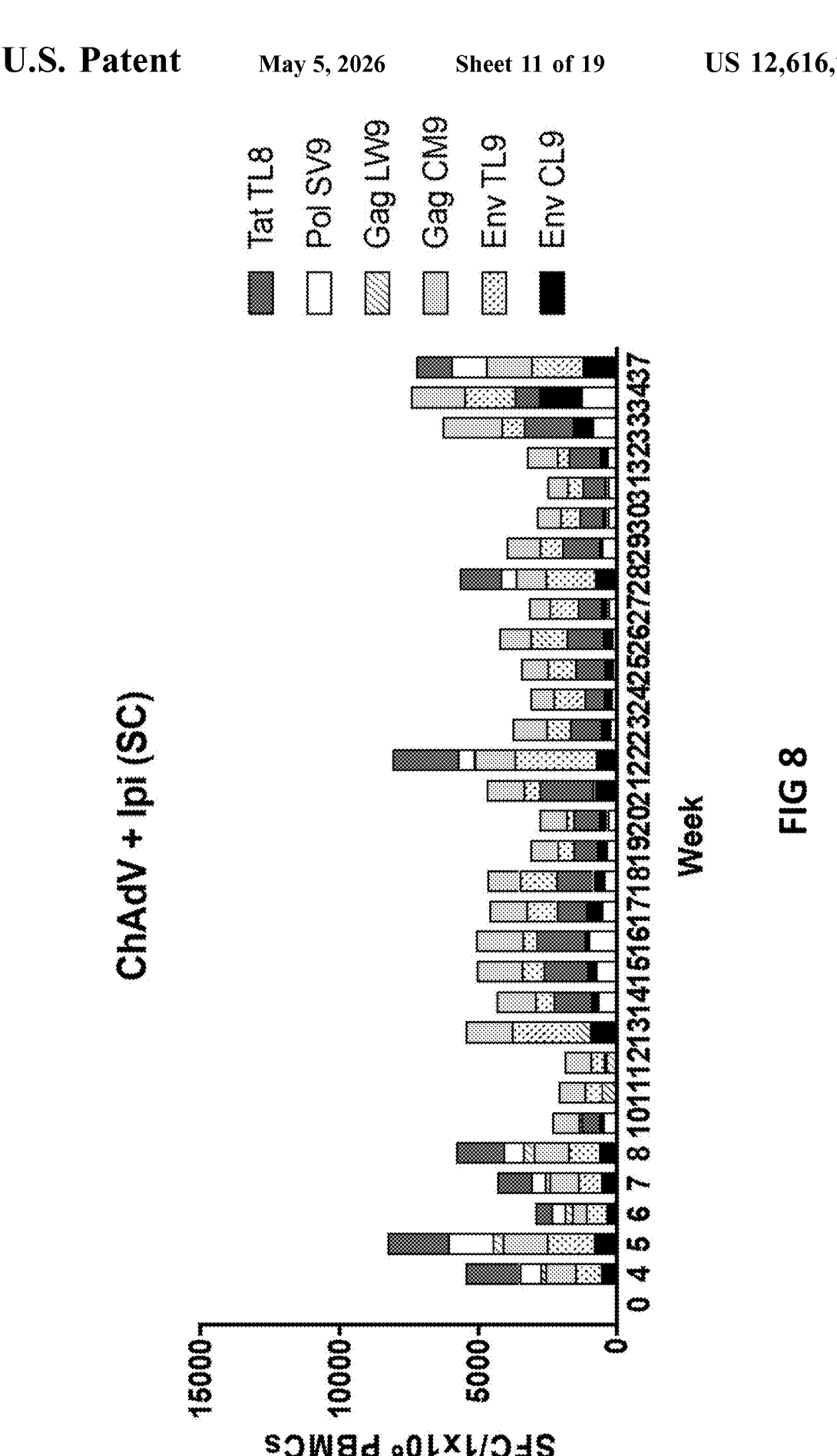
FIG. 8 shows a time course of CD8+ anti-epitope responses in *Rhesus macaques* dosed with chAd-MAG plus anti-CTLA4 antibody (Ipilimumab) delivered SC (Group 6). Mean SFC/1e6 splenocytes is shown.

The time course of CD8+ anti-epitope responses in the immunized NHPs are presented for chAd-MAG immunization alone (FIG. 6 and Table K), chAd-MAG immunization with the checkpoint inhibitor delivered IV (FIG. 7 and Table L), and chAd-MAG immunization with the checkpoint inhibitor delivered SC (FIG. 8 and Table M). The results demonstrate chAd68 vectors efficiently primed CD8+ responses in primates, alphavirus vectors efficiently boosted the chAD68 vaccine priming response, checkpoint inhibitor whether delivered IV or SC amplified both priming and boosting responses, and chAd vectors readministered post vaccination to effectively boosted the immune responses.

TABLE K

CD8+ anti-epitope responses in Rhesus Macaques dosed with chAd-MAG (Group 4). Mean SFC/1e6 splenocytes +/− the standard error is shown

| | | | Antigen | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 105.8 ± 68.1 | 473.3 ± 249.1 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |
| 25 | 136.4 ± 52.6 | 1207.1 ± 501.6 | 924 ± 358.5 | 6.2 ± 10.5 | 74.1 ± 34.4 | 484.6 ± 116.7 |
| 26 | 278.2 ± 114.4 | 1645 ± 661.7 | 1170.2 ± 469.9 | −2.9 ± 5.7 | 80.6 ± 55.8 | 784.4 ± 214.1 |
| 27 | 159 ± 56.8 | 961.7 ± 547.1 | 783.6 ± 366.4 | −5 ± 4.3 | 63.6 ± 27.5 | 402.9 ± 123.4 |
| 28 | 189.6 ± 75.7 | 1073.1 ± 508.8 | 668.3 ± 312.5 | −5.7 ± 4.1 | 80.3 ± 38.3 | 386.4 ± 122 |
| 29 | 155.3 ± 69.1 | 1102.9 ± 606.1 | 632.9 ± 235 | 34.5 ± 24.2 | 80 ± 35.5 | 422.5 ± 122.9 |
| 30 | 160.2 ± 59.9 | 859 ± 440.9 | 455 ± 209.1 | −3 ± 5.3 | 60.5 ± 28.4 | 302.7 ± 123.2 |
| 31 | 122.2 ± 49.7 | 771.1 ± 392.7 | 582.2 ± 233.5 | −5.7 ± 4.1 | 55.1 ± 27.3 | 295.2 ± 68.3 |
| 32 | 119.3 ± 28.3 | 619.4 ± 189.7 | 566 ± 222.1 | −3.7 ± 5.1 | 21.9 ± 4.5 | 320.5 ± 76.4 |
| 33 | 380.5 ± 122 | 1636.1 ± 391.4 | 1056.2 ± 205.7 | −5.7 ± 4.1 | 154.5 ± 38.5 | 988.4 ± 287.7 |
| 34 | 1410.8 ± 505.4 | 972.4 ± 301.5 | 319.6 ± 89.6 | −4.8 ± 4.2 | 141.1 ± 49.8 | 1375.5 ± 296.7 |
| 37 | 130.8 ± 29.2 | 500 ± 156.9 | 424.9 ± 148.9 | −3.5 ± 4.7 | 77.7 ± 24.6 | 207.1 ± 42.4 |
| 38 | 167.7 ± 54.8 | 1390.8 ± 504.7 | 830.4 ± 329.1 | −5.5 ± 4.1 | 111.8 ± 43.2 | 516 ± 121.7 |

35

TABLE L

CD8+ anti-epitope responses in Rhesus Macaques dosed with chAd-MAG plus anti-CTLA4 antibody (Ipilimumab) delivered IV. (Group 5). Mean SFC/1e6 splenocytes +/− the standard error is shown

| | | | Antigen | | | |
|---|---|---|---|---|---|---|
| Wk | Env CL9 | Env TL9 | Gag CM9 | Gag LW9 | Pol SV9 | Tat TL8 |
| 4 | 1848.1 ± 432.2 | 1295.7 ± 479.7 | 1709.8 ± 416.9 | 513.7 ± 219.8 | 838.5 ± 221.1 | 2514.6 ± 246.5 |
| 5 | 1844.1 ± 410.2 | 2367.5 ± 334.4 | 1983.1 ± 370.7 | 732.1 ± 249.4 | 1429.7 ± 275.3 | 2517.7 ± 286.5 |
| 6 | 822.4 ± 216.7 | 1131.2 ± 194.7 | 796.8 ± 185.8 | 226.8 ± 70 | 802.2 ± 101.4 | 913.5 ± 222.7 |
| 7 | 1147.2 ± 332.9 | 1066 ± 311.2 | 1149.8 ± 467.3 | 267.4 ± 162.6 | 621.5 ± 283.2 | 1552.2 ± 395.1 |
| 8 | 1192.7 ± 188.8 | 1461.5 ± 237.7 | 1566.9 ± 310.5 | 522.5 ± 118.6 | 662.3 ± 142.4 | 1706 ± 216.7 |
| 10 | 1249 ± 220.3 | 1170.6 ± 227.7 | 1297.3 ± 264.7 | −0.3 ± 4.4 | 551.8 ± 90.5 | 1425.3 ± 142.6 |
| 11 | 934.2 ± 221.7 | 808 ± 191.3 | 1003.1 ± 293.4 | 1.9 ± 4.3 | 364.2 ± 76.6 | 1270.8 ± 191.6 |
| 12 | 1106.2 ± 216.6 | 896.7 ± 190.7 | 1020.1 ± 243.3 | 1.3 ± 3.9 | 436.6 ± 90 | 1222 ± 155.4 |
| 13 | 2023.8 ± 556.3 | 3696.7 ± 1.7 | 2248.5 ± 436.4 | −4.5 ± 3.5 | 2614 ± 406.1 | 3700 ± 0 |
| 14 | 1278.7 ± 240 | 2639.5 ± 387 | 1654.6 ± 381.1 | −6 ± 2.1 | 988.8 ± 197.9 | 2288.3 ± 298.7 |
| 15 | 1458.9 ± 281.8 | 2932.5 ± 488.7 | 1893.4 ± 499 | 74.6 ± 15.6 | 1657.8 ± 508.9 | 2709.1 ± 428.7 |
| 16 | 1556.8 ± 243 | 2143.8 ± 295.2 | 2082.8 ± 234.2 | −5.8 ± 2.5 | 1014.6 ± 161.4 | 2063.7 ± 86.7 |
| 17 | 1527 ± 495.1 | 2213 ± 677.1 | 1767.7 ± 391.8 | 15.1 ± 5.9 | 633.8 ± 133.9 | 2890.8 ± 433.9 |
| 18 | 1068.2 ± 279.9 | 1940.9 ± 204.1 | 1114.1 ± 216.1 | −5.8 ± 2.5 | 396.6 ± 77.6 | 1659.4 ± 171.7 |
| 19 | 760.7 ± 362.2 | 1099.5 ± 438.4 | 802.7 ± 192.5 | −2.4 ± 3.3 | 262.2 ± 62.2 | 1118.6 ± 224.2 |
| 20 | 696.3 ± 138.2 | 954.9 ± 198 | 765.1 ± 248.4 | −1.4 ± 4.4 | 279.6 ± 89.3 | 1139 ± 204.5 |
| 21 | 1201.4 ± 327.9 | 3096 ± 1.9 | 1901 ± 412.1 | −5.8 ± 2.5 | 1676.3 ± 311.5 | 2809.3 ± 195.8 |
| 22 | 1442.5 ± 508.3 | 2944.7 ± 438.6 | 1528.4 ± 349.6 | 2.8 ± 5.1 | 940.7 ± 160.5 | 2306.3 ± 218.6 |
| 23 | 1400.4 ± 502.2 | 2757.1 ± 452.9 | 1604.2 ± 450.1 | −5.1 ± 2.3 | 708.1 ± 162.6 | 2100.4 ± 362.9 |
| 24 | 1351 ± 585.1 | 2264.5 ± 496 | 1080.6 ± 253.8 | 0.3 ± 6.5 | 444.2 ± 126.4 | 1823.7 ± 306.5 |
| 25 | 1211.5 ± 505.2 | 2160.4 ± 581.8 | 970.8 ± 235.9 | 2.5 ± 3.8 | 450.4 ± 126.9 | 1626.2 ± 261.3 |
| 26 | 1443 ± 492.5 | 2485 ± 588 | 1252.6 ± 326.4 | −0.2 ± 6 | 360.2 ± 92.3 | 2081.9 ± 331.1 |
| 27 | 896.2 ± 413.3 | 1686 ± 559.5 | 751 ± 192.1 | −3.7 ± 2.5 | 247.4 ± 82.8 | 1364.1 ± 232 |
| 28 | 1147.8 ± 456.9 | 1912.1 ± 417.1 | 930.3 ± 211.4 | −5.8 ± 2.5 | 423.9 ± 79.6 | 1649.3 ± 315 |
| 29 | 1038.5 ± 431.9 | 1915.2 ± 626.1 | 786.8 ± 205.9 | 23.5 ± 8.3 | 462.8 ± 64 | 1441.5 ± 249.7 |
| 30 | 730.5 ± 259.3 | 1078.6 ± 211.5 | 699.1 ± 156.2 | −4.4 ± 2.7 | 234.4 ± 43.9 | 1160.6 ± 112.6 |
| 31 | 750.4 ± 328.3 | 1431 ± 549.9 | 650.6 ± 141.1 | −5.2 ± 3 | 243.4 ± 56.4 | 868.9 ± 142.8 |

TABLE L-continued

CD8+ anti-epitope responses in Rhesus Macaques dosed with chAd-MAG plus anti-CTLA4 antibody
(Ipilimumab) delivered IV. (Group 5). Mean SFC/1e6 splenocytes +/− the standard error is shown

|  | Antigen | | | | | |
|---|---|---|---|---|---|---|
| Wk | Env CL9 | Env TL9 | Gag CM9 | Gag LW9 | Pol SV9 | Tat TL8 |
| 32 | 581.4 ± 227.7 | 1326.6 ± 505.2 | 573.3 ± 138 | −3.2 ± 4.2 | 160.8 ± 49.2 | 936.4 ± 110.4 |
| 33 | 2198.4 ± 403.8 | 3093.4 ± 123.3 | 2391.8 ± 378.4 | 7.1 ± 8.5 | 1598.1 ± 343.1 | 2827.5 ± 289.5 |
| 34 | 2654.3 ± 337 | 2709.9 ± 204.3 | 1297.5 ± 291.4 | 0.4 ± 4.2 | 1091.8 ± 242.9 | 1924 ± 245.7 |
| 37 | 846.8 ± 301.7 | 1706.9 ± 196 | 973.6 ± 149.3 | 50.5 ± 45.2 | 777.3 ± 140.2 | 1478.8 ± 94.3 |

TABLE M

CD8+ anti-epitope responses in Rhesus Macaques dosed with chAd-MAG plus anti-CTLA4 antibody
(Ipilimumab) delivered SC (Group 6). Mean SFC/1e6 splenocytes +/− the standard error is shown

|  | Antigen | | | | | |
|---|---|---|---|---|---|---|
| Wk | Env CL9 | Env TL9 | Gag CM9 | Gag LW9 | Pol SV9 | Tat TL8 |
| 4 | 598.3 ± 157.4 | 923.7 ± 306.8 | 1075.6 ± 171.8 | 180.5 ± 74.1 | 752.3 ± 245.8 | 1955.3 ± 444.4 |
| 5 | 842.2 ± 188.5 | 1703.7 ± 514.2 | 1595.8 ± 348.4 | 352.7 ± 92.3 | 1598.9 ± 416.8 | 2163.7 ± 522.1 |
| 6 | 396.4 ± 45.3 | 728.3 ± 232.7 | 503.8 ± 151.9 | 282 ± 69 | 463.1 ± 135.7 | 555.2 ± 191.5 |
| 7 | 584.2 ± 177 | 838.3 ± 254.9 | 1013.9 ± 349.4 | 173.6 ± 64.3 | 507.4 ± 165.7 | 1222.8 ± 368 |
| 8 | 642.9 ± 134 | 1128.6 ± 240.6 | 1259.1 ± 163.8 | 366.1 ± 72.8 | 726.7 ± 220.9 | 1695.6 ± 359.4 |
| 10 | 660.4 ± 211.4 | 746.9 ± 222.7 | 944.8 ± 210.2 | −1.2 ± 1.9 | 523.4 ± 230.7 | 787.3 ± 308.3 |
| 11 | 571.2 ± 162 | 609.4 ± 194.3 | 937.9 ± 186.5 | −8.9 ± 2.3 | 511.6 ± 229.6 | 1033.3 ± 315.7 |
| 12 | 485.3 ± 123.7 | 489.4 ± 142.7 | 919.3 ± 214.1 | −8.9 ± 2.3 | 341.6 ± 139.4 | 1394.7 ± 432.1 |
| 13 | 986.9 ± 154.5 | 2811.9 ± 411.3 | 1687.7 ± 344.3 | −4.1 ± 5.1 | 1368.5 ± 294.2 | 2751 ± 501.9 |
| 14 | 945.9 ± 251.4 | 2027.7 ± 492.8 | 1386.7 ± 326.7 | −5.7 ± 2.8 | 708.9 ± 277.1 | 1588.2 ± 440.1 |
| 15 | 1075.2 ± 322.4 | 2386 ± 580.7 | 1606.3 ± 368.1 | −5.4 ± 3.2 | 763.3 ± 248.8 | 1896.5 ± 507.8 |
| 16 | 1171.8 ± 341.6 | 2255.1 ± 439.6 | 1672.2 ± 342.3 | −7.8 ± 2.4 | 1031.6 ± 228.8 | 1896.4 ± 419.9 |
| 17 | 1118.2 ± 415.4 | 2156.3 ± 476 | 1345.3 ± 377.7 | −1.1 ± 6.7 | 573.7 ± 118.8 | 1614.4 ± 382.3 |
| 18 | 861.3 ± 313.8 | 2668.2 ± 366.8 | 1157.2 ± 259.6 | −8.9 ± 2.3 | 481.2 ± 164 | 1725.8 ± 511.4 |
| 19 | 719.2 ± 294.2 | 1447.2 ± 285 | 968 ± 294.5 | −2.2 ± 4.6 | 395.6 ± 106.1 | 1199.6 ± 289.2 |
| 20 | 651.6 ± 184 | 1189.8 ± 242.8 | 947.4 ± 249.8 | −8.9 ± 2.3 | 355 ± 106.3 | 1234.7 ± 361.7 |
| 21 | 810.3 ± 301.9 | 2576.2 ± 283.7 | 1334 ± 363.1 | −8.9 ± 2.3 | 892.2 ± 305 | 1904.4 ± 448.1 |
| 22 | 775 ± 196.4 | 2949 ± 409.7 | 1421.8 ± 309.7 | 38 ± 27.8 | 577 ± 144.2 | 2330.6 ± 572.3 |
| 23 | 584.9 ± 240.2 | 1977.9 ± 361.4 | 1209.8 ± 405.1 | −7.3 ± 3.2 | 273.7 ± 93.3 | 1430.6 ± 363.9 |
| 24 | 485.4 ± 194.4 | 1819.8 ± 325.5 | 837.2 ± 261.4 | −3.4 ± 4.1 | 234.4 ± 71.1 | 943.9 ± 243.3 |
| 25 | 452.3 ± 175 | 2072 ± 405.7 | 957.1 ± 293.1 | −8.9 ± 2.3 | 163 ± 43.2 | 1341.2 ± 394.7 |
| 26 | 517.9 ± 179.1 | 2616 ± 567.5 | 1126.6 ± 289 | −8.3 ± 2.3 | 199.9 ± 89.2 | 1615.7 ± 385.6 |
| 27 | 592.8 ± 171.7 | 1838.3 ± 372.4 | 749.3 ± 170.4 | −7.3 ± 2.5 | 325.5 ± 98.7 | 1110.7 ± 308.8 |
| 28 | 793 ± 228.5 | 1795.4 ± 332.3 | 1068.7 ± 210.3 | 2.5 ± 4.1 | 553.1 ± 144.3 | 1480.8 ± 357.1 |
| 29 | 661.8 ± 199.9 | 2140.6 ± 599.3 | 1202.7 ± 292.2 | −8.7 ± 2.8 | 558.9 ± 279.2 | 1424.2 ± 408.6 |
| 30 | 529.1 ± 163.3 | 1528.2 ± 249.8 | 840.5 ± 218.3 | −8.9 ± 2.3 | 357.7 ± 149.4 | 1029.3 ± 335 |
| 31 | 464.8 ± 152.9 | 1332.2 ± 322.7 | 726.3 ± 194.3 | −8.9 ± 2.3 | 354.3 ± 158.6 | 884.4 ± 282 |
| 32 | 612.9 ± 175.3 | 1584.2 ± 390.2 | 1058.3 ± 219.8 | −8.7 ± 2.8 | 364.6 ± 149.8 | 1388.8 ± 467.3 |
| 33 | 1600.2 ± 416.7 | 2597.4 ± 367.9 | 2086.4 ± 414.8 | −6.3 ± 3.3 | 893.8 ± 266 | 2490.6 ± 416.4 |
| 34 | 2814.6 ± 376.2 | 2713.6 ± 380.8 | 1888.8 ± 499.4 | −7.5 ± 3.1 | 1288.9 ± 438.9 | 2428.1 ± 458.9 |
| 37 | 1245.9 ± 471.7 | 1877.7 ± 291.2 | 1606.6 ± 441.9 | 14.2 ± 13 | 1227.5 ± 348.1 | 1260.7 ± 342 |

Memory Phenotyping in Indian *Rhesus macaques*

Figure 9:
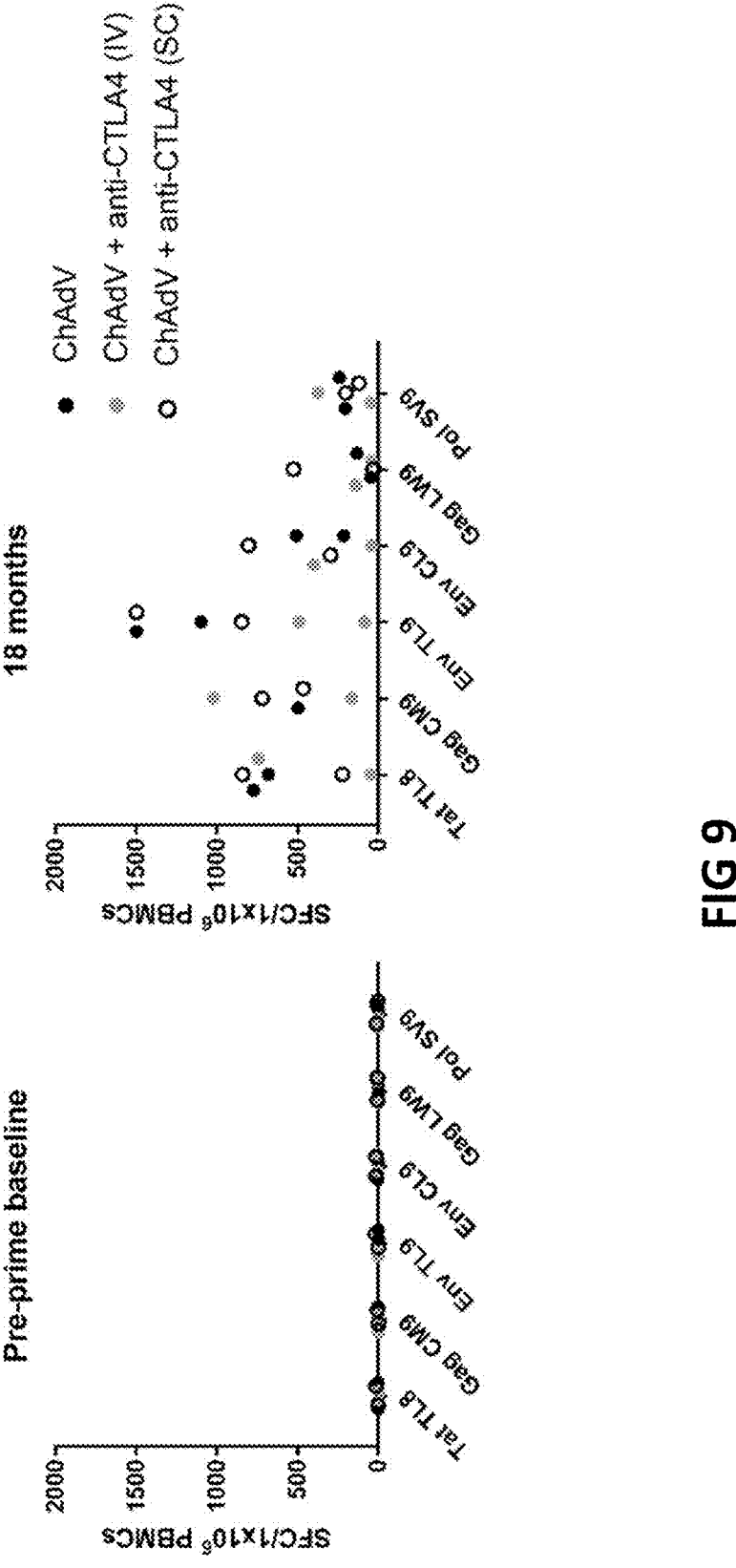
FIG. 9 shows antigen-specific memory responses generated by ChAdV68/samRNA vaccine protocol measured by ELISpot. Results are presented as individual dot plots, with each dot representing a single animal. Pre-immunization baseline (left panel) and memory response at 18 months post-prime (right panel) are shown.

*Rhesus macaque* were immunized with ChAdV68.5WTnt.MAG25mer/VEE-MAG25mer srRNA heterologous prime/boost regimen with or without anti-CTLA4, and boosted again with ChAdV68. 5WTnt.MAG25mer. Groups were assessed 11 months after the final ChAdV68 administration (study month 18). by ELISpot was performed as described. FIG. 9 and Table N shows cellular responses to six different Mamu-A*01 restricted epitopes as measured by ELISpot both pre-immunization (left panel) and after 18 months (right panel). The detection of responses to the restricted epitopes demonstrates antigen-specific memory responses were generated by ChAdV68/samRNA vaccine protocol.

Figure 10:
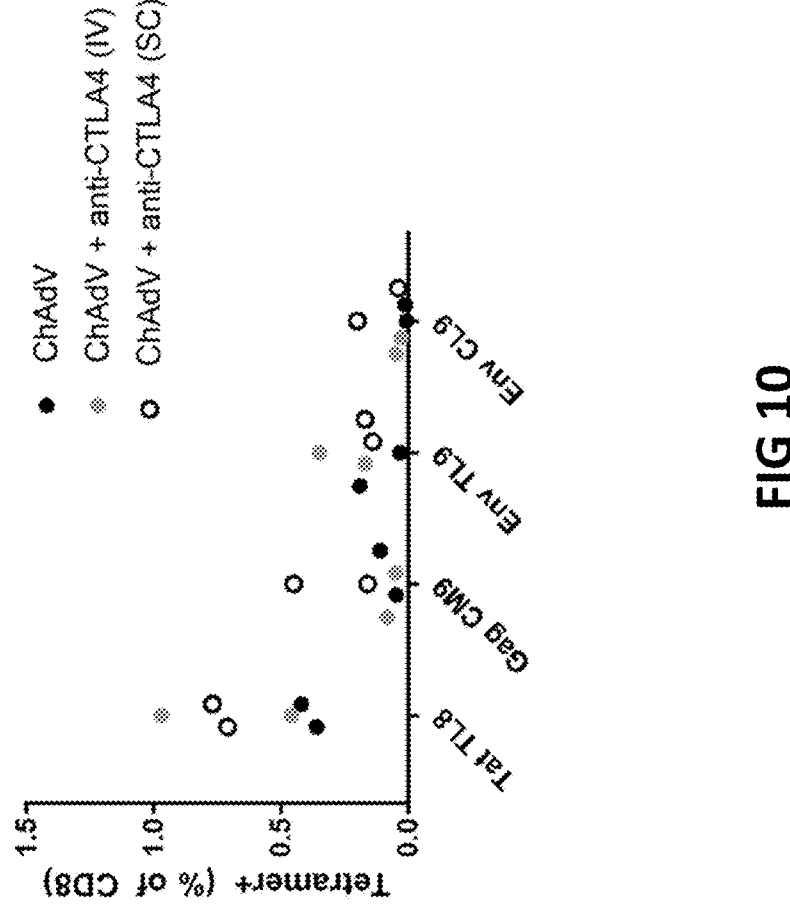
FIG. 10 shows memory cell phenotyping of antigen-specific CD8+ T-cells by flow cytometry using combinatorial tetramer staining and CD45RA/CCR7 co-staining.
Figure 11:
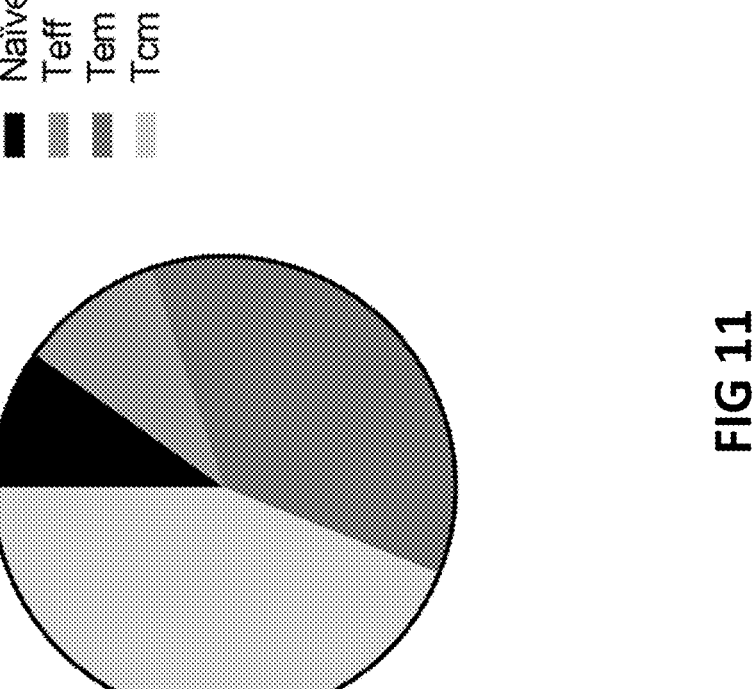
FIG. 11 shows the distribution of memory cell types within the sum of the four Mamu-A*01 tetramer+CD8+ T-cell populations at study month 18. Memory cells were characterized as follows: CD45RA+CCR7+=naïve, CD45RA+CCR7−=effector (Teff), CD45RA-CCR7+=central memory (Tcm), CD45RA-CCR7−=effector memory (Tem).

To assess memory, CD8+ T-cells recognizing 4 different rhesus *macaque* Mamu-A*01 class I epitopes encoded in the vaccines were monitored using dual-color Mamu-A*01 tetramer labeling, with each antigen being represented by a unique double positive combination, and allowed the identification of all 4 antigen-specific populations within a single sample. Memory cell phenotyping was performed by co-staining with the cell surface markers CD45RA and CCR7. FIG. 10 and Table O shows the results of the combinatorial tetramer staining and CD45RA/CCR7 co-staining for memory T-cells recognizing four different Mamu-A*01 restricted epitopes. The T cell phenotypes were also assessed by flow cytometry. FIG. 11 shows the distribution of memory cell types within the sum of the four Mamu-A*01 tetramer+CD8+ T-cell populations at study month 18. Memory cells were characterized as follows: CD45RA+ CCR7+=naïve, CD45RA+CCR7-=effector (Teff), CD45RA−CCR7+=central memory (Tcm), CD45RA−CCR7-=effector memory (Tem). Collectively, the results demonstrate that memory responses were detected at least one year following the last boost indicating long lasting immunity, including effector, central memory, and effector memory populations.

TABLE N

Mean spot forming cells (SFC) per $10^6$ PBMCs for each animal at
both pre-prime and memory assessment time points (18 months).

| | Pre-prime baseline | | | | | | 18 months | | | | | |
| Animal | Tat TL8 | Gag CM9 | Env TL9 | Env CL9 | Gag LW9 | Pol SV9 | Tat TL8 | Gag CM9 | Env TL9 | Env CL9 | Gag LW9 | Pol SV9 |
|---|---|---|---|---|---|---|---|---|---|---|---|---|
| 1 | 1.7 | 0.0 | 0.0 | 5.0 | 0.0 | 13.7 | 683.0 | 499.2 | 1100.3 | 217.5 | 47.7 | 205.3 |
| 2 | 0.0 | 0.0 | 0.0 | 0.2 | 0.1 | 0.0 | 773.4 | ND | 1500.0 | 509.3 | 134.5 | 242.5 |
| 3 | 0.0 | 0.0 | 6.7 | 6.8 | 10.2 | 3.3 | 746.3 | 167.5 | 494.1 | 402.8 | 140.6 | 376.0 |
| 4 | 0.0 | 0.0 | 0.0 | 0.0 | 0.0 | 0.0 | 47.6 | 1023.9 | 85.1 | 44.2 | 44.2 | 47.6 |
| 5 | 15.3 | 6.7 | 18.6 | 15.6 | 5.2 | 12.1 | 842.4 | 467.7 | 1500.0 | 805.9 | 527.8 | 201.8 |
| 6 | 3.1 | 0.0 | 0.0 | 15.5 | 6.9 | 5.3 | 224.3 | 720.3 | 849.0 | 296.9 | 32.4 | 121.9 |

ND = not determined due to technical exclusion

TABLE O

| Percent Mamu-A*01 tetramer positive out of live CD8+ cells | | | | |
| Animal | Tat TL8 | Gag CM9 | Env TL9 | Env CL9 |
|---|---|---|---|---|
| 1 | 0.42 | 0.11 | 0.19 | 0.013 |
| 2 | 0.36 | 0.048 | 0.033 | 0.00834 |
| 3 | 0.97 | 0.051 | 0.35 | 0.048 |
| 4 | 0.46 | 0.083 | 0.17 | 0.028 |
| 5 | 0.77 | 0.45 | 0.14 | 0.2 |
| 6 | 0.71 | 0.16 | 0.17 | 0.04 |

XVII. INFLUENZA STUDIES

Various dosing protocols using ChAdV68 and self-replicating RNA (srRNA) were evaluated for influenza vaccines.

Materials and Methods

Influenza ChAdV68 and SAM Vectors

ChAdV68 and SAM influenza vectors expressing influenza hemagglutinins (HA) from the following influenza A strains were made: H1N1 California7/09 and H7N9 Anhui1/13. The HA nucleotide sequences were codon optimized for optimized mammalian expression of the HA protein (see Sequences). The constructs were cloned by Gibson assembly into ChAdV68 and SAM plasmids. The ChAdV68 vector backbone used was the following: AC_000011.1 with E1 (nt 577 to 3403) and E3 (nt 27,125-31,825) sequences deleted; corresponding ATCC VR-594 nucleotides substituted at five positions; antigen under the control of the CMV promoter/enhancer inserted in place of deleted E1. ChAdV68 plasmids were PacI digested and transfected into 293F cells to produce ChAd-HA viral vectors. ChAd production was performed at the 400 mL scale in 293F suspension cells. Virus was purified by two rounds of discontinuous CsCl density gradients and the virus was purified and dialyzed into ARM buffer (10 mM Tris pH8.0, 25 mM NaCl, 2.5% Glycerol). Vector was diluted into ARM buffer to the target dose for administration to animals. The SAM vector backbone used was the following: Venezuelan Equine Encephalitis (VEE) (Kinney, 1986, Virology 152:400-413) based self-amplifying RNA (SAM) vector with sequences encoding the structural proteins of VEE located 3' of the 26S sub-genomic promoter were deleted (VEE sequences 7544 to 11,175 deleted; numbering based on Kinney et al 1986; SEQ ID NO:6) and replaced by antigen sequences. A high-quality full-length SAM encoding HA of H1N1 California7/09 or H7N9 Anhui1/13 strain was synthesized and co-transcriptionally capped in vitro and purified through silica columns. SAM was then encapsulated in lipid nanoparticles (LNP) and stored in a storage buffer.

In Vivo Evaluation in Balb/C Mice

For humoral assessment, ChAd-CA709-HA and ChAd-Anhui 1/13-HA vectors were dosed at either 5e10 VP or 1e9 VP/animal. Sera was harvested pre-injection and at day 28 post prime and at day 56, 4 weeks post SAM boost. Limiting dilutions of sera was analyzed for the ability to prevent hemagglutination of red blood cells and a hemagglutination inhibition (HAI) titer determined.

For T cell response assessment, Balb/c mice were immunized with 5e10 VP ChAd-CA709-HA or 10 μg SAM-CA709-HA and antigen specific T cell immune response were evaluated. At 2-weeks post prime, splenocytes were isolated and T cell response was assessed by overnight IFNγ ELISpot following stimulation with six minipools of overlapping peptides (15 AA long, 11 AA overlap) spanning the HA protein of influenza A CA/7/09.

Mice were also immunized in a ChAdV68-prime and SAM-boost regimen where mice were immunized with ChAd-HA (5e10 vp) and then boosted with SAM-HA at 8-weeks, with T cell responses assessed by IFNγ ELISpot at 2-weeks post boost (10 weeks post prime). T cell polyfunctionality was also assessed in splenocytes at 2-weeks post boost by intracellular cytokine staining (ICS) to identify T cells expressing IFNγ, TNFα or IL-2 post prime/boost with chAd & SAM-HA.

Results

Influenza vaccines were assessed in vivo.

Figure 12B:
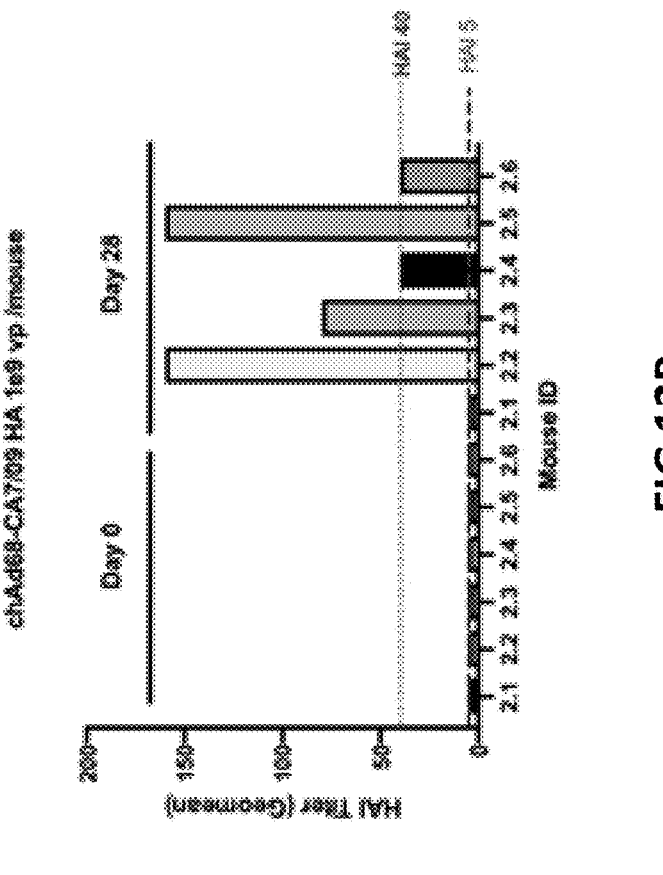
FIG. 12B shows HAI responses against influenza A HINI strain CA/7/09 post dosing with (B) 1e9 vp/animal. HAI 5 is the limit of detection. HAI 40 is a therapeutic threshold.
Figure 12A:
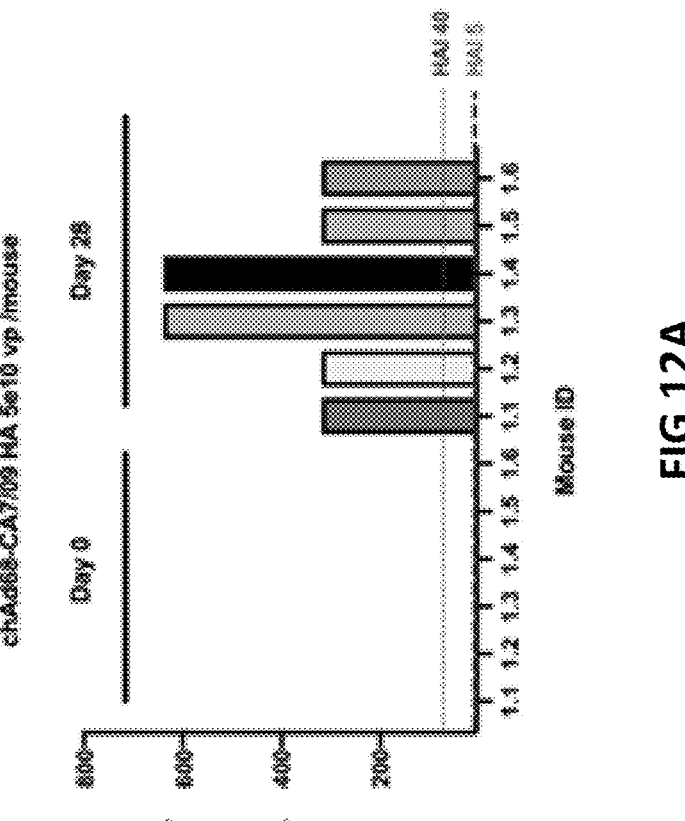
FIG. 12A shows HAI responses against influenza A H1N1 strain CA/7/09 post dosing with 5e10 vp/animals. HAI 5 is the limit of detection. HAI 40 is a therapeutic threshold.
Figures 13A, 13B:
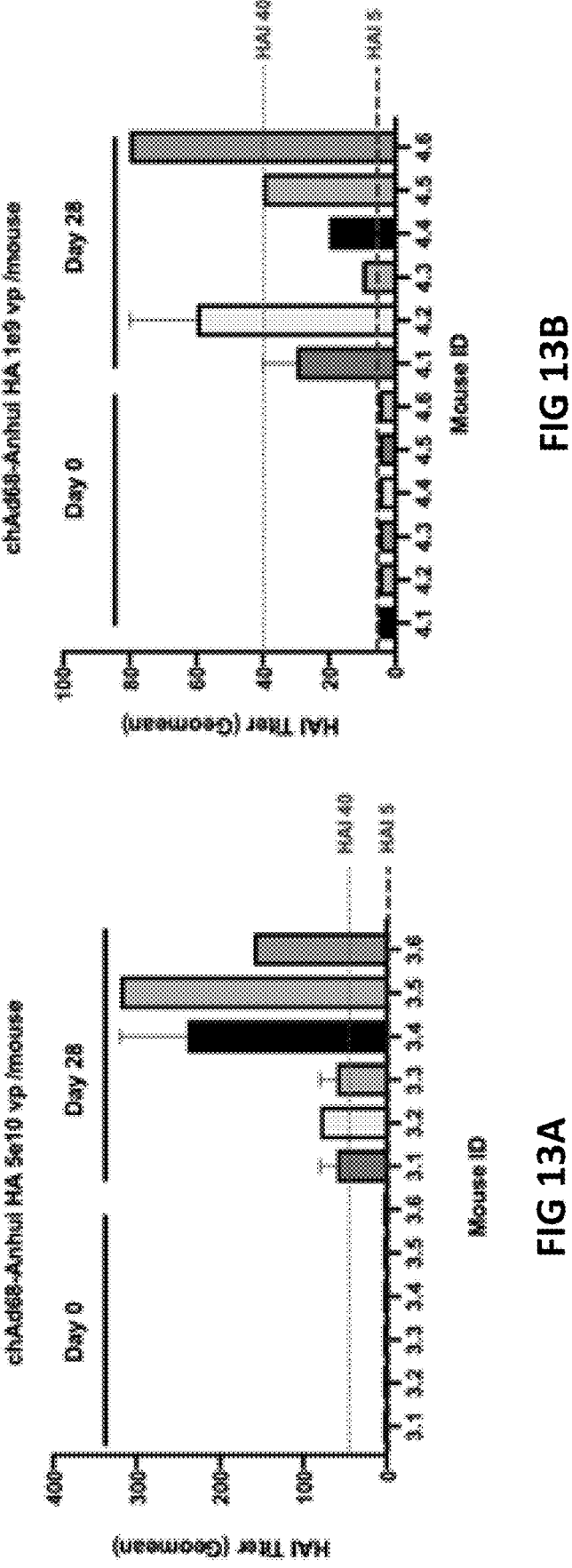
FIG. 13A shows HAI responses against influenza A H7N9 strain Anhui/1/13 post dosing with 5e10 vp/animal. HAI 5 is the limit of detection. HAI 40 is a therapeutic threshold. Note the vaccine is against Anhui/1/13 but the strain used in the HAI assay is the closely related A/Shanghai/2/13 HA on a PR8 influenza strain.
FIG. 13B shows HAI responses against influenza A H7N9 strain Anhui/1/13 post dosing with 1e9 vp/animal. HAI 5 is the limit of detection. HAI 40 is a therapeutic threshold. Note the vaccine is against Anhui/1/13 but the strain used in the HAI assay is the closely related A/Shanghai/2/13 HA on a PR8 influenza strain.

Shown in FIG. 12 and quantified in Table P are HAI titers for influenza A H1N1 strain CA/7/09 pre and post immunization. Mice administered with the high dose of 5e10 vp/animal (FIG. 12A) demonstrated 100% of animals seroconverted and had high titers >300 HAI and all animals had HAI titers>40 which is predicted to be protective. At the low dose (FIG. 12B), 5/6 animals had HAI titers>40 and these titers were greater than 4x the pre-samples indicating successful seroconversion that would likely be protective in vivo. Shown in FIG. 13 and quantified in Table Q are HAI titers for influenza A H7N9 Anhui1/13 strain pre and post immunization (FIG. 13A high dose; FIG. 13B low dose). A similar, but generally lower, response was observed against the H7N9 strain with all animals seroconverting at the high dose of 5e10 vp. The results demonstrate ChAd-HA priming induced strong humoral immune responses against H1N1 and H7N9 influenza strains.

Figures 14A, 14B:
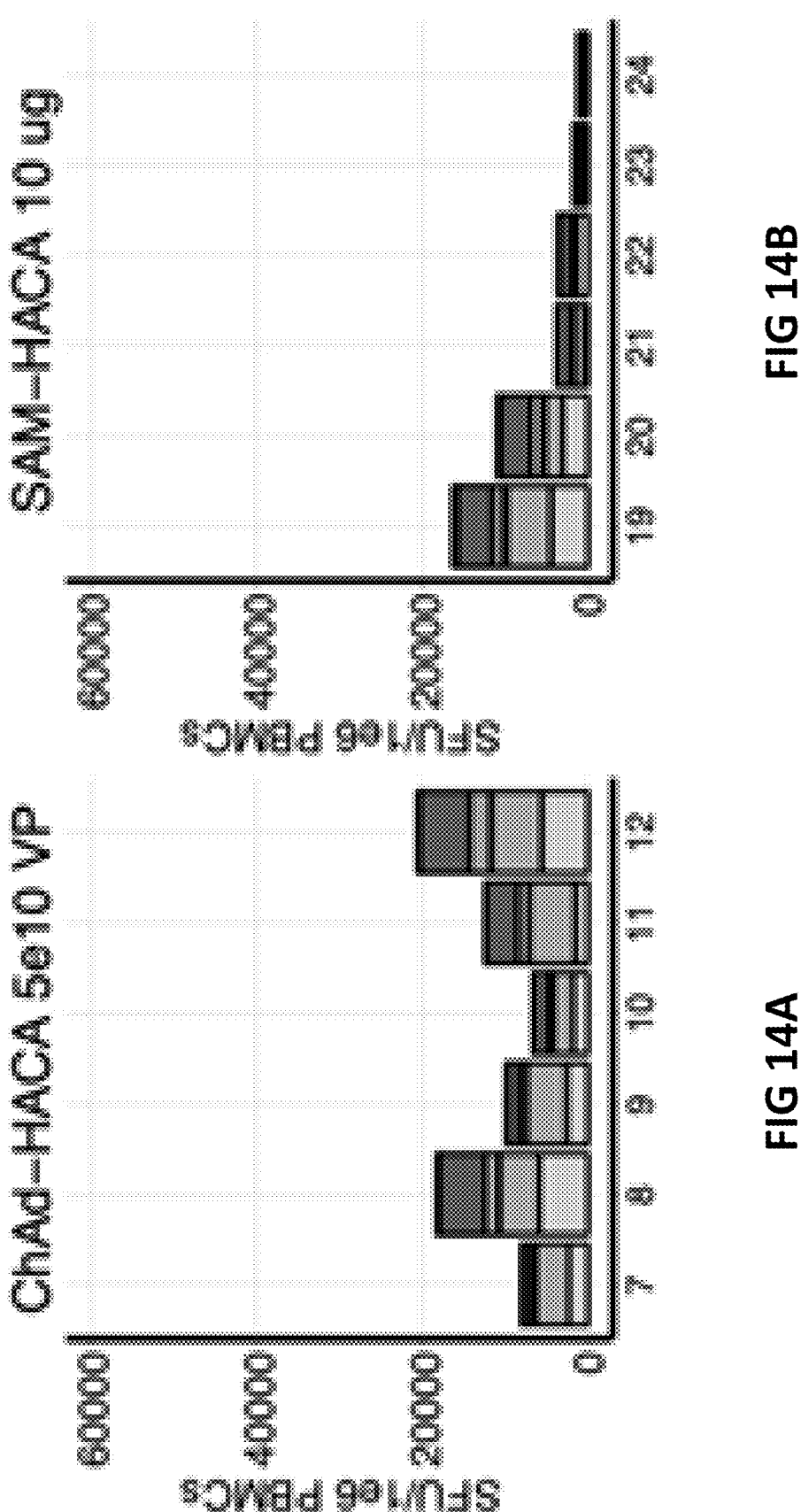
FIG. 14A shows anti-HA T-cell response for each mouse (n=6/group) 2-weeks post ChAd prime. Splenocytes were isolated ex vivo overnight IFNγ ELISpot performed using six overlapping peptide pools spanning the HA antigen. SFU/1e6 splenocytes, response to six pools are stacked.
FIG. 14B shows anti-HA T-cell response for each mouse (n=6/group) 2-weeks post SAM prime. Splenocytes were isolated ex vivo overnight IFNγ ELISpot performed using six overlapping peptide pools spanning the HA antigen. SFU/1e6 splenocytes, response to six pools are stacked.
Figure 14C:
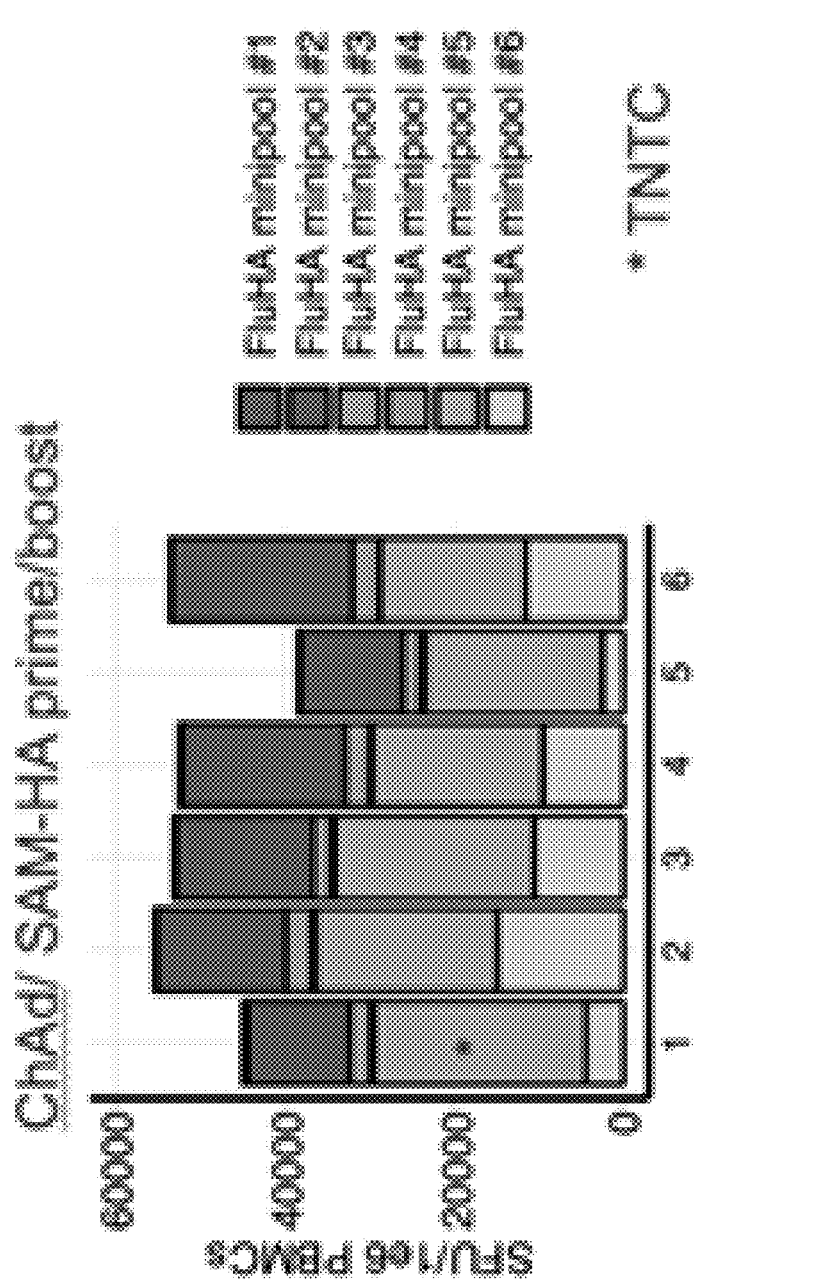
FIG. 14C shows anti-HA T-cell response for each mouse (n=6/group) 2-weeks post boost with SAM-HA (10-weeks post ChAd prime) (C). Splenocytes were isolated ex vivo overnight IFNγ ELISpot performed using six overlapping peptide pools spanning the HA antigen. SFU/1e6 splenocytes, response to six pools are stacked.
Figure 15B:
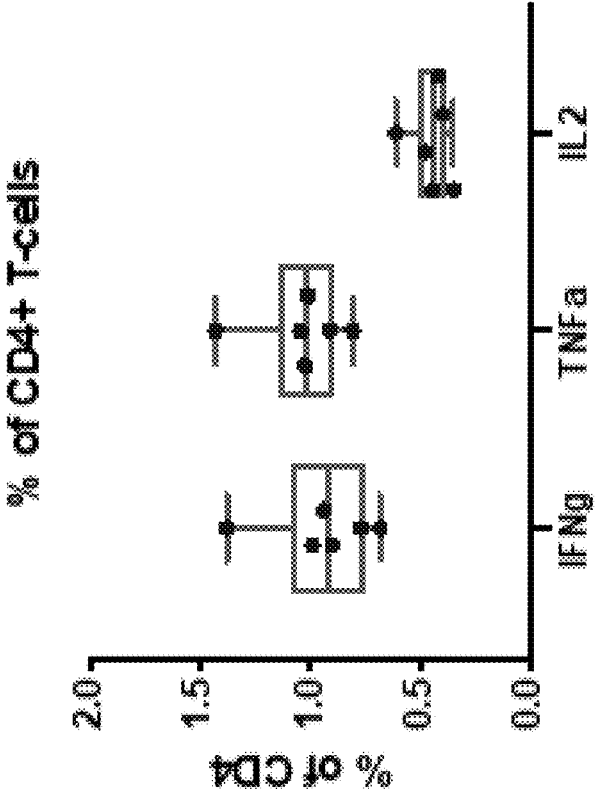
FIG. 15B shows T-cell responses post chAd prime/SAM boost (2-weeks post boost, 10 weeks post prime). Percentage of CD4+ cells expressing IFNg, TNFa and IL2 as measured by ICS post 5h ex vivo stimulation (sum of two overlapping peptide pools). Box and whiskers and median, IQR and range.
Figure 15A:
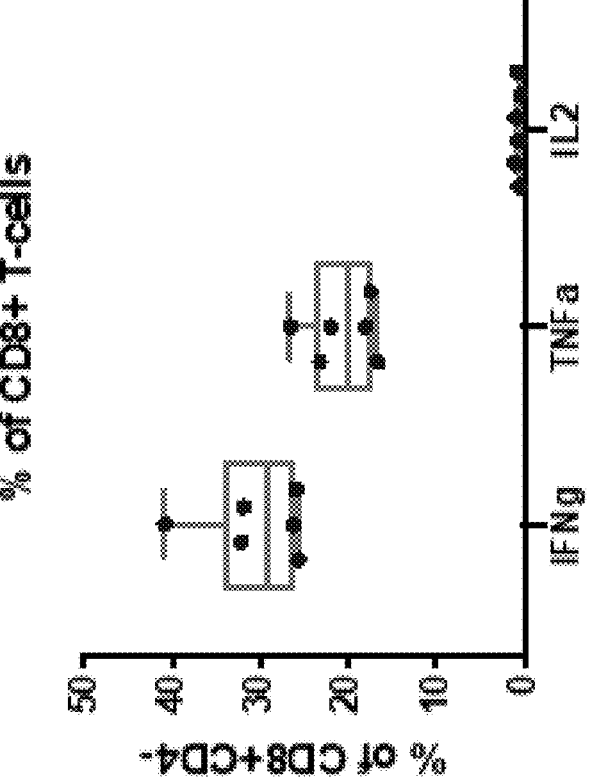
FIG. 15A shows T-cell responses post chAd prime/SAM boost (2-weeks post boost, 10 weeks post prime). Percentage of CD8+ expressing IFNg, TNFa and IL2 as measured by ICS post 5 h ex vivo stimulation (sum of two overlapping peptide pools). Box and whiskers and median, IQR and range.

Shown in FIG. 14 and quantified in Table R are anti-HA T cell responses for influenza A H1N1 strain CA/7/09 with either a ChAdV68-prime (FIG. 14A), SAM-prime (FIG. 14B), or ChAdV68-prime and SAM-boost (FIG. 14C). ChAdV68-prime produced a more potent T-cell response across peptide pools as measured by interferon gamma ELISpot. SAM-prime produced a more variable, and generally reduced, T-cell response across peptide pools as measured by interferon gamma ELISpot. ChAdV68-prime and SAM-boost showed significantly increased T cell responses compared to post prime responses with either vector. Shown in FIG. 15 and quantified in Table S are polyfunctional T cell responses for influenza A H1N1 strain CA/7/09 with a ChAdV68-prime and SAM-boost for CD8 T cells (FIG. 15A) and CD4 T cells (FIG. 15B). The T-cell response demonstrated a pronounced CD8 T cell bias. The results demonstrate the vaccine regimens induced strong, polyfunctional T cell responses against H1N1 influenza

TABLE Q

| H7N9 HAI titers pre and post immunization ("3-X" 5e10 VP; "4-X" 1e9 VP) | | |
|---|---|---|
| Mouse # | GMT Pre vaccination | GMT Post vaccination |
| 3-1 | 5 | 56.57 |
| 3-2 | 5 | 80 |
| 3-3 | 5 | 56.57 |
| 3-4 | 5 | 226.27 |
| 3-5 | 5 | 320 |
| 3-6 | 5 | 160 |
| 4-1 | 5 | 22.28 |
| 4-2 | 5 | 56.57 |
| 4-3 | 5 | 10 |
| 4-4 | 5 | 20 |
| 4-5 | 5 | 40 |
| 4-6 | 5 | 80 |

TABLE R

| H1N1 T Cell Responses (interferon gamma ELISpot) | | | | | | | | | | |
|---|---|---|---|---|---|---|---|---|---|---|
| | Animal | Minipool | | | | | | | | |
| Treatment | ID | 1 | 2 | 3 | 4 | 5 | 6 | SUM | Mean | SE |
| ChAd-HA | 7 | 34 | 966 | 638 | 7 | 4116 | 2304 | 8065 | 10630 | 1732 |
| 5e10 vp | 8 | 307 | 5526 | 1607 | 169 | 4790 | 5913 | 18312 | | |
| | 9 | 81 | 1538 | 745 | 38 | 4926 | 2600 | 9927 | | |
| | 10 | 59 | 1832 | 457 | 3 | 2463 | 1873 | 6687 | | |
| | 11 | 59 | 3855 | 1307 | 22 | 5630 | 1556 | 12430 | | |
| | 12 | 145 | 6100$^a$ | 2504 | 98 | 6100$^a$ | 5613 | 8360 | | |
| SAM-HA 10 ug | 21 | 487 | 4240 | 1373 | 374 | 5366 | 4515 | 16355 | 6313 | 2467 |
| | 22 | 354 | 3649 | 1451 | 231 | 2213 | 3101 | 11000 | | |
| | 23 | 49 | 1707 | 299 | 0 | 1332 | 476 | 3863 | | |
| | 24 | 138 | 1519 | 504 | 30 | 176 | 1339 | 3706 | | |
| | 25 | 104 | 648 | 217 | 0 | 87 | 666 | 1721 | | |
| | 26 | 112 | 400 | 213 | 30 | 215 | 261 | 1232 | | |
| ChAd-HA + | 1 | 696 | 11991 | 2356 | 525 | 25000$^a$ | 4441 | 20009 | 45546 | 5690 |
| SAM-HA | 2 | 247 | 15232 | 3041 | 454 | 21429 | 14969 | 55371 | | |
| prime/boost | 3 | 276 | 16216 | 2078 | 465 | 23563 | 10576 | 53174 | | |
| | 4 | 489 | 19196 | 2849 | 347 | 20170 | 9534 | 52584 | | |
| | 5 | 292 | 12085 | 2109 | 572 | 20931 | 2514 | 38503 | | |
| | 6 | 162 | 21544 | 2986 | 233 | 17148 | 11561 | 53635 | | | strains, in particular with ChAd-HA priming as well as subsequent boosting with a SAM-based vaccine.

TABLE P

| H1N1 HAI titers pre and post immunization ("1-X" 5e10 VP; "2-X" 1e9 VP) | | |
|---|---|---|
| Mouse # | GMT Pre vaccination | GMT Post vaccination |
| 1-1 | 5 | 320 |
| 1-2 | 5 | 320 |
| 1-3 | 5 | 640 |
| 1-4 | 5 | 640 |
| 1-5 | 5 | 320 |
| 1-6 | 5 | 320 |
| 2-1 | 5 | 5 |
| 2-2 | 5 | 160 |
| 2-3 | 5 | 80 |
| 2-4 | 5 | 40 |
| 2-5 | 5 | 160 |
| 2-6 | 5 | 40 |

TABLE S

| H1N1 Polyfunctional T Cell Responses (Cytokine ICS) | | | | | | |
|---|---|---|---|---|---|---|
| | % of CD8+ | | | % of CD4+ | | |
| | IFNg | TNFa | IL2 | IFNg | TNFa | IL2 |
| | 32.25 | 23.25 | 0.59 | 0.94 | 1.02 | 0.47 |
| | 25.67 | 16.70 | 0.47 | 0.90 | 1.01 | 0.44 |
| | 25.98 | 17.48 | 0.77 | 0.68 | 1.04 | 0.42 |
| | 31.97 | 22.10 | 0.55 | 1.38 | 1.43 | 0.61 |
| | 26.27 | 18.08 | 0.88 | 0.77 | 0.91 | 0.40 |
| | 40.89 | 26.66 | 1.02 | 0.99 | 0.81 | 0.35 |
| Mean | 30.51 | 20.71 | 0.71 | 0.94 | 1.04 | 0.45 |
| SE | 2.41 | 1.60 | 0.09 | 0.10 | 0.09 | 0.04 |

Cytokine responses are from individual animals and is the sum of the response to two overlapping peptide pools.

Certain Sequences

Vectors, cassettes, and antibodies referred to herein are described below and referred to by SEQ ID NO.

Tremelimumab VL (SEQ ID NO: 16)

Tremelimumab VH (SEQ ID NO: 17)

Tremelimumab VH CDR1 (SEQ ID NO: 18)

Tremelimumab VH CDR2 (SEQ ID NO: 19)

Tremelimumab VH CDR3 (SEQ ID NO: 20)

Tremelimumab VL CDR1 (SEQ ID NO: 21)

Tremelimumab VL CDR2 (SEQ ID NO: 22)

Tremelimumab VL CDR3 (SEQ ID NO: 23)

Durvalumab (MEDI4736) VL (SEQ ID NO: 24)

MEDI4736 VH (SEQ ID NO: 25)

MEDI4736 VH CDR1 (SEQ ID NO: 26)

MEDI4736 VH CDR2 (SEQ ID NO: 27)

MEDI4736 VH CDR3 (SEQ ID NO: 28)

MEDI4736 VL CDR1 (SEQ ID NO: 29)

MEDI4736 VL CDR2 (SEQ ID NO: 30)

MEDI4736 VL CDR3 (SEQ ID NO: 31)

UbA76-25 merPDTT nucleotide (SEQ ID NO: 32)

UbA76-25 merPDTT polypeptide (SEQ ID NO: 33)

MAG-25 merPDTT nucleotide (SEQ ID NO: 34)

MAG-25 merPDTT polypeptide (SEQ ID NO: 35)

Ub7625 merPDTT_NoSFL nucleotide (SEQ ID NO: 36)

Ub7625 merPDTT_NoSFL polypeptide (SEQ ID NO: 37)

ChAdV68.5WTnt.MAG25 mer (SEQ ID NO: 2); AC_000011.1 with E1 (nt 577 to 3403) and E3 (nt 27, 125-31, 825) sequences deleted; corresponding ATCC VR-594 nucleotides substituted at five positions; model neoantigen cassette under the control of the CMV promoter/enhancer inserted in place of deleted E1; SV40 polyA 3' of cassette Venezuelan equine encephalitis virus [VEE] (SEQ ID NO: 3) GenBank: L01442.2

VEE-MAG25mer (SEQ ID NO: 4); contains MAG-25merPDTT nucleotide (bases 30-1755)

Venezuelan equine encephalitis virus strain TC-83 [TC-83] (SEQ ID NO: 5) GenBank: L01443.1

VEE Delivery Vector (SEQ ID NO: 6); VEE genome with nucleotides 7544-11175 deleted [alphavirus structural proteins removed]

TC-83 Delivery Vector (SEQ ID NO: 7); TC-83 genome with nucleotides 7544-11175 deleted [alphavirus structural proteins removed]

VEE Production Vector (SEQ ID NO: 8); VEE genome with nucleotides 7544-11175 deleted, plus 5' T7-promoter, plus 3' restriction sites TC-83 Production Vector (SEQ ID NO: 9); TC-83 genome with nucleotides 7544-11175 deleted, plus 5' T7-promoter, plus 3' restriction sites VEE-UbAAY (SEQ ID NO: 14); VEE delivery vector with MHC class I mouse tumor epitopes SIINFEKL and AH1-A5 inserted VEE-Luciferase (SEQ ID NO: 15); VEE delivery vector with luciferase gene inserted at 7545 ubiquitin (SEQ ID NO: 38) >UbG76 0-228

Ubiquitin A76 (SEQ ID NO: 39) >UbA76 0-228

HLA-A2 (MHC class I) signal peptide (SEQ ID NO: 40) >MHC SignalPep 0-78

-continued

HLA-A2 (MHC class I) Trans Membrane domain (SEQ ID NO: 41) >HLA A2 TM Domain
0-201

IgK Leader Seq (SEQ ID NO: 42) >IgK Leader Seq 0-60

Human DC-Lamp (SEQ ID NO: 43) >HumanDCLAMP 0-3178

Mouse LAMP1 (SEQ ID NO: 44) >MouseLamp1 0-1858

Human Lamp1 cDNA (SEQ ID NO: 45) >Human Lamp1 0-2339

Tetanus toxoid nulceic acid sequence (SEQ ID NO: 46)

Tetanus toxoid amino acid sequence (SEQ ID NO: 47)

PADRE nulceotide sequence (SEQ ID NO: 48)

PADRE amino acid sequence (SEQ ID NO: 49)

WPRE (SEQ ID NO: 50) >WPRE 0-593

IRES (SEQ ID NO: 51) >eGFP_IRES_SEAP_Insert 1746-2335

GFP (SEQ ID NO: 52)

SEAP (SEQ ID NO: 53)

Firefly Luciferase (SEQ ID NO: 54)

FMDV 2A (SEQ ID NO: 55)

Ipilimumab Heavy Chain (SEQ ID NO: 29365)
QVQLVESGGGVVQPGRSLRLSCAASGFTFSSYTMHWVRQAPGKGLEWVTFISYDGNNKYYADSVKGRFTISRDN
SKNTLYLQMNSLRAEDTAIYYCARTGWLGPFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKRVEPKSCD
KTHTCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQGNVFSCSVMHEALHNHYTQKSLSL
SPGK (SEQ ID NO: 65)

Ipilimumab Light Chain (SEQ ID NO: 29366)
EIVLTQSPGTLSLSPGERATLSCRASQSVGSSYLAWYQQKPGQAPRLLIYGAFSRATGIPDRFSGSGSGTDFTL
TISRLEPEDFAVYYCQQYGSSPWTFGQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSENRGEC (SEQ
ID NO: 66)

Nivolumab Heavy Chain (SEQ ID NO: 29367)
QVQLVESGGGVVQPGRSLRLDCKASGITFSNSGMHWVRQAPGKGLEWVAVIWYDGSKRYYADSVKGRFTISRDN
SKNTLFLQMNSLRAEDTAVYYCATNDDYWGQGTLVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKVDKRVESKYGPPCPPC
PAPEFLGGPSVFLFPPKPKDTLMISRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVMHEALHNHYTQKSLSLSLGK
(SEQ ID NO: 67)

Nivolumab Light Chain (SEQ ID NO: 29368)
EIVLTQSPATLSLSPGERATLSCRASQSVSSYLAWYQQKPGQAPRLLIYDASNRATGIPARFSGSGSGTDFTLT
ISSLEPEDFAVYYCQQSSNWPRTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSENRGEC (SEQ ID
NO: 68)

Influenza A H1N1 CA/7/09 HA
ATGAAAGCTATCCTTGTAGTCCTTCTCTATACTTTTGCCACAGCTAACGCGGATACGCTGTGCATCGGGTATCA
CGCAAATAACTCCACCGATACGGTGGACACGGTGCTTGAGAAGAATGTAACTGTAACTCATTCCGTGAACTTGC
TGGAGGACAAACACAACGGGAAGTTGTGCAAGCTCAGGGGGGTCGCGCCGTTGCATTTGGGAAAATGTAATATC
GCTGGATGGATCTTGGGTAATCCCGAGTGCGAAAGCCTCAGCACCGCCAGCAGCTGGAGCTACATTGTGGAAAC
TCCCTCAAGCGATAACGGGACCTGTTACCCAGGGGATTTCATCGACTATGGAATTGCGGGAACAGTTGAGTT
CTGTGTGTCTTCATTTGAACGATTtGAAATTTTCCCCAAGACCAGTTCTTGGCCTAATCACGACTCTAACAAGGGT
GTTACGGCAGCATGCCCGCATGCCGGAGCAAAGAGTTTCTACAAAAAATTTGATCTGGTTGGTGAAGAAGGGCAA
CTCATACCCTAAGCTCAGTAAGTCTTATATCAATGACAAAGGAAAGAAGTACTGGTTTTGTGGGGAATCCACC
ATCCGTCCACATCTGCAGACCAACAGTCACTCTACCAGAACGCGGATGCCTACGTTTTTGTGGGAAGCTCAAGA
TATTCCAAAAAATTCAAGCCTGAGATTGCTATTCGCCCAAAGGTCCGCGACCAAGAAGGCAGGATGAATTACTA
CTGGACCTTGGTCGAGCCTGGTGATAAGATTACATTTGAAGCCACCGGTAACCTTGTTGTCCCGAGGTACGCCT
TCGCGATGGAGCGGAATGCAGGGTCAGGGATTATTATATCAGACACCCCAGTACACGACTGCAACACAACTTGT
CAGACCCCTAAGGGTGCCATCAATACATCCCTGCCGTTTCAGAATATCCATCCGATCACTATAGGCAAGTGTCC
AAAATATGTGAAGAGCACGAAGCTTAGGCTGGCGACCGGATTGCGGAACATACCTTCTATCCAGAGTCGCGGGC
TCTTCGGAGCTATCGCGGGCTTTATAGAGGGAGGATGGACTGGAATGGTAGATGGATGGTATGGTTACCACCAT
CAGAACGAACAGGGATCCGGGTACGCAGCAGATTTGAAATCAACACAGAACGCCATCGACGAGATCACCAATAA -continued

```
GGTGAACTCTGTAATTGAAAAAATGAATACGCAATTCACTGCAGTGGGGAAGGAATTCAACCATCTGGAGAAAC
GAATTGAAAACCTTAACAAGAAGGTAGATGACGGTTTCCTCGATATCTGGACATATAATGCAGAACTTTTGGTA
TTGCTGGAAAATGAACGGACCCTGGATTATCACGATTCAAACGTTAAAAATCTCTATGAGAAGGTTCGATCTCA
ACTGAAGAACAACGCCAAGGAAATAGGAAACGGATGTTTCGAGTTCTATCATAAATGCGATAACACATGCATGG
AGAGCGTCAAGAACGGTACCTACGACTATCCTAAGTATAGTGAGGAAGCCAAACTCAATAGGGAAGAGATCGAC
GGAGTCAAATTGGAATCAACGCGAATATATCAGATTCTTGCAATTTACAGCACTGTCGCGAGTAGCCTTGTGTT
GGTTGTGAGCCTCGGTGCTATTTCCTTTTGGATGTGCTCAAACGGCTCTCTCCAGTGTAGAATCTGCATTTGA
(SEQ ID NO: 69)

Influenza A H7N9 Anhui/1/13 HA
ATGAATACCCAAATATTGGTATTCGCTCTGATTGCAATTATTCCGACTAACGCAGATAAGATTTGCCTTGGCCA
CCATGCTGTGAGTAATGGAACTAAAGTTAACACACTTACCGAACGGGGCGTTGAAGTCGTGAACGCCACAGAGA
CAGTCGAGAGAACAAACATTCCACGAATATGCAGCAAAGGCAAACGAACTGTAGACCTCGGGCAATGCGGCCTC
CTCGGTACCATTACCGGTCCTCCGCAGTGTGACCAGTTTCTGGAGTTTTCAGCCGACCTCATCATTGAGCGACG
GGAGGGAAGCGACGTCTGCTACCCTGGGAAGTTCGTGAACGAAGAAGCGCTGCGGCAGATTTTGAGAGAAAGTG
GTGGTATAGATAAAGAGGCGATGGGCTTCACGTATTCCGGTATAAGGACAAATGGTGCCACGTCTGCATGCAGG
CGGAGCGGCAGCTCTTTTTACGCAGAGATGAAATGGCTGTTGTCAAACACCGATGATGCGGCTTTTCCTCAAAT
GACCAAAAGCTATAAGAACACCAGGAAATCCCCCGCACTCATAGTCTGGGGTATACATCACTCAGTGTCCACAG
CAGAACAAACGAAACTTTATGGGTCTGGCAACAAACTGGTGACAGTGGGGTCCTCTAACTATCAACAAAGCTTT
GTGCCATCACCAGGGGCTCGACCACAAGTAAACGGACTCAGTGGGCGGATCGACTTCCACTGGTTGATGCTCAA
TCCTAACGATACCGTTACCTTCTCTTTCAACGGAGCCTTCATAGCGCCTGACAGGGCCAGCTTTCTCAGGGGTA
AATCCATGGGGATACAGTCAGGGGTCCAGGTGGATGCCAATTGCGAAGGCGATTGCTATCACTCTGGCGGAACA
ATAATCTCCAATCTCCCGTTCCAGAATATTGACTCACGGGCAGTAGGGAAATGTCCCCGCTATGTCAAACAGAG
GAGCTTGCTGCTTGCAACCGGCATGAAGAACGTGCCTGAAATACCCAAAGGTAGGGGCCTTTTCGGGGCTATCG
CGGGATTTATCGAAAACGGGTGGGAGGGACTCATCGACGGCTGGTACGGCTTTAGGCATCAAAACGCGCAAGGT
GAAGGCACGGCAGCTGACTACAAGAGCACGCAGTCTGCCATCGATCAGATAACCGGGAAACTTAATCGCCTGAT
CGAAAAGACAAATCAGCAATTTGAACTCATCGACAATGAATTTAACGAAGTGGAGAAGCAAATTGGCAATGTCA
TCAACTGGACAAGAGACTCAATTACGGAAGTTTGGAGCTACAATGCTGAATTGCTTGTAGCAATGGAAAACCAG
CATACGATAGACCTGGCTGATTCTGAGATGGACAAGCTCTATGAGCGGGTAAAAAGGCAGCTCCGAGAAAACGC
CGAGGAGGACGGTACGGGATGCTTCGAGATTTTCCATAAGTGTGACGACGACTGTATGGCAAGTATCCGAAATA
ACACTTACGATCATTCAAAATACCGGGAGGAAGCTATGCAAAACAGAATACAGATTGACCCGGTTAAATTGAGC
AGCGGCTATAAAGATGTGATCCTGTGGTTTAGCTTCGGGAGCTTCCTGTTTCATTCTTCTGGCAATAGTTATGGG
TCTTGTATTTATTTGTGTAAAAAACGGGAATATGCGATGCACGATCTGTATCTGA
(SEQ ID NO: 70)
```

REFERENCES

1. Desrichard, A., Snyder, A. & Chan, T. A. Cancer Neoantigens and Applications for Immunotherapy. *Clin. Cancer Res. Off. J. Am. Assoc. Cancer Res.* (2015). doi:10.1158/1078-0432.CCR-14-3175

2. Schumacher, T. N. & Schreiber, R. D. Neoantigens in cancer immunotherapy. *Science* 348, 69-74 (2015).

3. Gubin, M. M., Artyomov, M. N., Mardis, E. R. & Schreiber, R. D. Tumor neoantigens: building a framework for personalized cancer immunotherapy. *J. Clin. Invest.* 125, 3413-3421 (2015).

4. Rizvi, N. A. et al. Cancer immunology. Mutational landscape determines sensitivity to PD-1 blockade in non-small cell lung cancer. *Science* 348, 124-128 (2015).

5. Snyder, A. et al. Genetic basis for clinical response to CTLA-4 blockade in melanoma. *N. Engl. J. Med.* 371, 2189-2199 (2014).

6. Carreno, B. M. et al. Cancer immunotherapy. A dendritic cell vaccine increases the breadth and diversity of melanoma neoantigen-specific T cells. *Science* 348, 803-808 (2015).

7. Tran, E. et al. Cancer immunotherapy based on mutation-specific CD4+ T cells in a patient with epithelial cancer. *Science* 344, 641-645 (2014).

8 Hacohen, N. & Wu, C. J.-Y. United States Patent Application: 20110293637-COMPOSITIONS AND METHODS OF IDENTIFYING TUMOR SPECIFIC NEOANTIGENS. (A1). at appft 1.uspto.gov/netacgi/nph-Parser?Sect1=PTO1&Sect2=HITOFF&d=PG01&p=1&u=/netahtml/PTO/srchnum.html&r=1&f=G&1=50&s1=20110293637.PGNR.

9. Lundegaard, C., Hoof, I., Lund, O. & Nielsen, M. State of the art and challenges in sequence based T-cell epitope prediction. *Immunome Res.* 6 Suppl 2, S3 (2010).

10. Yadav, M. et al. Predicting immunogenic tumour mutations by combining mass spectrometry and exome sequencing. *Nature* 515, 572-576 (2014).

11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).

12. Van Allen, E. M. et al. Genomic correlates of response to CTLA-4 blockade in metastatic melanoma. *Science* 350, 207-211 (2015).

13. Yoshida, K. & Ogawa, S. Splicing factor mutations and cancer. *Wiley Interdiscip. Rev. RNA* 5, 445-459 (2014).

14. Cancer Genome Atlas Research Network. Comprehensive molecular profiling of lung adenocarcinoma. *Nature* 511, 543-550 (2014).

15. Rajasagi, M. et al. Systematic identification of personal tumor-specific neoantigens in chronic lymphocytic leukemia. *Blood* 124, 453-462 (2014).

16. Downing, S. R. et al. U.S. Patent Application: 0120208706-OPTIMIZATION OF MULTIGENE ANALYSIS OF TUMOR SAMPLES. (A1). at appft1.uspto.gov/netacgi/nph-Parser?Sect1=PTO1&Sect2=HITOFF&d=PG01&p=1&u=/netahtml/PTO/srchnum.html&r=1&f=G&1=50&s1=20120208706.PGNR.

17. Target Capture for NextGen Sequencing—IDT. at www.idtdna.com/pages/products/nextgen/target-capture 18. Shukla, S. A. et al. Comprehensive analysis of cancer-associated somatic mutations in class I HLA genes. *Nat. Biotechnol.* 33, 1152-1158 (2015).

19. Cieslik, M. et al. The use of exome capture RNA-seq for highly degraded RNA with application to clinical cancer sequencing. *Genome Res.* 25, 1372-1381 (2015).

20. Bodini, M. et al. The hidden genomic landscape of acute myeloid leukemia: subclonal structure revealed by undetected mutations. *Blood* 125, 600-605 (2015).

21. Saunders, C. T. et al. Strelka: accurate somatic small-variant calling from sequenced tumor-normal sample pairs. *Bioinforma. Oxf. Engl.* 28, 1811-1817 (2012).

22. Cibulskis, K. et al. Sensitive detection of somatic point mutations in impure and heterogeneous cancer samples. *Nat. Biotechnol.* 31, 213-219 (2013).

23. Wilkerson, M. D. et al. Integrated RNA and DNA sequencing improves mutation detection in low purity tumors. *Nucleic Acids Res.* 42, e107 (2014).

24. Mose, L. E., Wilkerson, M. D., Hayes, D. N., Perou, C. M. & Parker, J. S. ABRA: improved coding indel detection via assembly-based realignment. *Bioinforma. Oxf. Engl.* 30, 2813-2815 (2014).

25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf. Engl.* 25, 2865-2871 (2009).

26. Lam, H. Y. K. et al. Nucleotide-resolution analysis of structural variants using BreakSeq and a breakpoint library. *Nat. Biotechnol.* 28, 47-55 (2010).

27. Frampton, G. M. et al. Development and validation of a clinical cancer genomic profiling test based on massively parallel DNA sequencing. *Nat. Biotechnol.* 31, 1023-1031 (2013).

28. Boegel, S. et al. HLA typing from RNA-Seq sequence reads. *Genome Med.* 4, 102 (2012).

29. Liu, C. et al. ATHLATES: accurate typing of human leukocyte antigen through exome sequencing. *Nucleic Acids Res.* 41, e142 (2013).

30. Mayor, N. P. et al. HLA Typing for the Next Generation. *PloS One* 10, e0127153 (2015).

31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).

32. Song, L. & Florea, L. CLASS: constrained transcript assembly of RNA-seq reads. *BMC Bioinformatics* 14 Suppl 5, S14 (2013).

33. Maretty, L., Sibbesen, J. A. & Krogh, A. Bayesian transcriptome assembly. *Genome Biol.* 15, 501 (2014).

34. Pertea, M. et al. StringTie enables improved reconstruction of a transcriptome from RNA-seq reads. *Nat. Biotechnol.* 33, 290-295 (2015).

35. Roberts, A., Pimentel, H., Trapnell, C. & Pachter, L. Identification of novel transcripts in annotated genomes using RNA-Seq. *Bioinforma. Oxf. Engl.* (2011). doi: 10.1093/bioinformatics/btr355

36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).

37. Rivas, M. A. et al. Human genomics. Effect of predicted protein-truncating genetic variants on the human transcriptome. *Science* 348, 666-669 (2015).

38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).

39. Anders, S., Pyl, P. T. & Huber, W. HTSeq—a Python framework to work with high-throughput sequencing data. *Bioinforma. Oxf. Engl.* 31, 166-169 (2015).

40. Furney, S. J. et al. SF3B1 mutations are associated with alternative splicing in uveal melanoma. *Cancer Discov.* (2013). doi:10.1158/2159-8290.CD-13-0330

41. Zhou, Q. et al. A chemical genetics approach for the functional assessment of novel cancer genes. *Cancer Res.* (2015). doi:10.1158/0008-5472.CAN-14-2930

42. Maguire, S. L. et al. SF3B1 mutations constitute a novel therapeutic target in breast cancer. *J. Pathol.* 235, 571-580 (2015).

43. Carithers, L. J. et al. A Novel Approach to High-Quality Postmortem Tissue Procurement: The GTEx Project. *Biopreservation Biobanking* 13, 311-319 (2015).

44. Xu, G. et al. RNA COMPASS: a dual approach for pathogen and host transcriptome analysis of RNA-seq datasets. *PloS One* 9, e89445 (2014).

45. Andreatta, M. & Nielsen, M. Gapped sequence alignment using artificial neural networks: application to the MHC class I system. *Bioinforma. Oxf. Engl.* (2015). doi:10.1093/bioinformatics/btv639

46. Jørgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).

47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).

48. Nielsen, M., Lundegaard, C., Lund, O. & Keşmir, C. The role of the proteasome in generating cytotoxic T-cell epitopes: insights obtained from improved predictions of proteasomal cleavage. *Immunogenetics* 57, 33-41 (2005).

49. Boisvert, F.-M. et al. A Quantitative Spatial Proteomics Analysis of Proteome Turnover in Human Cells. *Mol. Cell. Proteomics* 11, M111.011429-M111.011429 (2012).

50. Duan, F. et al. Genomic and bioinformatic profiling of mutational neoepitopes reveals new rules to predict anti-cancer immunogenicity. *J. Exp. Med.* 211, 2231-2248 (2014).

51. Janeway's Immunobiology: 9780815345312: Medicine & Health *Science* Books @ Amazon.com. at www.amazon.com/Janeways-Immunobiology-Kenneth-Murphy/dp/0815345313

52. Calis, J. J. A. et al. Properties of MHC Class I Presented Peptides That Enhance Immunogenicity. *PLoS Comput. Biol.* 9, e1003266 (2013).

53. Zhang, J. et al. Intratumor heterogeneity in localized lung adenocarcinomas delineated by multiregion sequencing. *Science* 346, 256-259 (2014)

54. Walter, M. J. et al. Clonal architecture of secondary acute myeloid leukemia. *N. Engl. J. Med.* 366, 1090-1098 (2012).

55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. *Science* 1992. 255:1261-1263.

56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.

57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.

58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9): 1308-18. doi: 10.1038/nprot.2015.086. Epub 2015 Aug. 6

59. Barnstable C J, Bodmer W F, Brown G. Galfre G, Milstein C, Williams A F, Ziegler A. Production of monoclonal antibodies to group A erythrocytes. HLA and other human cell surface antigens-new tools for genetic analysis. Cell. 1978 May; 14(1):9-20.

60. Goldman J M, Hibbin J, Kearney L, Orchard K, Th'ng K H, HLA-DR monoclonal antibodies inhibit the proliferation of normal and chronic granulocytic leukaemia myeloid progenitor cells. Br J Haematol. 1982 November: 52(3):411-20.

61. Eng J K, Jahan T A, Hoopmann M R, Comet: an open-source MS/MS sequence database search tool. Proteomics. 2013 January; 13(1):22-4. doi: 10.1002/pmic.201200439. Epub 2012 Dec. 4.

62. Eng J K, Hoopmann M R, Jahan T A, Egertson J D, Noble W S, MacCoss M J, A deeper look into Comet—implementation and features. J Am Soc Mass Spectrom. 2015 November; 26(11):1865-74. doi: 10.1007/s13361-015-1179-x. Epub 2015 Jun. 27.

63. Lukas Käll, Jesse Canterbury, Jason Weston, William Stafford Noble and Michael J. MacCoss. Semi-supervised learning for peptide identification from shotgun proteomics datasets. Nature Methods 4:923-925. November 2007

64. Lukas Käll, John D. Storey, Michael J. MacCoss and William Stafford Noble. Assigning confidence measures to peptides identified by tandem mass spectrometry. Journal of Proteome Research. 7(1):29-34. January 2008

65. Lukas Käll, John D. Storey and William Stafford Noble. Nonparametric estimation of posterior error probabilities associated with peptides identified by tandem mass spectrometry. Bioinformatics. 24(16):142-148. August 2008

66. Kinney R M, B J Johnson, V L Brown, D W Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.

67. Jill E Slansky, Frédérique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity. Volume 13. Issue 4. 1 Oct. 2000. Pages 529-538.

68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA.: 93(18): 9730-9735. 1996 Sep. 3.

69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. J Gen Virol 67:1951-1960. 1986.

70. Aarnoudse, C. A., Kruse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99. 7-13.

71. Alexander, J., Sidney, J., Southwood, S., Ruppert. J., Oseroff, C., Maewal, A., Snoke, K., Serra, H. M., Kubo, R. T., and Sette, A. (1994). Development of high potency universal DR-restricted helper epitopes by modification of high affinity DR-blocking peptides. Immunity 1. 751-761.

72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4. 4166.

73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24. 2102-2109.

74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450).

75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.

76. Janetzki, S., Price, L., Schroeder, H., Britten, C. M., Welters, M. J. P., and Hoos, A. (2015). Guidelines for the automated evaluation of Elispot assays. Nat Protoc 10, 1098-1115.

77. Lyons, G. E., Moore, T., Brasic, N., Li. M., Roszkowski, J. J., and Nishimura, M. I. (2006). Influence of human CD8 on antigen recognition by T-cell receptor-transduced cells. Cancer Res 66, 11455-11461.

78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. Blood 119, 368-376.

79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.

80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.

81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.

82. Pushko P. Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.

83. Strauss, J H and E G Strauss. The alphaviruses: gene expression, replication, and evolution. Microbiol Rev. 1994 September; 58(3):491-562.

84. Rhême C. Ehrengruber M U, Grandgirard D. Alphaviral cytotoxicity and its implication in vector development. Exp Physiol. 2005 January; 90(1):45-52. Epub 2004 Nov. 12.

85. Riley, Michael K. II, and Wilfred Vermerris. Recent Advances in Nanomaterials for Gene Delivery—A Review. Nanomaterials 2017, 7(5), 94.

86. Frolov I, Hardy R, Rice C M. Cis-acting RNA elements at the 5' end of Sindbis virus genome RNA regulate minus- and plus-strand RNA synthesis. RNA. 2001 November; 7(11):1638-51.

87. Jose J, Snyder J E, Kuhn R J. A structural and functional perspective of alphavirus replication and assembly. Future Microbiol. 2009 September; 4(7):837-56.

88. Bo Li and C. olin N. Dewey. RSEM: accurate transcript quantification from RNA-Seq data with or without a referenfe genome. BMC Bioinformatics, 12:323, August 2011

89. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sébastien Lemieux, Pierre Thibault, and Claude Perreault. MHC class I-associated peptides derive from selective regions of the human genome. The Journal of Clinical Investigation, 2016, 90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.

91. Mommen G P., Marino, F., Meiring H D., Poelen, M C., van Gaans-van den Brink, J A., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423 April 2016.

92. Sebastian Kreiter, Mathias Vormehr, Niels van de Roemer, Mustafa Diken, Martin Lower, Jan Diekmann, Sebastian Boegel, Barbara Schrörs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to caner. Nature 520, 692-696, April 2015.

93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.

94. Andreatta M., Karosiene E., Rasmussen M., Stryhn A., Buus S., Nielsen M. Accurate pan-specific prediction of peptide-MHC class II binding affinity with improved binding core identification. Immunogenetics 67(11-12) 641-650, November 2015.

95. Nielsen, M., Lund, O. NN-align. An artificial neural network-based alignment algorithm for MHC class II peptide binding prediction. BMC Bioinformatics 10:296, September 2009.

96. Nielsen, M., Lundegaard, C., Lund, O. Prediction of MHC class II binding affinity using SMM-align, a novel stabilization matrix alignment method. BMC Bioinformatics 8:238, July 2007.

97. Zhang, J., et al. PEAKS DB: de novo sequencing assisted database search for sensitive and accurate peptide identification. Molecular & Cellular Proteomics. 11(4):1-8. Jan. 2, 2012.

98. Jensen, Kamilla Kjaergaard, et al. "Improved Methods for Prediting Peptide Binding Affinity to MHC Class II Molecules." Immunology, 2018, doi:10.1111/imm.12889.

99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. Nat. Biotechnol. 30, 413-421

100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271.e11.

101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nat. Biotechnol. 33, 1152-1158.

102. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

103. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

What is claimed is:

1. A composition for delivery of a self-replicating alphavirus-based expression system, wherein the composition for delivery of the self-replicating alphavirus-based expression system comprises:

(A) the self-replicating alphavirus-based expression system, wherein the self-replicating alphavirus-based expression system comprises one or more vectors, wherein the one or more vectors comprises:

(a) an RNA alphavirus backbone, wherein the RNA alphavirus backbone comprises:

(i) at least one promoter nucleotide sequence, and (ii) at least one polyadenylation (poly(A)) sequence; and (b) a cassette, wherein the cassette comprises:

(i) at least one antigen-encoding nucleic acid sequence comprising:

a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, b. optionally a 5' linker sequence, and c. optionally a 3' linker sequence;

(ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, wherein an ordered sequence of each element of the cassette in the composition for delivery of the self-replicating alphavirus-based expression system is described in the formula, from 5' to 3', comprising:

$$P_a\text{-}(L5_b\text{-}N_c\text{-}L3_d)_X\text{-}(G5_e\text{-}U_f)_Y\text{-}G3_g$$

wherein P comprises the second promoter nucleotide sequence, where a=0 or 1,

N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1, G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an MHC class I epitope-encoding nucleic acid sequence, and Y=0, 1, or 2, where for each Y the corresponding $U_f$ is an MHC class II epitope-encoding nucleic acid sequence optionally wherein:

(a) for each X the corresponding $N_c$ is a distinct MHC class I epitope encoding nucleic acid sequence; and/or (b) for each Y the corresponding $U_f$ is a distinct MHC class II antigen-encoding nucleic acid sequence; and/or (c) wherein:

a=0, b=1, d=1, e=1, g=1, h=1, X=20, Y=2, the at least one promoter nucleotide sequence is a single 26S promoter nucleotide sequence provided by the backbone, the at least one polyadenylation poly(A) sequence is a poly(A) sequence of at least 100 consecutive A nucleotides provided by the backbone, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 2 amino acids in length, L3 is a native 3' linker sequence that encodes a native C-terminal acid sequence of the MHC I epitope, and wherein the 3' linker sequence encodes a peptide that is at least 2 amino acids in length, U is each of a PADRE class II sequence and a Tetanus toxoid MHC class II sequence, wherein the alphavirus vector is a Venezuelan equine encephalitis virus vector, each of the MHC class I antigen-encoding nucleic acid sequences encodes a polypeptide that is between 13 and 25 amino acids in length, and optionally wherein at least two of the antigen-encoding nucleic acid sequences encode polypeptide sequences or portions thereof that are presented by MHC class I on the tumor cell surface, and (B) a lipid-nanoparticle (LNP), wherein the LNP encapsulates the self-replicating alphavirus-based expression system.

2. The composition of claim 1, wherein the nucleic acid sequence encoding the peptide comprises encoding a peptide selected from: an epitope, a full-length protein, a protein subunit, a protein domain, and combinations thereof of the protein expressed in the infectious disease organism.

3. The composition of claim 1, wherein the nucleic acid sequence encoding the peptide comprises two or more distinct epitope-encoding nucleic acid sequences, between 1-10, between 1-20, between 1-30, between 1-40, between 1-50, between 1-100, between 1-200, between 1-300, between 1-400, between 1-500, between 2-10, between 2-20, between 2-30, between 2-40, between 2-50, between 2-100, between 2-200, between 2-300, between 2-400, or between 2-500 distinct epitope-encoding nucleic acid sequences distinct epitope-encoding nucleic acid sequences.

4. The composition of claim 1, wherein the encoded peptide or peptides is capable of stimulating an immune response, a T cell response, a B cell response, and/or a T cell response and a B cell response.

5. The composition of claim 1, wherein the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, a orthymyxoviridae family virus, and tuberculosis.

6. The composition of claim 1, wherein the LNP comprises a lipid selected from the group consisting of:
an ionizable amino lipid, a phosphatidylcholine, cholesterol, a PEG-based coat lipid, or a combination thereof; or
the LNP comprises an ionizable amino lipid, a phosphatidylcholine, cholesterol, and a PEG-based coat lipid; and
optionally wherein the ionizable amino lipids comprise MC3-like (dilinoleylmethyl-4-dimethylaminobutyrate) molecules; and/or
the LNP-encapsulated expression system has a diameter of about 100 nm.

7. The composition of claim 1, wherein the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus, optionally wherein
a. the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus, or
b. the RNA alphavirus backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus; optionally wherein sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof; and/or the RNA alphavirus backbone comprises does not encode structural virion proteins capsid, E2 and E1, optionally wherein the antigen cassette is inserted in place of structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus; and/or the insertion of the antigen cassette provides for transcription of a polycistronic RNA comprising the nsP1-4 genes and the at least one antigen-encoding nucleic acid sequence, wherein the nsP1-4 genes and the at least one antigen-encoding nucleic acid sequence are in separate open reading frames; and optionally wherein the Venezuelan equine encephalitis virus comprises:
the sequence of SEQ ID NO:3 or SEQ ID NO:5, optionally further comprising a deletion between base pair 7544 and 11175, or the sequence set forth in SEQ ID NO:6 or SEQ ID NO:7, optionally
wherein the antigen cassette is inserted at position 7544 to replace the deletion between base pairs 7544 and 11175 as set forth in the sequence of SEQ ID NO:3 or SEQ ID NO:5.

8. The composition of claim 1, wherein the at least one promoter nucleotide sequence is:
the native 26S promoter nucleotide sequence encoded by the RNA alphavirus backbone or wherein the at least one promoter nucleotide sequence is an exogenous RNA promoter; and/or
wherein the second promoter nucleotide sequence is a 26S promoter nucleotide sequence, or comprises multiple 26S promoter nucleotide sequences, wherein each 26S promoter nucleotide sequence provides for transcription of one or more of the separate open reading frames; and/or
the at least one promoter nucleotide sequence or the second promoter nucleotide sequence is inducible or non-inducible; and/or
the at least one poly(A) sequence comprises a poly(A) sequence native to the backbone or exogenous to the backbone; and/or
the at least one poly(A) sequence is operably linked to at least one of the at least one antigen-encoding nucleic acid sequences; and/or
the at least one poly(A) sequence is at least 20, at least 30, at least 40, at least 50, at least 60, at least 70, at least 80, or at least 90 consecutive A nucleotides or at least 100 consecutive A nucleotides.

9. The composition of claim 1, wherein the epitope-encoding nucleic acid sequence comprises a MHC class I epitope-encoding nucleic acid sequence, and wherein the MHC class I epitope-encoding nucleic acid sequence is selected by performing the steps of:
(a) obtaining at least one of exome, transcriptome, or whole genome nucleotide sequencing data from the infectious disease organism, wherein the infectious disease organism nucleotide sequencing data is used to obtain data representing peptide sequences of each of a set of epitopes;
(b) inputting the peptide sequence of each epitope into a presentation model to generate a set of numerical likelihoods that each of the epitopes is presented by one or more of the MHC alleles on the infected cell surface, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence optionally wherein each of the MHC class I epitope-encoding nucleic acid sequences is selected by performing the above steps (a)-(c); and/or a number of the set of selected epitopes is 2-20; and/or the presentation model represents dependence between:

(a) presence of a pair of a particular one of the MHC alleles and a particular amino acid at a particular position of a peptide sequence, and (b) likelihood of presentation on the tumor cell surface, by the particular one of the MHC alleles of the pair, of such a peptide sequence comprising the particular amino acid at the particular position; and/or selecting the set of selected epitopes comprises selecting epitopes that have an increased likelihood of being presented on the tumor cell surface relative to unselected epitopes based on the presentation model; and/or selecting the set of selected epitopes comprises selecting epitopes that have an increased likelihood of being capable of inducing a tumor-specific immune response in the subject relative to unselected epitopes based on the presentation model; and/or selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC); and/or selecting the set of selected epitopes comprises selecting epitopes that have a decreased likelihood of being subject to inhibition via central or peripheral tolerance relative to unselected epitopes based on the presentation model; and/or the set of selected epitopes comprises selecting epitopes that have a decreased likelihood of being capable of inducing an autoimmune response to normal tissue in the subject relative to unselected epitopes based on the presentation model; and/or exome or transcriptome nucleotide sequencing data is obtained by performing sequencing on the tumor tissue, optionally wherein the sequencing is next generation sequencing (NGS) or any massively parallel sequencing approach.

10. The composition of claim 1, wherein:

the cassette comprises junctional epitope sequences formed by adjacent sequences in the cassette, optionally wherein at least one or each junctional epitope sequence has an affinity of greater than 500 nM for MHC and/or wherein each junctional epitope sequence is non-self; and/or the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject, optionally wherein the non-therapeutic predicted MHC class I or class II epitope sequence is a junctional epitope sequence formed by adjacent sequences in the cassette; and/or the prediction is based on presentation likelihoods generated by inputting sequences of the non-therapeutic epitopes into a presentation model; and/or an order of the antigen-encoding nucleic acid sequences in the cassette is determined by a series of steps comprising:

(a) generating a set of candidate cassette sequences corresponding to different orders of the antigen-encoding nucleic acid sequences;

(b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine.

11. The composition of claim 1, wherein the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

12. The composition of claim 1, wherein:

one or more of the epitope-encoding nucleic acid sequences are derived from an infection in or an infected cell of a subject; or each of the epitope-encoding nucleic acid sequences are derived from an infection in or an infected cell of a subject; or one or more of the epitope-encoding nucleic acid sequences are not derived from an infection in or an infected cell of a subject; or each of the epitope-encoding nucleic acid sequences are not derived from an infection in or an infected cell of a subject.

13. A method for stimulating an immune response in a subject, the method comprising administering to the subject the composition for delivery of the self-replicating alphavirus-based expression system of claim 1, and optionally administering to the subject a composition for delivery of a chimpanzee adenovirus (ChAdV)-based expression system, and, optionally wherein the composition for delivery of the ChAdV-based expression system is administered as a priming dose and either the composition for delivery of the ChAdV-based expression system or the composition for delivery of the self-replicating alphavirus-based expression system is administered as one or more boosting doses, or the composition for delivery of the self-replicating alphavirus-based expression system is administered as a priming dose either the composition for delivery of the ChAdV-based expression system or the composition for delivery of the self-replicating alphavirus-based expression system is administered as one or more boosting doses; and/or optionally wherein two or more, or 1, 2, 3, 4, 5, 6, 7, or 8 boosting doses are administered; and/or optionally wherein the cassette of the composition for delivery of the ChAdV-based expression system is identical to the cassette of the composition for delivery of the self-replicating alphavirus-based expression system.

14. The method of claim 13, wherein the composition for delivery of the self-replicating alphavirus-based expression system of claim 1 is administered as the priming dose and administered as one or more boosting doses.

15. A composition for delivery of a self-replicating alphavirus-based expression system, wherein the composition for delivery of the self-replicating alphavirus-based expression system comprises:

(A) the self-replicating alphavirus-based expression system, wherein the self-replicating alphavirus-based expression system comprises one or more vectors, wherein the one or more vectors comprises:

(a) an RNA alphavirus backbone, wherein the RNA alphavirus backbone comprises:

(i) at least one promoter nucleotide sequence, and (ii) at least one polyadenylation (poly(A)) sequence; and (b) a cassette, wherein the cassette comprises:

(i) at least one antigen-encoding nucleic acid sequence comprising:

a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, b. optionally a 5' linker sequence, and c. optionally a 3' linker sequence;

(ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, wherein the at least one promoter nucleotide sequence is:

the native 26S promoter nucleotide sequence encoded by the RNA alphavirus backbone or wherein the at least one promoter nucleotide sequence is an exogenous RNA promoter; and/or wherein the second promoter nucleotide sequence is a 26S promoter nucleotide sequence, or comprises multiple 26S promoter nucleotide sequences, wherein each 26S promoter nucleotide sequence provides for transcription of one or more of the separate open reading frames; and/or the at least one promoter nucleotide sequence or the second promoter nucleotide sequence is inducible or non-inducible; and/or the at least one poly(A) sequence comprises a poly(A) sequence native to the backbone or exogenous to the backbone; and/or the at least one poly(A) sequence is operably linked to at least one of the at least one antigen-encoding nucleic acid sequences; and/or the at least one poly(A) sequence is at least 20, at least 30, at least 40, at least 50, at least 60, at least 70, at least 80, or at least 90 consecutive A nucleotides or at least 100 consecutive A nucleotides, and (B) a lipid-nanoparticle (LNP), wherein the LNP encapsulates the self-replicating alphavirus-based expression system.

16. A method for stimulating an immune response in a subject, the method comprising administering to the subject the composition for delivery of the self-replicating alphavirus-based expression system of claim 15, and optionally administering to the subject a composition for delivery of a chimpanzee adenovirus (ChAdV)-based expression system, and, optionally wherein the composition for delivery of the ChAdV-based expression system is administered as a priming dose and either the composition for delivery of the ChAdV-based expression system or the composition for delivery of the self-replicating alphavirus-based expression system is administered as one or more boosting doses, or the composition for delivery of the self-replicating alphavirus-based expression system is administered as a priming dose either the composition for delivery of the ChAdV-based expression system or the composition for delivery of the self-replicating alphavirus-based expression system is administered as one or more boosting doses; and/or optionally wherein two or more, or 1, 2, 3, 4, 5, 6, 7, or 8 boosting doses are administered; and/or optionally wherein the cassette of the composition for delivery of the ChAdV-based expression system is identical to the cassette of the composition for delivery of the self-replicating alphavirus-based expression system.

17. A composition for delivery of a self-replicating alphavirus-based expression system, wherein the composition for delivery of the self-replicating alphavirus-based expression system comprises:

(A) the self-replicating alphavirus-based expression system, wherein the self-replicating alphavirus-based expression system comprises one or more vectors, wherein the one or more vectors comprises:

(a) an RNA alphavirus backbone, wherein the RNA alphavirus backbone comprises:

(i) at least one promoter nucleotide sequence, and (ii) at least one polyadenylation (poly(A)) sequence; and (b) a cassette, wherein the cassette comprises:

(i) at least one antigen-encoding nucleic acid sequence comprising:

a. a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, b. optionally a 5' linker sequence, and c. optionally a 3' linker sequence;

(ii) optionally, a second promoter nucleotide sequence operably linked to the at least one antigen-encoding nucleic acid sequence; and (iii) optionally, at least one second poly(A) sequence, wherein the second poly(A) sequence is a native poly(A) sequence or an exogenous poly(A) sequence to the alphavirus, wherein the cassette comprises junctional epitope sequences formed by adjacent sequences in the cassette, optionally wherein:

at least one or each junctional epitope sequence has an affinity of greater than 500 nM for MHC and/or wherein each junctional epitope sequence is non-self; and/or the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject, optionally wherein the non-therapeutic predicted MHC class I or class II epitope sequence is a junctional epitope sequence formed by adjacent sequences in the cassette; and/or the prediction is based on presentation likelihoods generated by inputting sequences of the non-therapeutic epitopes into a presentation model; and/or an order of the antigen-encoding nucleic acid sequences in the cassette is determined by a series of steps comprising:

(a) generating a set of candidate cassette sequences corresponding to different orders of the antigen-encoding nucleic acid sequences;

(b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine, and (B) a lipid-nanoparticle (LNP), wherein the LNP encapsulates the self-replicating alphavirus-based expression system.

18. A method for stimulating an immune response in a subject, the method comprising administering to the subject the composition for delivery of the self-replicating alphavirus-based expression system of claim 17, and optionally administering to the subject a composition for delivery of a chimpanzee adenovirus (ChAdV)-based expression system, and, optionally wherein the composition for delivery of the ChAdV-based expression system is administered as a priming dose and either the composition for delivery of the ChAdV-based expression system or the composition for delivery of the self-replicating alphavirus-based expression system is administered as one or more boosting doses, or the composition for delivery of the self-replicating alphavirus-based expression system is administered as a priming dose either the composition for delivery of the ChAdV-based expression system or the composition for delivery of the self-replicating alphavirus-based expression system is administered as one or more boosting doses; and/or optionally wherein two or more, or 1, 2, 3, 4, 5, 6, 7, or 8 boosting doses are administered; and/or optionally wherein the cassette of the composition for delivery of the ChAdV-based expression system is identical to the cassette of the composition for delivery of the self-replicating alphavirus-based expression system.

\* \* \* \* \*